US012692322B2

(12) United States Patent
Mulvihill et al.

(10) Patent No.: US 12,692,322 B2
(45) Date of Patent: Jul. 28, 2026

(54) ***KRAS* SPECIFIC ANTIBODIES AND USES THEREOF**

(71) Applicant: Genentech, Inc., South San Francisco, CA (US)

(72) Inventors: Melinda M Mulvihill, S. San Francisco, CA (US); John Gerard Quinn, S. San Francisco, CA (US); Micah Steffek, San Francisco, CA (US); Weiru Wang, S. San Francisco, CA (US); John Bruning, S. San Francisco, CA (US); Christopher Williamson Davies, Oakland, CA (US); Marie Evangelista, San Francisco, CA (US); James Thomas Koerber, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 867 days.

(21) Appl. No.: 17/243,129

(22) Filed: Apr. 28, 2021

(65) Prior Publication Data

US 2022/0112308 A1 Apr. 14, 2022

Related U.S. Application Data

(60) Provisional application No. 63/018,356, filed on Apr. 30, 2020.

(51) Int. Cl.

| | |
|---|---|
| ***C07K 16/40*** | (2006.01) |
| ***C12N 15/10*** | (2006.01) |
| ***G01N 33/573*** | (2006.01) |

(52) U.S. Cl.

CPC .......... *C07K 16/40* (2013.01); *C12N 15/1037* (2013.01); *G01N 33/573* (2013.01);

(Continued)

(58) Field of Classification Search

CPC ................ C07K 16/40; C07K 2317/56; C07K 2317/565; C07K 2317/76; C07K 2317/90;

(Continued)

(56) References Cited

U.S. PATENT DOCUMENTS

| | | | | |
|---|---|---|---|---|
| 9,334,331 | B2 * | 5/2016 | Igawa | C07K 16/36 |
| 10,287,345 | B2 * | 5/2019 | Donovan | A61P 21/04 |

(Continued)

FOREIGN PATENT DOCUMENTS

| | | | |
|---|---|---|---|
| EP | 3173428 | A1 | 5/2017 |
| WO | 2018/069871 | A1 | 4/2018 |

(Continued)

OTHER PUBLICATIONS

Warram JM, de Boer E, Sorace AG, Chung TK, Kim H, Pleijhuis RG, van Dam GM, Rosenthal EL. Antibody-based imaging strategies for cancer. Cancer Metastasis Rev. Sep. 2014;33(2-3):809-22. doi: 10.1007/s10555-014-9505-5. PMID: 24913898; PMCID: PMC4116453. (Year: 2014).*

(Continued)

*Primary Examiner* — Joanne Hama
*Assistant Examiner* — Hannah Sunshine
(74) *Attorney, Agent, or Firm* — Genentech, Inc.; Richard G. A. Bone

(57) ABSTRACT

Provided herein are anti-KRas antibodies that bind to mutant KRas-GDP and alkylated mutant KRas-GDP and methods of using the same. Also provide herein are method of screening for KRas inhibitors and methods of measuring binding of KRas to the antibodies described herein.

50 Claims, 33 Drawing Sheets

Specification includes a Sequence Listing.

(52) U.S. Cl.
CPC .... *C07K 2317/56* (2013.01); *C07K 2317/565* (2013.01); *C07K 2317/76* (2013.01); *C07K 2317/90* (2013.01); *G01N 2333/914* (2013.01)

(58) Field of Classification Search
CPC ............ C07K 2317/34; C07K 2317/55; C07K 2317/92; C07K 16/32; C07K 2317/73; C12N 15/1037; G01N 33/573; G01N 2333/914; G01N 33/57484; A61P 35/00; A61K 2039/505
See application file for complete search history.

(56) References Cited

U.S. PATENT DOCUMENTS

| | | | | |
|---|---|---|---|---|
| 2005/0142593 A1* | 6/2005 | Bensimon | ............ | C12Q 1/6804 435/6.16 |
| 2017/0158777 A1* | 6/2017 | Kim | ............... | C12Y 306/05002 |

FOREIGN PATENT DOCUMENTS

| | | | |
|---|---|---|---|
| WO | WO-2018112420 A1 * | 6/2018 | ........... A61K 31/415 |
| WO | 2019/107812 | 6/2019 | |

OTHER PUBLICATIONS

Koide S. Engineering of recombinant crystallization chaperones. Curr Opin Struct Biol. Aug. 2009; 19(4):449-57. doi: 10.1016/j.sbi.2009.04.008. Epub May 26, 2009. PMID: 19477632; PMCID: PMC2736338. (Year: 2009).*

Tanaka T, Lobato MN, Rabbitts TH. Single domain intracellular antibodies: a minimal fragment for direct in vivo selection of antigen-specific intrabodies. J Mol Biol. Aug. 29, 2003;331(5):1109-20. doi: 10.1016/s0022-2836(03)00836-2. PMID: 12927545. (Year: 2003).*

Chiu ML, Goulet DR, Teplyakov A, Gilliland GL. Antibody Structure and Function: The Basis for Engineering Therapeutics. Antibodies (Basel). Dec. 3, 2019;8(4):55. doi: 10.3390/antib8040055. PMID: 31816964; PMCID: PMC6963682. (Year: 2019).*

Clark LA, Demarest SJ, Eldredge J, Jarpe MB, Li Y, Simon K, van Vlijmen HW. Influence of canonical structure determining residues on antibody affinity and stability. J Struct Biol. Feb. 2014;185(2):223-7. doi: 10.1016/j.jsb.2013.08.009. Epub Aug. 29, 2013. PMID: 23994046. (Year: 2013).*

Hummer AM, Abanades B, Deane CM. Advances in computational structure-based antibody design. Curr Opin Struct Biol. Jun. 2022; 74:102379. doi: 10.1016/j.sbi.2022.102379. Epub Apr. 28, 2022. PMID: 35490649. (Year: 2022).*

"International Search Report—PCT/US2021/029517" (w/Written Opinion),:1-25 (Sep. 21, 2021).

Khan, I., et al., "Therapeutic targeting of RAS: New hope for drugging the 'undruggable'" Biochim Biophys Acta Mol Cell Res 1867(2):118570(1-16) (Feb. 1, 2020).

Shin, S., et al., "Antibody targeting intracellular oncogenic Ras mutants exerts anti-tumour effects after systemic administration" Nat Commun 8:15090 (1-14) (May 10, 2017).

Tanaka, T., et al., "Tumour prevention by a single antibody domain targeting the interaction of signal transduction proteins with Ras" EMBO J 26(13):3250-3259 (Jul. 11, 2007).

* cited by examiner

SEQUENCE LISTING

<160> NUMBER OF SEQ ID NOS: 110

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

```
Arg Ala Ser Gln Gly Ile Arg Asn Asp Leu Gly
1               5                   10
```

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 2

```
Ala Ala Ser Ser Leu Gln Ser
1               5
```

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 3

```
Leu Gln Asp His Asp Tyr Pro Leu Thr
1               5
```

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 4

```
Ser Tyr Ser Met Asn
1               5
```

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 5

```
Tyr Ile Ser Ser Ser Ser Ser Thr Ile Tyr Tyr Ala Asp Ser Val Lys
1               5                   10                  15

Gly
```

<210> SEQ ID NO 6
<211> LENGTH: 10
<212> TYPE: PRT
<213> ORGANISM: Artificial Sequence -continued
<220> FEATURE:
<223> OTHER INFORMATION: Description of Artificial Sequence: Synthetic
      peptide

<400> SEQUENCE: 6

```
Gly Phe Tyr Val Arg Asn Trp Phe Asp Pro
1               5                   10
```

<210> SEQ ID NO 7
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp His Asp Tyr Pro Leu
                85                  90                  95

Thr Phe Gly Gln Gly Thr Lys Val Glu Ile Lys
            100                 105
```

<210> SEQ ID NO 8
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Phe Tyr Val Arg Asn Trp Phe Asp Pro Trp Gly Gln Gly
            100                 105                 110

Thr Leu Val Thr Val Ser Ser
        115
```

<210> SEQ ID NO 9
<211> LENGTH: 13

<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

Ser Gly Ser Ser Ser Asn Ile Gly Ser Asn Tyr Val Tyr
1 5 10

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

Arg Asn Asn Gln Arg Pro Ser
1 5

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 11

Ala Ala Trp Asp Glu Arg Leu Ser Gly Trp Val
1 5 10

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 12

Ser Ser Asn Trp Trp Ser
1 5

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 13

Glu Ile Tyr His Ser Gly Ser Thr Asn Tyr Asn Pro Ser Leu Lys Ser
1 5 10 15

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic peptide

<400> SEQUENCE: 14

Gly Ser Ser Ser Trp Tyr Asp Leu Gly Pro Phe Asp Tyr 1 5 10

<210> SEQ ID NO 15
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

Ser Val Leu Thr Gln Pro Pro Ser Ala Ser Gly Thr Pro Gly Gln Arg
1 5 10 15

Val Thr Ile Ser Cys Ser Gly Ser Ser Ser Asn Ile Gly Ser Asn Tyr
20 25 30

Val Tyr Trp Tyr Gln Gln Leu Pro Gly Thr Ala Pro Lys Leu Leu Ile
35 40 45

Tyr Arg Asn Asn Gln Arg Pro Ser Gly Val Pro Asp Arg Phe Ser Gly
50 55 60

Ser Lys Ser Gly Thr Ser Ala Ser Leu Ala Ile Ser Gly Leu Arg Ser
65 70 75 80

Glu Asp Glu Ala Asp Tyr Tyr Cys Ala Ala Trp Asp Glu Arg Leu Ser
85 90 95

Gly Trp Val Phe Gly Gly Gly Thr Lys Leu Thr Val Leu
100 105

<210> SEQ ID NO 16
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

Glu Val Gln Leu Gln Glu Ser Gly Pro Gly Leu Val Lys Pro Pro Gly
1 5 10 15

Thr Leu Ser Leu Thr Cys Ala Val Ser Gly Gly Ser Ile Ser Ser Ser
20 25 30

Asn Trp Trp Ser Trp Val Arg Gln Pro Pro Gly Lys Gly Leu Glu Trp
35 40 45

Ile Gly Glu Ile Tyr His Ser Gly Ser Thr Asn Tyr Asn Pro Ser Leu
50 55 60

Lys Ser Arg Val Thr Ile Ser Val Asp Lys Ser Lys Asn Gln Phe Ser
65 70 75 80

Leu Lys Leu Ser Ser Val Thr Ala Ala Asp Thr Ala Val Tyr Tyr Cys
85 90 95

Ala Arg Gly Ser Ser Ser Trp Tyr Asp Leu Gly Pro Phe Asp Tyr Trp
100 105 110

Gly Gln Gly Thr Leu Val Thr Val Ser Ser
115 120

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 17

Arg Ala Ser Gln Gly Ile Ser Ser Tyr Leu Ala
1 5 10

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

Ala Ala Ser Ser Leu Gln Ser
1 5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 19

Gln Gln Tyr Tyr Ser Tyr Pro Phe Thr
1 5

<210> SEQ ID NO 20
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 20

Ser Tyr Ala Met Ser
1 5

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 21

Ala Ile Ser Ser Ser Gly Ser Ser Thr Tyr Tyr Ala Asp Ser Val Lys
1 5 10 15

Gly

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 22

Asp Gln Gly Gly Tyr Gly Tyr Pro Gly Glu Ser Trp Phe Asp Tyr
1 5 10 15

<210> SEQ ID NO 23
<211> LENGTH: 107

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 23

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Tyr Pro Phe
                85                  90                  95

Thr Phe Gly Gln Gly Thr Lys Val Glu Ile Lys
            100                 105
```

<210> SEQ ID NO 24
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 24

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Ser Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gln Gly Gly Tyr Gly Tyr Pro Gly Glu Ser Trp Phe Asp
            100                 105                 110

Tyr Trp Gly Gln Gly Thr Leu Val Thr Val Ser Ser
        115                 120
```

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 25

```
Arg Ala Ser Gln Ser Ile Ser Ser Tyr Leu Asn
1               5                   10
```

-continued

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Ala Ala Ser Ser Leu Gln Ser
1 5

<210> SEQ ID NO 27
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 27

Gln Gln Ser Tyr Ser Pro Pro Trp Thr
1 5

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

Ser Tyr Ser Met Asn
1 5

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 29

Ser Ile Ser Ser Ser Ser Ser Tyr Ile Tyr Tyr Ala Asp Ser Val Lys
1 5 10 15

Gly

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 30

Ala Phe Tyr Ser Tyr Met Asp Val
1 5

<210> SEQ ID NO 31
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Pro Pro Trp
                85                  90                  95

Thr Phe Gly Gln Gly Thr Lys Val Glu Ile Lys
            100                 105

<210> SEQ ID NO 32
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ala Phe Tyr Ser Tyr Met Asp Val Trp Gly Gln Gly Thr Leu
            100                 105                 110

Val Thr Val Ser Ser
        115

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 33

Arg Ser Ser Gln Ser Leu Leu His Ser Asn Gly Tyr Asn Tyr Leu Asp
1               5                   10                  15

<210> SEQ ID NO 34
<211> LENGTH: 7
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 34

Leu Gly Ser Asn Arg Ala Ser
1 5

<210> SEQ ID NO 35
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 35

Met Gln Ala Leu Gln Thr Pro Leu Thr
1 5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 36

Ser Ser Asn Trp Trp Ser
1 5

<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 37

Glu Ile Tyr His Ser Gly Ser Thr Asn Tyr Asn Pro Ser Leu Lys Ser
1 5 10 15

<210> SEQ ID NO 38
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 38

Glu Arg Thr Ile Leu Thr Gly Tyr Tyr Gly Phe Asp Tyr
1 5 10

<210> SEQ ID NO 39
<211> LENGTH: 112
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 39

Asp Ile Val Met Thr Gln Ser Pro Leu Ser Leu Pro Val Thr Pro Gly
1 5 10 15

Glu Pro Ala Ser Ile Ser Cys Arg Ser Ser Gln Ser Leu Leu His Ser

```
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gln Gly Thr Lys Val Glu Ile Lys
            100                 105                 110


<210> SEQ ID NO 40
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Val Gln Leu Gln Glu Ser Gly Pro Gly Leu Val Lys Pro Pro Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Arg Thr Ile Leu Thr Gly Tyr Tyr Gly Phe Asp Tyr Trp
            100                 105                 110

Gly Gln Gly Thr Leu Val Thr Val Ser Ser
        115                 120


<210> SEQ ID NO 41
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ser Gly Ser Ser Ser Asn Ile Gly Asn Asn Tyr Val Ser
1               5                   10


<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asp Asn Asn Lys Arg Pro Ser
1               5
```

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 43

```
Gly Thr Trp Asp Ser Ser Leu Thr Gly Tyr Val
1               5                   10
```

<210> SEQ ID NO 44
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 44

```
Ser Tyr Ala Ile Ser
1               5
```

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 45

```
Gly Ile Ile Pro Ile Phe Gly Thr Ala Asn Tyr Ala Gln Lys Phe Gln
1               5                   10                  15

Gly
```

<210> SEQ ID NO 46
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 46

```
Tyr Tyr Asp Phe Trp Ser Gly Tyr Pro Gly Gly Leu Phe Asp Val
1               5                   10                  15
```

<210> SEQ ID NO 47
<211> LENGTH: 109
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

```
Ser Val Leu Thr Gln Pro Pro Ser Val Ser Ala Ala Pro Gly Gln Lys
1               5                   10                  15

Val Thr Ile Ser Cys Ser Gly Ser Ser Ser Asn Ile Gly Asn Asn Tyr
            20                  25                  30

Val Ser Trp Tyr Gln Gln Leu Pro Gly Thr Ala Pro Lys Leu Leu Ile
        35                  40                  45
```

-continued

```
Tyr Asp Asn Asn Lys Arg Pro Ser Gly Ile Pro Asp Arg Phe Ser Gly
    50                  55                  60

Ser Lys Ser Gly Thr Ser Ala Thr Leu Gly Ile Thr Gly Leu Gln Thr
65                  70                  75                  80

Gly Asp Glu Ala Asp Tyr Tyr Cys Gly Thr Trp Asp Ser Ser Leu Thr
                85                  90                  95

Gly Tyr Val Phe Gly Gly Gly Thr Lys Leu Thr Val Leu
            100                 105


<210> SEQ ID NO 48
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Phe Trp Ser Gly Tyr Pro Gly Gly Leu Phe Asp
            100                 105                 110

Val Trp Gly Gln Gly Thr Leu Val Thr Val Ser Ser
        115                 120


<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ser Gly Ser Ser Ser Asn Ile Gly Asn Asn Tyr Val Ser
1               5                   10


<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Asp Asn Asn Lys Arg Pro Ser
1               5


<210> SEQ ID NO 51
<211> LENGTH: 11
<212> TYPE: PRT
```

<213> ORGANISM: Artificial Sequence
<220> FEATURE:
<223> OTHER INFORMATION: Description of Artificial Sequence: Synthetic
peptide

<400> SEQUENCE: 51

Gly Thr Trp Asp Ser Ser Leu Thr Gly Trp Val
1 5 10

<210> SEQ ID NO 52
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 52

Ser Tyr Ala Ile Ser
1 5

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 53

Gly Ile Ile Pro Ile Phe Gly Thr Ala Asn Tyr Ala Gln Lys Phe Gln
1 5 10 15

Gly

<210> SEQ ID NO 54
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 54

Tyr Tyr Asp Phe Trp Ser Gly Tyr Pro Gly Gly Leu Phe Asp Val
1 5 10 15

<210> SEQ ID NO 55
<211> LENGTH: 109
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 55

Ser Val Leu Thr Gln Pro Pro Ser Val Ser Ala Ala Pro Gly Gln Lys
1 5 10 15

Val Thr Ile Ser Cys Ser Gly Ser Ser Ser Asn Ile Gly Asn Asn Tyr
20 25 30

Val Ser Trp Tyr Gln Gln Leu Pro Gly Thr Ala Pro Lys Leu Leu Ile
35 40 45

Tyr Asp Asn Asn Lys Arg Pro Ser Gly Ile Pro Asp Arg Phe Ser Gly
50 55 60

Ser Lys Ser Gly Thr Ser Ala Thr Leu Gly Ile Thr Gly Leu Gln Thr
65 70 75 80

```
Gly Asp Glu Ala Asp Tyr Tyr Cys Gly Thr Trp Asp Ser Ser Leu Thr
                85                  90                  95

Gly Trp Val Phe Gly Gly Gly Thr Lys Leu Thr Val Leu
            100                 105


<210> SEQ ID NO 56
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Tyr Tyr Asp Phe Trp Ser Gly Tyr Pro Gly Gly Leu Phe Asp
            100                 105                 110

Val Trp Gly Gln Gly Thr Leu Val Thr Val Ser Ser
        115                 120


<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Gly Asp Ser Leu Arg Ser Tyr Tyr Ala Ser
1               5                   10


<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gly Lys Asn Asn Arg Pro Ser
1               5


<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 59

Asn Ser Arg Asp Ser Ser Gly Asn His Trp Val
1 5 10

<210> SEQ ID NO 60
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 60

Ser Tyr Ser Met Asn
1 5

<210> SEQ ID NO 61
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 61

Ser Ile Ser Ser Ser Ser Ser Tyr Ile Tyr Tyr Ala Asp Ser Val Lys
1 5 10 15

Gly

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 62

Thr Asn Asn Tyr Gly Tyr Arg Tyr Phe Asp Tyr
1 5 10

<210> SEQ ID NO 63
<211> LENGTH: 105
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 63

Leu Thr Gln Asp Pro Ala Val Ser Val Ala Leu Gly Gln Thr Val Arg
1 5 10 15

Ile Thr Cys Gln Gly Asp Ser Leu Arg Ser Tyr Tyr Ala Ser Trp Tyr
20 25 30

Gln Gln Lys Pro Gly Gln Ala Pro Val Leu Val Ile Tyr Gly Lys Asn
35 40 45

Asn Arg Pro Ser Gly Ile Pro Asp Arg Phe Ser Gly Ser Ser Ser Gly
50 55 60

Asn Thr Ala Ser Leu Thr Ile Thr Gly Ala Gln Ala Glu Asp Glu Ala
65 70 75 80

Asp Tyr Tyr Cys Asn Ser Arg Asp Ser Ser Gly Asn His Trp Val Phe
85 90 95

Gly Gly Gly Thr Lys Leu Thr Val Leu 100 105

<210> SEQ ID NO 64
<211> LENGTH: 120
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 64

Glu Val Gln Leu Val Glu Ser Gly Gly Gly Leu Val Lys Pro Gly Gly
1 5 10 15

Ser Leu Arg Leu Ser Cys Ala Ala Ser Gly Phe Thr Phe Ser Ser Tyr
20 25 30

Ser Met Asn Trp Val Arg Gln Ala Pro Gly Lys Gly Leu Glu Trp Val
35 40 45

Ser Ser Ile Ser Ser Ser Ser Ser Tyr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Thr Asn Asn Tyr Gly Tyr Arg Tyr Phe Asp Tyr Trp Gly Gln
100 105 110

Gly Thr Leu Val Thr Val Ser Ser
115 120

<210> SEQ ID NO 65
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 65

Gln Gly Asp Ser Leu Arg Ser Tyr Tyr Ala Ser
1 5 10

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 66

Gly Lys Asn Asn Arg Pro Ser
1 5

<210> SEQ ID NO 67
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 67

Asn Ser Arg Asp Ser Thr Asp Asn His Leu Trp Val
1 5 10

-continued

<210> SEQ ID NO 68
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 68

Ser Tyr Ser Met Asn
1 5

<210> SEQ ID NO 69
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 69

Ser Ile Ser Ser Ser Ser Ser Tyr Ile Tyr Tyr Ala Asp Ser Val Lys
1 5 10 15

Gly

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 70

Ala Thr Ser Ser Gly Tyr Tyr Tyr Phe Asp Tyr
1 5 10

<210> SEQ ID NO 71
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 71

Glu Leu Thr Gln Asp Pro Ala Val Ser Val Ala Leu Gly Gln Thr Val
1 5 10 15

Arg Ile Thr Cys Gln Gly Asp Ser Leu Arg Ser Tyr Tyr Ala Ser Trp
20 25 30

Tyr Gln Gln Lys Pro Gly Gln Ala Pro Val Leu Val Ile Tyr Gly Lys
35 40 45

Asn Asn Arg Pro Ser Gly Ile Pro Asp Arg Phe Ser Gly Ser Ser Ser
50 55 60

Gly Asn Thr Ala Ser Leu Thr Ile Thr Gly Ala Gln Ala Glu Asp Glu
65 70 75 80

Ala Asp Tyr Tyr Cys Asn Ser Arg Asp Ser Thr Asp Asn His Leu Trp
85 90 95

Val Phe Gly Gly Gly Thr Lys Leu Thr Val Leu
100 105

<210> SEQ ID NO 72
<211> LENGTH: 120

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 72

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ala Thr Ser Ser Gly Tyr Tyr Tyr Phe Asp Tyr Trp Gly Gln
            100                 105                 110

Gly Thr Leu Val Thr Val Ser Ser
        115                 120
```

<210> SEQ ID NO 73
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 73

```
Ser Gly Ser Ser Ser Asn Ile Gly Asn Asn Tyr Val Ser
1               5                   10
```

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 74

```
Asp Asn Asn Lys Arg Pro Ser
1               5
```

<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 75

```
Gly Thr Trp Asp Asn Ser Leu Ser Val Trp Val
1               5                   10
```

<210> SEQ ID NO 76
<211> LENGTH: 5
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 76

Ser Tyr Ser Met Asn
1               5


<210> SEQ ID NO 77
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Tyr Ile Ser Ser Ser Ser Ser Thr Ile Tyr Tyr Ala Asp Ser Val Lys
1               5                   10                  15

Gly


<210> SEQ ID NO 78
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Lys Gly Ile Val Gly Trp Gly Phe Phe Gly Met Asp Val
1               5                   10


<210> SEQ ID NO 79
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 79

Ser Val Leu Thr Gln Pro Pro Ser Val Ser Ala Ala Pro Gly Gln Lys
1               5                   10                  15

Val Thr Ile Ser Cys Ser Gly Ser Ser Ser Asn Ile Gly Asn Asn Tyr
            20                  25                  30

Val Ser Trp Tyr Gln Gln Leu Pro Gly Thr Ala Pro Lys Leu Leu Ile
        35                  40                  45

Tyr Asp Asn Asn Lys Arg Pro Ser Gly Ile Pro Asp Arg Phe Ser Gly
    50                  55                  60

Ser Lys Ser Gly Thr Ser Ala Thr Leu Gly Ile Thr Gly Leu Gln Thr
65                  70                  75                  80

Gly Asp Glu Ala Asp Tyr Tyr Cys Gly Thr Trp Asp Asn Ser Leu Ser
                85                  90                  95

Val Trp Val Phe Gly Gly Gly Thr Lys Leu Thr Val Leu
            100                 105


<210> SEQ ID NO 80
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 80

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ser Met Asn Trp Val Arg Gln Ala Pro Gly Lys Gly Leu Glu Trp Val
35 40 45

Ser Tyr Ile Ser Ser Ser Ser Ser Thr Ile Tyr Tyr Ala Asp Ser Val
50 55 60

Lys Gly Arg Phe Thr Ile Ser Arg Asp Asn Ala Lys Asn Ser Leu Tyr
65 70 75 80

Leu Gln Met Asn Ser Leu Arg Ala Glu Asp Thr Ala Val Tyr Tyr Cys
85 90 95

Ala Arg Gly Lys Gly Ile Val Gly Trp Gly Phe Phe Gly Met Asp Val
100 105 110

Trp Gly Gln Gly Thr Leu Val Thr Val Ser Ser
115 120

<210> SEQ ID NO 81
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 81

Ser Gly Ser Ser Ser Asn Ile Gly Ser Asn Tyr Val Tyr
1 5 10

<210> SEQ ID NO 82
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 82

Arg Asn Asn Gln Arg Pro Ser
1 5

<210> SEQ ID NO 83
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 83

Ala Ala Trp Asp Asp Ser Leu Ser Gly Trp Val
1 5 10

<210> SEQ ID NO 84
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 84

```
Ser Tyr Ser Met Asn
1               5


<210> SEQ ID NO 85
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Tyr Ile Ser Ser Ser Ser Ser Thr Ile Tyr Tyr Ala Asp Ser Val Lys
1               5                   10                  15

Gly


<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ser Phe Gly Pro Tyr Ala Phe Asp Val
1               5


<210> SEQ ID NO 87
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Val Leu Thr Gln Pro Pro Ser Ala Ser Gly Thr Pro Gly Gln Arg Val
1               5                   10                  15

Thr Ile Ser Cys Ser Gly Ser Ser Ser Asn Ile Gly Ser Asn Tyr Val
            20                  25                  30

Tyr Trp Tyr Gln Gln Leu Pro Gly Thr Ala Pro Lys Leu Leu Ile Tyr
        35                  40                  45

Arg Asn Asn Gln Arg Pro Ser Gly Val Pro Asp Arg Phe Ser Gly Ser
    50                  55                  60

Lys Ser Gly Thr Ser Ala Ser Leu Ala Ile Ser Gly Leu Arg Ser Glu
65                  70                  75                  80

Asp Glu Ala Asp Tyr Tyr Cys Ala Ala Trp Asp Asp Ser Leu Ser Gly
                85                  90                  95

Trp Val Phe Gly Gly Gly Thr Lys Leu Thr Val Leu
            100                 105


<210> SEQ ID NO 88
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Ser Ser Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Ser Phe Gly Pro Tyr Ala Phe Asp Val Trp Gly Gln Gly Thr
            100                 105                 110

Leu Val Thr Val Ser Ser
        115


<210> SEQ ID NO 89
<211> LENGTH: 189
<212> TYPE: PRT
<213> ORGANISM: Homo sapiens

<400> SEQUENCE: 89

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys
                165                 170                 175

Thr Pro Gly Cys Val Lys Ile Lys Lys Cys Ile Ile Met
            180                 185


<210> SEQ ID NO 90
<211> LENGTH: 188
<212> TYPE: PRT
<213> ORGANISM: Homo sapiens

<400> SEQUENCE: 90

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30
```

```
Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185
```

<210> SEQ ID NO 91
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 91

```
Gly Ser Ser Ile Trp Ser Ser Asn
1               5
```

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 92

```
Gly Ser Asn Ile Ser Ser Ser Asn
1               5
```

<210> SEQ ID NO 93
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 93

```
Gly Ser Ser Ile Phe Ser Ser Asn
1               5
```

<210> SEQ ID NO 94
<211> LENGTH: 8
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 94

Gly Ser Ser Ile Met Ser Ser Asn
1               5

<210> SEQ ID NO 95
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Ser Ser Ile Tyr Ser Ser Asn
1               5

<210> SEQ ID NO 96
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Gly Asn Ile Trp Ser Ser Asn
1               5

<210> SEQ ID NO 97
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Lys Gly Ser Ile Trp Ala Ser His
1               5

<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Lys Gly Ser Ile Trp Ser Ser Asn
1               5

<210> SEQ ID NO 99
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Glu Val Gln Leu Gln Glu Ser Gly Pro Gly Leu Val Lys Pro Pro Gly
1               5                   10                  15

Thr Leu Ser Leu Thr Cys Ala Val Ser Gly Ser Ser Ile Trp Ser Ser

```
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Ser Ser Ser Trp Tyr Asp Leu Gly Pro Phe Asp Tyr Trp
            100                 105                 110

Gly Gln Gly Thr Leu Val Thr Val Ser Ser
        115                 120


<210> SEQ ID NO 100
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Glu Val Gln Leu Gln Glu Ser Gly Pro Gly Leu Val Lys Pro Pro Gly
1               5                   10                  15

Thr Leu Ser Leu Thr Cys Ala Val Ser Gly Ser Asn Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Ser Ser Ser Trp Tyr Asp Leu Gly Pro Phe Asp Tyr Trp
            100                 105                 110

Gly Gln Gly Thr Leu Val Thr Val Ser Ser
        115                 120


<210> SEQ ID NO 101
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Glu Val Gln Leu Gln Glu Ser Gly Pro Gly Leu Val Lys Pro Pro Gly
1               5                   10                  15

Thr Leu Ser Leu Thr Cys Ala Val Ser Gly Ser Ser Ile Phe Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
```

```
65                  70                  75                  80

Leu Lys Leu Ser Ser Val Thr Ala Ala Asp Thr Ala Val Tyr Tyr Cys
                85                  90                  95

Ala Arg Gly Ser Ser Ser Trp Tyr Asp Leu Gly Pro Phe Asp Tyr Trp
            100                 105                 110

Gly Gln Gly Thr Leu Val Thr Val Ser Ser
        115                 120


<210> SEQ ID NO 102
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Glu Val Gln Leu Gln Glu Ser Gly Pro Gly Leu Val Lys Pro Pro Gly
1               5                   10                  15

Thr Leu Ser Leu Thr Cys Ala Val Ser Gly Ser Ser Ile Met Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Ser Ser Ser Trp Tyr Asp Leu Gly Pro Phe Asp Tyr Trp
            100                 105                 110

Gly Gln Gly Thr Leu Val Thr Val Ser Ser
        115                 120


<210> SEQ ID NO 103
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Glu Val Gln Leu Gln Glu Ser Gly Pro Gly Leu Val Lys Pro Pro Gly
1               5                   10                  15

Thr Leu Ser Leu Thr Cys Ala Val Ser Gly Ser Ser Ile Tyr Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Gly Ser Ser Ser Trp Tyr Asp Leu Gly Pro Phe Asp Tyr Trp
            100                 105                 110

Gly Gln Gly Thr Leu Val Thr Val Ser Ser
```

115 120

<210> SEQ ID NO 104
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 104

Glu Val Gln Leu Gln Glu Ser Gly Pro Gly Leu Val Lys Pro Pro Gly
1 5 10 15

Thr Leu Ser Leu Thr Cys Ala Val Ser Gly Gly Asn Ile Trp Ser Ser
20 25 30

Asn Trp Trp Ser Trp Val Arg Gln Pro Pro Gly Lys Gly Leu Glu Trp
35 40 45

Ile Gly Glu Ile Tyr His Ser Gly Ser Thr Asn Tyr Asn Pro Ser Leu
50 55 60

Lys Ser Arg Val Thr Ile Ser Val Asp Lys Ser Lys Asn Gln Phe Ser
65 70 75 80

Leu Lys Leu Ser Ser Val Thr Ala Ala Asp Thr Ala Val Tyr Tyr Cys
85 90 95

Ala Arg Gly Ser Ser Ser Trp Tyr Asp Leu Gly Pro Phe Asp Tyr Trp
100 105 110

Gly Gln Gly Thr Leu Val Thr Val Ser Ser
115 120

<210> SEQ ID NO 105
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 105

Glu Val Gln Leu Gln Glu Ser Gly Pro Gly Leu Val Lys Pro Pro Gly
1 5 10 15

Thr Leu Ser Leu Thr Cys Ala Val Ser Lys Gly Ser Ile Trp Ala Ser
20 25 30

His Trp Trp Ser Trp Val Arg Gln Pro Pro Gly Lys Gly Leu Glu Trp
35 40 45

Ile Gly Glu Ile Tyr His Ser Gly Ser Thr Asn Tyr Asn Pro Ser Leu
50 55 60

Lys Ser Arg Val Thr Ile Ser Val Asp Lys Ser Lys Asn Gln Phe Ser
65 70 75 80

Leu Lys Leu Ser Ser Val Thr Ala Ala Asp Thr Ala Val Tyr Tyr Cys
85 90 95

Ala Arg Gly Ser Ser Ser Trp Tyr Asp Leu Gly Pro Phe Asp Tyr Trp
100 105 110

Gly Gln Gly Thr Leu Val Thr Val Ser Ser
115 120

<210> SEQ ID NO 106
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 106

Glu Val Gln Leu Gln Glu Ser Gly Pro Gly Leu Val Lys Pro Pro Gly
1 5 10 15

Thr Leu Ser Leu Thr Cys Ala Val Ser Lys Gly Ser Ile Trp Ser Ser
20 25 30

Asn Trp Trp Ser Trp Val Arg Gln Pro Pro Gly Lys Gly Leu Glu Trp
35 40 45

Ile Gly Glu Ile Tyr His Ser Gly Ser Thr Asn Tyr Asn Pro Ser Leu
50 55 60

Lys Ser Arg Val Thr Ile Ser Val Asp Lys Ser Lys Asn Gln Phe Ser
65 70 75 80

Leu Lys Leu Ser Ser Val Thr Ala Ala Asp Thr Ala Val Tyr Tyr Cys
85 90 95

Ala Arg Gly Ser Ser Ser Trp Tyr Asp Leu Gly Pro Phe Asp Tyr Trp
100 105 110

Gly Gln Gly Thr Leu Val Thr Val Ser Ser
115 120

<210> SEQ ID NO 107
<211> LENGTH: 230
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 107

Glu Val Gln Leu Gln Glu Ser Gly Pro Gly Leu Val Lys Pro Pro Gly
1 5 10 15

Thr Leu Ser Leu Thr Cys Ala Val Ser Gly Gly Ser Ile Ser Ser Ser
20 25 30

Asn Trp Trp Ser Trp Val Arg Gln Pro Pro Gly Lys Gly Leu Glu Trp
35 40 45

Ile Gly Glu Ile Tyr His Ser Gly Ser Thr Asn Tyr Asn Pro Ser Leu
50 55 60

Lys Ser Arg Val Thr Ile Ser Val Asp Lys Ser Lys Asn Gln Phe Ser
65 70 75 80

Leu Lys Leu Ser Ser Val Thr Ala Ala Asp Thr Ala Val Tyr Tyr Cys
85 90 95

Ala Arg Gly Ser Ser Ser Trp Tyr Asp Leu Gly Pro Phe Asp Tyr Trp
100 105 110

Gly Gln Gly Thr Leu Val Thr Val Ser Ser Ala Ser Thr Lys Gly Pro
115 120 125

Ser Val Phe Pro Leu Ala Pro Ser Ser Lys Ser Thr Ser Gly Gly Thr
130 135 140

Ala Ala Leu Gly Cys Leu Val Lys Asp Tyr Phe Pro Glu Pro Val Thr
145 150 155 160

Val Ser Trp Asn Ser Gly Ala Leu Thr Ser Gly Val His Thr Phe Pro
165 170 175

Ala Val Leu Gln Ser Ser Gly Leu Tyr Ser Leu Ser Ser Val Val Thr
180 185 190

Val Pro Ser Ser Ser Leu Gly Thr Gln Thr Tyr Ile Cys Asn Val Asn
195 200 205

His Lys Pro Ser Asn Thr Lys Val Asp Lys Lys Val Glu Pro Lys Ser

```
    210                 215                 220

Cys Asp Lys Thr His Thr
225                 230


<210> SEQ ID NO 108
<211> LENGTH: 427
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Gly Leu Asn Asp Ile Phe Glu Ala Gln Lys Ile Glu Trp His Glu Gly
1               5                   10                  15

Ser Glu Asn Leu Tyr Phe Gln Ser Thr Glu Tyr Lys Leu Val Val Val
            20                  25                  30

Gly Ala Gly Gly Val Gly Lys Ser Ala Leu Thr Ile Gln Leu Ile Gln
        35                  40                  45

Asn His Phe Val Asp Glu Tyr Asp Pro Thr Ile Glu Asp Ser Tyr Arg
    50                  55                  60

Lys Gln Val Val Ile Asp Gly Glu Thr Ser Leu Leu Asp Ile Leu Asp
65                  70                  75                  80

Thr Ala Gly Gln Glu Glu Tyr Ser Ala Met Arg Asp Gln Tyr Met Arg
                85                  90                  95

Thr Gly Glu Gly Phe Leu Leu Val Phe Ala Ile Asn Asn Thr Lys Ser
            100                 105                 110

Phe Glu Asp Ile His His Tyr Arg Glu Gln Ile Lys Arg Val Lys Asp
        115                 120                 125

Ser Glu Asp Val Pro Met Val Leu Val Gly Asn Lys Ser Asp Leu Pro
    130                 135                 140

Ser Arg Thr Val Asp Thr Lys Gln Ala Gln Asp Leu Ala Arg Ser Tyr
145                 150                 155                 160

Gly Ile Pro Phe Ile Glu Thr Ser Ala Lys Thr Arg Gln Gly Val Asp
                165                 170                 175

Asp Ala Phe Tyr Thr Leu Val Arg Glu Ile Arg Lys His Lys Glu Lys
            180                 185                 190

Gly Gly Gly Gly Ser Gly Gly Gly Gly Ser Gly Gly Gly Gly Ser Gly
        195                 200                 205

Gly Gly Gly Ser Ser Val Leu Thr Gln Pro Pro Ser Ala Ser Gly Thr
    210                 215                 220

Pro Gly Gln Arg Val Thr Ile Ser Cys Ser Gly Ser Ser Ser Asn Ile
225                 230                 235                 240

Gly Ser Asn Tyr Val Tyr Trp Tyr Gln Gln Leu Pro Gly Thr Ala Pro
                245                 250                 255

Lys Leu Leu Ile Tyr Arg Asn Asn Gln Arg Pro Ser Gly Val Pro Asp
            260                 265                 270

Arg Phe Ser Gly Ser Lys Ser Gly Thr Ser Ala Ser Leu Ala Ile Ser
        275                 280                 285

Gly Leu Arg Ser Glu Asp Glu Ala Asp Tyr Tyr Cys Ala Ala Trp Asp
    290                 295                 300

Glu Arg Leu Ser Gly Trp Val Phe Gly Gly Gly Thr Lys Leu Thr Val
305                 310                 315                 320

Leu Gly Gln Pro Lys Ala Ala Pro Ser Val Thr Leu Phe Pro Pro Ser
                325                 330                 335
```

-continued

```
Ser Glu Glu Leu Gln Ala Asn Lys Ala Thr Leu Val Cys Leu Ile Ser
            340                 345                 350

Asp Phe Tyr Pro Gly Ala Val Thr Val Ala Trp Lys Ala Asp Ser Ser
        355                 360                 365

Pro Val Lys Ala Gly Val Glu Thr Thr Thr Pro Ser Lys Gln Ser Asn
    370                 375                 380

Asn Lys Tyr Ala Ala Ser Ser Tyr Leu Ser Leu Thr Pro Glu Gln Trp
385                 390                 395                 400

Lys Ser His Lys Ser Tyr Ser Cys Gln Val Thr His Glu Gly Ser Thr
                405                 410                 415

Val Glu Lys Thr Val Ala Pro Thr Glu Cys Ser
            420                 425


<210> SEQ ID NO 109
<211> LENGTH: 442
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Gly Leu Asn Asp Ile Phe Glu Ala Gln Lys Ile Glu Trp His Glu Gly
1               5                   10                  15

Ser Glu Asn Leu Tyr Phe Gln Ser Thr Glu Tyr Lys Leu Val Val Val
            20                  25                  30

Gly Ala Gly Gly Val Gly Lys Ser Ala Leu Thr Ile Gln Leu Ile Gln
        35                  40                  45

Asn His Phe Val Asp Glu Tyr Asp Pro Thr Ile Glu Asp Ser Tyr Arg
    50                  55                  60

Lys Gln Val Val Ile Asp Gly Glu Thr Ser Leu Leu Asp Ile Leu Asp
65                  70                  75                  80

Thr Ala Gly Gln Glu Glu Tyr Ser Ala Met Arg Asp Gln Tyr Met Arg
                85                  90                  95

Thr Gly Glu Gly Phe Leu Leu Val Phe Ala Ile Asn Asn Thr Lys Ser
            100                 105                 110

Phe Glu Asp Ile His His Tyr Arg Glu Gln Ile Lys Arg Val Lys Asp
        115                 120                 125

Ser Glu Asp Val Pro Met Val Leu Val Gly Asn Lys Ser Asp Leu Pro
    130                 135                 140

Ser Arg Thr Val Asp Thr Lys Gln Ala Gln Asp Leu Ala Arg Ser Tyr
145                 150                 155                 160

Gly Ile Pro Phe Ile Glu Thr Ser Ala Lys Thr Arg Gln Gly Val Asp
                165                 170                 175

Asp Ala Phe Tyr Thr Leu Val Arg Glu Ile Arg Lys His Lys Glu Lys
            180                 185                 190

Gly Gly Gly Gly Ser Gly Gly Gly Gly Ser Gly Gly Gly Gly Ser Gly
        195                 200                 205

Gly Gly Gly Ser Glu Val Gln Leu Gln Glu Ser Gly Pro Gly Leu Val
    210                 215                 220

Lys Pro Pro Gly Thr Leu Ser Leu Thr Cys Ala Val Ser Gly Gly Ser
225                 230                 235                 240

Ile Ser Ser Ser Asn Trp Trp Ser Trp Val Arg Gln Pro Pro Gly Lys
                245                 250                 255

Gly Leu Glu Trp Ile Gly Glu Ile Tyr His Ser Gly Ser Thr Asn Tyr
            260                 265                 270
```

Asn Pro Ser Leu Lys Ser Arg Val Thr Ile Ser Val Asp Lys Ser Lys
275 280 285

Asn Gln Phe Ser Leu Lys Leu Ser Ser Val Thr Ala Ala Asp Thr Ala
290 295 300

Val Tyr Tyr Cys Ala Arg Gly Ser Ser Ser Trp Tyr Asp Leu Gly Pro
305 310 315 320

Phe Asp Tyr Trp Gly Gln Gly Thr Leu Val Thr Val Ser Ser Ala Ser
325 330 335

Thr Lys Gly Pro Ser Val Phe Pro Leu Ala Pro Ser Ser Lys Ser Thr
340 345 350

Ser Gly Gly Thr Ala Ala Leu Gly Cys Leu Val Lys Asp Tyr Phe Pro
355 360 365

Glu Pro Val Thr Val Ser Trp Asn Ser Gly Ala Leu Thr Ser Gly Val
370 375 380

His Thr Phe Pro Ala Val Leu Gln Ser Ser Gly Leu Tyr Ser Leu Ser
385 390 395 400

Ser Val Val Thr Val Pro Ser Ser Ser Leu Gly Thr Gln Thr Tyr Ile
405 410 415

Cys Asn Val Asn His Lys Pro Ser Asn Thr Lys Val Asp Lys Lys Val
420 425 430

Glu Pro Lys Ser Cys Asp Lys Thr His Thr
435 440

<210> SEQ ID NO 110
<211> LENGTH: 215
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 110

Ser Val Leu Thr Gln Pro Pro Ser Ala Ser Gly Thr Pro Gly Gln Arg
1 5 10 15

Val Thr Ile Ser Cys Ser Gly Ser Ser Ser Asn Ile Gly Ser Asn Tyr
20 25 30

Val Tyr Trp Tyr Gln Gln Leu Pro Gly Thr Ala Pro Lys Leu Leu Ile
35 40 45

Tyr Arg Asn Asn Gln Arg Pro Ser Gly Val Pro Asp Arg Phe Ser Gly
50 55 60

Ser Lys Ser Gly Thr Ser Ala Ser Leu Ala Ile Ser Gly Leu Arg Ser
65 70 75 80

Glu Asp Glu Ala Asp Tyr Tyr Cys Ala Ala Trp Asp Glu Arg Leu Ser
85 90 95

Gly Trp Val Phe Gly Gly Gly Thr Lys Leu Thr Val Leu Gly Gln Pro
100 105 110

Lys Ala Ala Pro Ser Val Thr Leu Phe Pro Pro Ser Ser Glu Glu Leu
115 120 125

Gln Ala Asn Lys Ala Thr Leu Val Cys Leu Ile Ser Asp Phe Tyr Pro
130 135 140

Gly Ala Val Thr Val Ala Trp Lys Ala Asp Ser Ser Pro Val Lys Ala
145 150 155 160

Gly Val Glu Thr Thr Thr Pro Ser Lys Gln Ser Asn Asn Lys Tyr Ala
165 170 175

Ala Ser Ser Tyr Leu Ser Leu Thr Pro Glu Gln Trp Lys Ser His Lys

-continued

```
          180                 185                 190

Ser Tyr Ser Cys Gln Val Thr His Glu Gly Ser Thr Val Glu Lys Thr
        195                 200                 205

Val Ala Pro Thr Glu Cys Ser
    210                 215
```

*KRAS* SPECIFIC ANTIBODIES AND USES THEREOF

CROSS REFERENCE TO RELATED APPLICATIONS

The application claims the benefit of U.S. Provisional Application No. 63/018,356, filed Apr. 30, 2020, which is incorporated herein in its entirety and for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: P35630US_SEQLIST.TXT, date recorded: Mar. 23, 2021, size: 60,938 bytes).

FIELD OF THE INVENTION

The present invention relates to KRas specific antibodies and methods of using the same.

BACKGROUND OF THE INVENTION

KRAS is one of the most frequently mutated oncogenes in cancer (Kranenburg, O., *Biochim. Biophys. Acta* 2005 1756). KRAS encodes one of the Ras family of guanosine triphosphatases (GTPases) that function in transmitting signals from cell surface receptors to intracellular effector pathways (Pylayeva-Gupta, Y. et al. *Nat Rev Cancer* 2011 11). Ras GTPases cycle between an active, guanosine 5'-triphosphate (GTP)-bound state and an inactive, guanosine 5'-diphosphate (GDP)-bound, state. In cancer, oncogenic mutations in KRas, including KRAS$^{G12C}$-driven tumors, impair its GTPase activity and result in the accumulation of the GTP-bound, activated form of KRas. As a result, pathways downstream of KRas are constitutively activated, leading to the promotion of proliferation and the suppression of apoptosis (Pylayeva-Gupta, Y. et al. *Nat Rev Cancer* 2011 11).

Despite its long-recognized prevalence in cancer, for many years KRas was not considered to be a druggable target (McCormick, F. *Clin Cancer Res* 2015 21:8). Beyond KRAS$^{G12C}$ there are other alleles of KRAS that are associated with cancer (Haigis, K M, *Trends Cancer* 2017 3:10). Accordingly, there exists a need in the art for KRas-specific antibodies that specifically bind to the KRas bound to GDP (KRas-GDP) with a higher affinity than to the KRas bound to GTP (KRas-GTP).

SUMMARY OF THE INVENTION

In one aspect, the present invention provides an isolated antibody or antigen binding fragment thereof that binds to a human KRas, wherein the antibody specifically binds to the KRas bound to GDP (KRas-GDP) with a higher affinity than to the KRas bound to GTP (KRas-GTP).

In some embodiments, the antibody or antigen binding fragment thereof is a KRas alkylated conformation specific antibody.

In some embodiments, the antibody or antigen binding fragment thereof opens and stabilizes the SWII pocket.

In some embodiments, the human KRas is a KRas mutant selected from the group consisting of KRas$^{G12C}$, KRas$^{G12V}$, KRas$^{G12R}$, KRas$^{Q61H}$, KRas$^{G12D}$ and, KRas$^{G13D}$.

In some embodiments, the human KRas is a KRas mutant selected from the group consisting of KRas$^{G12C}$, KRas$^{G12V}$, KRas$^{G12D}$, and KRas$^{G13D}$.

In some embodiments, the KRas mutant is KRas$^{G12C}$.

In some embodiments, the KRas$^{G12C}$-GDP is alkylated with a KRas$^{G12C}$ specific covalent inhibitor.

In some embodiments, the isolated antibody or antigen binding fragment is an alkylated conformation specific KRas antibody that binds to KRas$^{G12C}$-GDP alkylated with MRTX849, AMG-510, GDC-6036, ARS-3248, LY3499446, or JNJ-74699157.

In some embodiments, the antibody or antigen binding fragment thereof stabilizes the SWII pocket of a KRas mutant protein.

In some embodiments, the antibody or antigen binding fragment thereof comprises (a) a light chain variable region comprising:
  (i) CDR-L1 comprising the amino acid sequence SGSSSNIGSNYVY (SEQ ID NO:9);
  (ii) CDR-L2 comprising the amino acid sequence RNNQRPS (SEQ ID NO:10);
  (iii) CDR-L3 comprising the amino acid sequence AAWDERLSGWV (SEQ ID NO:11); and
(b) a heavy chain variable region comprising:
  (i) CDR-H1 comprising the amino acid sequence SSNWWS (SEQ ID NO:12);
  (ii) CDR-H2 comprising the amino acid sequence EIYHSGSTNYNPSLKS (SEQ ID NO:13); and
  (iii) CDR-H3 comprising the amino acid sequence GSSSWYDLGPFDY (SEQ ID NO: 14).

In some embodiments, the light chain variable region comprises the amino acid sequence of SEQ ID NO:15 and the heavy chain variable region comprises the amino acid sequence of SEQ ID NO:16.

In some embodiments, the antibody comprises (a) a light chain variable region comprising:
  (i) CDR-L1 comprising the amino acid sequence RASQGIRNDLG (SEQ ID NO:1);
  (ii) CDR-L2 comprising the amino acid sequence AASSLQS (SEQ ID NO:2);
  (iii) CDR-L3 comprising the amino acid sequence LQDHDYPLT (SEQ ID NO:3); and
(b) a heavy chain variable region comprising:
  (i) CDR-H1 comprising the amino acid sequence SYSMN (SEQ ID NO:4);
  (ii) CDR-H2 comprising the amino acid sequence YISSSSSTIYYADSVKG (SEQ ID NO:5); and
  (iii) CDR-H3 comprising the amino acid sequence GFYVRNWFDP (SEQ ID NO:6).

In some embodiments, the light chain variable region comprises the amino acid sequence of SEQ ID NO:7 and the heavy chain variable region comprises the amino acid sequence of SEQ ID NO:8.

In some embodiments, the antibody or antigen binding fragment thereof comprises (a) a light chain variable region comprising:
  (i) CDR-L1 comprising the amino acid sequence RASQGISSYLA (SEQ ID NO: 17);
  (ii) CDR-L2 comprising the amino acid sequence AASSLQS (SEQ ID NO:18);
  (iii) CDR-L3 comprising the amino acid sequence QQYYSYPFT (SEQ ID NO:19); and
(b) a heavy chain variable region comprising:
  (i) CDR-H1 comprising the amino acid sequence SYAMS (SEQ ID NO:20);
  (ii) CDR-H2 comprising the amino acid sequence AISSGSSTYYADSVKG (SEQ ID NO:21); and (iii) CDR-H3 comprising the amino acid sequence DQGGYGYPGESWFDY (SEQ ID NO:22).

In some embodiments, the light chain variable region comprises the amino acid sequence of SEQ ID NO:23 and the heavy chain variable region comprises the amino acid sequence of SEQ ID NO:24.

In some embodiments, the antibody or antigen binding fragment thereof comprises (a) a light chain variable region comprising:
(i) CDR-L1 comprising the amino acid sequence RASQSISSYLN (SEQ ID NO:25);
(ii) CDR-L2 comprising the amino acid sequence AASSLQS (SEQ ID NO:26);
(iii) CDR-L3 comprising the amino acid sequence QQSYSPPWT (SEQ ID NO:27); and
(b) a heavy chain variable region comprising:
(i) CDR-H1 comprising the amino acid sequence SYSMN (SEQ ID NO:28);
(ii) CDR-H2 comprising the amino acid sequence SISSSSYIYYADSVKG (SEQ ID NO:29); and
(iii) CDR-H3 comprising the amino acid sequence AFYSYMDV (SEQ ID NO:30).

In some embodiments, the light chain variable region comprises the amino acid sequence of SEQ ID NO:31 and the heavy chain variable region comprises the amino acid sequence of SEQ ID NO:32.

In some embodiments, the antibody or antigen binding fragment thereof comprises (a) a light chain variable region comprising:
(i) CDR-L1 comprising the amino acid sequence RSSQSLLHSNGYNYLD (SEQ ID NO:33);
(ii) CDR-L2 comprising the amino acid sequence LGSNRAS (SEQ ID NO:34);
(iii) CDR-L3 comprising the amino acid sequence MQALQTPLT (SEQ ID NO:35); and
(b) a heavy chain variable region comprising:
(i) CDR-H1 comprising the amino acid sequence SSNWWS (SEQ ID NO:36);
(ii) CDR-H2 comprising the amino acid sequence EIYHSGSTNYNPSLKS (SEQ ID NO:37); and
(iii) CDR-H3 comprising the amino acid sequence ERTILTGYYGFDY (SEQ ID NO:38).

In some embodiments, the light chain variable region comprises the amino acid sequence of SEQ ID NO:39 and the heavy chain variable region comprises the amino acid sequence of SEQ ID NO:40.

In some embodiments, the antibody or antigen binding fragment thereof comprises (a) a light chain variable region comprising:
(i) CDR-L1 comprising the amino acid sequence SGSSSNIGNNYVS (SEQ ID NO:41);
(ii) CDR-L2 comprising the amino acid sequence DNNKRPS (SEQ ID NO:42);
(iii) CDR-L3 comprising the amino acid sequence GTWDSSLTGYV (SEQ ID NO:43); and
(b) a heavy chain variable region comprising:
(i) CDR-H1 comprising the amino acid sequence SYAIS (SEQ ID NO:44);
(ii) CDR-H2 comprising the amino acid sequence GIIPIFGTANYAQKFQG (SEQ ID NO:45); and
(iii) CDR-H3 comprising the amino acid sequence YYDFWSGYPGGLFDV (SEQ ID NO:46).

In some embodiments, the light chain variable region comprises the amino acid sequence of SEQ ID NO:47 and the heavy chain variable region comprises the amino acid sequence of SEQ ID NO:48.

In some embodiments, the antibody comprises (a) a light chain variable region comprising:
(i) CDR-L1 comprising the amino acid sequence SGSSSNIGSNYVY (SEQ ID NO:81);
(ii) CDR-L2 comprising the amino acid sequence RNNQRPS (SEQ ID NO:82);
(iii) CDR-L3 comprising the amino acid sequence AAWDDSLSGWV (SEQ ID NO:83); and
(b) a heavy chain variable region comprising:
(i) CDR-H1 comprising the amino acid sequence SYSMN (SEQ ID NO:84);
(ii) CDR-H2 comprising the amino acid sequence YISSSSSTIYYADSVKG (SEQ ID NO:85); and
(iii) CDR-H3 comprising the amino acid sequence SFGPYAFDV (SEQ ID NO:86).

In some embodiments, the light chain variable region comprises the amino acid sequence of SEQ ID NO:87 and the heavy chain variable region comprises the amino acid sequence of SEQ ID NO:88.

In some embodiments, the antibody or antigen binding fragment thereof comprises (a) a light chain variable region comprising:
(i) CDR-L1 comprising the amino acid sequence SGSSSNIGNNYVS (SEQ ID NO:49);
(ii) CDR-L2 comprising the amino acid sequence DNNKRPS (SEQ ID NO:50);
(iii) CDR-L3 comprising the amino acid sequence GTWDSSLTGWV (SEQ ID NO:51); and
(b) a heavy chain variable region comprising:
(i) CDR-H1 comprising the amino acid sequence SYAIS (SEQ ID NO:52);
(ii) CDR-H2 comprising the amino acid sequence GIIPIFGTANYAQKFQG (SEQ ID NO:53); and
(iii) CDR-H3 comprising the amino acid sequence YYDFWSGYPGGLFDV (SEQ ID NO:54).

In some embodiments, the light chain variable region comprises the amino acid sequence of SEQ ID NO:55 and the heavy chain variable region comprises the amino acid sequence of SEQ ID NO:56.

In some embodiments, the antibody or antigen binding fragment thereof comprises (a) a light chain variable region comprising:
(i) CDR-L1 comprising the amino acid sequence QGDSLRSYYAS (SEQ ID NO:57);
(ii) CDR-L2 comprising the amino acid sequence GKNNRPS (SEQ ID NO:58);
(iii) CDR-L3 comprising the amino acid sequence NSRDSSGNHWV (SEQ ID NO:59); and
(b) a heavy chain variable region comprising:
(i) CDR-H1 comprising the amino acid sequence SYSMN (SEQ ID NO:60);
(ii) CDR-H2 comprising the amino acid sequence SISSSSYIYYADSVKG (SEQ ID NO: 61); and
(iii) CDR-H3 comprising the amino acid sequence TNNYGYRYFDY (SEQ ID NO:62).

In some embodiments, the light chain variable region comprises the amino acid sequence of SEQ ID NO:63 and the heavy chain variable region comprises the amino acid sequence of SEQ ID NO:64.

In some embodiments, the antibody or antigen binding fragment thereof comprises (a) a light chain variable region comprising:
(i) CDR-L1 comprising the amino acid sequence QGDSLRSYYAS (SEQ ID NO:65);
(ii) CDR-L2 comprising the amino acid sequence GKNNRPS (SEQ ID NO:66);
(iii) CDR-L3 comprising the amino acid sequence NSRDSTDNHLWV (SEQ ID NO:67); and (b) a heavy chain variable region comprising:
(i) CDR-H1 comprising the amino acid sequence SYSMN (SEQ ID NO:68);
(ii) CDR-H2 comprising the amino acid sequence SISSSSSYIYYADSVKG (SEQ ID NO:69); and
(iii) CDR-H3 comprising the amino acid sequence ATSSGYYYFDY (SEQ ID NO:70).

In some embodiments, the light chain variable region comprises the amino acid sequence of SEQ ID NO:71 and the heavy chain variable region comprises the amino acid sequence of SEQ ID NO:72.

In some embodiments, the antibody or antigen binding fragment thereof comprises
(a) a light chain variable region comprising:
(i) CDR-L1 comprising the amino acid sequence SGSSSNIGNNYVS (SEQ ID NO:73);
(ii) CDR-L2 comprising the amino acid sequence DNNKRPS (SEQ ID NO:74);
(iii) CDR-L3 comprising the amino acid sequence GTWDNSLSVWV (SEQ ID NO:75); and
(b) a heavy chain variable region comprising:
(i) CDR-H1 comprising the amino acid sequence SYSMN (SEQ ID NO:76);
(ii) CDR-H2 comprising the amino acid sequence YISSSSSTIYYADSVKG (SEQ ID NO:77); and
(iii) CDR-H3 comprising the amino acid sequence GKGIVGWGFFGMDV (SEQ ID NO:78).

In some embodiments, the light chain variable region comprises the amino acid sequence of SEQ ID NO:79 and the heavy chain variable region comprises the amino acid sequence of SEQ ID NO:80.

In another aspect, the present invention provides an isolated antibody or antigen binding fragment thereof that binds to human KRas-GDP, wherein the isolated antibody or antigen binding fragment thereof binds to amino acids W99, K5, L6, V7, S39, D54, L54, Y71, T74, and/or G75 of human KRas.

In another aspect, the present invention provides isolated nucleic acid(s) encoding a KRas antibody light chain variable domain and a heavy chain variable domain of the antibody or antigen binding fragment provided herein. In another aspect, the present invention provides a vector comprising the nucleic acid(s). In another aspect, the present invention provides a host cell comprising the vector.

In some embodiments, the antibody or antigen binding fragment thereof is conjugated to a detectable label.

In some embodiments, the present invention provides a process for making an antibody or fragment thereof that binds to KRas-GDP comprising culturing a host cell of paragraph under conditions suitable for expression of the vector encoding the antibody and recovering the antibody.

In another aspect, the present invention provides a method of screening for an antibody that binds to KRas$^{G12C}$-GDP with higher affinity than KRas$^{G12C}$-GTP comprising
(a) contacting an antibody library with
i) KRas$^{G12C}$-GDP,
ii) alkylated KRas$^{G12C}$-GDP with a KRas$^{G12C}$ specific covalent inhibitor, and
iii) KRas$^{G12C}$ bound to a non-hydrolysable GTP analog and
(b) selecting an antibody that binds to the alkylated KRas$^{G12C}$-GDP and the unalkylated KRas$^{G12C}$-GDP with higher affinity than KRas$^{G12C}$ bound to the non-hydrolysable GTP analog.

In some embodiments, the library is a synthetic phage library.

In another aspect, the present invention provides a method for detecting KRas-GDP in a biological sample comprising contacting the biological sample with a KRas antibody or antigen binding fragment provided herien.

In some embodiments, the method further comprises contacting the biological sample with an antibody that binds to KRas-GTP, wherein the amount of KRas-GDP and the amount of KRas-GTP are determined.

In another aspect, the present invention provides a kit comprising the KRas antibody or antigen binding fragment thereof of any one of paragraphs [0006]-[0037] conjugated to a detectable label and instructions for detecting said antibody or antigen binding fragment thereof.

In another aspect, the present invention provides a method of obtaining an inhibitor of a KRas mutant comprising contacting an anti-KRas antibody or antigen binding fragment thereof with the KRas mutant, screening compounds, and identifying compounds that bind to the KRas mutant bound to the antibody or antigen binding fragment thereof.

In some embodiments, the compounds comprise molecules that covalently modify KRas at the SWII pocket.

In some embodiments, the compounds comprise a covalent inhibitor that alkylates at least one residue in the SWII pocket.

In some embodiments, the compounds comprise molecules that non-covalently modify KRas at the SWII pocket.

In some embodiments, the KRas mutant is KRas$^{G12C}$, KRas$^{G12V}$, KRas$^{G12D}$, KRas$^{G13D}$, KRas$^{G12R}$, or KRas$^{Q61H}$.

In one aspect, the present invention provides a method of detecting alkylation of KRas comprising contacting a biological sample with an anti-KRas antibody or antigen binding fragment and detecting the antibody or antigen binding fragment thereof bound to alkylated KRas.

In some embodiments, the detection comprises detection of KRas$^{G12C}$.

In some embodiments, the antibody or antigen binding fragment thereof is a KRas alkylated conformation specific antibody.

In another aspect, the present invention provides a method of detecting alkylation of KRas in a mammal comprising administering an anti-KRas antibody or antigen binding fragment thereof to the mammal and detecting the antibody or antigen binding fragment thereof bound to the alkylated KRas.

In another aspect, the present invention provides a method of detecting alkylation of KRas in a patient treated with a KRas inhibitor, the method comprising:
(a) obtaining a sample from the patient;
(b) contacting the sample with an anti-KRas antibody;
(c) measuring an amount of KRas bound by the antibody or antigen binding fragment thereof.

In some embodiments, the KRas inhibitor is MRTX849, AMG-510, GDC-6036, ARS-3248, LY3499446, or JNJ-74699157.

In some embodiments, the amount of KRas bound by the antibody or antigen binding fragment thereof determines a dosage of the KRas inhibitor to administer to the patient.

In some embodiments, the detection comprises detection of KRas$^{G12C}$.

In some embodiments, the antibody or antigen binding fragment thereof is a KRas alkylated conformation specific antibody.

In some embodiments, the mammal is a human.

In one aspect, the present invention provides a method of detecting alkylation of KRas$^{G12C}$ in a subject treated with a KRas$^{G12C}$ specific covalent inhibitor, the method comprising:

(a) administering an anti-KRas antibody or antigen binding fragment to the subject after treatment with the $KRas^{G12C}$ specific covalent inhibitor; and (b) detecting the antibody or antigen binding fragment thereof bound to the alkylated KRas.

In some embodiments, the $KRas^{G12C}$ specific covalent inhibitor is ARS-1952, ARS-853, ARS-1620, MRTX849, AMG-510, GDC-6036, ARS-3248, LY3499446, or JNJ-74699157.

In some embodiments, the antibody or antigen binding fragment thereof is a KRas alkylated conformation specific antibody.

In one aspect, the present invention provides a method of treating a $KRas^{G12C}$ mediated cancer, the method comprising administering to a patient having such a cancer, an anti-KRas antibody or antigen binding fragment thereof.

In some embodiments, the $KRas^{G12C}$ mediated cancer is NSCLC, colon cancer, or pancreatic cancer.

In another aspect, the present invention provides a crystallization chaperone comprising an anti-KRas antibody or antigen binding fragment thereof.

In another aspect, the present invention provides a method from crystallizing KRas, wherein the KRas is optionally bound to a KRas inhibitor, the method comprising contacting an anti-KRas antibody or antigen binding fragment thereof with KRas and resolving a crystal structure of the complex.

In some embodiments, the KRas is $KRas^{G12C}$, $KRas^{G12D}$, $KRas^{G12V}$, $KRas^{G12R}$, $KRas^{G13D}$, or $KRas^{Q61H}$.

In another aspect, the present invention provides a biosensing surface for measuring binding of compounds to a KRas wherein:

(i) the biosensing surface comprises a hydrogel into which a KRas protein and an anti-KRas antibody or antigen binding fragment are co-localized;

(ii) the KRas and the antibody or antigen binding fragment thereof have sufficient degrees of freedom within the hydrogen to engage each other to form affinity complexes;

(iii) the local concentration of the KRas and the antibody or antigen binding fragment thereof exceeds the dissociation affinity constant by at least 10-fold, wherein the local concentration promotes formation of the affinity complex;

(iv) the fraction of unbound KRas protein and anti-KRas antibody is less than about 50%;

(v) the KRas inhibitor compound is injected onto the biosensing surface for at least 5 seconds; and (vi) wherein binding of the KRas inhibitor compound to the anti-KRas antibody is measured over at least one sensing channel.

In some embodiments, the hydrogel is about 10 nm-500 nm, 10 nm-300 nm, 10-250 nm, or about 10-200 nm in thickness.

In some embodiments, the present invention provides a biosensing surface for measuring binding of compounds to a KRas wherein KRas is biotinylated.

In some embodiments, the present invention provides a biosensing surface for measuring binding of compounds to a KRas wherein the biosensing surface is attached to a BIACORE sensor chip.

In another aspect, the present invention provides a method of screening compounds for anti-KRas inhibitor activity, the method comprising measuring the binding of a compound to KRas, wherein the KRas is bound to an anti-KRas antibody, and wherein the binding is measured using a biosensing surface.

In another aspect, the present invention provides a method of measuring binding of a KRas mutant protein to an anti-KRas antibody described herein, wherein the method comprises:

(i) contacting a biosensing surface with KRas to form a KRas-bound biosensing surface;

(ii) contacting the KRas-bound biosensing surface with an anti-KRas antibody or antigen binding fragment thereof, wherein the antibody or antigen binding fragment thereof is at a molar excess compared to the KRas protein; and (iii) detecting the binding and affinity of the antibody or antigen binding fragment thereof to KRas using surface plasmon resonance.

In another aspect, the present invention provides a method of measuring binding of a KRas mutant protein to an anti-KRas antibody described herein, wherein the method comprises:

(i) contacting a biosensing surface with an anti-KRas antibody or antigen binding fragment thereof to form an anti-KRas antibody-bound biosensing surface;

(ii) contacting the anti-KRas antibody-bound biosensing surface with KRas, wherein the antibody or antigen binding fragment thereof is at a molar excess compared to the KRas protein; and (iii) detecting the binding and affinity of the antibody or antigen binding fragment thereof to KRas using surface plasmon resonance.

It is to be understood that one, some, or all of the properties of the various embodiments described herein may be combined to form other embodiments of the present invention.

BRIEF DESCRIPTION OF THE DRAWINGS

FIG. 6A shows the 2H11 Fab bound to $KRas^{G12C}$-GDP (upper structure). The KRas structure is shown in ribbons, SWII (SW2) is labeled, GDP is shown in sticks, Mg2+ is shown in sphere, and the Cys12 residue is heighted with thicker sticks. The 2H11 Fab is shown in transparent surface and ribbons. The lower structure in FIG. 6A is surface mapping of the KRas epitope for 2H11, rotated relative to the upper structure. FIG. 6B shows a close up view of the antibody-antigen interface. Complementarity determining regions (CDRs) making direct contact with KRas are shown in ribbons. Dotted lines indicate hydrogen bonds, and SWI, SWII, CDRs, GDP, and Cys12 are indicated. The anchoring HC.Trp99 is shown in thick sticks. FIG. 6C shows a comparison of the $KRas^{G12C}$/2H11 complex in the presence and absence of GNE-1952. The GNE-1952 compound is shown as a stick diagram. The SWII residues of both structures are shown in thin sticks, and Cys12 and His95 are indicated. FIG. 6D shows an alignment of the 2H11 anti-KRas antibody bound to $KRas^{G12C}$-GDP and DCAI compound bound to KRas. FIG. 6E shows an alignment of the 1A5 anti-KRas antibody bound to $KRas^{G12C}$-GDP and GNE-1952 $KRas^{G12C}$-GDP. FIG. 6F shows a comparison between the structure of iDab6 and 2H11 in binding the KRas SWI.

DETAILED DESCRIPTION OF EMBODIMENTS OF THE INVENTION

I. Definitions

Figure 1A:
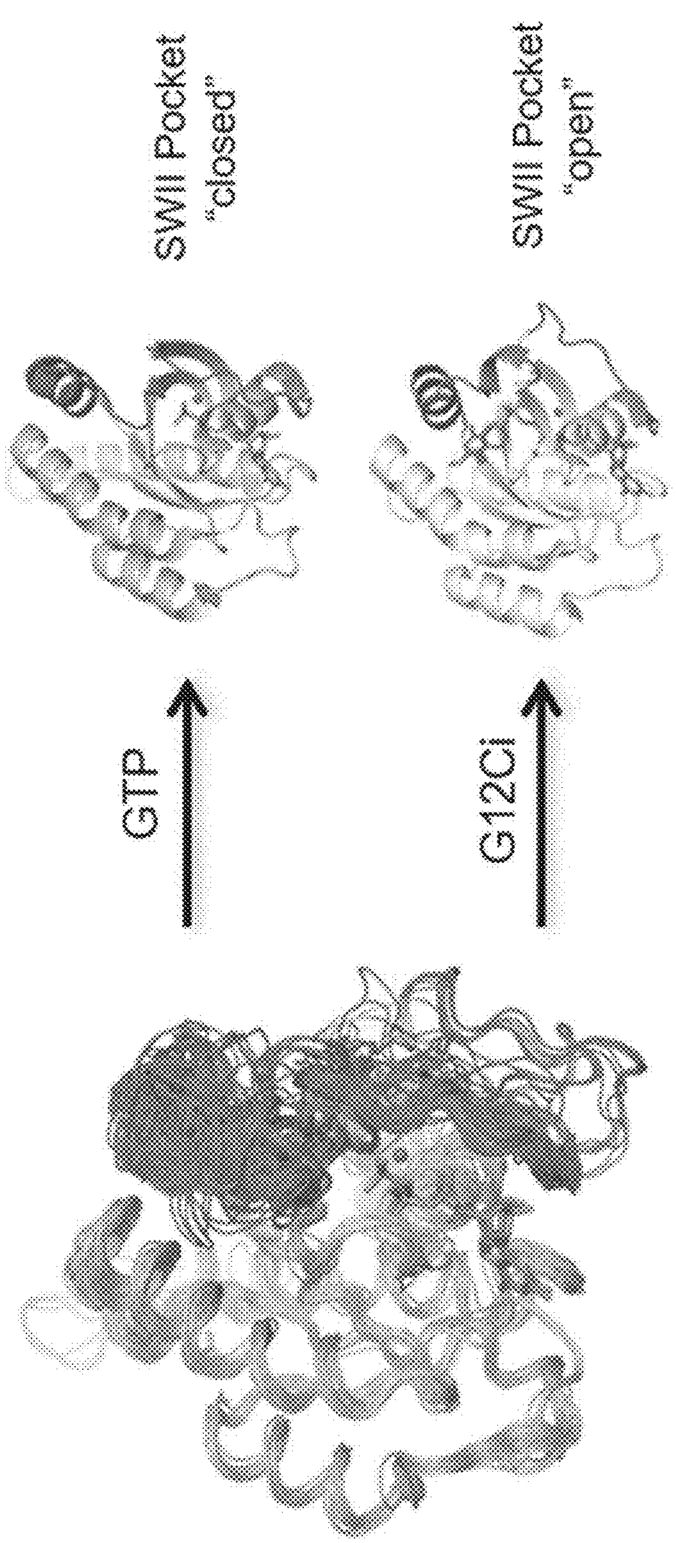
FIG. 1A shows an overlay of Ras crystal structures.

Unless defined otherwise, technical and scientific terms used herein have the same meaning as commonly understood by one of ordinary skill in the art to which this invention belongs. All references cited herein, including patent applications and publications, are incorporated by reference in their entirety.

For purposes of interpreting this specification, the following definitions will apply and whenever appropriate, terms used in the singular will also include the plural and vice versa. It is to be understood that the terminology used herein is for the purpose of describing particular embodiments only, and is not intended to be limiting. In the event that any definition set forth below conflicts with any document incorporated herein by reference, the definition set forth below shall control.

"KRas" used herein refers to a human KRas protein. In some embodiments, human KRas comprises the amino acid sequence of SEQ ID NO:90. In some embodiments, the KRas protein is a mutant (e.g. "mutant KRas" or "KRas mutant"). In some embodiments, the mutant KRas comprises one or more mutations relative to the amino acid sequence of SEQ ID NO:90. In some embodiments, the KRas mutant is an oncogenic mutant. In some embodiments, the KRas protein is a naturally occurring KRas mutant. In some embodiments, the KRas protein is $KRas^{G12C}$ (i.e. KRas with a cysteine substitution at position 12). In some embodiments, the KRas protein is $KRas^{G12V}$, $KRas^{G12R}$, $KRas^{Q61H}$, or $KRas^{G13D}$. "KRas-GDP" used herein refers to KRas bound to guanosine 5'-diphosphate (GDP). In some embodiments, KRas-GDP is inactive KRas. In some embodiments, inactive KRas is not able to bind a RAF kinase, such as c-Raf, and allosterically activate its kinase activity. In some embodiments, inactive KRas does not activate an effector pathway downstream to KRas. In some embodiments, inactive KRas does not activate the mitogen-activated protein (MAP) kinase cascade. In some embodiments, inactive KRas does not activate a signaling cascade that promotes proliferation. In some embodiments, inactive KRas does not activate a signaling cascade that suppresses apoptosis. In some embodiments, inactive KRas does not activate a signaling cascade that promotes the transcription of the glucose transporter GLUT1.

"KRas-GTP" used herein refers to KRas bound to guanosine 5'-triphosphate (GTP). In some embodiments, KRas-GTP is active KRas. In some embodiments, active KRas is able to bind a RAF kinase, such as c-Raf, and allosterically activate its kinase activity. In some embodiments active KRas activates an effector pathway downstream to KRas. In some embodiments, active KRas activates the mitogen-activated protein (MAP) kinase cascade. In some embodiments, active KRas activates a signaling cascade that promotes proliferation. In some embodiments, active KRas activates a signaling cascade that suppresses apoptosis. In some embodiments, active KRas activates a signaling cascade that promotes the transcription of the glucose transporter GLUT1.

An "anti-KRas antibody" used herein, is one that binds to a human KRas-GDP with sufficient specificity and affinity to be useful in detection of KRas-GDP, detection of alkylated KRas-GDP and/or stabilization of KRas-GDP. In one embodiment, the extent of binding of an anti-KRas antibody to an unrelated, KRas protein is less than about 10% of the binding of the antibody to KRas as measured, e.g., by a radioimmunoassay (RIA). In certain embodiments, an antibody that binds to KRas has a dissociation constant ($K_D$) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

Antibodies that "stabilize KRas-GDP" as used herein refers to antibodies which are able to bind to KRas-GDP and preferentially lock KRas in its GDP bound state over its GTP bound state. In some embodiments, an antibody that stabilizes KRas-GDP is also referred to as a CLAMP (i.e., a "Conformation Locking Antibodies for Molecular Probe discovery").

"Affinity" refers to the strength of the sum total of noncovalent interactions between a single binding site of a molecule (e.g., an antibody) and its binding partner (e.g., an antigen, such as KRas, KRas-GDP, and/or alkylated KRas). Unless indicated otherwise, as used herein, "binding affinity" refers to intrinsic binding affinity, which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Specific illustrative and exemplary embodiments for measuring binding affinity are described herein. In some embodiments, affinity is measured using a surface plasmon resonance (SPR) assay. In some embodiments, affinity is measured using a SPR assay using a BIACORE®-T200, BIACORE®-S200, BIACORE®-8k, BIACORE®-2000 or a BIACORE®-3000 instrument. In some embodiments, affinity is measured by enzyme-linked immunosorbent assay (ELISA).

As used herein, a first molecule binds to a second molecule with a "higher affinity" than it does a third molecule when it has a lower dissociation constant ($K_D$) for binding the second molecule than the third molecule.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; single-chain antibody molecules (e.g. scFv); and multispecific antibodies formed from antibody fragments. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an $F(ab')_2$ fragment that has two antigen-combining sites and is still capable of cross-linking antigen.

The term "monoclonal antibody," as used herein, refers to an antibody obtained from a population of substantially homogeneous antibodies, i.e., the individual antibodies comprising the population are identical and/or bind the same epitope, except for possible variant antibodies, e.g, containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (x) and lambda (k), based on the amino acid sequence of its constant domain.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "chimeric" antibody refers to an antibody in which a portion of the heavy and/or light chain is derived from a particular source or species, while the remainder of the heavy and/or light chain is derived from a different source or species.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda MD (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, $6^{th}$ ed., W.H. Freeman and Co., page 91 (2007)). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).)

Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest,* 5th Ed. Public Health Service, National Institutes of Health, Bethesda, MD (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

The term "detecting" is used in the broadest sense to include both qualitative and quantitative measurements of a target molecule. In one aspect, the detecting method as described herein is used to identify the mere presence of KRas, KRas-GDP, and/or alkylated KRas in a biological sample. In another aspect, the method is used to test whether KRas, KRas-GDP, and/or alkylated KRas in a sample is present at a detectable level. In yet another aspect, the method can be used to quantify the amount of KRas, KRas-GDP, and/or alkylated KRas in a sample and further to compare the KRas, KRas-GDP, and/or alkylated KRas levels from different samples.

The term "biological sample" refers to any biological substance that may contain KRas, KRas-GDP, and/or alkylated KRas. A sample can be biological fluid, such as whole blood or whole blood components including red blood cells, white blood cells, platelets, serum and plasma, ascites, vitreous fluid, lymph fluid, synovial fluid, follicular fluid, seminal fluid, amniotic fluid, milk, saliva, sputum, tears, perspiration, mucus, cerebrospinal fluid, and other constituents of the body that may contain KRas, KRas-GDP, and/or alkylated KRas. In various embodiments, the sample is a body sample from any animal. In some embodiments, the sample is from a mammal. In some embodiments, the sample is from a human subject. In some embodiments, the biological sample is from clinical patients or patients treated with a therapeutic KRas antibody. In some embodiments, the biological sample is from clinical patients or patients treated with a KRas alkylating agent. In certain embodiments, the biological sample is serum or plasma. In certain embodiments, the biological sample is serum from a clinical patient.

The term "capture reagent" refers to a reagent (e.g., an antibody) or mixture of such reagent that bind to a target (e.g., KRas, KRas-GDP, and/or alkylated KRas) of interest and are capable of binding and capturing the target (e.g., KRas, KRas-GDP, and/or alkylated KRas) of interest in a biological sample such that under suitable conditions, the complex of capture reagent and target (e.g., KRas, KRas-GDP, and/or alkylated KRas) of interest can be separated from the rest of the sample. In certain embodiments, the capture reagent is immobilized or immobilizable.

The "Fab" fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The term "Fc region" herein is used to define a C-terminal region of an immunoglobulin heavy chain that contains at least a portion of the constant region. The term includes native sequence Fc regions and variant Fc regions. In certain embodiments, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest,* 5th Ed. Public Health Service, National Institutes of Health, Bethesda, MD, 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-KRas antibody" refers to one or more nucleic acid molecules encoding the heavy and light chains (or fragments thereof) of an anti-KRas antibody, including such nucleic acid molecule(s) in a single vector or separate vectors, and such nucleic acid molecule(s) present at one or more locations in a host cell.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, California, or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

A "therapeutically effective amount" is at least the minimum concentration required to effect a measurable improvement or prevention of a particular disorder. A therapeutically effective amount herein may vary according to factors such as the disease state, age, sex, and weight of the patient, and the ability of the antibody to elicit a desired response in the individual. A therapeutically effective amount is also one in which any toxic or detrimental effects of the antibody are outweighed by the therapeutically beneficial effects.

The term "pharmaceutical formulation" or "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable carrier" or an "effective amount" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, antibodies of the invention are used to delay development of a disease or to slow the progression of a disease, such as cancer.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

A "KRas inhibitor" as referred to herein refers to, in the case of $KRas^{G12C}$ a covalent inhibitor that alkylates $KRas^{G12C}$, specifically at the Cys12 residue. As used herein in reference to $KRas^{G12D}$ or $KRas^{G13D}$ a KRas inhibitor can refer to a covalent inhibitor (e.g. a molecule that covalently binds to Asp12 or Asp13) or a non-covalent inhibitor that specifically binds to a given KRas mutant as described herein. As used herein in reference to $KRas^{G12V}$, $KRas^{G12R}$, $KRas^{G12D}$, $KRas^{G13D}$, and $KRas^{Q61H}$, a KRas inhibitor can refer to a non-covalent inhibitor that specifically binds to a given KRas mutant as described herein.

AMG-510 refers to a compound having the structure:

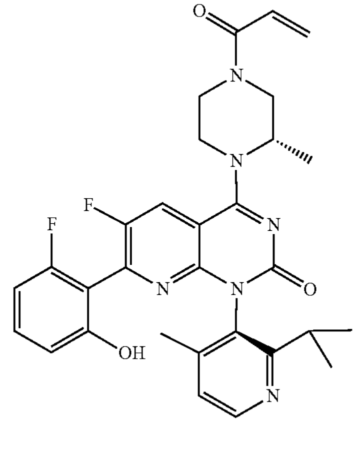

and having the chemical name 4-((S)-4-acryloyl-2-methylpiperazin-1-yl)-6-fluoro-7-(2-fluoro-6-hydroxyphenyl)-1-(2-isopropyl-4-methylpyridin-3-yl)pyrido[2,3-d]pyrimidin-2(1H)-one.

MRTX-849 refers to a compound having the structure:

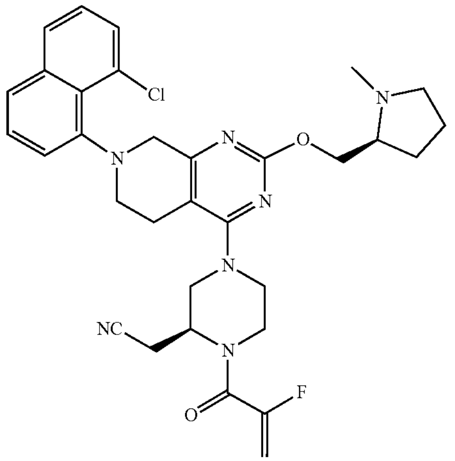 [SMILES: C=C(F)C(=O)N1CCN(c2nc(OC[C@@H]3CCCN3C)nc3c2CCN(c2cccc4cccc(Cl)c24)C3)C[C@@H]1CC#N]

and having the chemical name 2-((S)-4-(7-(8-chloronaphthalen-1-yl)-2-(((S)-1-methylpyrrolidin-2-yl)methoxy)-5,6,7,8-tetrahydropyrido[3,4-d]pyrimidin-4-yl)-1-(2-fluoroacryloyl)piperazin-2-yl)acetonitrile.

ARS-1620 refers to a compound having the structure:

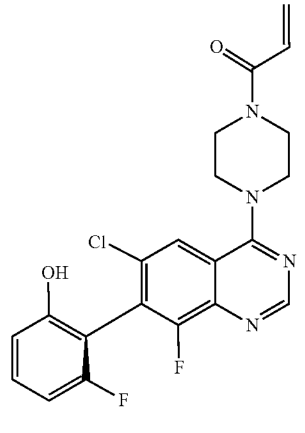

and having the chemical name (R)-1-(4-(6-chloro-8-fluoro-7-(2-fluoro-6-hydroxyphenyl)quinazolin-4-yl)piperazin-1-yl)prop-2-en-1-one.

ARS-853 refers to a compound having the structure:

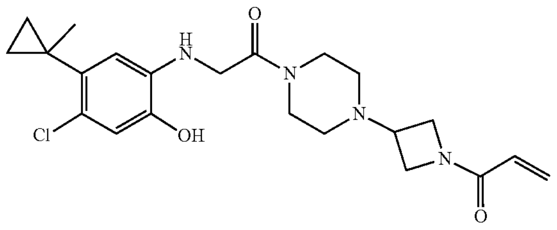 [SMILES: C=CC(=O)N1CC(N2CCN(C(=O)CNc3cc(C4(C)CC4)c(Cl)cc3O)CC2)C1]

and having the chemical name 1-(3-(4-((4-chloro-2-hydroxy-5-(1-methylcyclopropyl)phenyl)glycyl)piperazin-1-yl)azetidin-1-yl)prop-2-en-1-one.

GNE-1952 refers to a compound having the structure:

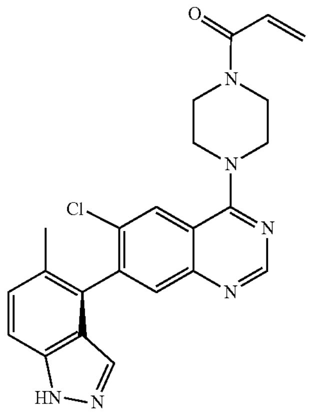

and having the chemical name (R)-1-(4-(6-chloro-7-(5-methyl-TH-indazol-4-yl)quinazolin-4-yl)piperazin-1-yl) prop-2-en-1-one.

As used herein, the singular form "a", "an", and "the" includes plural references unless indicated otherwise.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the invention described herein include "comprising," "consisting," and "consisting essentially of" aspects and embodiments.

II. Compositions and Methods

A. Anti-KRas Antibodies i. Human KRas Protein

In one aspect, the present disclosure provides antibodies that interact with or otherwise bind to a region, such as an epitope, within a human KRas protein. KRas protein is a 21 kilodalton monomeric GTPase that is part of the RAS/MAPK signaling pathway. KRas is a proto-oncogene and is the most frequently mutated oncogene in human cancers (Haigis, K M, *Trends Cancer* 2017 3:10).

In some embodiments, Human KRas is variously referred to as C-K-RAS, c-K-ras protein, c-K-ras2 protein, c-Kirsten-ras protein, cellular c-Ki-ras2 proto-oncogene, K-ras p21 protein, KI-RAS, Kirsten rat sarcoma viral oncogene homolog, KRAS1, PR310 c-K-ras oncogene, RASK2, RASK_HUMAN, transforming protein p21, v-Ki-ras2 Kirsten rat sarcoma viral oncogene homolog, NS, NS3, OES, CFC2, RALD, K-Ras, KRAS1, KRAS2, K-RAS2A, K_RAS2B, and K-RAS4B.

There are two splice isoforms of human KRas mRNA that result in two variants of the KRas protein. The variant termed "KRas isoform b" is the predominant variant, and is comprised of five exons. Isoform b lacks exon 4a and terminates in exon 4b. The second variant (isoform a) is a rare variant comprised of six exons, including exon 4a, and terminating in exon 4a. In the present disclosure, the term "KRas" refers to isoform b, unless otherwise specified.

The amino acid sequence of human KRas isoform b is set forth below as SEQ ID NO:90.

```
MTEYKLVVVGAGGVGKSALTIQLIQNHFVDEYDPT
IEDSYRKQVVIDGETCLLDILDTAGQEEYSAMRDQ
YMRTGEGFLCVFAINNTKSFEDIHHYREQIKRVKD
SEDVPMVLVGNKCDLPSRTVDTKQAQDLARSYGIP
FIETSAKIRQGVDDAFYTLVREIRKHKEKMSKDGK
KKKKKSKTKCVIM
```

The amino acid sequence of human KRas isoform a is set forth below as SEQ ID NO:89.

```
MTEYKLVVVGAGGVGKSALTIQLIQNHFVDEYDPT
IEDSYRKQVVIDGETCLLDILDTAGQEEYSAMRDQ
YMRTGEGFLCVFAINNTKSFEDIHHYREQIKRVKD
SEDVPMVLVGNKCDLPSRTVDTKQAQDLARSYGIP
FIETSAKTRQRVEDAFYTLVREIRQYRLKKISKEE
KTPGCVKIKKCIIM
```

Mutations in KRas and their relationships to various phenotypes, including cancer phenotypes, have been described (see Online Mendelian Inheritance in Man entry number 190070). Several mutant alleles of human KRas have been classified as pathogenic by an expert panel for the FDA Recognition of Public Human Genetic Variant Databases. This includes the coding sequence variants D153V, G60R, T58I, P34L, Q22R, V141, and K5N. In some embodiments, the KRas is a mutant KRas having a mutation corresponding to G12A, G12C, G12D, G12R, G12S, G12V, G13A, G13C, G13D, G13R, G13S, G13V, Q61E, Q61H, Q61K, Q61L, Q61P, Q61R, A146T, A146P, A146V, or A146T. In some embodiments of the present disclosure, additional mutant alleles of KRas are used, including, for example, $KRas^{G12C}$, $KRas^{G12D}$, $KRas^{G13D}$, $KRas^{G13C}$, $KRas^{G12V}$, $KRas^{G12R}$, and $KRas^{Q61H}$.

In some embodiments, KRas couples cell surface receptors to intracellular effector pathways by cycling between "on" and "off" conformations that are conferred by the binding of GTP and GDP, respectively. In some embodiments, KRas is bound to GDP; in these embodiments, it is termed KRas-GDP, or inactive KRas. In other embodiments, KRas is bound to GTP; in these embodiments, it is termed KRas-GTP, or active KRas. The transition between these two states is regulated by guanine nucleotide exchange factors (GEFs), that promote the activation of Ras proteins by stimulating GDP for GTP exchange, and by GTPase-activating proteins (GAPs), that accelerate Ras-mediated GTP hydrolysis (Pylayeva-Gupta, Y. et al. *Nat Rev Cancer* 2011 11). In some embodiments, oncogenic mutations in KRas disrupt its ability to transition between KRas-GDP and KRas-GTP. In some embodiments, oncogenic substitutions in residues G12 and G13 prevent the formation of van der Waals bonds between KRas and a GAP through steric hindrance and so perturb the proper orientation of the catalytic glutamine (Q61) in RAS, which results in the pronounced attenuation of GTP hydrolysis (Pylayeva-Gupta, Y. et al. *Nat Rev Cancer* 2011 11; Scheffzek K, et al. *Science* 1997 277). As a result, in some embodiments KRas is constitutively active.

KRas has an allosteric pocket that is revealed only in its GDP-bound state (Ostream, J. M. et al., *Nature* 2013 28 503:7477). This pocket is known as the switch-II pocket, S-IIP, or SWII. One exemplary mutant allele of KRas, $KRas^{G12C}$, has been targeted via the covalent binding of inhibitors to the Cys12 residue. These inhibitors stabilize the opening of the SWII pocket (Ostream, J. M. et al., *Nature* 2013 28 503:7477; Patricelli, M. P., et al., *Cancer Discov.* 2016 6; Lito, P., et al., *Science* 2016 351). The mechanism of action of such SWII covalent binders (also known as SWII ligands) is thought to be through stabilization of the transient SWII pocket via initial weak binding to the pocket followed by alkylation of Cys12 (Patricelli, M. P., et al., *Cancer Discov.* 2016 6). This locks $KRas^{G12C}$-GDP in an inactive state, inhibiting tumor growth in pre-clinical models, and has shown promising clinical activity (Patricelli, M. P., et al., *Cancer Discov.* 2016 6; Fakih, M. et al., *J Clin Oncol* 2019 37).

ii. Anti-KRas Antibodies

Anti-KRas antibodies or antigen binding fragments thereof that bind to a human KRas protein are described herein. In some embodiments, the anti-KRas antibody binds a KRas protein, wherein the KRas protein comprises the amino acid sequence SEQ ID NO:90. In some embodiments, the anti-KRas antibody binds to human KRas wherein the antibody binds to the KRas bound to GDP (KRas-GDP) with a higher affinity than to the KRas bound to GTP (KRas-GTP). In some embodiments, the anti-KRas antibody binds to KRas-GDP with a lower dissociation constant ($K_D$) than to KRas-GTP. In some embodiments, the anti-KRas antibody binds to KRas-GDP with a lower dissociation constant ($K_D$) at 25° C. than to KRas-GTP. In some embodiments, the anti-KRas antibody binds to KRas-GDP with a lower dissociation constant ($K_D$), as determined by surface plasmon resonance, than to KRas-GTP. In some embodiments, the anti-KRas antibody binds to KRas-GDP with a lower dissociation constant ($K_D$), as determined by surface plasmon resonance at 25° C., than to KRas-GTP. In some embodiments, the anti-KRas antibody binds to KRas-GDP with a lower dissociation constant ($K_D$) than the anti-KRas antibody binds to KRas-GTP. In some embodiments, the anti-KRas antibody binds to KRas-GDP more specifically than it does to KRas-GTP. In some embodiments, the anti-KRas antibody binds to KRas-GDP more strongly than it does to KRas-GTP. In some embodiments, the anti-KRas antibody binds to KRas-GDP with a higher association constant or affinity constant than to KRas-GTP. In some embodiments, the anti-KRas antibody preferentially binds KRas-GDP over KRas-GTP.

In some embodiments, the anti-KRas antibody shows no detectable binding to KRas GTP. In some embodiments, the anti-KRas antibody has at least a 10 fold, at least a 100 fold, at least a 1000 fold, or at least a 10,000 fold greater affinity for KRas-GDP compared to KRas-GTP. In some embodiments, the anti-KRas antibody has a 10 to 10,000 fold greater affinity for KRas-GDP compared to KRas-GTP. In some embodiments, the anti-KRas antibody has a 10 to 1,000,000 fold greater affinity for KRas-GDP compared to KRas-GTP.

In some embodiments, the anti-KRas antibody binds to human KRas wherein the antibody binds to the KRas bound to GTP (KRas-GTP) with a higher affinity than to the KRas bound to GDP (KRas-GDP). In some embodiments, the anti-KRas antibody binds to KRas-GTP with a lower dissociation constant ($K_D$) than to KRas-GDP. In some embodiments, the anti-KRas antibody binds to KRas-GTP with a lower dissociation constant ($K_D$) at 25° C. than to KRas-GDP. In some embodiments, the anti-KRas antibody binds to KRas-GTP with a lower dissociation constant ($K_D$), as determined by surface plasmon resonance, than to KRas-GDP. In some embodiments, the anti-KRas antibody binds to KRas-GTP with a lower dissociation constant ($K_D$), as determined by surface plasmon resonance at 25° C., than to KRas-GDP. In some embodiments, the anti-KRas antibody binds to KRas-GTP with a lower dissociation constant ($K_D$) than the anti-KRas antibody binds to KRas-GDP. In some embodiments, the anti-KRas antibody binds to KRas-GTP more specifically than it does to KRas-GDP. In some embodiments, the anti-KRas antibody binds to KRas-GTP more strongly than it does to KRas-GDP. In some embodiments, the anti-KRas antibody binds to KRas-GTP with a higher association constant or affinity constant than to KRas-GDP. In some embodiments, the anti-KRas antibody preferentially binds KRas-GTP over KRas-GDP.

In some embodiments, the anti-KRas antibody binds to inactive KRas with a higher affinity than to active KRas. In some embodiments, the anti-KRas antibody binds to inactive KRas more stably than it binds active KRas. In some embodiments, the anti-KRas antibody binds to inactive KRas with a lower $K_D$ than it does to active KRas. In some embodiments, the anti-KRas antibody binds specifically to inactive KRas. In some embodiments, the anti-KRas antibody binds to inactive KRas with greater specificity than active KRas. In some embodiments, the anti-KRas antibody binds to inactive KRas more strongly than to active KRas. In some embodiments, the anti-KRas antibody preferentially binds inactive KRas over active KRas.

In some embodiments, the present disclosure provides anti-KRas antibodies that bind and/or induce certain conformations of KRas. In particular, provided herein are anti-KRas antibodies that open and/or stabilize the SWII pocket. In some embodiments, the anti-KRas antibodies provided herein stabilize the SWII pocket. In some embodiments, the anti-KRas antibodies stabilize an open conformation of KRas. In some embodiments, the anti-KRas antibodies opens and stabilize the SWII pocket. In some embodiments, the anti-KRas antibodies stabilize an inactive conformation of KRas. In some embodiments, the anti-KRas antibodies open and stabilize the SWII pocket such that a KRas inhibitor can bind. In some embodiments, the anti-KRas antibody preferentially binds to the open confirmation of KRas. In some embodiments, the anti-KRas antibody binds to KRas-GDP in an open or closed conformation. In some embodiments, the anti-KRas antibody binds to KRas-GTP in an open or closed conformation. In some embodiments, the anti-KRas antibody improves the binding of molecules to the SWII pocket. In some embodiments, the anti-KRas antibody improves the binding of inhibitors to the SWII pocket. In some embodiments, the anti-KRas antibody improves the binding of ligands to the SWII pocket. In some embodiments, the anti-KRas antibody improves the binding of a covalent KRas inhibitor (e.g. a KRas inhibitor that alkylates Cys12) in the SWII pocket. In some embodiments, the anti-KRas antibody binds $KRas^{G12C}$ and improves covalent binding (e.g. alkylation) of residue Cys12. In some embodiments, the anti-KRas antibody binds $KRas^{G12D}$ and improves covalent binding of residue Asp12. In some embodiments, the anti-KRas antibody binds $KRas^{G13D}$ and improves covalent binding of residue Asp13.

In some embodiments, the anti-KRas antibody improves the binding of a non-covalent KRas inhibitor (e.g. a KRas inhibitor that non-covalently binds to residue 12 or 13) in the SWII pocket). In some embodiments, the anti-KRas antibody binds $KRas^{G12D}$ and improves non-covalent binding of residue Asp12. In some embodiments, the anti-KRas antibody binds $KRas^{G12D}$ and improves covalent binding of residue Asp12. In some embodiments, the anti-KRas antibody binds $KRas^{G12V}$ and improves non-covalent binding of residue Val12. In some embodiments, the anti-KRas antibody binds $KRas^{G12R}$ and improves non-covalent binding of residue Arg12. In some embodiments, the anti-KRas antibody binds $KRas^{G13D}$ and improves non-covalent binding of residue Asp13. In some embodiments, the anti-KRas antibody binds $KRas^{G13D}$ and improves covalent binding of residue Asp13. In some embodiments, the anti-KRas antibody binds $KRas^{Q61H}$ and improves non-covalent binding of residue His61.

In some embodiments, the present disclosure provides anti-KRas antibodies that cause KRas to be in a certain conformation more frequently. In some embodiments, the anti-KRas antibody causes KRas to occupy a certain conformation. In particular, provided herein are anti-KRas antibodies that cause KRas to comprise an open SWII pocket more frequently. In some embodiments, the anti-KRas antibodies cause KRas to be in an open conformation more frequently. In some embodiments, the anti-KRas antibodies cause the KRas SWII pocket to be opened and/or stabilized more frequently. In some embodiments, the anti-KRas antibodies cause the SWII pocket to be open and stabilized more frequently such that a KRas inhibitor can bind. In such embodiments, the anti-KRas antibodies described herein can make the residue at position 12 more accessible to and/or stabilized by an inhibitor. In some embodiments, the anti-KRas antibody makes it more likely that ligands will bind to the SWII pocket. In some embodiments, the anti-KRas antibody makes it more likely that the SWII pocket will be bound by a covalent KRas inhibitor (e.g. alkylated). In some embodiments, the anti-KRas antibody binds $KRas^{G12C}$ and makes it more likely that residue Cys12 will be bound by a covalent inhibitor (e.g. alkylated). In some embodiments, the anti-KRas antibody makes it more likely that the SWII pocket will be bound by a non-covalent KRas inhibitor. In some embodiments, the anti-KRas antibody binds $KRas^{G12D}$ and makes it more likely that residue Asp12 will be bound by a non-covalent inhibitor. In some embodiments, the anti-KRas antibody binds $KRas^{G12V}$ and makes it more likely that residue Val12 will be bound by a non-covalent inhibitor. In some embodiments, the anti-KRas antibody binds $KRas^{G12R}$ and makes it more likely that residue Arg12 will be bound by a non-covalent inhibitor. In some embodiments, the anti-KRas antibody binds $KRas^{G13D}$ and makes it more likely that residue Asp13 will be bound by a non-covalent inhibitor. In some embodiments, the anti-KRas antibody binds $KRas^{Q61H}$ and makes it more likely that residue His61 will be bound by a non-covalent inhibitor.

In some embodiments, the present disclosure provides anti-KRas antibodies that affect the conformation of KRas. In some embodiments, the anti-KRas antibody affects the structure of the KRas protein. In some embodiments, the anti-KRas antibody alters the relative frequency with which KRas occupies a specific conformation. In some embodiments, the anti-KRas antibody alters the preference of KRas for specific conformations. In some embodiments, the anti-KRas antibody allosterically regulates KRas structure. In particular, provided herein are anti-KRas antibodies that promote the opening of SWII pocket. In some embodiments, the anti-KRas antibodies provided herein promote the stabilization of the SWII pocket. In some embodiments, the anti-KRas antibodies provided herein promote the stabilization of the SWII pocket in $KRas^{G12C}$. In some embodiments, the anti-KRas antibodies provided herein promote the stabilization of the SWII pocket in $KRas^{G12D}$. In some embodiments, the anti-KRas antibodies provided herein promote the stabilization of the SWII pocket in $KRas^{G12V}$. In some embodiments, the anti-KRas antibodies provided herein promote the stabilization of the SWII pocket in $KRas^{G12R}$. In some embodiments, the anti-KRas antibodies provided herein promote the stabilization of the SWII pocket in $KRas^{G13D}$. In some embodiments, the anti-KRas antibodies provided herein promote the stabilization of the SWII pocket in $KRas^{Q61H}$. In some embodiments, the anti-KRas antibodies promote the stabilization of an open conformation of KRas. In some embodiments, the anti-KRas antibodies promote the opening and stabilization of the SWII pocket. In some embodiments, the anti-KRas antibodies promote the stabilization of an inactive conformation of KRas. In some embodiments, the anti-KRas antibodies promote the opening and stabilization of the SWII pocket such that a KRas inhibitor can bind. In some embodiments, the anti-KRas antibody promotes the binding of ligands to the SWII pocket. In some embodiments, the anti-KRas antibody promotes the binding of inhibitors to the SWII pocket. In some embodiments, the anti-KRas antibody promotes the binding of ligands to the SWII pocket. In some embodiments, the anti-KRas antibody promotes the covalent alkylation of the SWII pocket. In some embodiments, the anti-KRas antibody binds $KRas^{G12C}$ and promotes the alkylation of residue Cys12. In some embodiments, the anti-KRas antibody promotes binding by a non-covalent KRas inhibitor. In some embodiments, the anti-KRas antibody binds $KRas^{G12D}$ and antibody promotes binding to residue Asp12 by a non-covalent inhibitor. In some embodiments, the anti-KRas antibody binds $KRas^{G12V}$ and antibody promotes binding to residue Val12 by a non-covalent inhibitor. In some embodiments, the anti-KRas antibody binds $KRas^{G12R}$ and antibody promotes binding to residue Arg12 by a non-covalent inhibitor. In some embodiments, the anti-KRas antibody binds $KRas^{G13D}$ and antibody promotes binding to residue Asp13 by a non-covalent inhibitor. In some embodiments, the anti-KRas antibody binds $KRas^{Q61H}$ and antibody promotes binding to residue His61 by a non-covalent inhibitor.

In some embodiments, the present disclosure provides anti-KRas antibodies that bind and/or induce certain conformations of KRas. In particular, provided herein are anti-KRas antibodies that impede the closing of the SWII pocket. In some embodiments, the anti-KRas antibodies provided herein prevent the closing of the SWII pocket. In some embodiments, the anti-KRas antibodies provided herein prevent the closing of the SWII pocket in $KRas^{G12C}$. In some embodiments, the anti-KRas antibodies provided herein prevent the closing of the SWII pocket in $KRas^{G12D}$. In some embodiments, the anti-KRas antibodies provided herein prevent the closing of the SWII pocket in $KRas^{G12V}$. In some embodiments, the anti-KRas antibodies provided herein prevent the closing of the SWII pocket in $KRas^{G12R}$. In some embodiments, the anti-KRas antibodies provided herein prevent the closing of the SWII pocket in $KRas^{G13D}$. In some embodiments, the anti-KRas antibodies provided herein prevent the closing of the SWII pocket in $KRas^{Q61H}$. In some embodiments, the anti-KRas antibodies impede or prevent KRas adopting a closed conformation. In some embodiments, the anti-KRas antibodies impede or prevent the closed conformation of the SWII pocket. In some embodiments, the anti-KRas antibodies impede or prevent the closing of the SWII pocket such that a KRas inhibitor can bind. In some embodiments, the anti-KRas antibody preferentially binds to the non-closed confirmation of KRas. In some embodiments, the anti-KRas antibody preferentially binds to the confirmation of the KRas SWII pocket that is not closed. In some embodiments, the anti-KRas antibody causes KRas to be less likely to be in the closed conformation. In some embodiments, the anti-KRas antibody causes KRas to be in the closed conformation less frequently.

In some embodiments, binding of the anti-KRas antibodies disclosed herein results in the induction of certain conformations of KRas. In particular, binding of the anti-KRas antibodies disclosed herein results in an open SWII pocket. In some embodiments, the anti-KRas antibodies provided herein results in an open SWII pocket in $KRas^{G12C}$. In some embodiments, the anti-KRas antibodies provided herein results in an open SWII pocket in $KRas^{G12D}$. In some embodiments, the anti-KRas antibodies provided herein results in an open SWII pocket in $KRas^{G12V}$. In some embodiments, the anti-KRas antibodies provided herein results in an open SWII pocket in $KRas^{G12R}$. In some embodiments, the anti-KRas antibodies provided herein results in an open SWII pocket in $KRas^{G13D}$. In some embodiments, the anti-KRas antibodies provided herein results in an open SWII pocket in $KRas^{Q61H}$. In some embodiments, binding of the anti-KRas antibody results in a stably open SWII pocket. In some embodiments, binding of the anti-KRas antibody results in a SWII pocket that is more likely to be open. In some embodiments, binding of the anti-KRas antibody results in the opening of the SWII pocket. In some embodiments, binding of the anti-KRas antibody results in the stabilization of the SWII pocket. In some embodiments, binding of the anti-KRas antibody results in the stabilization of an open conformation of KRas. In some embodiments, binding of the anti-KRas antibody results in the opening and stabilization of the SWII pocket. In some embodiments, binding of the anti-KRas antibody results in the stabilization of an inactive conformation of KRas. In some embodiments, binding of the anti-KRas antibody results in the opening and stabilization of the SWII pocket such that a KRas inhibitor can bind. In some embodiments, binding of the anti-KRas antibody results in the improved binding of inhibitors to the SWII pocket. In some embodiments, binding of the anti-KRas antibody results in the improved binding of ligands to the SWII pocket. In some embodiments, binding of the anti-KRas antibody results in the improved covalent alkylation of the SWII pocket. In some embodiments, binding of the anti-KRas antibody to $KRas^{G12C}$ results in improved alkylation of residue Cys12.

In some embodiments, the present disclosure provides anti-KRas antibodies that specifically bind and/or induce specific conformations of KRas. In particular, provided herein are anti-KRas antibodies that specifically open the SWII pocket. In some embodiments, the anti-KRas antibodies provided herein specifically stabilize the SWII pocket. In some embodiments, the anti-KRas antibodies provided herein specifically stabilize the SWII pocket of $KRas^{G12D}$. In some embodiments, the anti-KRas antibodies provided herein specifically stabilize the SWII pocket of $KRas^{G12V}$. In some embodiments, the anti-KRas antibodies provided herein specifically stabilize the SWII pocket of $KRas^{G12R}$. In some embodiments, the anti-KRas antibodies provided herein specifically stabilize the SWII pocket of $KRas^{G13D}$. In some embodiments, the anti-KRas antibodies provided herein specifically stabilize the SWII pocket of $KRas^{Q61H}$. In some embodiments, the anti-KRas antibodies specifically stabilize an open conformation of KRas. In some embodiments, the anti-KRas antibodies specifically open and stabilize the SWII pocket. In some embodiments, the anti-KRas antibodies specifically stabilize an inactive conformation of KRas. In some embodiments, the anti-KRas antibodies specifically open and stabilize the SWII pocket such that a KRas inhibitor can bind. In some embodiments, the anti-KRas antibody specifically binds to the open conformation of KRas.

In some embodiments of the present disclosure, the anti-KRas antibodies are KRas alkylated conformation-specific antibodies. In some embodiments, KRas alkylated conformation-specific antibodies are referred to as Class I antibodies, and include, for example, antibodies 1A5, 1D6, 2C1, 1A6, 1F4, and 1B7. In some embodiments, KRas alkylated conformation-specific antibodies bind KRas covalently bound to a KRas inhibitor (e.g. where Cys12 is alkylated by the covalent inhibitor). In some embodiments, KRas alkylated conformation-specific antibodies bind in the presence of a covalently bound SWII inhibitor. In some embodiments, KRas alkylated conformation-specific antibodies bind in the presence of a covalently bound SWII ligand. In some embodiments, KRas is covalently bound (e.g. alkylated) to a KRas inhibitor selected from the group consisting of MRTX849, AMG-510, GDC-6036, ARS-3248, LY3499446, LY3537982, or JNJ-74699157. In another embodiment, KRas is covalently bound to a compound such as ARS1620 or GNE1952. In some embodiments, KRas alkylated conformation-specific antibodies bind KRas in which the SWII pocket is in the open conformation. In some embodiments, KRas alkylated conformation-specific antibodies stabilize the SWII pocket. In some embodiments, the KRas alkylated conformation-specific antibodies described herein stabilize the SWII pocket of $KRas^{G12D}$. In some embodiments, the KRas alkylated conformation-specific antibodies described herein stabilize the SWII pocket of $KRas^{G12V}$ In some embodiments, the KRas alkylated conformation-specific antibodies described herein stabilize the SWII pocket of $KRas^{G12R}$. In some embodiments, the KRas alkylated conformation-specific antibodies described herein stabilize the SWII pocket of $KRas^{G13D}$ In some embodiments, the KRas alkylated conformation-specific antibodies described herein stabilize the SWII pocket of $KRas^{Q61H}$. In some embodiments, KRas alkylated conformation-specific antibodies stabilize the SWII pocket in an open conformation. In some embodiments, KRas alkylated conformation-specific antibodies are used to detect the alkylation of KRas. In some embodiments, KRas alkylated conformation-specific antibodies described herein are used to detect the binding of $KRas^{G12C}$ to covalent inhibitors. In some embodiments, KRas alkylated conformation-specific antibodies may be used to detect alkylated $KRas^{G12C}$-GDP in vivo in tumor cells. In some embodiments, KRas alkylated conformation-specific antibodies may be used to detect alkylated $KRas^{G12C}$-GTP in vivo in tumor cells. In some such embodiments, the detection is used to monitor alkylation of $KRas^{G12C}$ in a patient being treated with a KRas inhibitor (e.g. MRTX849, AMG-510, GDC-6036, ARS-3248, LY3499446, LY3537982, or JNJ-74699157).

In some embodiments the alkylated conformation-specific anti-KRas antibody has at least 5 fold, at least 2 fold, at least 10 fold, at least 50 fold, at least 100 fold, at least 1000 fold greater affinity for an open conformation of KRas compared to a closed conformation. In some embodiments, the alkylated conformation-specific anti-KRas antibody has 2 to 1000 fold increased affinity for an open conformation of KRas compared to a closed conformation. In some embodiments, the alkylated conformation-specific anti-KRas antibody has 10 to 1000 fold increased affinity for an open conformation of KRas compared to a closed conformation. In some embodiments, the alkylated conformation-specific anti-KRas antibody has 10 to 10000 fold increased affinity for an open conformation of KRas compared to a closed conformation. In some embodiments, the alkylated conformation-specific anti-KRas antibody has 10 to 100000 fold increased affinity for an open conformation of KRas compared to a closed conformation.

In some embodiments of the present disclosure, the alkylated conformation-specific anti-KRas antibodies stabilize the open conformation of the SWII pocket of KRas as described herein. In some embodiments, the anti-KRas antibody is a class I or a class II antibody. In some embodiments, the anti-KRas antibody is 1A5. In some embodiments, the anti-KRas antibody is 1D6. In some embodiments, the antibody is 2C1. In some embodiments, the anti-KRas antibody is 1A6. In some embodiments, the antibody is 1B7. In some embodiments, the anti-KRas antibody is 1E5. In some embodiments, the anti-KRas antibody is 2H11. In some embodiments, the anti-KRas antibody is 2A3. In some embodiments, the anti-KRas antibody is 3A12. In some embodiments, the anti-KRas antibody is 4G12. In some embodiments, the anti-KRas antibody is 1F4. In some embodiments, the anti-KRas antibody is Ab1. In some embodiments, the anti-KRas antibody is Ab2. In some embodiments, the anti-KRas antibody is Ab3. In some embodiments, the anti-KRas antibody is Ab4. In some embodiments, the anti-KRas antibody is Ab5. In some embodiments, the anti-KRas antibody is Ab6. In some embodiments, the anti-KRas antibody is Ab7. In some embodiments, the anti-KRas antibody is Ab8.

In some embodiments of the present disclosure, the anti-KRas antibody is an alkylated conformation-specific KRas antibody. In some embodiments, alkylated conformation-specific KRas antibodies bind KRas and induce a conformation of KRas in which the SWII pocket is open. In some embodiments, the alkylated conformation-specific KRas antibody initially binds KRas with a closed SWII pocket, and induces a conformational change in KRas such that the SWII pocket opens. In some embodiments, binding of the alkylated conformation-specific KRas antibody causes the SWII pocket to open. In some embodiments, the alkylated conformation-specific KRas antibody promotes the opening of the SWII pocket. In some embodiments, the alkylated conformation-specific KRas antibody alters the conformation of KRas. In some embodiments, the alkylation-inducing KRas antibody is a Class II antibody. In some embodiments, the KRas alkylated conformation-specific antibody is a Class II antibody. In some embodiments, the anti-KRas antibody is 1E5, 2H11, 2A3, 3A12, 1F4, or 4G12. In some embodiments, the anti-KRas antibody is 1E5, 2H11, 2A3, 3A12, 1F4, 4G12, Ab1, Ab2, Ab3, Ab4, Ab5, Ab6, Ab7, or Ab8. In some embodiments, the anti-KRas antibody is 2H11, Ab1, Ab2, Ab3, Ab4, Ab5, Ab6, Ab7, or Ab8. In some embodiments, the anti-KRas antibody is Ab1, Ab2, Ab3, Ab4, Ab5, Ab6, Ab7, or Ab8. In some embodiments, the anti-KRas antibody is 1E5. In some embodiments, the anti-KRas antibody is 2H11. In some embodiments, the anti-KRas antibody is 2A3. In some embodiments, the anti-KRas antibody is 3A12. In some embodiments, the anti-KRas antibody is 4G12. In some embodiments, the anti-KRas antibody is 1F4. In some embodiments, the anti-KRas antibody is Ab1. In some embodiments, the anti-KRas antibody is Ab2. In some embodiments, the anti-KRas antibody is Ab3. In some embodiments, the anti-KRas antibody is Ab4. In some embodiments, the anti-KRas antibody is Ab5. In some embodiments, the anti-KRas antibody is Ab6. In some embodiments, the anti-KRas antibody is Ab7. In some embodiments, the anti-KRas antibody is Ab8.

In some embodiments, alkylated conformation-specific KRas antibodies of the present disclosure stabilize the open conformation of the SWII pocket in the absence of a covalently-bound $KRas^{G12C}$ inhibitor or SWII ligand. In some embodiments, the anti-KRas antibody initially binds KRas with an open SWII pocket, and stabilizes SWII pocket as described herein. In some embodiments, alkylated conformation-specific KRas antibodies of the present disclosure stabilize the open conformation of the SWII pocket in the absence of a non-covalently-bound $KRas^{G12C}$ inhibitor or SWII ligand In some embodiments, the open conformation of the SWII pocket is considered stabilized when it is more likely to be in an open state than it is in a wild-type KRas protein not bound by such an antibody. In some embodiments, the open conformation of the SWII pocket is considered to be induced when the open conformation is present more frequently than it normally would be. In some embodiments, the anti-KRas antibody locks the KRas SWII pocket in an open conformation. In some embodiments, the anti-KRas antibody prevents the SWII pocket from closing. In some embodiments, alkylated conformation-specific KRas antibodies improve the non-covalent affinity of a number G12C inhibitors for $KRas^{G12C}$ and wild-type KRas.

In some embodiments, the alkylation-inducing anti-KRas antibody binds to unalkylated KRas-GDP and alkylated KRas-GDP with about the same affinity. In some embodiments, the anti-KRas antibody binds to unalkylated KRas-GDP and alkylated KRas-GDP with affinities within 10 fold, within 5 fold, or within 2 fold of each other. In some embodiments, the anti-KRas antibody binds to unalkylated KRas-GDP and alkylated KRas-GDP with affinities within between 10 and 2 fold of each other.

In some embodiments, the invention provides anti-KRas antibodies or antigen binding fragments thereof that bind to a human KRas wherein the human KRas is a KRas mutant. In some embodiments of the present disclosure, the KRas mutant is $KRas^{G12C}$ Mutations in codon 12 of KRas predominate in the cancers in which KRAS are most common (i.e., pancreatic ductal adenocarcinoma (PDAC), colorectal cancer (CRC), and non-small cell lung cancer (NSCLC)) (Haigis, K M, *Trends Cancer* 2017 3:10). $KRas^{G12C}$ is a particular allele of KRAS that has been targeted by compounds that covalently bind the mutated residue Cys12, as described above.

In some embodiments, anti-KRas antibodies of the present disclosure bind KRas mutant proteins. In some embodiments of the present disclosure, the KRas mutant is $KRas^{G12V}$. In some embodiments, the KRas mutant is $KRas^{G12R}$. In some embodiments, the KRas mutant is $KRas^{Q61H}$. In some embodiments, the KRas mutant is $KRas^{G12D}$ In some embodiments, the KRas mutant is $KRas^{G13D}$.

In some embodiments, the isolated antibody or antigen binding fragment is an alkylated conformation-specific KRas antibody that binds to $KRas^{G12C}$-GDP covalently bound (e.g. alkylated) with a small molecule. In some embodiments, an anti-KRas antibody is an alkylated conformation-specific KRas antibody that binds to $KRas^{G12C}$-GDP covalently bound by a small molecule. In some embodiments, $KRas^{G12C}$-GDP is covalently bound (e.g. alkylated) with MRTX849. In some embodiments, $KRas^{G12C}$-GDP is covalently bound (e.g. alkylated) with AMG-510. In some embodiments, $KRas^{G12C}$-GDP is covalently bound (e.g. alkylated) with GDC-6036. In some embodiments, $KRas^{G12C}$-GDP is covalently bound (e.g. alkylated) with ARS-3248. In some embodiments, $KRas^{G12C}$-GDP is covalently bound (e.g. alkylated) with LY3499446. In some embodiments, $KRas^{G12C}$-GDP is covalently bound (e.g. alkylated) with JNJ-74699157. In some embodiments, $KRas^{G12C}$-GDP is covalently bound (e.g. alkylated) with MRTX849, AMG-510, GDC-6036, ARS-3248, LY3499446, LY3537982, or JNJ-74699157.

In some embodiments, the isolated antibody or antigen binding fragment is an alkylated conformation-specific KRas antibody that binds to $KRas^{G12C}$-GDP covalently bound (e.g. alkylated) with a small molecule, in a clinical sample as described herein. In some embodiments, an anti-KRas antibody is an alkylated conformation-specific KRas antibody that binds to $KRas^{G12C}$-GDP covalently bound by a small molecule in a tumor sample taken from a patient as described herein. In some such embodiments, $KRas^{G12C}$-GDP is covalently bound (e.g. alkylated) with MRTX849. In some such embodiments, $KRas^{G12C}$-GDP is covalently bound (e.g. alkylated) with AMG-510. In some such embodiments, $KRas^{G12C}$-GDP is covalently bound (e.g. alkylated) with GDC-6036. In some such embodiments, $KRas^{G12C}$-GDP is covalently bound (e.g. alkylated) with ARS-3248. In some such embodiments, $KRas^{G12C}$-GDP is covalently bound (e.g. alkylated) with LY3499446. In some such embodiments, $KRas^{G12C}$-GDP is covalently bound (e.g. alkylated) with JNJ-74699157. In some such embodiments, $KRas^{G12C}$-GDP is covalently bound (e.g. alkylated) with MRTX849, AMG-510, GDC-6036, ARS-3248, LY3499446, LY3537982, or JNJ-74699157. In some embodiments, the isolated antibody or antigen binding fragment is an alkylated conformation-specific KRas antibody that binds to KRas-GDP as described herein and is used in a biomarker ass for determination of the level of target engagement as described herein.

In some embodiments, the anti-KRas antibody binds $KRas^{G12C}$-GDP. In some embodiments, the anti-KRas antibody binds $KRas^{G12C}$-GDP with a higher affinity when the $KRas^{G12C}$-GDP is alkylated than when the $KRas^{G12C}$-GDP is not alkylated. In some embodiments, the anti-KRas antibody binds $KRas^{G12D}$-GDP. In some embodiments, the anti-KRas antibody binds $KRas^{G12V}$-GDP. In some embodiments, the anti-KRas antibody binds $KRas^{G12R}$-GDP. In some embodiments, the anti-KRas antibody binds $KRas^{G13D}$-GDP. In some embodiments, the anti-KRas antibody binds $KRas^{Q61H}$-GDP. In some embodiments, the anti-KRas antibody binds said mutant KRas-GDP with a higher affinity when the mutant KRas-GDP is bound by a covalent or non-covalent KRas inhibitor than when the mutant KRas-GDP is not bound by a covalent or non-covalent KRas inhibitor.

In some embodiments, the alkylated conformation-specific anti-KRas antibody has at least 5 fold, at least 2 fold, at least 10 fold, at least 50 fold, at least 100 fold, at least 1000 fold greater affinity for alkylated KRas-GDP over unalkylated KRas-GDP. In some embodiments, the alkylated conformation-specific anti-KRas antibody has 2 to 1000 fold increased affinity for alkylated KRas-GDP over unalkylated KRas-GDP. In some embodiments, the alkylated conformation-specific anti-KRas antibody has 10 to 1000 fold increased affinity for alkylated KRas-GDP over unalkylated KRas-GDP. In some embodiments, the alkylated conformation-specific anti-KRas antibody has 10 to 1000 fold increased affinity for alkylated KRas-GDP over unalkylated KRas-GDP. In some embodiments, the alkylated conformation-specific anti-KRas antibody has 10 to 10000 fold increased affinity for alkylated KRas-GDP over unalkylated KRas-GDP. In some embodiments, the alkylated conformation-specific anti-KRas antibody has 10 to 100000 fold increased affinity for alkylated KRas-GDP over unalkylated KRas-GDP.

In some embodiments, the alkylated conformation-specific anti-KRas antibody has at least 5 fold, at least 2 fold, at least 10 fold, at least 50 fold, at least 100 fold, at least 1000 fold greater affinity for alkylated KRas-GTP over unalkylated KRas-GTP. In some embodiments, the alkylated conformation-specific anti-KRas antibody has 2 to 1000 fold increased affinity for alkylated KRas-GTP over unalkylated KRas-GTP. In some embodiments, the alkylated conformation-specific anti-KRas antibody has 10 to 1000 fold increased affinity for alkylated KRas-GTP over unalkylated KRas-GTP. In some embodiments, the alkylated conformation-specific anti-KRas antibody has 10 to 1000 fold increased affinity for alkylated KRas-GTP over unalkylated KRas-GTP. In some embodiments, the alkylated conformation-specific anti-KRas antibody has 10 to 10000 fold increased affinity for alkylated KRas-GTP over unalkylated KRas-GTP. In some embodiments, the alkylated conformation-specific anti-KRas antibody has 10 to 100000 fold increased affinity for alkylated KRas-GTP over unalkylated KRas-GTP.

In some embodiments, the isolated antibody or antigen binding fragment is an anti-KRas antibody that binds to $KRas^{G12D}$-GDP non-covalently bound to a small molecule. In some embodiments, the isolated antibody or antigen binding fragment is an anti-KRas antibody that binds to $KRas^{G12D}$-GTP non-covalently bound to a small molecule. In some embodiments, the isolated antibody or antigen binding fragment is an anti-KRas antibody that binds to $KRas^{G12V}$-GDP non-covalently bound to a small molecule. In some embodiments, the isolated antibody or antigen binding fragment is an anti-KRas antibody that binds to $KRas^{G12V}$-GTP non-covalently bound to a small molecule. In some embodiments, the isolated antibody or antigen binding fragment is an anti-KRas antibody that binds to $KRas^{G12R}$-GDP non-covalently bound to a small molecule. In some embodiments, the isolated antibody or antigen binding fragment is an anti-KRas antibody that binds to $KRas^{G12R}$-GTP non-covalently bound to a small molecule. In some embodiments, the isolated antibody or antigen binding fragment is an anti-KRas antibody that binds to $KRas^{Q61H}$-GDP non-covalently bound to a small molecule. In some embodiments, the isolated antibody or antigen binding fragment is an anti-KRas antibody that binds to $KRas^{Q61H}$-GTP non-covalently bound to a small molecule. In some embodiments, the isolated antibody or antigen binding fragment is an anti-KRas antibody that binds to $KRas^{G13D}$-GDP non-covalently bound to a small molecule.

In some embodiments, the isolated antibody or antigen binding fragment is an anti-KRas antibody that binds to $KRas^{G13D}$-GTP non-covalently bound to a small molecule.

In some embodiments, the anti-KRas antibody comprises one, two, three, four, five, or six CDRs of antibody 2H11 as shown in Table 2 and Table 3. In some embodiments, the anti-KRas antibody comprises the VH and/or the VL of antibody 2H11 as shown in Table 4 and Table 5. In a particular embodiment, an anti-KRas antibody comprising one, two, three, four, five, or six CDRs of antibody 2H11, and/or the VH and/or the VL of antibody 2H11 binds KRas mutant $KRas^{G12C}$. In some embodiments, the anti-KRas antibody is an alkylated-conformation specific KRas antibody. In some embodiments, the anti-KRas antibody opens and stabilizes the SWII pocket of KRas.

In some embodiments, the anti-KRas antibody comprises one, two, three, four, five, or six CDRs of antibody Ab1 as shown in Table 2 and Table 3. In some embodiments, the anti-KRas antibody comprises the VH and/or the VL of antibody Ab1 as shown in Table 4 and Table 5. In a particular embodiment, an anti-KRas antibody comprising one, two, three, four, five, or six CDRs of antibody Ab1, and/or the VH and/or the VL of antibody Ab1 binds KRas mutant $KRas^{G12C}$. In some embodiments, the antibody Ab1 is an alkylated-conformation specific KRas antibody. In some embodiments, the antibody Ab1 opens and stabilizes the SWII pocket of KRas.

In some embodiments, the anti-KRas antibody comprises one, two, three, four, five, or six CDRs of antibody Ab2 as shown in Table 2 and Table 3. In some embodiments, the anti-KRas antibody comprises the VH and/or the VL of antibody Ab2 as shown in Table 4 and Table 5. In a particular embodiment, an anti-KRas antibody comprising one, two, three, four, five, or six CDRs of antibody Ab2, and/or the VH and/or the VL of antibody Ab2 binds KRas mutant $KRas^{G12C}$. In some embodiments, the antibody Ab2 is an alkylated-conformation specific KRas antibody. In some embodiments, the antibody Ab2 opens and stabilizes the SWII pocket of KRas.

In some embodiments, the anti-KRas antibody comprises one, two, three, four, five, or six CDRs of antibody Ab3 as shown in Table 2 and Table 3. In some embodiments, the anti-KRas antibody comprises the VH and/or the VL of antibody Ab3 as shown in Table 4 and Table 5. In a particular embodiment, an anti-KRas antibody comprising one, two, three, four, five, or six CDRs of antibody Ab3, and/or the VH and/or the VL of antibody Ab3 binds KRas mutant $KRas^{G12C}$. In some embodiments, the antibody Ab3 is an alkylated-conformation specific KRas antibody. In some embodiments, the antibody Ab3 opens and stabilizes the SWII pocket of KRas.

In some embodiments, the anti-KRas antibody comprises one, two, three, four, five, or six CDRs of antibody Ab4 as shown in Table 2 and Table 3. In some embodiments, the anti-KRas antibody comprises the VH and/or the VL of antibody Ab4 as shown in Table 4 and Table 5. In a particular embodiment, an anti-KRas antibody comprising one, two, three, four, five, or six CDRs of antibody Ab4, and/or the VH and/or the VL of antibody Ab4 binds KRas mutant $KRas^{G12C}$. In some embodiments, the antibody Ab4 is an alkylated-conformation specific KRas antibody. In some embodiments, the antibody Ab4 opens and stabilizes the SWII pocket of KRas.

In some embodiments, the anti-KRas antibody comprises one, two, three, four, five, or six CDRs of antibody Ab5 as shown in Table 2 and Table 3. In some embodiments, the anti-KRas antibody comprises the VH and/or the VL of antibody Ab5 as shown in Table 4 and Table 5. In a particular embodiment, an anti-KRas antibody comprising one, two, three, four, five, or six CDRs of antibody Ab5, and/or the VH and/or the VL of antibody Ab5 binds KRas mutant $KRas^{G12C}$. In some embodiments, the antibody Ab5 is an alkylated-conformation specific KRas antibody. In some embodiments, the antibody Ab5 opens and stabilizes the SWII pocket of KRas.

In some embodiments, the anti-KRas antibody comprises one, two, three, four, five, or six CDRs of antibody Ab6 as shown in Table 2 and Table 3. In some embodiments, the anti-KRas antibody comprises the VH and/or the VL of antibody Ab6 as shown in Table 4 and Table 5. In a particular embodiment, an anti-KRas antibody comprising one, two, three, four, five, or six CDRs of antibody Ab6, and/or the VH and/or the VL of antibody Ab6 binds KRas mutant $KRas^{G12C}$. In some embodiments, the antibody Ab6 is an alkylated-conformation specific KRas antibody. In some embodiments, the antibody Ab6 opens and stabilizes the SWII pocket of KRas.

In some embodiments, the anti-KRas antibody comprises one, two, three, four, five, or six CDRs of antibody Ab7 as shown in Table 2 and Table 3. In some embodiments, the anti-KRas antibody comprises the VH and/or the VL of antibody Ab7 as shown in Table 4 and Table 5. In a particular embodiment, an anti-KRas antibody comprising one, two, three, four, five, or six CDRs of antibody Ab7, and/or the VH and/or the VL of antibody Ab7 binds KRas mutant $KRas^{G12C}$. In some embodiments, the antibody Ab7 is an alkylated-conformation specific KRas antibody. In some embodiments, the antibody Ab7 opens and stabilizes the SWII pocket of KRas.

In some embodiments, the anti-KRas antibody comprises one, two, three, four, five, or six CDRs of antibody Ab8 as shown in Table 2 and Table 3. In some embodiments, the anti-KRas antibody comprises the VH and/or the VL of antibody Ab8 as shown in Table 4 and Table 5. In a particular embodiment, an anti-KRas antibody comprising one, two, three, four, five, or six CDRs of antibody Ab8, and/or the VH and/or the VL of antibody Ab8 binds KRas mutant $KRas^{G12C}$. In some embodiments, the antibody Ab8 is an alkylated-conformation specific KRas antibody. In some embodiments, the antibody Ab8 opens and stabilizes the SWII pocket of KRas.

In some embodiments, the anti-KRas antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:16. In certain embodiments, a VH sequence contains substitutions (e.g., conservative substitutions), insertions, or deletions relative to the amino acid sequence of SEQ ID NO:16, but retains the ability to bind KRas as the anti-KRas antibody comprising SEQ ID NO:16. In certain embodiments, a total of 1 to 13 amino acids have been substituted, inserted and/or deleted in SEQ ID NO: 16. In certain embodiments, substitutions, insertions, or deletions occur in regions outside the CDRs (i.e., in the FRs). In a particular embodiment, the VH comprises one, two or three CDRs selected from the group consisting of: (a) a CDR-H1 comprising the amino acid sequence of SEQ ID NO:12, (b) a CDR-H2 comprising the amino acid sequence of SEQ ID NO:13, and (c) a CDR-H3 comprising the amino acid sequence of SEQ ID NO:14.

In some embodiments, the anti-KRas antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:99. In certain embodiments, a VH sequence contains substitutions (e.g., conservative substitutions), insertions, or deletions relative to the amino acid sequence of SEQ ID NO:99, but retains the ability to bind KRas as the anti-KRas antibody comprising SEQ ID NO:99. In certain embodiments, a total of 1 to 13 amino acids have been substituted, inserted and/or deleted in SEQ ID NO:99. In certain embodiments, substitutions, insertions, or deletions occur in regions outside the CDRs (i.e., in the FRs). In a particular embodiment, the VH comprises one, two or three CDRs selected from the group consisting of: (a) a CDR-H1 comprising the amino acid sequence of SEQ ID NO:91, (b) a CDR-H2 comprising the amino acid sequence of SEQ ID NO:13, and (c) a CDR-H3 comprising the amino acid sequence of SEQ ID NO:14.

In some embodiments, the anti-KRas antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:100. In certain embodiments, a VH sequence contains substitutions (e.g., conservative substitutions), insertions, or deletions relative to the amino acid sequence of SEQ ID NO:100, but retains the ability to bind KRas as the anti-KRas antibody comprising SEQ ID NO:100. In certain embodiments, a total of 1 to 13 amino acids have been substituted, inserted and/or deleted in SEQ ID NO:100. In certain embodiments, substitutions, insertions, or deletions occur in regions outside the CDRs (i.e., in the FRs). In a particular embodiment, the VH comprises one, two or three CDRs selected from the group consisting of (a) a CDR-H1 comprising the amino acid sequence of SEQ ID NO:92, (b) a CDR-H2 comprising the amino acid sequence of SEQ ID NO:13, and (c) a CDR-H3 comprising the amino acid sequence of SEQ ID NO:14.

In some embodiments, the anti-KRas antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:101. In certain embodiments, a VH sequence contains substitutions (e.g., conservative substitutions), insertions, or deletions relative to the amino acid sequence of SEQ ID NO:101, but retains the ability to bind KRas as the anti-KRas antibody comprising SEQ ID NO:101. In certain embodiments, a total of 1 to 13 amino acids have been substituted, inserted and/or deleted in SEQ ID NO:101. In certain embodiments, substitutions, insertions, or deletions occur in regions outside the CDRs (i.e., in the FRs). In a particular embodiment, the VH comprises one, two or three CDRs selected from the group consisting of: (a) a CDR-H1 comprising the amino acid sequence of SEQ ID NO:93, (b) a CDR-H2 comprising the amino acid sequence of SEQ ID NO:13, and (c) a CDR-H3 comprising the amino acid sequence of SEQ ID NO:14.

In some embodiments, the anti-KRas antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:102. In certain embodiments, a VH sequence contains substitutions (e.g., conservative substitutions), insertions, or deletions relative to the amino acid sequence of SEQ ID NO:102, but retains the ability to bind KRas as the anti-KRas antibody comprising SEQ ID NO:102. In certain embodiments, a total of 1 to 13 amino acids have been substituted, inserted and/or deleted in SEQ ID NO:102. In certain embodiments, substitutions, insertions, or deletions occur in regions outside the CDRs (i.e., in the FRs). In a particular embodiment, the VH comprises one, two or three CDRs selected from the group consisting of: (a) a CDR-H1 comprising the amino acid sequence of SEQ ID NO:94, (b) a CDR-H2 comprising the amino acid sequence of SEQ ID NO:13, and (c) a CDR-H3 comprising the amino acid sequence of SEQ ID NO:14.

In some embodiments, the anti-KRas antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:103. In certain embodiments, a VH sequence contains substitutions (e.g., conservative substitutions), insertions, or deletions relative to the amino acid sequence of SEQ ID NO:103, but retains the ability to bind KRas as the anti-KRas antibody comprising SEQ ID NO:103. In certain embodiments, a total of 1 to 13 amino acids have been substituted, inserted and/or deleted in SEQ ID NO:103. In certain embodiments, substitutions, insertions, or deletions occur in regions outside the CDRs (i.e., in the FRs). In a particular embodiment, the VH comprises one, two or three CDRs selected from the group consisting of: (a) a CDR-H1 comprising the amino acid sequence of SEQ ID NO:95, (b) a CDR-H2 comprising the amino acid sequence of SEQ ID NO:13, and (c) a CDR-H3 comprising the amino acid sequence of SEQ ID NO:14.

In some embodiments, the anti-KRas antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:104. In certain embodiments, a VH sequence contains substitutions (e.g., conservative substitutions), insertions, or deletions relative to the amino acid sequence of SEQ ID NO:104, but retains the ability to bind KRas as the anti-KRas antibody comprising SEQ ID NO:104. In certain embodiments, a total of 1 to 13 amino acids have been substituted, inserted and/or deleted in SEQ ID NO:104. In certain embodiments, substitutions, insertions, or deletions occur in regions outside the CDRs (i.e., in the FRs). In a particular embodiment, the VH comprises one, two or three CDRs selected from the group consisting of: (a) a CDR-H1 comprising the amino acid sequence of SEQ ID NO:96, (b) a CDR-H2 comprising the amino acid sequence of SEQ ID NO:13, and (c) a CDR-H3 comprising the amino acid sequence of SEQ ID NO:14.

In some embodiments, the anti-KRas antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:105. In certain embodiments, a VH sequence contains substitutions (e.g., conservative substitutions), insertions, or deletions relative to the amino acid sequence of SEQ ID NO:105, but retains the ability to bind KRas as the anti-KRas antibody comprising SEQ ID NO:105. In certain embodiments, a total of 1 to 13 amino acids have been substituted, inserted and/or deleted in SEQ ID NO:105. In certain embodiments, substitutions, insertions, or deletions occur in regions outside the CDRs (i.e., in the FRs). In a particular embodiment, the VH comprises one, two or three CDRs selected from the group consisting of (a) a CDR-H1 comprising the amino acid sequence of SEQ ID NO:97, (b) a CDR-H2 comprising the amino acid sequence of SEQ ID NO:13, and (c) a CDR-H3 comprising the amino acid sequence of SEQ ID NO:14.

In some embodiments, the anti-KRas antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:106. In certain embodiments, a VH sequence contains substitutions (e.g., conservative substitutions), insertions, or deletions relative to the amino acid sequence of SEQ ID NO:106, but retains the ability to bind KRas as the anti-KRas antibody comprising SEQ ID NO:106. In certain embodiments, a total of 1 to 13 amino acids have been substituted, inserted and/or deleted in SEQ ID NO:106. In certain embodiments, substitutions, insertions, or deletions occur in regions outside the CDRs (i.e., in the FRs). In a particular embodiment, the VH comprises one, two or three CDRs selected from the group consisting of: (a) a CDR-H1 comprising the amino acid sequence of SEQ ID NO:98, (b) a CDR-H2 comprising the amino acid sequence of SEQ ID NO:13, and (c) a CDR-H3 comprising the amino acid sequence of SEQ ID NO:14.

In another aspect, an anti-KRas antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:15. In certain embodiments, a VL sequence contains substitutions (e.g., conservative substitutions), insertions, or deletions relative to the amino acid sequence of SEQ ID NO:15, but retains the ability to bind KRas as the anti-KRas antibody comprising SEQ ID NO:15. In certain embodiments, a total of 1 to 11 amino acids have been substituted, inserted and/or deleted in SEQ ID NO:15. In certain embodiments, the substitutions, insertions, or deletions occur in regions outside the CDRs (i.e., in the FRs). In a particular embodiment, the VL comprises one, two or three CDRs selected from the group consisting of (a) a CDR-L1 comprising the amino acid sequence of SEQ ID NO:9; (b) a CDR-L2 comprising the amino acid sequence of SEQ ID NO:10; and (c) a CDR-L3 comprising the amino acid sequence of SEQ ID NO:11.

In one embodiment, the anti-KRas antibody comprises a VL comprising the amino acid sequence of SEQ ID NO:15 and a VH comprising the amino acid sequence of SEQ ID NO: 16. In one embodiment, the anti-KRas antibody comprises a VL comprising the amino acid sequence of SEQ ID NO:15 and a VH comprising the amino acid sequence of SEQ ID NO:99. In one embodiment, the anti-KRas antibody comprises a VL comprising the amino acid sequence of SEQ ID NO:15 and a VH comprising the amino acid sequence of SEQ ID NO: 100. In one embodiment, the anti-KRas antibody comprises a VL comprising the amino acid sequence of SEQ ID NO:15 and a VH comprising the amino acid sequence of SEQ ID NO:101. In one embodiment, the anti-KRas antibody comprises a VL comprising the amino acid sequence of SEQ ID NO:15 and a VH comprising the amino acid sequence of SEQ ID NO: 102. In one embodiment, the anti-KRas antibody comprises a VL comprising the amino acid sequence of SEQ ID NO:15 and a VH comprising the amino acid sequence of SEQ ID NO: 103. In one embodiment, the anti-KRas antibody comprises a VL comprising the amino acid sequence of SEQ ID NO:15 and a VH comprising the amino acid sequence of SEQ ID NO: 104. In one embodiment, the anti-KRas antibody comprises a VL comprising the amino acid sequence of SEQ ID NO:15 and a VH comprising the amino acid sequence of SEQ ID NO: 105. In one embodiment, the anti-KRas antibody comprises a VL comprising the amino acid sequence of SEQ ID NO:15 and a VH comprising the amino acid sequence of SEQ ID NO: 106.

In another aspect, an anti-KRas antibody is provided, wherein the antibody comprises a VH comprising a CDR-H1 comprising the amino acid sequence of SEQ ID NO:12, a CDR-H2 comprising the amino acid sequence of SEQ ID NO:13, and a CDR-H3 comprising the amino acid sequence of SEQ ID NO:14; and a VL comprising a CDR-L1 comprising the amino acid sequence of SEQ ID NO:9, a CDR-L2 comprising the amino acid sequence of SEQ ID NO:10, and a CDR-L3 comprising the amino acid sequence of SEQ ID NO:11.

In another aspect, an anti-KRas antibody is provided, wherein the antibody comprises a VH comprising a CDR-H1 comprising the amino acid sequence of SEQ ID NO:91, a CDR-H2 comprising the amino acid sequence of SEQ ID NO:13, and a CDR-H3 comprising the amino acid sequence of SEQ ID NO:14; and a VL comprising a CDR-L1 comprising the amino acid sequence of SEQ ID NO:9, a CDR-L2 comprising the amino acid sequence of SEQ ID NO:10, and a CDR-L3 comprising the amino acid sequence of SEQ ID NO:11.

In another aspect, an anti-KRas antibody is provided, wherein the antibody comprises a VH comprising a CDR-H1 comprising the amino acid sequence of SEQ ID NO:92, a CDR-H2 comprising the amino acid sequence of SEQ ID NO:13, and a CDR-H3 comprising the amino acid sequence of SEQ ID NO:14; and a VL comprising a CDR-L1 comprising the amino acid sequence of SEQ ID NO:9, a CDR-L2 comprising the amino acid sequence of SEQ ID NO:10, and a CDR-L3 comprising the amino acid sequence of SEQ ID NO:11.

In another aspect, an anti-KRas antibody is provided, wherein the antibody comprises a VH comprising a CDR-H1 comprising the amino acid sequence of SEQ ID NO:93, a CDR-H2 comprising the amino acid sequence of SEQ ID NO:13, and a CDR-H3 comprising the amino acid sequence of SEQ ID NO:14; and a VL comprising a CDR-L1 comprising the amino acid sequence of SEQ ID NO:9, a CDR-L2 comprising the amino acid sequence of SEQ ID NO:10, and a CDR-L3 comprising the amino acid sequence of SEQ ID NO:11.

In another aspect, an anti-KRas antibody is provided, wherein the antibody comprises a VH comprising a CDR-H1 comprising the amino acid sequence of SEQ ID NO:94, a CDR-H2 comprising the amino acid sequence of SEQ ID NO:13, and a CDR-H3 comprising the amino acid sequence of SEQ ID NO:14; and a VL comprising a CDR-L1 comprising the amino acid sequence of SEQ ID NO:9, a CDR-L2 comprising the amino acid sequence of SEQ ID NO:10, and a CDR-L3 comprising the amino acid sequence of SEQ ID NO:11.

In another aspect, an anti-KRas antibody is provided, wherein the antibody comprises a VH comprising a CDR-H1 comprising the amino acid sequence of SEQ ID NO:95, a CDR-H2 comprising the amino acid sequence of SEQ ID NO:13, and a CDR-H3 comprising the amino acid sequence of SEQ ID NO:14; and a VL comprising a CDR-L1 comprising the amino acid sequence of SEQ ID NO:9, a CDR-L2 comprising the amino acid sequence of SEQ ID NO:10, and a CDR-L3 comprising the amino acid sequence of SEQ ID NO:11.

In another aspect, an anti-KRas antibody is provided, wherein the antibody comprises a VH comprising a CDR-H1 comprising the amino acid sequence of SEQ ID NO:96, a CDR-H2 comprising the amino acid sequence of SEQ ID NO:13, and a CDR-H3 comprising the amino acid sequence of SEQ ID NO:14; and a VL comprising a CDR-L1 comprising the amino acid sequence of SEQ ID NO:9, a CDR-L2 comprising the amino acid sequence of SEQ ID NO:10, and a CDR-L3 comprising the amino acid sequence of SEQ ID NO:11.

In another aspect, an anti-KRas antibody is provided, wherein the antibody comprises a VH comprising a CDR- H1 comprising the amino acid sequence of SEQ ID NO:97, a CDR-H2 comprising the amino acid sequence of SEQ ID NO:13, and a CDR-H3 comprising the amino acid sequence of SEQ ID NO:14; and a VL comprising a CDR-L1 comprising the amino acid sequence of SEQ ID NO:9, a CDR-L2 comprising the amino acid sequence of SEQ ID NO:10, and a CDR-L3 comprising the amino acid sequence of SEQ ID NO:11.

In another aspect, an anti-KRas antibody is provided, wherein the antibody comprises a VH comprising a CDR-H1 comprising the amino acid sequence of SEQ ID NO:98, a CDR-H2 comprising the amino acid sequence of SEQ ID NO:13, and a CDR-H3 comprising the amino acid sequence of SEQ ID NO:14; and a VL comprising a CDR-L1 comprising the amino acid sequence of SEQ ID NO:9, a CDR-L2 comprising the amino acid sequence of SEQ ID NO:10, and a CDR-L3 comprising the amino acid sequence of SEQ ID NO:11.

In another aspect, an anti-KRas antibody is provided, wherein the antibody comprises a VH CDR1, a VH CDR2, and a VH CDR3, respectively comprising the amino acid sequences of a CDR1, a CDR2, and a CDR3 within a VH having the sequence set forth in SEQ ID NO:16; and a VL CDR1, a VL CDR2, and a VL CDR3, respectively comprising the amino acid sequences of a CDR1, a CDR2, and a CDR3 within a VL having the sequence set forth in SEQ ID NO:15.

In another aspect, an anti-KRas antibody is provided, wherein the antibody comprises a VH CDR1, a VH CDR2, and a VH CDR3, respectively comprising the amino acid sequences of a CDR1, a CDR2, and a CDR3 within a VH having the sequence set forth in SEQ ID NO:99; and a VL CDR1, a VL CDR2, and a VL CDR3, respectively comprising the amino acid sequences of a CDR1, a CDR2, and a CDR3 within a VL having the sequence set forth in SEQ ID NO:15.

In another aspect, an anti-KRas antibody is provided, wherein the antibody comprises a VH CDR1, a VH CDR2, and a VH CDR3, respectively comprising the amino acid sequences of a CDR1, a CDR2, and a CDR3 within a VH having the sequence set forth in SEQ ID NO:100; and a VL CDR1, a VL CDR2, and a VL CDR3, respectively comprising the amino acid sequences of a CDR1, a CDR2, and a CDR3 within a VL having the sequence set forth in SEQ ID NO:15.

In another aspect, an anti-KRas antibody is provided, wherein the antibody comprises a VH CDR1, a VH CDR2, and a VH CDR3, respectively comprising the amino acid sequences of a CDR1, a CDR2, and a CDR3 within a VH having the sequence set forth in SEQ ID NO:101; and a VL CDR1, a VL CDR2, and a VL CDR3, respectively comprising the amino acid sequences of a CDR1, a CDR2, and a CDR3 within a VL having the sequence set forth in SEQ ID NO:15.

In another aspect, an anti-KRas antibody is provided, wherein the antibody comprises a VH CDR1, a VH CDR2, and a VH CDR3, respectively comprising the amino acid sequences of a CDR1, a CDR2, and a CDR3 within a VH having the sequence set forth in SEQ ID NO:102; and a VL CDR1, a VL CDR2, and a VL CDR3, respectively comprising the amino acid sequences of a CDR1, a CDR2, and a CDR3 within a VL having the sequence set forth in SEQ ID NO:15.

In another aspect, an anti-KRas antibody is provided, wherein the antibody comprises a VH CDR1, a VH CDR2, and a VH CDR3, respectively comprising the amino acid sequences of a CDR1, a CDR2, and a CDR3 within a VH having the sequence set forth in SEQ ID NO:103; and a VL CDR1, a VL CDR2, and a VL CDR3, respectively comprising the amino acid sequences of a CDR1, a CDR2, and a CDR3 within a VL having the sequence set forth in SEQ ID NO:15.

In another aspect, an anti-KRas antibody is provided, wherein the antibody comprises a VH CDR1, a VH CDR2, and a VH CDR3, respectively comprising the amino acid sequences of a CDR1, a CDR2, and a CDR3 within a VH having the sequence set forth in SEQ ID NO:104; and a VL CDR1, a VL CDR2, and a VL CDR3, respectively comprising the amino acid sequences of a CDR1, a CDR2, and a CDR3 within a VL having the sequence set forth in SEQ ID NO:15.

In another aspect, an anti-KRas antibody is provided, wherein the antibody comprises a VH CDR1, a VH CDR2, and a VH CDR3, respectively comprising the amino acid sequences of a CDR1, a CDR2, and a CDR3 within a VH having the sequence set forth in SEQ ID NO:105; and a VL CDR1, a VL CDR2, and a VL CDR3, respectively comprising the amino acid sequences of a CDR1, a CDR2, and a CDR3 within a VL having the sequence set forth in SEQ ID NO:15.

In another aspect, an anti-KRas antibody is provided, wherein the antibody comprises a VH CDR1, a VH CDR2, and a VH CDR3, respectively comprising the amino acid sequences of a CDR1, a CDR2, and a CDR3 within a VH having the sequence set forth in SEQ ID NO:106; and a VL CDR1, a VL CDR2, and a VL CDR3, respectively comprising the amino acid sequences of a CDR1, a CDR2, and a CDR3 within a VL having the sequence set forth in SEQ ID NO:15.

In some embodiments, the anti-KRas antibody comprises one, two, three, four, five, or six CDRs of antibody 1A5 as shown in Table 2 and Table 3. In some embodiments, the anti-KRas antibody comprises the VH and/or the VL of antibody 1A5 as shown in Table 4 and Table 5. In a particular embodiment, an anti-KRas antibody comprising one, two, three, four, five, or six CDRs of antibody 1A5, and/or the VH and/or the VL of antibody 1A5 binds KRas mutant $KRas^{G12C}$. In some embodiments, the anti-KRas antibody is an alkylated-conformation specific KRas antibody. In some embodiments, the anti-KRas antibody stabilizes the SWII pocket of KRas.

In some embodiments, the anti-KRas antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:8. In certain embodiments, a VH sequence contains substitutions (e.g., conservative substitutions), insertions, or deletions relative to the amino acid sequence of SEQ ID NO:8, but retains the ability to bind KRas as the anti-KRas antibody comprising SEQ ID NO:8. In certain embodiments, a total of 1 to 13 amino acids have been substituted, inserted and/or deleted in SEQ ID NO:8. In certain embodiments, substitutions, insertions, or deletions occur in regions outside the CDRs (i.e., in the FRs). In a particular embodiment, the VH comprises one, two or three CDRs selected from the group consisting of: (a) a CDR-H1 comprising the amino acid sequence of SEQ ID NO:4, (b) a CDR-H2 comprising the amino acid sequence of SEQ ID NO:5, and (c) a CDR-H3 comprising the amino acid sequence of SEQ ID NO:6.

In another aspect, an anti-KRas antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:7. In certain embodiments, a VL sequence contains substitutions (e.g., conservative substitutions), insertions, or deletions relative to the amino acid sequence of SEQ ID NO:7, but retains the ability to bind KRas as the anti-KRas antibody comprising SEQ ID NO:7. In certain embodiments, a total of 1 to 11 amino acids have been substituted, inserted and/or deleted in SEQ ID NO:7. In certain embodiments, the substitutions, insertions, or deletions occur in regions outside the CDRs (i.e., in the FRs). In a particular embodiment, the VL comprises one, two or three CDRs selected from the group consisting of (a) a CDR-L1 comprising the amino acid sequence of SEQ ID NO:1; (b) a CDR-L2 comprising the amino acid sequence of SEQ ID NO:2; and (c) a CDR-L3 comprising the amino acid sequence of SEQ ID NO:3.

In one embodiment, the anti-KRas antibody comprises a VL comprising the amino acid sequence of SEQ ID NO:7 and a VH comprising the amino acid sequence of SEQ ID NO:8.

In another aspect, an anti-KRas antibody is provided, wherein the antibody comprises a VH comprising a CDR-H1 comprising the amino acid sequence of SEQ ID NO:4, a CDR-H2 comprising the amino acid sequence of SEQ ID NO:5, and a CDR-H3 comprising the amino acid sequence of SEQ ID NO:6; and a VL comprising a CDR-L1 comprising the amino acid sequence of SEQ ID NO:1, a CDR-L2 comprising the amino acid sequence of SEQ ID NO:2, and a CDR-L3 comprising the amino acid sequence of SEQ ID NO:3.

In another aspect, an anti-KRas antibody is provided, wherein the antibody comprises a VH CDR1, a VH CDR2, and a VH CDR3, respectively comprising the amino acid sequences of a CDR1, a CDR2, and a CDR3 within a VH having the sequence set forth in SEQ ID NO:8; and a VL CDR1, a VL CDR2, and a VL CDR3, respectively comprising the amino acid sequences of a CDR1, a CDR2, and a CDR3 within a VL having the sequence set forth in SEQ ID NO:7.

In some embodiments, the anti-KRas antibody comprises one, two, three, four, five, or six CDRs of antibody 1D6 as shown in Table 2 and Table 3. In some embodiments, the anti-KRas antibody comprises the VH and/or the VL of antibody 1D6 as shown in Table 4 and Table 5. In a particular embodiment, an anti-KRas antibody comprising one, two, three, four, five, or six CDRs of antibody 1D6, and/or the VH and/or the VL of antibody 1D6 binds KRas mutant $KRas^{G12C}$. In some embodiments, the anti-KRas antibody is an alkylated-conformation specific KRas antibody. In some embodiments, the anti-KRas antibody stabilizes the SWII pocket of KRas.

In some embodiments, the anti-KRas antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:24. In certain embodiments, a VH sequence contains substitutions (e.g., conservative substitutions), insertions, or deletions relative to the amino acid sequence of SEQ ID NO: 24, but retains the ability to bind KRas as the anti-KRas antibody comprising SEQ ID NO:24. In certain embodiments, a total of 1 to 13 amino acids have been substituted, inserted and/or deleted in SEQ ID NO: 24. In certain embodiments, substitutions, insertions, or deletions occur in regions outside the CDRs (i.e., in the FRs). In a particular embodiment, the VH comprises one, two or three CDRs selected from the group consisting of (a) a CDR-H1 comprising the amino acid sequence of SEQ ID NO:20, (b) a CDR-H2 comprising the amino acid sequence of SEQ ID NO:21, and (c) a CDR-H3 comprising the amino acid sequence of SEQ ID NO:22.

In another aspect, an anti-KRas antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:23. In certain embodiments, a VL sequence contains substitutions (e.g., conservative substitutions), insertions, or deletions relative to the amino acid sequence of SEQ ID NO:23, but retains the ability to bind KRas as the anti-KRas antibody comprising SEQ ID NO:23. In certain embodiments, a total of 1 to 11 amino acids have been substituted, inserted and/or deleted in SEQ ID NO:23. In certain embodiments, the substitutions, insertions, or deletions occur in regions outside the CDRs (i.e., in the FRs). In a particular embodiment, the VL comprises one, two or three CDRs selected from the group consisting of (a) a CDR-L1 comprising the amino acid sequence of SEQ ID NO:17; (b) a CDR-L2 comprising the amino acid sequence of SEQ ID NO:18; and (c) a CDR-L3 comprising the amino acid sequence of SEQ ID NO:19.

In one embodiment, the anti-KRas antibody comprises a VL comprising the amino acid sequence of SEQ ID NO:23 and a VH comprising the amino acid sequence of SEQ ID NO:24.

In another aspect, an anti-KRas antibody is provided, wherein the antibody comprises a VH comprising a CDR-H1 comprising the amino acid sequence of SEQ ID NO:20, a CDR-H2 comprising the amino acid sequence of SEQ ID NO:21, and a CDR-H3 comprising the amino acid sequence of SEQ ID NO:22; and a VL comprising a CDR-L1 comprising the amino acid sequence of SEQ ID NO:17, a CDR-L2 comprising the amino acid sequence of SEQ ID NO:18, and a CDR-L3 comprising the amino acid sequence of SEQ ID NO:19.

In another aspect, an anti-KRas antibody is provided, wherein the antibody comprises a VH CDR1, a VH CDR2, and a VH CDR3, respectively comprising the amino acid sequences of a CDR1, a CDR2, and a CDR3 within a VH having the sequence set forth in SEQ ID NO: 24; and a VL CDR1, a VL CDR2, and a VL CDR3, respectively comprising the amino acid sequences of a CDR1, a CDR2, and a CDR3 within a VL having the sequence set forth in SEQ ID NO: 23.

In some embodiments, the anti-KRas antibody comprises one, two, three, four, five, or six CDRs of antibody 2C1 as shown in Table 2 and Table 3. In some embodiments, the anti-KRas antibody comprises the VH and/or the VL of antibody 2C1 as shown in Table 4 and Table 5. In a particular embodiment, an anti-KRas antibody comprising one, two, three, four, five, or six CDRs of antibody 2C1, and/or the VH and/or the VL of antibody 2C1 binds KRas mutant $KRas^{G12C}$. In some embodiments, the anti-KRas antibody is an alkylated-conformation specific KRas antibody. In some embodiments, the anti-KRas antibody stabilizes the SWII pocket of KRas.

In some embodiments, the anti-KRas antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:32. In certain embodiments, a VH sequence contains substitutions (e.g., conservative substitutions), insertions, or deletions relative to the amino acid sequence of SEQ ID NO:32, but retains the ability to bind KRas as the anti-KRas antibody comprising SEQ ID NO:32. In certain embodiments, a total of 1 to 13 amino acids have been substituted, inserted and/or deleted in SEQ ID NO:32. In certain embodiments, substitutions, insertions, or deletions occur in regions outside the CDRs (i.e., in the FRs). In a particular embodiment, the VH comprises one, two or three CDRs selected from the group consisting of (a) a CDR-H1 comprising the amino acid sequence of SEQ ID NO:28, (b) a CDR-H2 comprising the amino acid sequence of SEQ ID NO:29, and (c) a CDR-H3 comprising the amino acid sequence of SEQ ID NO:30.

In another aspect, an anti-KRas antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:31. In certain embodiments, a VL sequence contains substitutions (e.g., conservative substitutions), insertions, or deletions relative to the amino acid sequence of SEQ ID NO:31, but retains the ability to bind KRas as the anti-KRas antibody comprising SEQ ID NO:31. In certain embodiments, a total of 1 to 11 amino acids have been substituted, inserted and/or deleted in SEQ ID NO:31. In certain embodiments, the substitutions, insertions, or deletions occur in regions outside the CDRs (i.e., in the FRs). In a particular embodiment, the VL comprises one, two or three CDRs selected from the group consisting of (a) a CDR-L1 comprising the amino acid sequence of SEQ ID NO:25; (b) a CDR-L2 comprising the amino acid sequence of SEQ ID NO:26; and (c) a CDR-L3 comprising the amino acid sequence of SEQ ID NO:27.

In one embodiment, the anti-KRas antibody comprises a VL comprising the amino acid sequence of SEQ ID NO:31 and a VH comprising the amino acid sequence of SEQ ID NO:32.

In another aspect, an anti-KRas antibody is provided, wherein the antibody comprises a VH comprising a CDR-H1 comprising the amino acid sequence of SEQ ID NO:28, a CDR-H2 comprising the amino acid sequence of SEQ ID NO:29, and a CDR-H3 comprising the amino acid sequence of SEQ ID NO:30; and a VL comprising a CDR-L1 comprising the amino acid sequence of SEQ ID NO:25, a CDR-L2 comprising the amino acid sequence of SEQ ID NO:26, and a CDR-L3 comprising the amino acid sequence of SEQ ID NO:27.

In another aspect, an anti-KRas antibody is provided, wherein the antibody comprises a VH CDR1, a VH CDR2, and a VH CDR3, respectively comprising the amino acid sequences of a CDR1, a CDR2, and a CDR3 within a VH having the sequence set forth in SEQ ID NO:32; and a VL CDR1, a VL CDR2, and a VL CDR3, respectively comprising the amino acid sequences of a CDR1, a CDR2, and a CDR3 within a VL having the sequence set forth in SEQ ID NO:31.

In some embodiments, the anti-KRas antibody comprises one, two, three, four, five, or six CDRs of antibody 4G12 as shown in Table 2 and Table 3. In some embodiments, the anti-KRas antibody comprises the VH and/or the VL of antibody 4G12 as shown in Table 4 and Table 5. In a particular embodiment, an anti-KRas antibody comprising one, two, three, four, five, or six CDRs of antibody 4G12, and/or the VH and/or the VL of antibody 4G12 binds KRas mutant $KRas^{G12C}$. In some embodiments, the anti-KRas antibody is an alkylated-conformation specific KRas antibody. In some embodiments, the anti-KRas antibody opens and stabilizes the SWII pocket of KRas.

In some embodiments, the anti-KRas antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:40. In certain embodiments, a VH sequence contains substitutions (e.g., conservative substitutions), insertions, or deletions relative to the amino acid sequence of SEQ ID NO:40, but retains the ability to bind KRas as the anti-KRas antibody comprising SEQ ID NO:40. In certain embodiments, a total of 1 to 13 amino acids have been substituted, inserted and/or deleted in SEQ ID NO:40. In certain embodiments, substitutions, insertions, or deletions occur in regions outside the CDRs (i.e., in the FRs). In a particular embodiment, the VH comprises one, two or three CDRs selected from the group consisting of: (a) a CDR-H1 comprising the amino acid sequence of SEQ ID NO:36, (b) a CDR-H2 comprising the amino acid sequence of SEQ ID NO:37, and (c) a CDR-H3 comprising the amino acid sequence of SEQ ID NO:38.

In another aspect, an anti-KRas antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:39. In certain embodiments, a VL sequence contains substitutions (e.g., conservative substitutions), insertions, or deletions relative to the amino acid sequence of SEQ ID NO:39, but retains the ability to bind KRas as the anti-KRas antibody comprising SEQ ID NO:39. In certain embodiments, a total of 1 to 11 amino acids have been substituted, inserted and/or deleted in SEQ ID NO:39. In certain embodiments, the substitutions, insertions, or deletions occur in regions outside the CDRs (i.e., in the FRs). In a particular embodiment, the VL comprises one, two or three CDRs selected from the group consisting of (a) a CDR-L1 comprising the amino acid sequence of SEQ ID NO:33; (b) a CDR-L2 comprising the amino acid sequence of SEQ ID NO:34; and (c) a CDR-L3 comprising the amino acid sequence of SEQ ID NO:35.

In one embodiment, the anti-KRas antibody comprises a VL comprising the amino acid sequence of SEQ ID NO:39 and a VH comprising the amino acid sequence of SEQ ID NO:40.

In another aspect, an anti-KRas antibody is provided, wherein the antibody comprises a VH comprising a CDR-H1 comprising the amino acid sequence of SEQ ID NO:36, a CDR-H2 comprising the amino acid sequence of SEQ ID NO:37, and a CDR-H3 comprising the amino acid sequence of SEQ ID NO:38; and a VL comprising a CDR-L1 comprising the amino acid sequence of SEQ ID NO:33, a CDR-L2 comprising the amino acid sequence of SEQ ID NO:34, and a CDR-L3 comprising the amino acid sequence of SEQ ID NO:35.

In another aspect, an anti-KRas antibody is provided, wherein the antibody comprises a VH CDR1, a VH CDR2, and a VH CDR3, respectively comprising the amino acid sequences of a CDR1, a CDR2, and a CDR3 within a VH having the sequence set forth in SEQ ID NO:40; and a VL CDR1, a VL CDR2, and a VL CDR3, respectively comprising the amino acid sequences of a CDR1, a CDR2, and a CDR3 within a VL having the sequence set forth in SEQ ID NO:39.

In some embodiments, the anti-KRas antibody comprises one, two, three, four, five, or six CDRs of antibody 1A6 as shown in Table 2 and Table 3. In some embodiments, the anti-KRas antibody comprises the VH and/or the VL of antibody 1A6 as shown in Table 4 and Table 5. In a particular embodiment, an anti-KRas antibody comprising one, two, three, four, five, or six CDRs of antibody 1A6, and/or the VH and/or the VL of antibody 1A6 binds KRas mutant $KRas^{G12C}$. In some embodiments, the anti-KRas antibody is an alkylated-conformation specific KRas antibody. In some embodiments, the anti-KRas antibody stabilizes the SWII pocket of KRas.

In some embodiments, the anti-KRas antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:48. In certain embodiments, a VH sequence contains substitutions (e.g., conservative substitutions), insertions, or deletions relative to the amino acid sequence of SEQ ID NO:48, but retains the ability to bind KRas as the anti-KRas antibody comprising SEQ ID NO:48. In certain embodiments, a total of 1 to 13 amino acids have been substituted, inserted and/or deleted in SEQ ID NO:48. In certain embodiments, substitutions, insertions, or deletions occur in regions outside the CDRs (i.e., in the FRs). In a particular embodiment, the VH comprises one, two or three CDRs selected from the group consisting of (a) a CDR-H1 comprising the amino acid sequence of SEQ ID NO:44, (b) a CDR-H2 comprising the amino acid sequence of SEQ ID NO:45, and (c) a CDR-H3 comprising the amino acid sequence of SEQ ID NO:46.

In another aspect, an anti-KRas antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:47. In certain embodiments, a VL sequence contains substitutions (e.g., conservative substitutions), insertions, or deletions relative to the amino acid sequence of SEQ ID NO:47, but retains the ability to bind KRas as the anti-KRas antibody comprising SEQ ID NO:47. In certain embodiments, a total of 1 to 11 amino acids have been substituted, inserted and/or deleted in SEQ ID NO:47. In certain embodiments, the substitutions, insertions, or deletions occur in regions outside the CDRs (i.e., in the FRs). In a particular embodiment, the VL comprises one, two or three CDRs selected from the group consisting of (a) a CDR-L1 comprising the amino acid sequence of SEQ ID NO:41; (b) a CDR-L2 comprising the amino acid sequence of SEQ ID NO:42; and (c) a CDR-L3 comprising the amino acid sequence of SEQ ID NO:43.

In one embodiment, the anti-KRas antibody comprises a VL comprising the amino acid sequence of SEQ ID NO:47 and a VH comprising the amino acid sequence of SEQ ID NO:48.

In another aspect, an anti-KRas antibody is provided, wherein the antibody comprises a VH comprising a CDR-H1 comprising the amino acid sequence of SEQ ID NO:44, a CDR-H2 comprising the amino acid sequence of SEQ ID NO:45, and a CDR-H3 comprising the amino acid sequence of SEQ ID NO:46; and a VL comprising a CDR-L1 comprising the amino acid sequence of SEQ ID NO:41, a CDR-L2 comprising the amino acid sequence of SEQ ID NO:42, and a CDR-L3 comprising the amino acid sequence of SEQ ID NO:43.

In another aspect, an anti-KRas antibody is provided, wherein the antibody comprises a VH CDR1, a VH CDR2, and a VH CDR3, respectively comprising the amino acid sequences of a CDR1, a CDR2, and a CDR3 within a VH having the sequence set forth in SEQ ID NO:48; and a VL CDR1, a VL CDR2, and a VL CDR3, respectively comprising the amino acid sequences of a CDR1, a CDR2, and a CDR3 within a VL having the sequence set forth in SEQ ID NO:47.

In some embodiments, the anti-KRas antibody comprises one, two, three, four, five, or six CDRs of antibody 1F4 as shown in Table 2 and Table 3. In some embodiments, the anti-KRas antibody comprises the VH and/or the VL of antibody 1F4 as shown in Table 4 and Table 5. In a particular embodiment, an anti-KRas antibody comprising one, two, three, four, five, or six CDRs of antibody 1F4, and/or the VH and/or the VL of antibody 1F4 binds KRas mutant $KRas^{G12C}$. In some embodiments, the anti-KRas antibody is an alkylation specific KRas antibody. In some embodiments, the anti-KRas antibody stabilizes the SWII pocket of KRas.

In some embodiments, the anti-KRas antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:88. In certain embodiments, a VH sequence contains substitutions (e.g., conservative substitutions), insertions, or deletions relative to the amino acid sequence of SEQ ID NO:88, but retains the ability to bind KRas as the anti-KRas antibody comprising SEQ ID NO:88. In certain embodiments, a total of 1 to 13 amino acids have been substituted, inserted and/or deleted in SEQ ID NO:88. In certain embodiments, substitutions, insertions, or deletions occur in regions outside the CDRs (i.e., in the FRs). In a particular embodiment, the VH comprises one, two or three CDRs selected from the group consisting of (a) a CDR-H1 comprising the amino acid sequence of SEQ ID NO:84, (b) a CDR-H2 comprising the amino acid sequence of SEQ ID NO:85, and (c) a CDR-H3 comprising the amino acid sequence of SEQ ID NO:86.

In another aspect, an anti-KRas antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:87. In certain embodiments, a VL sequence contains substitutions (e.g., conservative substitutions), insertions, or deletions relative to the amino acid sequence of SEQ ID NO:87, but retains the ability to bind KRas as the anti-KRas antibody comprising SEQ ID NO:87. In certain embodiments, a total of 1 to 11 amino acids have been substituted, inserted and/or deleted in SEQ ID NO:87. In certain embodiments, the substitutions, insertions, or deletions occur in regions outside the CDRs (i.e., in the FRs). In a particular embodiment, the VL comprises one, two or three CDRs selected from the group consisting of (a) a CDR-L1 comprising the amino acid sequence of SEQ ID NO:81; (b) a CDR-L2 comprising the amino acid sequence of SEQ ID NO:82; and (c) a CDR-L3 comprising the amino acid sequence of SEQ ID NO:83.

In one embodiment, the anti-KRas antibody comprises a VL comprising the amino acid sequence of SEQ ID NO:87 and a VH comprising the amino acid sequence of SEQ ID NO:88.

In another aspect, an anti-KRas antibody is provided, wherein the antibody comprises a VH comprising a CDR-H1 comprising the amino acid sequence of SEQ ID NO:84, a CDR-H2 comprising the amino acid sequence of SEQ ID NO:85, and a CDR-H3 comprising the amino acid sequence of SEQ ID NO:86; and a VL comprising a CDR-L1 comprising the amino acid sequence of SEQ ID NO:81, a CDR-L2 comprising the amino acid sequence of SEQ ID NO:82, and a CDR-L3 comprising the amino acid sequence of SEQ ID NO:83.

In another aspect, an anti-KRas antibody is provided, wherein the antibody comprises a VH CDR1, a VH CDR2, and a VH CDR3, respectively comprising the amino acid sequences of a CDR1, a CDR2, and a CDR3 within a VH having the sequence set forth in SEQ ID NO:88; and a VL CDR1, a VL CDR2, and a VL CDR3, respectively comprising the amino acid sequences of a CDR1, a CDR2, and a CDR3 within a VL having the sequence set forth in SEQ ID NO:87.

In some embodiments, the anti-KRas antibody comprises one, two, three, four, five, or six CDRs of antibody 1B7 as shown in Table 2 and Table 3. In some embodiments, the anti-KRas antibody comprises the VH and/or the VL of antibody 1B7 as shown in Table 4 and Table 5. In a particular embodiment, an anti-KRas antibody comprising one, two, three, four, five, or six CDRs of antibody 1B7, and/or the VH and/or the VL of antibody 1B7 binds KRas mutant $KRas^{G12C}$. In some embodiments, the anti-KRas antibody is an alkylated-conformation specific KRas antibody. In some embodiments, the anti-KRas antibody stabilizes the SWII pocket of KRas.

In some embodiments, the anti-KRas antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:56. In certain embodiments, a VH sequence contains substitutions (e.g., conservative substitutions), insertions, or deletions relative to the amino acid sequence of SEQ ID NO:56, but retains the ability to bind KRas as the anti-KRas antibody comprising SEQ ID NO:56. In certain embodiments, a total of 1 to 13 amino acids have been substituted, inserted and/or deleted in SEQ ID NO:56. In certain embodiments, substitutions, insertions, or deletions occur in regions outside the CDRs (i.e., in the FRs). In a particular embodiment, the VH comprises one, two or three CDRs selected from the group consisting of (a) a CDR-H1 comprising the amino acid sequence of SEQ ID NO:52, (b) a CDR-H2 comprising the amino acid sequence of SEQ ID NO:53, and (c) a CDR-H3 comprising the amino acid sequence of SEQ ID NO:54.

In another aspect, an anti-KRas antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:55. In certain embodiments, a VL sequence contains substitutions (e.g., conservative substitutions), insertions, or deletions relative to the amino acid sequence of SEQ ID NO:55, but retains the ability to bind KRas as the anti-KRas antibody comprising SEQ ID NO:55. In certain embodiments, a total of 1 to 11 amino acids have been substituted, inserted and/or deleted in SEQ ID NO:55. In certain embodiments, the substitutions, insertions, or deletions occur in regions outside the CDRs (i.e., in the FRs). In a particular embodiment, the VL comprises one, two or three CDRs selected from the group consisting of (a) a CDR-L1 comprising the amino acid sequence of SEQ ID NO:49; (b) a CDR-L2 comprising the amino acid sequence of SEQ ID NO:50; and (c) a CDR-L3 comprising the amino acid sequence of SEQ ID NO:51.

In one embodiment, the anti-KRas antibody comprises a VL comprising the amino acid sequence of SEQ ID NO:55 and a VH comprising the amino acid sequence of SEQ ID NO:56.

In another aspect, an anti-KRas antibody is provided, wherein the antibody comprises a VH comprising a CDR-H1 comprising the amino acid sequence of SEQ ID NO:52, a CDR-H2 comprising the amino acid sequence of SEQ ID NO:53, and a CDR-H3 comprising the amino acid sequence of SEQ ID NO:54; and a VL comprising a CDR-L1 comprising the amino acid sequence of SEQ ID NO:49, a CDR-L2 comprising the amino acid sequence of SEQ ID NO:50, and a CDR-L3 comprising the amino acid sequence of SEQ ID NO:51.

In another aspect, an anti-KRas antibody is provided, wherein the antibody comprises a VH CDR1, a VH CDR2, and a VH CDR3, respectively comprising the amino acid sequences of a CDR1, a CDR2, and a CDR3 within a VH having the sequence set forth in SEQ ID NO:56; and a VL CDR1, a VL CDR2, and a VL CDR3, respectively comprising the amino acid sequences of a CDR1, a CDR2, and a CDR3 within a VL having the sequence set forth in SEQ ID NO:55.

In some embodiments, the anti-KRas antibody comprises one, two, three, four, five, or six CDRs of antibody 1E5 as shown in Table 2 and Table 3. In some embodiments, the anti-KRas antibody comprises the VH and/or the VL of antibody 1E5 as shown in Table 4 and Table 5. In a particular embodiment, an anti-KRas antibody comprising one, two, three, four, five, or six CDRs of antibody 1E5, and/or the VH and/or the VL of antibody 1E5 binds KRas mutant $KRas^{G12C}$. In some embodiments, the anti-KRas antibody is an alkylated-conformation specific KRas antibody. In some embodiments, the anti-KRas antibody opens and stabilizes the SWII pocket of KRas.

In some embodiments, the anti-KRas antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:64. In certain embodiments, a VH sequence contains substitutions (e.g., conservative substitutions), insertions, or deletions relative to the amino acid sequence of SEQ ID NO:64, but retains the ability to bind KRas as the anti-KRas antibody comprising SEQ ID NO:64. In certain embodiments, a total of 1 to 13 amino acids have been substituted, inserted and/or deleted in SEQ ID NO:64. In certain embodiments, substitutions, insertions, or deletions occur in regions outside the CDRs (i.e., in the FRs). In a particular embodiment, the VH comprises one, two or three CDRs selected from the group consisting of (a) a CDR-H1 comprising the amino acid sequence of SEQ ID NO:60, (b) a CDR-H2 comprising the amino acid sequence of SEQ ID NO:61, and (c) a CDR-H3 comprising the amino acid sequence of SEQ ID NO:62.

In another aspect, an anti-KRas antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:63. In certain embodiments, a VL sequence contains substitutions (e.g., conservative substitutions), insertions, or deletions relative to the amino acid sequence of SEQ ID NO:63, but retains the ability to bind KRas as the anti-KRas antibody comprising SEQ ID NO:63. In certain embodiments, a total of 1 to 11 amino acids have been substituted, inserted and/or deleted in SEQ ID NO:63. In certain embodiments, the substitutions, insertions, or deletions occur in regions outside the CDRs (i.e., in the FRs). In a particular embodiment, the VL comprises one, two or three CDRs selected from the group consisting of (a) a CDR-L1 comprising the amino acid sequence of SEQ ID NO:57; (b) a CDR-L2 comprising the amino acid sequence of SEQ ID NO:58; and (c) a CDR-L3 comprising the amino acid sequence of SEQ ID NO:59.

In one embodiment, the anti-KRas antibody comprises a VL comprising the amino acid sequence of SEQ ID NO:63 and a VH comprising the amino acid sequence of SEQ ID NO:64.

In another aspect, an anti-KRas antibody is provided, wherein the antibody comprises a VH comprising a CDR-H1 comprising the amino acid sequence of SEQ ID NO:60, a CDR-H2 comprising the amino acid sequence of SEQ ID NO:61, and a CDR-H3 comprising the amino acid sequence of SEQ ID NO:62; and a VL comprising a CDR-L1 comprising the amino acid sequence of SEQ ID NO:57, a CDR-L2 comprising the amino acid sequence of SEQ ID NO:58, and a CDR-L3 comprising the amino acid sequence of SEQ ID NO:59.

In another aspect, an anti-KRas antibody is provided, wherein the antibody comprises a VH CDR1, a VH CDR2, and a VH CDR3, respectively comprising the amino acid sequences of a CDR1, a CDR2, and a CDR3 within a VH having the sequence set forth in SEQ ID NO:64; and a VL CDR1, a VL CDR2, and a VL CDR3, respectively comprising the amino acid sequences of a CDR1, a CDR2, and a CDR3 within a VL having the sequence set forth in SEQ ID NO:63.

In some embodiments, the anti-KRas antibody comprises one, two, three, four, five, or six CDRs of antibody 2A3 as shown in Table 2 and Table 3. In some embodiments, the anti-KRas antibody comprises the VH and/or the VL of antibody 2A3 as shown in Table 4 and Table 5. In a particular embodiment, an anti-KRas antibody comprising one, two, three, four, five, or six CDRs of antibody 2A3, and/or the VH and/or the VL of antibody 2A3 binds KRas mutant $KRas^{G12C}$. In some embodiments, the anti-KRas antibody is an alkylated-conformation specific KRas antibody. In some embodiments, the anti-KRas antibody opens and stabilizes the SWII pocket of KRas.

In some embodiments, the anti-KRas antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:72. In certain embodiments, a VH sequence contains substitutions (e.g., conservative substitutions), insertions, or deletions relative to the amino acid sequence of SEQ ID NO:72, but retains the ability to bind KRas as the anti-KRas antibody comprising SEQ ID NO:72. In certain embodiments, a total of 1 to 13 amino acids have been substituted, inserted and/or deleted in SEQ ID NO:72. In certain embodiments, substitutions, insertions, or deletions occur in regions outside the CDRs (i.e., in the FRs). In a particular embodiment, the VH comprises one, two or three CDRs selected from the group consisting of: (a) a CDR-H1 comprising the amino acid sequence of SEQ ID NO:68, (b) a CDR-H2 comprising the amino acid sequence of SEQ ID NO:69, and (c) a CDR-H3 comprising the amino acid sequence of SEQ ID NO:70.

In another aspect, an anti-KRas antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:71. In certain embodiments, a VL sequence contains substitutions (e.g., conservative substitutions), insertions, or deletions relative to the amino acid sequence of SEQ ID NO:71, but retains the ability to bind KRas as the anti-KRas antibody comprising SEQ ID NO:71. In certain embodiments, a total of 1 to 11 amino acids have been substituted, inserted and/or deleted in SEQ ID NO:71. In certain embodiments, the substitutions, insertions, or deletions occur in regions outside the CDRs (i.e., in the FRs). In a particular embodiment, the VL comprises one, two or three CDRs selected from the group consisting of (a) a CDR-L1 comprising the amino acid sequence of SEQ ID NO:65; (b) a CDR-L2 comprising the amino acid sequence of SEQ ID NO:66; and (c) a CDR-L3 comprising the amino acid sequence of SEQ ID NO:67.

In one embodiment, the anti-KRas antibody comprises a VL comprising the amino acid sequence of SEQ ID NO:71 and a VH comprising the amino acid sequence of SEQ ID NO:72.

In another aspect, an anti-KRas antibody is provided, wherein the antibody comprises a VH comprising a CDR-H1 comprising the amino acid sequence of SEQ ID NO:68, a CDR-H2 comprising the amino acid sequence of SEQ ID NO:69, and a CDR-H3 comprising the amino acid sequence of SEQ ID NO:70; and a VL comprising a CDR-L1 comprising the amino acid sequence of SEQ ID NO:65, a CDR-L2 comprising the amino acid sequence of SEQ ID NO:66, and a CDR-L3 comprising the amino acid sequence of SEQ ID NO:67.

In another aspect, an anti-KRas antibody is provided, wherein the antibody comprises a VH CDR1, a VH CDR2, and a VH CDR3, respectively comprising the amino acid sequences of a CDR1, a CDR2, and a CDR3 within a VH having the sequence set forth in SEQ ID NO:72; and a VL CDR1, a VL CDR2, and a VL CDR3, respectively comprising the amino acid sequences of a CDR1, a CDR2, and a CDR3 within a VL having the sequence set forth in SEQ ID NO:71.

In some embodiments, the anti-KRas antibody comprises one, two, three, four, five, or six CDRs of antibody 3A12 as shown in Table 2 and Table 3. In some embodiments, the anti-KRas antibody comprises the VH and/or the VL of antibody 3A12 as shown in Table 4 and Table 5. In a particular embodiment, an anti-KRas antibody comprising one, two, three, four, five, or six CDRs of antibody 3A12, and/or the VH and/or the VL of antibody 3A12 binds KRas mutant $KRas^{G12C}$. In some embodiments, the anti-KRas antibody is an alkylated-conformation specific KRas antibody. In some embodiments, the anti-KRas antibody opens and stabilizes the SWII pocket of KRas.

In some embodiments, the anti-KRas antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:80. In certain embodiments, a VH sequence contains substitutions (e.g., conservative substitutions), insertions, or deletions relative to the amino acid sequence of SEQ ID NO:80, but retains the ability to bind KRas as the anti-KRas antibody comprising SEQ ID NO:80. In certain embodiments, a total of 1 to 13 amino acids have been substituted, inserted and/or deleted in SEQ ID NO:80. In certain embodiments, substitutions, insertions, or deletions occur in regions outside the CDRs (i.e., in the FRs). In a particular embodiment, the VH comprises one, two or three CDRs selected from the group consisting of (a) a CDR-H1 comprising the amino acid sequence of SEQ ID NO:76, (b) a CDR-H2 comprising the amino acid sequence of SEQ ID NO:77, and (c) a CDR-H3 comprising the amino acid sequence of SEQ ID NO:78.

In another aspect, an anti-KRas antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:79. In certain embodiments, a VL sequence contains substitutions (e.g., conservative substitutions), insertions, or deletions relative to the amino acid sequence of SEQ ID NO:79, but retains the ability to bind KRas as the anti-KRas antibody comprising SEQ ID NO:79. In certain embodiments, a total of 1 to 11 amino acids have been substituted, inserted and/or deleted in SEQ ID NO:79. In certain embodiments, the substitutions, insertions, or deletions occur in regions outside the CDRs (i.e., in the FRs). In a particular embodiment, the VL comprises one, two or three CDRs selected from the group consisting of (a) a CDR-L1 comprising the amino acid sequence of SEQ ID NO:73; (b) a CDR-L2 comprising the amino acid sequence of SEQ ID NO:74; and (c) a CDR-L3 comprising the amino acid sequence of SEQ ID NO:75.

In one embodiment, the anti-KRas antibody comprises a VL comprising the amino acid sequence of SEQ ID NO:79 and a VH comprising the amino acid sequence of SEQ ID NO:80.

In another aspect, an anti-KRas antibody is provided, wherein the antibody comprises a VH comprising a CDR-H1 comprising the amino acid sequence of SEQ ID NO:76, a CDR-H2 comprising the amino acid sequence of SEQ ID NO:77, and a CDR-H3 comprising the amino acid sequence of SEQ ID NO:78; and a VL comprising a CDR-L1 comprising the amino acid sequence of SEQ ID NO:73, a CDR-L2 comprising the amino acid sequence of SEQ ID NO:74, and a CDR-L3 comprising the amino acid sequence of SEQ ID NO:75.

In another aspect, an anti-KRas antibody is provided, wherein the antibody comprises a VH CDR1, a VH CDR2, and a VH CDR3, respectively comprising the amino acid sequences of a CDR1, a CDR2, and a CDR3 within a VH having the sequence set forth in SEQ ID NO:80; and a VL CDR1, a VL CDR2, and a VL CDR3, respectively comprising the amino acid sequences of a CDR1, a CDR2, and a CDR3 within a VL having the sequence set forth in SEQ ID NO:79.

In another aspect, an anti-KRas antibody is provided, wherein the antibody comprises a VH as in any of the embodiments provided above, and a VL as in any of the embodiments provided above.

In a further aspect of the invention, an anti-KRas antibody according to any of the above embodiments is a monoclonal antibody, including a chimeric, humanized or human antibody. In some embodiments, an anti-KRas antibody is an antibody fragment, e.g., a Fv, Fab, Fab', scFv, diabody, or $F(ab')_2$ fragment. In another embodiment, the anti-KRas antibody is a full-length antibody, e.g., an intact IgG1 antibody or other antibody class or isotype as defined herein.

In one embodiment of the invention, an anti-KRas antibody according to the above embodiments binds to an amino acid epitope or epitopes of human KRas. In some embodiments, an anti-KRas antibody binds to one or more, two or more, three or more, four or more, five or more, or 6 or more, or all of the amino acids W99, K5, L6, V7, S39, D54, L54, Y71, T74, and/or G75 of human KRas, wherein human KRas comprises the amino acid sequence SEQ ID NO:90. In some embodiments, the anti-KRas antibody binds to W99 of human KRas. In some embodiments the anti-KRas antibody binds to residues from SW1 and SW2 of human KRas. In some embodiments, the anti-KRas antibody binds to SW2 of human KRas. In some embodiments, the anti-KRas antibody binds to the amino acid residues listed in Tables A-D, below. In some embodiments, the anti-KRas antibody binds within 3.5, 4.0, or 4.5 angstroms (Å) of the residues listed in Table A. In some embodiments, the anti-KRas antibody binds within 3.5, 4.0, or 4.5 Å of the residues listed in Table B. In some embodiments, the anti-KRas antibody binds within 3.5, 4.0, or 4.5 Å of the residues listed in Table C. In some embodiments, the anti-KRas antibody binds within 3.5, 4.0, or 4.5 Å of the residues listed in Table D.

TABLE A

| Contact Residues for 2H11 | | |
|---|---|---|
| Within 3.5 Å | Within 4.0 Å | Within 4.5 Å |
| LYS-5 | LYS-5 | LYS-5 |
| LEU-6 | LEU-6 | LEU-6 |
| VAL-7 | VAL-7 | VAL-7 |
| ILE-36 | GLN-25 | GLN-25 |
| ASP-38 | TYR-32 | TYR-32 |
| SER-39 | ILE-36 | ASP-33 |
| ARG-41 | ASP-38 | ILE-36 |
| ASP-54 | SER-39 | ASP-38 |
| MET-67 | TYR-40 | SER-39 |
| TYR-71 | ARG-41 | TYR-40 |
| THR-74 | ASP-54 | ARG-41 |
| | LEU-56 | ASP-54 |
| | SER-65 | ILE-55 |
| | MET-67 | LEU-56 |
| | TYR-71 | SER-65 |
| | THR-74 | MET-67 |
| | GLY-75 | GLN-70 |
| | | TYR-71 |
| | | THR-74 |
| | | GLY-75 |

TABLE B

| Contact residues for 2C1 | | |
|---|---|---|
| Within 3.5 Å | Within 4.0 Å | Within 4.5 Å |
| GLU-62 | GLU-62 | GLU-62 |
| GLU-63 | GLU-63 | GLU-63 |
| TYR-64 | TYR-64 | TYR-64 |
| LYS-88 | LYS-88 | THR-87 |
| ASP-92 | GLU-91 | LYS-88 |
| HIS-94 | ASP-92 | GLU-91 |
| HIS-95 | HIS-94 | ASP-92 |
| GLU-98 | HIS-95 | HIS-94 |
| GLN-99 | GLU-98 | HIS-95 |
| ARG-102 | GLN-99 | GLU-98 |
| | ARG-102 | GLN-99 |
| | TYR-137 | LYS-101 |
| | | ARG-102 |
| | | TYR-137 |

TABLE C

| Contact residues for 1E5 | | |
|---|---|---|
| Within 3.5 Å | Within 4.0 Å | Within 4.5 Å |
| GLU-31 | GLU-3 | GLU-3 |
| TYR-32 | LYS-5 | LYS-5 |
| ASP-33 | GLN-25 | GLN-25 |
| GLU-37 | GLU-31 | GLU-31 |
| ASP-38 | TYR-32 | TYR-32 |
| SER-39 | ASP-33 | ASP-33 |
| TYR-40 | PRO-34 | PRO-34 |
| ARG-41 | THR-35 | THR-35 |
| ASP-54 | ILE-36 | ILE-36 |
| ALA-59 | GLU-37 | GLU-37 |
| GLN-61 | ASP-38 | ASP-38 |
| GLU-63 | SER-39 | SER-39 |
| ARG-68 | TYR-40 | TYR-40 |
| TYR-71 | ARG-41 | ARG-41 |
| | ASP-54 | LYS-42 |
| | LEU-56 | ASP-54 |

TABLE C-continued

| Contact residues for 1E5 | | |
|---|---|---|
| Within 3.5 Å | Within 4.0 Å | Within 4.5 Å |
| | ALA-59 | LEU-56 |
| | GLN-61 | ALA-59 |
| | GLU-63 | GLY-60 |
| | ARG-68 | GLN-61 |
| | TYR-71 | GLU-63 |
| | | MET-67 |
| | | ARG-68 |
| | | TYR-71 |

TABLE D

| Contact residues for 3A12 | | |
|---|---|---|
| Within 3.5 Å | Within 4.0 Å | Within 4.5 Å |
| LYS-5 | LYS-5 | LYS-5 |
| LEU-6 | LEU-6 | LEU-6 |
| VAL-7 | VAL-7 | VAL-7 |
| GLU-37 | TYR-32 | TYR-32 |
| ASP-38 | THR-35 | ASP-33 |
| SER-39 | GLU-37 | THR-35 |
| TYR-40 | ASP-38 | ILE-36 |
| ARG-41 | SER-39 | GLU-37 |
| ASP-54 | TYR-40 | ASP-38 |
| GLU-63 | ARG-41 | SER-39 |
| TYR-64 | ASP-54 | TYR-40 |
| MET-67 | LEU-56 | ARG-41 |
| GLN-70 | GLU-63 | ASP-54 |
| TYR-71 | TYR-64 | ILE-55 |
| THR-74 | MET-67 | LEU-56 |
| | GLN-70 | GLU-63 |
| | TYR-71 | TYR-64 |
| | THR-74 | MET-67 |
| | GLY-75 | GLN-70 |
| | | TYR-71 |
| | | THR-74 |
| | | GLY-75 |

Figure 11A:
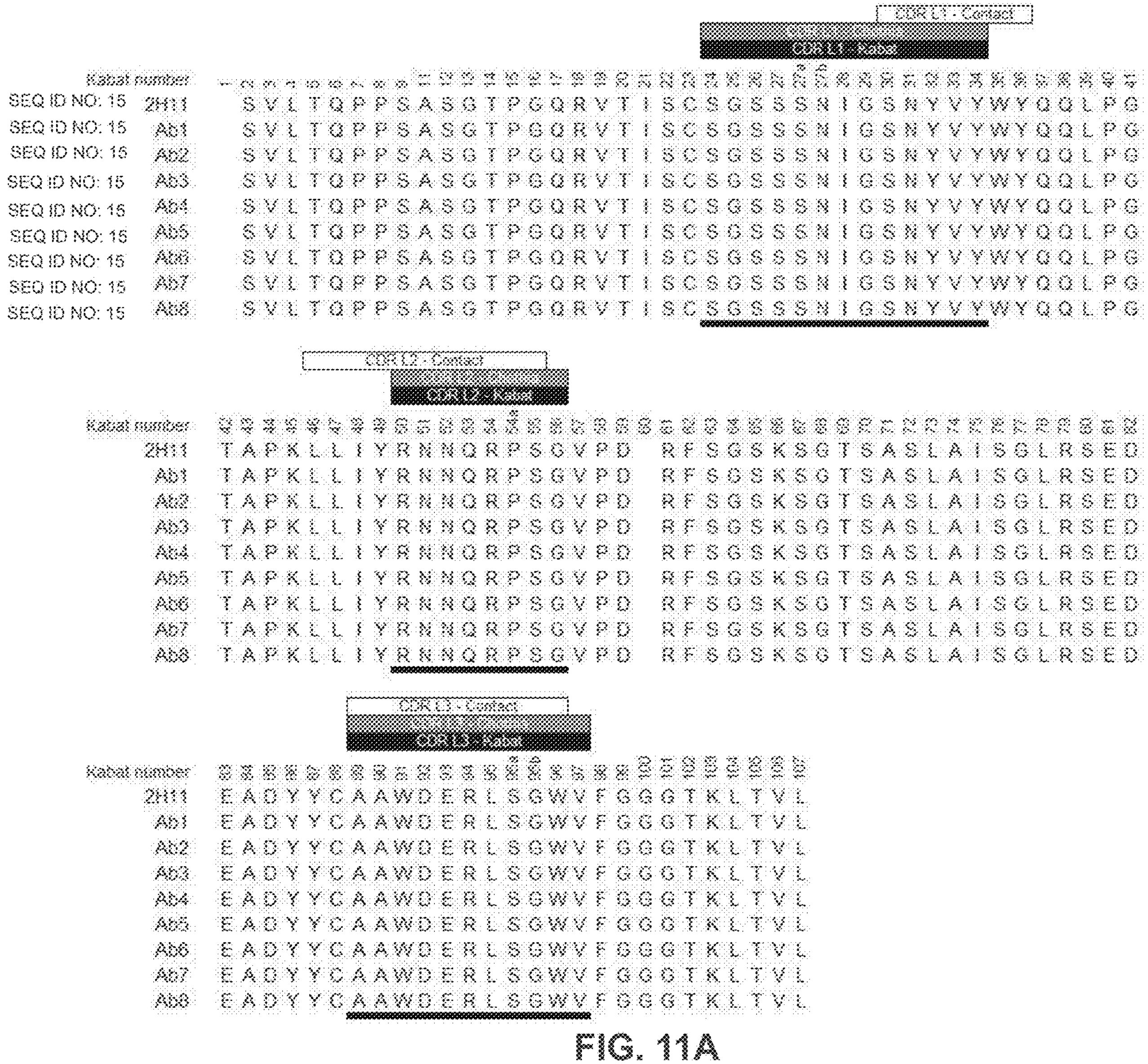
FIG. 11A shows the alignment of the light chain CDR sequences of 2H11 and antibody variants Ab1, Ab2, Ab3, Ab4. Ab5. Ab6. Ab7 and Ab8 with L1, L2, and L3 regions noted for both Kabat and Chlothia numbering. Contact residues for each CDR are also noted.
Figure 11B:
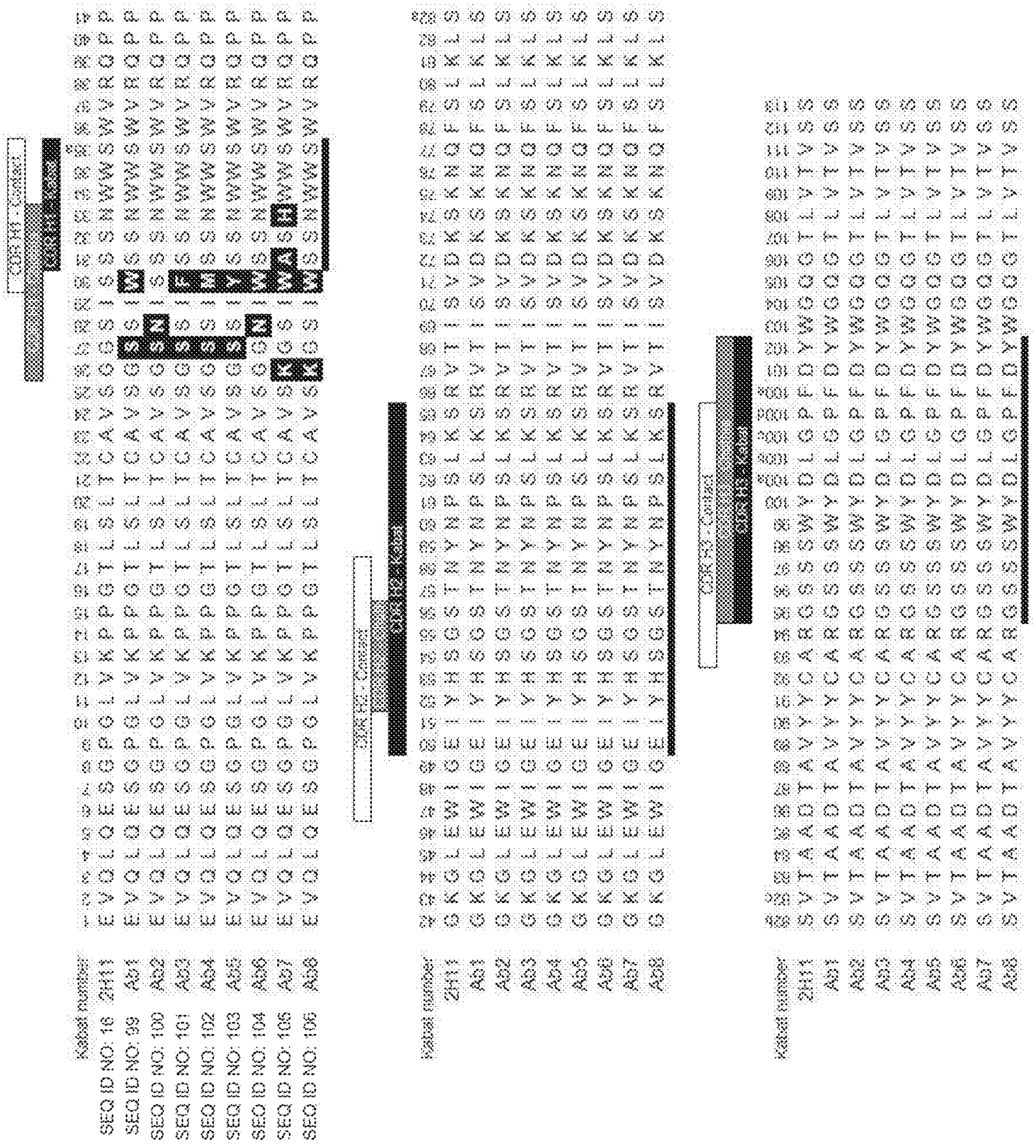
FIG. 11B shows the alignment of the heavy chain CDR sequences of 2H11 and antibody variants Ab1, Ab2, Ab3, Ab4. Ab5. Ab6. Ab7 and Ab8 with H1, H2, and H3 regions noted for both Kabat and Chlothia numbering. Contact residues for each CDR are also noted.

In some embodiments, the contact residues for Ab1, Ab2, Ab3, Ab4, Ab5, Ab6, Ab7, and Ab8 are as set forth in FIG. 11A and FIG. 11B.

In another aspect provided herein is fusion protein comprising a KRas protein (e.g. SEQ ID NO:90) or a fragment thereof and a Fab, scFv, or IgG of an antibody described herein. In one such embodiment, the fusion protein comprises a KRas protein or fragment thereof as described herein a linker comprising (Gly-Ser)$_n$ where n is at least 1, and an Fab, scFv, or IgG as described herein. In one such embodiment, n is an integer of 1-5, 1-8, 1-10, or 1-20. In one embodiment, the KRas protein or fragment thereof is fused to the N-terminus of a Fab described herein. In one such embodiment, there is a linker between the KRas and the N-terminus of the Fab. In another embodiment, the KRas protein or fragment thereof is linked to the C-terminus of the Fab. In one such embodiment, there is a linker as described herein between the N-terminus of the KRas protein and the C-terminus of the Fab.

In one embodiment of the fusion proteins described herein, the Fab comprises the HC sequence:

```
                              (SEQ ID NO: 107)
EVQLQESGPGLVKPPGILSLICAVSGGSISSSNWW

SWVRQPPGKGLEWIGEIYHSGSTNYNPSLKSRVTI

SVDKSKNQFSLKLSSVTAADTAVYYCARGSSSWYD
```

-continued

```
LGPFDYWGQGTLVTVSSASTKGPSVFPLAPSSKST

SGGTAALGCLVKDYFPEPVTVSWNSGALTSGVHTF

PAVLQSSGLYSLSSVVTVPSSSLGTQTYICNVNHK

PSNTKVDKKVEPKSCDKTHT

and the LC sequence:
                              (SEQ ID NO: 108)
GLNDIFEAQKIEWHEGSENLYFQSTEYKLVVVGAG

GVGKSALTIQLIQNHFVDEYDPTIEDSYRKQVVID

GETSLLDILDTAGQEEYSAMRDQYMRTGEGFLLVF

AINNTKSFEDIHHYREQIKRVKDSEDVPMVLVGNK

SDLPSRTVDTKQAQDLARSYGIPFIETSAKTRQGV

DDAFYILVREIRKHKEKGGGGSGGGGSGGGGSGGG

GSSVLIQPPSASGTPGQRVTISCSGSSSNIGSNYV

YWYQQLPGTAPKLLIYRNNQRPSGVPDRFSGSKSG

TSASLAISGLRSEDEADYYCAAWDERLSGWVFGGG

TKLTVLGQPKAAPSVTLFPPSSEELQANKATLVCL

ISDFYPGAVTVAWKADSSPVKAGVETTTPSKQSNN

KYAASSYLSLTPEQWKSHKSYSCQVTHEGSTVEKT

VAPTECS.
```

In another embodiment of the fusion proteins described herein, the Fab comprises the HC sequence:

```
                              (SEQ ID NO: 109)
GLNDIFEAQKIEWHEGSENLYFQSTEYKLVVVGAG

GVGKSALTIQLIQNHFVDEYDPTIEDSYRKQVVID

GETSLLDILDTAGQEEYSAMRDQYMRTGEGFLLVF

AINNTKSFEDIHHYREQIKRVKDSEDVPMVLVGNK

SDLPSRTVDTKQAQDLARSYGIPFIETSAKTRQGV

DDAFYTLVREIRKHKEKGGGGSGGGGSGGGGSGGG

GSEVQLQESGPGLVKPPGILSLICAVSGGSISSSN

WWSWVRQPPGKGLEWIGEIYHSGSTNYNPSLKSRV

TISVDKSKNQFSLKLSSVTAADTAVYYCARGSSSW

YDLGPFDYWGQGTLVTVSSASTKGPSVFPLAPSSK

STSGGTAALGCLVKDYFPEPVTVSWNSGALTSGVH

TFPAVLQSSGLYSLSSVVTVPSSSLGTQTYICNVN

HKPSNTKVDKKVEPKSCDKTHT

and the LC sequence:
                              (SEQ ID NO: 110)
SVLTQPPSASGTPGQRVTISCSGSSSNIGSNYVYW

YQQLPGTAPKLLIYRNNQRPSGVPDRFSGSKSGTS

ASLAISGLRSEDEADYYCAAWDERLSGWVFGGGTK
```

-continued

LTVLGQPKAAPSVTLFPPSSEELQANKATLVCLIS

DFYPGAVTVAWKADSSPVKAGVETTTPSKQSNNKY

AASSYLSLTPEQWKSHKSYSCQVTHEGSTVEKTVA

PTECS.

In a further aspect of the invention, an anti-KRas antibody according to any of the above embodiments or described herein is conjugated to a heterologous moiety, agent, or label. Examples of suitable labels are those numerous labels known for use in immunoassay, including moieties that may be detected directly, such as fluorochrome, chemiluminscent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores such as rare-earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, HRP, alkaline phosphatase, beta-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin (detectable by, e.g., avidin, streptavidin, streptavidin-HRP, and streptavidin-β-galactosidase with MUG), spin labels, bacteriophage labels, stable free radicals, and the like.

In another aspect, provided herein is a composition comprising one or more of the anti-KRas antibodies according to any of the above embodiments or described herein. Also provided herein is a nucleic acid encoding the anti-KRas antibodies described herein, a vector comprising the nucleic acid, and a host cell comprising the vector. In some embodiments, the host cell is isolated or purified. In some embodiments, the host cell is a cell culture medium.

iii. Methods of Production

1. Polyclonal Antibodies

The antibodies of the invention may comprise polyclonal antibodies. Methods of preparing polyclonal antibodies are known to the skilled artisan. Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include human KRas, or fusion proteins thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation. The mammal can then be bled, and the serum assayed for anti-KRas antibody titer. If desired, the mammal can be boosted until the antibody titer increases or plateaus.

2. Monoclonal Antibodies

The antibodies of the invention may alternatively be monoclonal antibodies. Monoclonal antibodies may be made using the hybridoma method first described by Kohler et al., Nature, 256:495 (1975), or may be made by recombinant DNA methods (see, e.g. U.S. Pat. No. 4,816,567).

In the hybridoma method, a mouse or other appropriate host animal, such as a hamster, is immunized as described above to elicit lymphocytes that produce or are capable of producing antibodies that will specifically bind to the protein used for immunization. Alternatively, lymphocytes may be immunized in vitro. After immunization, lymphocytes are isolated and then fused with a myeloma cell line using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium which medium contains one or more substances that inhibit the growth or survival of the unfused, parental myeloma cells (also referred to as fusion partner). For example, if the parental myeloma cells lack the enzyme hypoxanthine guanine phosphoribosyl transferase (HGPRT or HPRT), the selective culture medium for the hybridomas typically will include hypoxanthine, aminopterin, and thymidine (HAT medium), which substances prevent the growth of HGPRT-deficient cells.

Fusion partner myeloma cells are those that fuse efficiently, support stable high-level production of antibody by the selected antibody-producing cells, and are sensitive to a selective medium that selects against the unfused parental cells. Myeloma cell lines are murine myeloma lines, such as those derived from MOPC-21 and MPC-11 mouse tumors available from the Salk Institute Cell Distribution Center, San Diego, California USA, and SP-2 and derivatives e.g., X63-Ag8-653 cells available from the American Type Culture Collection, Manassas, Virginia, USA. Human myeloma and mouse-human heteromyeloma cell lines also have been described for the production of human monoclonal antibodies (Kozbor, J. Immunol., 133:3001 (1984); and Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. The binding specificity of monoclonal antibodies produced by hybridoma cells may be determined by immunoprecipitation or by an in vitro binding assay, such as radioimmunoassay (RIA) or enzyme-linked immunosorbent assay (ELISA). The binding affinity of the monoclonal antibody can, for example, be determined by the Scatchard analysis described in Munson et al., Anal. Biochem., 107:220 (1980).

Once hybridoma cells that produce antibodies of the desired specificity, affinity, and/or activity are identified, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal e.g., by i.p. injection of the cells into mice.

The monoclonal antibodies secreted by the subclones are suitably separated from the culture medium, ascites fluid, or serum by conventional antibody purification procedures such as, for example, affinity chromatography (e.g., using protein A or protein G-Sepharose) or ion-exchange chromatography, hydroxylapatite chromatography, gel electrophoresis, dialysis, etc.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a source of such DNA. Once isolated, the DNA may be placed into expression vectors, which are then transfected into host cells such as *E. coli* cells, simian COS cells, Chinese Hamster Ovary (CHO) cells, or myeloma cells that do not otherwise produce antibody protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Pliickthun, Immunol. Revs. 130:151-188 (1992).

In a further embodiment, monoclonal antibodies or antibody fragments can be isolated from antibody phage libraries generated using the techniques described in McCafferty et al., Nature, 348:552-554 (1990). Clackson et al., Nature, 352:624-628 (1991) and Marks et al., J. Mol. Biol., 222: 581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res. 21:2265-2266 (1993)). Thus, these techniques are viable alternatives to traditional monoclonal antibody hybridoma techniques for isolation of monoclonal antibodies.

In principle, synthetic antibody clones are selected by screening phage libraries containing phage that display various fragments of antibody variable region (Fv) fused to phage coat protein. Such phage libraries are screened for against the desired antigen. Clones expressing Fv fragments capable of binding to the desired antigen are adsorbed to the antigen and thus separated from the non-binding clones in the library. The binding clones are then eluted from the antigen, and can be further enriched by additional cycles of antigen adsorption/elution.

Variable domains can be displayed functionally on phage, either as single-chain Fv (scFv) fragments, in which VH and VL are covalently linked through a short, flexible peptide, or as Fab fragments, in which they are each fused to a constant domain and interact non-covalently, as described in Winter et al., Ann. Rev. Immunol., 12: 433-455 (1994).

Repertoires of VH and VL genes can be separately cloned by polymerase chain reaction (PCR) and recombined randomly in phage libraries, which can then be searched for antigen-binding clones as described in Winter et al., Ann. Rev. Immunol., 12: 433-455 (1994). Libraries from immunized sources provide high-affinity antibodies to the immunogen without the requirement of constructing hybridomas. Alternatively, the naive repertoire can be cloned to provide a single source of human antibodies to a wide range of non-self and also self antigens without any immunization as described by Griffiths et al., EMBO J, 12: 725-734 (1993). Finally, naive libraries can also be made synthetically by cloning the unrearranged V-gene segments from stem cells, and using PCR primers containing random sequence to encode the highly variable CDR3 regions and to accomplish rearrangement in vitro as described by Hoogenboom and Winter, J. Mol. Biol., 227: 381-388 (1992).

Screening of the libraries can be accomplished by various techniques known in the art. For example, human KRas can be used to coat the wells of adsorption plates, expressed on host cells affixed to adsorption plates or used in cell sorting, or conjugated to biotin for capture with streptavidin-coated beads, or used in any other method for panning display libraries.

The selection of antibodies with slow dissociation kinetics (and good binding affinities) can be promoted by use of long washes and monovalent phage display as described in Bass et al., Proteins, 8: 309-314 (1990) and in WO 92/09690, and a low coating density of antigen as described in Marks et al., Biotechnol., 10: 779-783 (1992).

Any of the anti-KRas antibodies of the invention can be obtained by designing a suitable antigen screening procedure to select for the phage clone of interest followed by construction of a full length anti-KRas antibody clone using the Fv sequences from the phage clone of interest and suitable constant region (Fc) sequences described in Kabat et al., Sequences of Proteins of Immunological Interest, Fifth Edition, NIH Publication 91-3242, Bethesda MD (1991), vols. 1-3.

3. Selection of Conformation-Specific Anti-KRas Antibodies

Methods provided herein can be used to screen for an antibody that binds to certain conformations of human KRas. In one embodiment, the methods can be used to screen for an antibody that binds to KRas$^{G12C}$-GDP with higher affinity than KRas$^{G12C}$-GTP. For example, the method may comprise (a) contacting an antibody library with i) KRas$^{G12C}$-GDP, ii) alkylated KRas$^{G12C}$-GDP, and iii) KRas$^{G12C}$ bound to a non-hydrolysable GTP analog and (b) selecting an antibody that binds to the alkylated KRas$^{G12C}$-GDP and the unalkylated KRas$^{G12C}$-GDP with higher affinity than KRas$^{G12C}$ bound to the non-hydrolysable GTP analog.

For example, an in vitro selection strategy may be used using synthetic antibody libraries and human KRas$^{G12C}$ in distinct conformations. For example, KRas$^{G12C}$ that is either alkylated or not alkylated and bound to GDP, and unalkylated KRas$^{G12C}$ bound to GMPPcp (a non-hydrolysable GTP mimetic) may be used. Biopanning may be performed in which synthetic phage libraries are incubated in solution with biotinylated KRas$^{G12C}$-GDP alkylated with GNE-1952, a small molecule G12C inhibitor (Li Liansheng et al., WO2017058768A1). Other small molecules such as ARS-853 and ARS-1620 may be used to covalently bind Cys12 and thereby lock KRas$^{G12C}$ in the open SWII conformation. In order to drive selections towards the unique conformation of alkylated KRas$^{G12C}$-GDP, selections may be done in the presence of excess of non-biotinylated KRas$^{G12C}$-GDP and KRas$^{G12C}$-GMPPcp in solution. Thus, because KRas$^{G12C}$-GDP may be biotinylated and collected, antibodies specific to the open conformation KRas$^{G12C}$-GDP+GNE-1952, and not KRas$^{G12C}$-GDP and KRas$^{G12C}$-GMPPcp, may be enriched.

Conformation-specific anti-KRas antibody selection may be performed, for example, using existing synthetic Fab phage display libraries (C. V. Lee et al., *J Mol Biol* 2004; 340:1073-1093; W. C. Liang et al., *J Mol Biol* 2007; 366:815-829). The pooled library may be cycled through three to four rounds of binding in solution to biotinylated KRas$^{G12Ci}$-GDP+GNE1952 (ranging from 500 nM initially down to 10 nM). The solution may be captured on NeutrAvidin beads (Promega), blocked with 5 uM biotin, washed 3 times for 30 s each in PBS+0.5% BSA+0.1% Tween 20 (PBSBT), and eluted with 100 mM HCl. The eluted phage may be neutralized with 1M TRIS-HCl pH 8.0 prior to overnight amplification in *E. coli* XL1-blue (Stratagene) with the addition of M13-KO7 helper phage (New England Biolabs). In order to enrich for binders specific to the alkylated KRas$^{G12C}$, selections may be done in the presence of excess of either soluble KRas$^{G12C}$-GDP or KRas$^{G12C}$-GMPPcp at 1 μM. After selections, individual colonies may be picked and grown overnight at 30° C. in 96-well deep well plates in 2×YT media supplemented with carbenicillin and helper phage. Phage supernatant may be used in phage ELISAs against KRas$^{G12Ci}$-GDP+GNE1952, KRas$^{G12C}$-GDP, and KRas$^{G12C}$-GMPPcp to identify clones specific to the conformation-specific KRas target.

iv. Recombinant Methods and Compositions

Antibodies may be produced using recombinant methods and compositions, e.g., as described in U.S. Pat. No. 4,816,567. In one embodiment, isolated nucleic acid encoding an anti-KRas antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., YO, NSO, Sp20 cell). In one embodiment, a method of making an anti-KRas antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-KRas antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, NJ, 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, Nat. Biotech. 22:1409-1414 (2004), and Li et al., Nat. Biotech. 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV 1 line transformed by SV40 (COS-7); human embryonic kidney line (293 or 293 cells as described, e.g., in Graham et al., J Gen Viral. 36:59 (1977); baby hamster kidney cells (BHK); mouse sertoli cells (TM4 cells as described, e.g., in Mather, Biol. Reprod. 23:243-251 (1980); monkey kidney cells (CV 1); African green monkey kidney cells (VERO-76); human cervical carcinoma cells (HELA); canine kidney cells (MOCK; buffalo rat liver cells (BRL 3A); human lung cells (W138); human liver cells (Hep 02); mouse mammary tumor (MMT 060562); TRI cells, as described, e.g., in Mather et al., Annals N. Y. Acad. Sci. 383:44-68 (1982); MRC 5 cells; and FS4 cells. Other useful mammalian host cell lines include Chinese hamster ovary (CHO) cells, including DHFK CHO cells (Urlaub et al., Proc. Natl. Acad. Sci. USA 77:4216 (1980)); and myeloma cell lines such as YO, NSO and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, NJ), pp. 255-268 (2003).

v. Assays

Anti-KRas antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc. Binding affinity can be measured by common methods known in the art. In one embodiment, the $K_D$ of an antibody is measured by a radiolabeled antigen binding assay (RIA) performed with the Fab version of the antibody and antigen molecule as described by the following assay that measures solution binding affinity of Fabs for antigen by equilibrating Fab with a minimal concentration of ($m^1I$)-labeled antigen in the presence of a titration series of unlabeled antigen, then capturing bound antigen with an anti-Fab antibody-coated plate (Chen, et al., (1999) J. Mol. Biol 293:865-881). To establish conditions for the assay, microtiter plates (Dynex) are coated overnight with 5 ug/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbant plate (Nunc #269620), 100 pM or 26 pM [125I]-antigen are mixed with serial dilutions of a Fab of interest (consistent with assessment of an anti-VEGF antibody, Fab-12, in Presta et al., (1997) *Cancer Res.* 57:4593-4599). The Fab of interest is then incubated overnight; however, the incubation may continue for a longer period (e.g., 65 hours) to ensure that equilibrium is reached. Thereafter, the mixtures are transferred to the capture plate for incubation at room temperature for one hour. The solution is then removed and the plate washed eight times with 0.1% Tween-20 in PBS. When the plates have dried, 150 ul/well of scintillant (MicroScint-20; Packard) is added, and the plates are counted on a Topcount gamma counter (Packard) for ten minutes. Concentrations of each Fab that give less than or equal to 20% of maximal binding are chosen for use in competitive binding assays.

According to another embodiment, the $K_D$ is measured by using surface-plasmon resonance assays using a BIACORE®-2000 or a BIACORE®-3000 instrument (BIAcore, Inc., Piscataway, N.J.) at 25° C. with immobilized antigen CM5 chips at 10 response units (RU). In some embodiments, carboxymethylated dextran biosensor chips (CM5, BIAcore Inc.) are activated with N-ethyl-N'-(3-dimethylaminopropyl)-carbodiimide hydrochloride (EDC) and N-hydroxysuccinimide (NHS) according to the supplier's instructions. Antigen can be diluted with, for example, 10 mM sodium acetate, pH 4.8, to a concentration of about 3-10 μg/ml (e.g., 5 μg/ml (0.2 μM)) before injection at a flow rate of about 3-10 μL/minute (e.g., 5 μL/minute) to achieve approximately 10 response units (RU) of the coupled protein. Following the injection of antigen, ethanolamine (e.g., 1 mM) can be injected to block unreacted groups. For kinetics measurements, two-fold serial dilutions of a Fab such as those described herein (at a concentration of, for example, 0.78 nM to 500 nM) can be injected in PBS with TWEEN 20™ surfactant (PBST) (e.g., at 0.05%) at 25° C. The injection can be at a flow rate of approximately 10-50 μL/min (e.g., 25 μL/min). Association rates ($k_{on}$) and dissociation rates ($k_{off}$) can be calculated using, for example, a one-to-one Langmuir binding model (BIAcore® Evaluation Software version 3.2) by simultaneously fitting the association and dissociation sensorgrams. The equilibrium dissociation constant ($K_D$) can be calculated as the ratio $k_{off}/k_{on}$. See, e.g., Chen et al., J. Mol. Biol. 293:865-881 (1999). If the on-rate exceeds $10^6 M^{-1} s^{-1}$ by the surface-plasmon resonance assay above, then the on-rate can be determined by using a fluorescent quenching technique that measures the increase or decrease in fluorescence-emission intensity (e.g., excitation=295 nm; emission=340 nm, 16 nm band-pass) at 25° C. of an anti-antigen antibody (Fab form) at a concentration of 10-50 nM (e.g., 20 nM) in, for example, PBS at a pH of about 6.8-7.5 (e.g., 7.2). The measurements can be performed in the presence of increasing concentrations of antigen as measured in a spectrometer, such as a stop-flow-equipped spectrophotometer (Aviv Instruments) or a 8000-series SLM-AMINCO™ spectrophotometer (ThermoSpectronic) with a stirred cuvette.

In another aspect, competition assays may be used to identify another anti-KRas antibody that competes for binding of human KRas with any of anti-KRas antibodies described herein. In certain embodiments, such a competing antibody binds to the same epitope (e.g., a linear or a conformational epitope) of KRas. Detailed exemplary methods for mapping an epitope to which an antibody binds are provided in Morris (1996) "Epitope Mapping Protocols," in Methods in Molecular Biology vol. Humana Press, Totowa, NJ).

In an exemplary competition assay, immobilized human KRas protein is incubated in a solution comprising a first labeled antibody (e.g., a first labeled anti-KRas antibody) that binds to KRas, respectively and a second unlabeled antibody (e.g., a second unlabeled anti-KRas antibody) that is being tested for its ability to compete with the first antibody for binding to KRas. The second antibody may be present in a hybridoma supernatant. As a control, immobilized KRas is incubated in a solution comprising the first labeled antibody but not the second unlabeled antibody. After incubation under conditions permissive for binding of the first antibody to KRas, excess unbound antibody is removed, and the amount of label associated with immobilized KRas is measured. If the amount of label associated with immobilized KRas is substantially reduced in the test sample relative to the control sample, then that indicates that the second antibody is competing with the first antibody for binding to KRas. See Harlow and Lane (1988) Antibodies: A Laboratory Manual ch. 14 (Cold Spring Harbor Laboratory, Cold Spring Harbor, NY). Competition assays can also be performed in a manner as described above with FACS using cells transfected with KRas and expressed on the cell surface. Additionally, ELISA with KRas can also be used in a competition assay.

In another aspect, gel shift assays may be used to identify an interaction between an anti-KRas antibody of the invention and a target protein, such as human KRas. In an exemplary gel shift assay, human KRas is pre-incubated with an anti-KRas antibody. The pre-incubated KRas and control KRas that have not been pre-incubated with an anti-KRas antibody are subjected to gel electrophoresis and probed secondary antibodies. The mobility of the pre-incubated KRas and the KRas are compared, wherein a difference in the mobility of the pre-incubated KRas and the control KRas indicates an interaction between KRas and the anti-KRas antibody.

2. Crystal Structure

In some embodiments, the crystal structure of an anti-KRas antibody of the invention in complex with human KRas is solved. For example, KRas and an anti-KRas antibody may be purified and crystallized in a complex, and their structure may be determined by X-ray crystallography.

B. Methods of Using Anti-KRas Antibodies

In certain embodiments, any of the anti-KRas antibodies, or compositions comprising such antibodies as provided herein are useful for detecting the presence of KRas, KRas-GDP, and/or alkylated KRas in a biological sample. In certain embodiments any of the anti-KRas antibodies or compositions comprising such antibodies as provided herein are useful to quantitate KRas, KRas-GDP, and/or alkylated KRas in a sample. In some embodiments, any of the anti-KRas antibodies or compositions comprising such antibodies as provided herein are useful to quantitate $KRas^{G12C}$, $KRas^{G12C}$-GDP, and/or alkylated $KRas^{G12C}$ in a sample. In some embodiments, any of the anti-KRas antibodies or compositions comprising such antibodies as provided herein are useful to quantitate $KRas^{G12V}$ or $KRas^{G12V}$-GDP. In some embodiments, any of the anti-KRas antibodies or compositions comprising such antibodies as provided herein are useful to quantitate $KRas^{G12R}$ or $KRas^{G12R}$-GDP. In some embodiments, any of the anti-KRas antibodies or compositions comprising such antibodies as provided herein are useful to quantitate $KRas^{G12D}$ or $KRas^{G12D}$-GDP. In some embodiments, any of the anti-KRas antibodies or compositions comprising such antibodies as provided herein are useful to quantitate $KRas^{G13D}$ or $KRas^{G13D}$-GDP. In some embodiments, any of the anti-KRas antibodies or compositions comprising such antibodies as provided herein are useful to quantitate $KRas^{Q61H}$ or $KRas^{Q61H}$-GDP.

In certain embodiments, any of the anti-KRas antibodies, or compositions comprising such antibodies as provided herein are useful for detecting the presence of KRas, KRas-GTP, and/or alkylated KRas in a biological sample. In certain embodiments any of the anti-KRas antibodies or compositions comprising such antibodies as provided herein are useful to quantitate KRas, KRas-GTP, and/or alkylated KRas in a sample. In some embodiments, any of the anti-KRas antibodies or compositions comprising such antibodies as provided herein are useful to quantitate $KRas^{G12C}$, $KRas^{G12C}$-GTP, and/or alkylated $KRas^{G12C}$ in a sample. In some embodiments, any of the anti-KRas antibodies or compositions comprising such antibodies as provided herein are useful to quantitate $KRas^{G12V}$ or $KRas^{G12V}$-GTP. In some embodiments, any of the anti-KRas antibodies or compositions comprising such antibodies as provided herein are useful to quantitate $KRas^{G12R}$ or $KRas^{G12R}$-GTP. In some embodiments, any of the anti-KRas antibodies or compositions comprising such antibodies as provided herein are useful to quantitate $KRas^{G12D}$ or $KRas^{G12D}$-GTP. In some embodiments, any of the anti-KRas antibodies or compositions comprising such antibodies as provided herein are useful to quantitate $KRas^{G13D}$ or $KRas^{G13D}$-GTP. In some embodiments, any of the anti-KRas antibodies or compositions comprising such antibodies as provided herein are useful to quantitate $KRas^{Q61H}$ or $KRas^{Q61H}$-GTP.

In one aspect provided herein is a method of measuring target engagement of one or more KRas inhibitors described herein to a KRas protein (e.g. $KRas^{G12C}$). In one embodiment, the method comprises: (a) obtaining a sample (e.g. a tumor sample as described herein) from a patient described herein; (b) contacting the sample with an anti-KRas antibody or antigen-binding fragment thereof described herein; and (c) measuring the level of KRas bound by the anti-KRas antibody. In one such embodiment, the KRas inhibitor is MRTX849, AMG-510, GDC-6036, ARS-3248, LY3499446, LY3537982, or JNJ-74699157.

In some embodiments provided herein is a biomarker assay for measuring target engagement of one or more KRas inhibitors described herein to a KRas protein (e.g. $KRas^{G12C}$). In some such embodiments, the biomarker assay measures target engagement in a clinical setting from a clinical sample taken from a patient treated with one or more KRas inhibitors selected from the group consisting of MRTX849, AMG-510, GDC-6036, ARS-3248, LY3499446, LY3537982, and JNJ-74699157. In some such embodiments, the biomarker assay is used to determine a dosage of a KRas inhibitor described herein to such patients In certain embodiments, labeled anti-KRas antibodies which can be used to detect or quantify KRas, KRas-GDP, and/or alkylated KRas as described herein are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, J3-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

In certain embodiments, labeled anti-KRas antibodies which can be used to detect or quantify KRas, KRas-GTP, and/or alkylated KRas as described herein are provided. Labels include, but are not limited to, those described hereinabove.

In certain embodiments any of the anti-KRas antibodies, or compositions comprising such antibodies, as provided herein, are useful for detecting the presence of KRas, such as KRas-GDP, and/or alkylated KRas in an immunoassay, including specifically $KRas^{G12C}$, $KRas^{G12D}$, $KRas^{G12V}$, $KRas^{G12R}$, $KRas^{G13D}$, or $KRas^{Q61H}$ as described herein. In some embodiments, the anti-KRas antibodies, or compositions comprising such antibodies, as provided herein, are useful for detecting the presence of KRas, alkylated $KRas^{G12C}$ in an immunoassay. In some embodiments, the anti-KRas antibodies, or compositions comprising such antibodies, as provided herein, are useful for detecting the presence of KRas, such as KRas-GDP, and/or $KRas^{G12D}$ or $KRas^{G13D}$ bound to a covalent KRas inhibitor as described herein.

As described below, the anti-KRas antibodies, or compositions comprising such antibodies, can be used in a variety of different assays, including but not limited to ELISA, and immunohistochemistry.

In certain embodiments any of the anti-KRas antibodies, or compositions comprising such antibodies, as provided herein, are useful for detecting the presence of KRas, such as KRas-GTP, and/or alkylated KRas in an immunoassay, including specifically $KRas^{G12C}$, $KRas^{G12D}$, $KRas^{G12V}$, $KRas^{G12R}$, $KRas^{G13D}$, or $KRas^{Q61H}$ as described herein. In some embodiments, the anti-KRas antibodies, or compositions comprising such antibodies, as provided herein, are useful for detecting the presence of KRas, such as KRas-GTP, and/or $KRas^{G12D}$ or $KRas^{G13D}$ bound to a covalent KRas inhibitor as described herein.

i. ELISA (Enzyme-Linked Immunosorbent Assay)

In some embodiments, the anti-KRas antibodies are used in an ELISA assay to detect the presence and/or amount of KRas, KRas-GDP, KRas-GTP, and/or alkylated KRas, including specifically $KRas^{G12C}$, $KRas^{G12D}$, $KRas^{G12V}$, $KRas^{G12R}$ $KRas^{G13D}$, or $KRas^{Q61H}$ as described herein. Accordingly, provided herein is a method of detecting KRas, KRas GDP, KRas-GTP, and/or alkylated KRAS comprising an ELISA assay that utilizes anti-KRas antibodies as capture reagents for KRas, KRas-GDP, KRas-GTP, and/or alkylated KRas. In the first step of the assay the biological sample suspected of containing or containing KRas, KRas-GDP, KRas-GTP, and/or alkylated KRas is contacted and incubated with the capture (or coat) antibodies so that the capture antibodies capture or bind to KRas, KRas-GDP, KRas-GTP, and/or alkylated KRas so that it can be detected in a detection step. The detection step involves use of a detectable antibody, which, when contacted with any of KRas, KRas-GDP, KRas-GTP, and/or alkylated KRas, binds to KRas, KRas-GDP, KRas-GTP, and/or alkylated KRas, if present. A detection means is used to detect the label on the antibody and hence the presence or amount of KRas, KRas-GDP, KRas-GTP, and/or alkylated KRas present.

In certain embodiments, the assay utilizes the following steps.

First Step

In the first step of the assay herein, the biological sample suspected of containing or containing KRas, KRas-GDP, KRas-GTP, and/or alkylated KRas, including specifically $KRas^{G12C}$, $KRas^{G12D}$, $KRas^{G12V}$, $KRas^{G12R}$, $KRas^{G13D}$, or $KRas^{Q61H}$ as described herein, is contacted and incubated with the immobilized capture (or coat) reagents, which are anti-KRas antibodies. In some embodiments, these anti-KRas antibodies are monoclonal antibodies, and may be from any species. In some embodiments, these anti-KRas antibodies are rodent antibodies, in further embodiments murine or rat, and in further embodiments murine antibodies.

In various embodiments, the anti-KRas is any anti-KRas antibody disclosed herein. The anti-KRas antibody may be any of the Class I or Class II antibodies disclosed herein. For example, in some embodiments the anti-KRas antibody comprises a light chain variable region comprising a CDR-L1 comprising the amino acid sequence SGSSSNIGSNYVY (SEQ ID NO:9), a CDR-L2 comprising the amino acid sequence RNNQRPS (SEQ ID NO:10), and a CDR-L3 comprising the amino acid sequence AAWDERLSGWV (SEQ ID NO:11) and a heavy chain variable region comprising a CDR-H1 comprising the amino acid sequence SSNWWS (SEQ ID NO:12), a CDR-H2 comprising the amino acid sequence EIYHSGSTNYNPSLKS (SEQ ID NO:13), and a CDR-H3 comprising the amino acid sequence GSSSWYDLGPFDY (SEQ ID NO:14). In some embodiments the anti-KRas antibody comprises a light chain variable region comprising a CDR-L1 comprising the amino acid sequence SGSSSNIGSNYVY (SEQ ID NO:9), a CDR-L2 comprising the amino acid sequence RNNQRPS (SEQ ID NO:10), and a CDR-L3 comprising the amino acid sequence AAWDERLSGWV (SEQ ID NO:11) and a heavy chain variable region comprising a CDR-H1 comprising the amino acid sequence GSSIWSSN (SEQ ID NO:91), a CDR-H2 comprising the amino acid sequence EIYHSGSTNYNPSLKS (SEQ ID NO:13), and a CDR-H3 comprising the amino acid sequence GSSSWYDLGPFDY (SEQ ID NO:14). In some embodiments the anti-KRas antibody comprises a light chain variable region comprising a CDR-L1 comprising the amino acid sequence SGSSSNIGSNYVY (SEQ ID NO:9), a CDR-L2 comprising the amino acid sequence RNNQRPS (SEQ ID NO:10), and a CDR-L3 comprising the amino acid sequence AAWDERLSGWV (SEQ ID NO: 11) and a heavy chain variable region comprising a CDR-H1 comprising the amino acid sequence GSNISSSN (SEQ ID NO:92), a CDR-H2 comprising the amino acid sequence EIYHSGSTNYNPSLKS (SEQ ID NO:13), and a CDR-H3 comprising the amino acid sequence GSSSWYDLGPFDY (SEQ ID NO:14). In some embodiments the anti-KRas antibody comprises a light chain variable region comprising a CDR-L1 comprising the amino acid sequence SGSSSNIGSNYVY (SEQ ID NO:9), a CDR-L2 comprising the amino acid sequence RNNQRPS (SEQ ID NO:10), and a CDR-L3 comprising the amino acid sequence AAWDERLSGWV (SEQ ID NO: 11) and a heavy chain variable region comprising a CDR-H1 comprising the amino acid sequence GSSIFSSN (SEQ ID NO:93), a CDR-H2 comprising the amino acid sequence EIYHSGSTNYNPSLKS (SEQ ID NO:13), and a CDR-H3 comprising the amino acid sequence GSSSWYDLGPFDY (SEQ ID NO:14). In some embodiments the anti-KRas antibody comprises a light chain variable region comprising a CDR-L1 comprising the amino acid sequence SGSSSNIGSNYVY (SEQ ID NO:9), a CDR-L2 comprising the amino acid sequence RNNQRPS (SEQ ID NO:10), and a CDR-L3 comprising the amino acid sequence AAWDERLSGWV (SEQ ID NO: 11) and a heavy chain variable region comprising a CDR-H1 comprising the amino acid sequence GSSIMSSN (SEQ ID NO:94), a CDR-H2 comprising the amino acid sequence EIYHSGSTNYNPSLKS (SEQ ID NO:13), and a CDR-H3 comprising the amino acid sequence GSSSWYDLGPFDY (SEQ ID NO:14). In some embodiments the anti-KRas antibody comprises a light chain variable region comprising a CDR-L1 comprising the amino acid sequence SGSSSNIGSNYVY (SEQ ID NO:9), a CDR-L2 comprising the amino acid sequence RNNQRPS (SEQ ID NO:10), and a CDR-L3 comprising the amino acid sequence AAWDERLSGWV (SEQ ID NO: 11) and a heavy chain variable region comprising a CDR-H1 comprising the amino acid sequence GSSIYSSN (SEQ ID NO:95), a CDR-H2 comprising the amino acid sequence EIYHSGSTNYNPSLKS (SEQ ID NO:13), and a CDR-H3 comprising the amino acid sequence GSSSWYDLGPFDY (SEQ ID NO:14). In some embodiments the anti-KRas antibody comprises a light chain variable region comprising a CDR-L1 comprising the amino acid sequence SGSSSNIGSNYVY (SEQ ID NO:9), a CDR-L2 comprising the amino acid sequence RNNQRPS (SEQ ID NO:10), and a CDR-L3 comprising the amino acid sequence AAWDERLSGWV (SEQ ID NO: 11) and a heavy chain variable region comprising a CDR-H1 comprising the amino acid sequence GGNIWSSN (SEQ ID NO:96), a CDR-H2 comprising the amino acid sequence EIYHSGSTNYNPSLKS (SEQ ID NO:13), and a CDR-H3 comprising the amino acid sequence GSSSWYDLGPFDY (SEQ ID NO:14). In some embodiments the anti-KRas antibody comprises a light chain variable region comprising a CDR-L1 comprising the amino acid sequence SGSSSNIGSNYVY (SEQ ID NO:9), a CDR-L2 comprising the amino acid sequence RNNQRPS (SEQ ID NO:10), and a CDR-L3 comprising the amino acid sequence AAWDERLSGWV (SEQ ID NO: 11) and a heavy chain variable region comprising a CDR-H1 comprising the amino acid sequence KGSIWASH (SEQ ID NO:97), a CDR-H2 comprising the amino acid sequence EIYHSGSTNYNPSLKS (SEQ ID NO:13), and a CDR-H3 comprising the amino acid sequence GSSSWYDLGPFDY (SEQ ID NO:14). In some embodiments the anti-KRas antibody comprises a light chain variable region comprising a CDR-L1 comprising the amino acid sequence SGSSSNIGSNYVY (SEQ ID NO:9), a CDR-L2 comprising the amino acid sequence RNNQRPS (SEQ ID NO:10), and a CDR-L3 comprising the amino acid sequence AAWDERLSGWV (SEQ ID NO: 11) and a heavy chain variable region comprising a CDR-H1 comprising the amino acid sequence GSSIWSSN KGSIWSSN (SEQ ID NO:98), a CDR-H2 comprising the amino acid sequence EIYHSGSTNYNPSLKS (SEQ ID NO:13), and a CDR-H3 comprising the amino acid sequence GSSSWYDLGPFDY (SEQ ID NO:14). In some embodiments, the anti-KRas antibody comprises a light chain variable region comprising a CDR-L1 comprising the amino acid sequence RASQGIRNDLG (SEQ ID NO:1), a CDR-L2 comprising the amino acid sequence AASSLQS (SEQ ID NO: 2), and a CDR-L3 comprising the amino acid sequence LQDHDYPLT (SEQ ID NO:3), and a heavy chain variable region comprising a CDR-H1 comprising the amino acid sequence SYSMN (SEQ ID NO:4), a CDR-H2 comprising the amino acid sequence YISSSSSTIYYADSVKG (SEQ ID NO: 5), and a CDR-H3 comprising the amino acid sequence GFYVRNWFDP (SEQ ID NO:6). In some embodiments, the anti-KRas antibody comprises a light chain variable region comprising a CDR-L1 comprising the amino acid sequence RASQGISSYLA (SEQ ID NO:17), a CDR-L2 comprising the amino acid sequence AASSLQS (SEQ ID NO:18), and a CDR-L3 comprising the amino acid sequence QQYYSYPFT (SEQ ID NO:19), and a heavy chain variable region comprising a CDR-H1 comprising the amino acid sequence SYAMS (SEQ ID NO:20), a CDR-H2 comprising the amino acid sequence AISSSGSSTYYADSVKG (SEQ ID NO:21), and a CDR-H3 comprising the amino acid sequence DQGGYGYPGESWFDY (SEQ ID NO:22). In some embodiments, the anti-KRas antibody comprises a light chain variable region comprising a CDR-L1 comprising the amino acid sequence RASQSISSYLN (SEQ ID NO:25), a CDR-L2 comprising the amino acid sequence AASSLQS (SEQ ID NO:26), and a CDR-L3 comprising the amino acid sequence QQSYSPPWT (SEQ ID NO:27), and a heavy chain variable region comprising a CDR-H1 comprising the amino acid sequence SYSMN (SEQ ID NO:28), a CDR-H2 comprising the amino acid sequence SISSSSSYIYYADSVKG (SEQ ID NO:29), and a CDR-H3 comprising the amino acid sequence AFYSYMDV (SEQ ID NO:30). In some embodiments, the anti-KRas antibody comprises a light chain variable region comprising a CDR-L1 comprising the amino acid sequence RSSQSLLHSNGYNYLD (SEQ ID NO:33), a CDR-L2 comprising the amino acid sequence LGSNRAS (SEQ ID NO:34), and a CDR-L3 comprising the amino acid sequence MQALQTPLT (SEQ ID NO:35), and a heavy chain variable region comprising a CDR-H1 comprising the amino acid sequence SSNWWS (SEQ ID NO:36), a CDR-H2 comprising the amino acid sequence EIYHSGSTNYNPSLKS (SEQ ID NO:37), and a CDR-H3 comprising the amino acid sequence ERTILTGYYGFDY (SEQ ID NO:38). In some embodiments, the anti-KRas antibody comprises a light chain variable region comprising a CDR-L1 comprising the amino acid sequence SGSSSNIGNNYVS (SEQ ID NO:41), a CDR-L2 comprising the amino acid sequence DNNKRPS (SEQ ID NO:42), and CDR-L3 comprising the amino acid sequence GTWDSSLTGYV (SEQ ID NO: 43), and a heavy chain variable region comprising a CDR-H1 comprising the amino acid sequence SYAIS (SEQ ID NO:44), a CDR-H2 comprising the amino acid sequence GIIPIFGTANYAQKFQG (SEQ ID NO:45), and a CDR-H3 comprising the amino acid sequence YYDFWSGYPGGLFDV (SEQ ID NO:46). In some embodiments, the anti-KRas antibody comprises a light chain variable region comprising a CDR-L1 comprising the amino acid sequence SGSSSNIGSNYVY (SEQ ID NO:81), a CDR-L2 comprising the amino acid sequence RNNQRPS (SEQ ID NO:82), and a CDR-L3 comprising the amino acid sequence AAWDDSLSGWV (SEQ ID NO: 83) and a heavy chain variable region comprising a CDR-H1 comprising the amino acid sequence SYSMN (SEQ ID NO:84), a CDR-H2 comprising the amino acid sequence YISSSSSTIYYADSVKG (SEQ ID NO:85), and a CDR-H3 comprising the amino acid sequence SFGPYAFDV (SEQ ID NO:86). In some embodiments, the anti-KRas antibody comprises a light chain variable region comprising a CDR-L1 comprising the amino acid sequence SGSSSNIGNNYVS (SEQ ID NO:49), a CDR-L2 comprising the amino acid sequence DNNKRPS (SEQ ID NO:50), and a CDR-L3 comprising the amino acid sequence GTWDSSLTGWV (SEQ ID NO: 51), and a heavy chain variable region comprising a CDR-H1 comprising the amino acid sequence SYAIS (SEQ ID NO:52), a CDR-H2 comprising the amino acid sequence GIIPIFGTANYAQKFQG (SEQ ID NO:53), and a CDR-H3 comprising the amino acid sequence YYDFWSGYPGGLFDV (SEQ ID NO:54). In some embodiments, the anti-KRas antibody comprises a light chain variable region comprising a CDR-L1 comprising the amino acid sequence QGDSLRSYYAS (SEQ ID NO:57), a CDR-L2 comprising the amino acid sequence GKNNRPS (SEQ ID NO:58), and a CDR-L3 comprising the amino acid sequence NSRDSSGNHWV (SEQ ID NO: 59), and a heavy chain variable region comprising a CDR-H1 comprising the amino acid sequence SYSMN (SEQ ID NO:60), a CDR-H2 comprising the amino acid sequence SISSSSSYIYYADSVKG (SEQ ID NO:61), and a CDR-H3 comprising the amino acid sequence TNNYGYRYFDY (SEQ ID NO:62). In some embodiments, the anti-KRas antibody comprises a light chain variable region comprising a CDR-L1 comprising the amino acid sequence QGDSLRSYYAS (SEQ ID NO:65), a CDR-L2 comprising the amino acid sequence GKNNRPS (SEQ ID NO:66), and a CDR-L3 comprising the amino acid sequence NSRDSTDNHLWV (SEQ ID NO: 67), and a heavy chain variable region comprising a CDR-H1 comprising the amino acid sequence SYSMN (SEQ ID NO:68), a CDR-H2 comprising the amino acid sequence SISSSSSYIYYADSVKG (SEQ ID NO:69), and a CDR-H3 comprising the amino acid sequence ATSSGYYYFDY (SEQ ID NO:70). In some embodiments, the anti-KRas antibody comprises a light chain variable region comprising a CDR-L1 comprising the amino acid sequence SGSSSNIGNNYVS (SEQ ID NO:73), a CDR-L2 comprising the amino acid sequence DNNKRPS (SEQ ID NO:74), and a CDR-L3 comprising the amino acid sequence GTWDNSLSVWV (SEQ ID NO: 75), and a heavy chain variable region comprising a CDR-H1 comprising the amino acid sequence SYSMN (SEQ ID NO:76), a CDR-H2 comprising the amino acid sequence YISSSSSTIYYADSVKG (SEQ ID NO:77), and a CDR-H3 comprising the amino acid sequence GKGIVGWGFFGMDV (SEQ ID NO:78).

Immobilization conventionally is accomplished by insolubilizing the capture reagents either before the assay procedure, as by adsorption to a water-insoluble matrix or surface (U.S. Pat. No. 3,720,760) or non-covalent or covalent coupling (for example, using glutaraldehyde or carbodiimide cross-linking, with or without prior activation of the support with, e.g., nitric acid and a reducing agent as described in U.S. Pat. No. 3,645,852 or in Rotmans et al.; J. Immunol. Methods, 57:87-98 (1983)), or afterward, e.g., by immunoprecipitation. In some embodiments, the capture antibody is conjugated to biotin and is bound to a streptavidin coated surface. In other embodiments, the capture antibody is conjugated to a protein tag, such as a His tag or GST, and is bound to a suitable surface, e.g., a nickel or copper coated surface, or a glutathione coated surface.

The solid phase used for immobilization may be any inert support or carrier that is essentially water insoluble and useful in immunometric assays, including supports in the form of, e.g., surfaces, particles, porous matrices, etc. Examples of commonly used supports include small sheets, SEPHADEX® gels, polyvinyl chloride, plastic beads, and assay plates or test tubes manufactured from polyethylene, polypropylene, polystyrene, and the like, including 96-well microtiter plates, as well as particulate materials such as filter paper, agarose, cross-linked dextran, and other polysaccharides. Alternatively, reactive water-insoluble matrices such as cyanogen-bromide-activated carbohydrates and the reactive substrates described in U.S. Pat. Nos. 3,969,287; 3,691,016; 4,195,128; 4,247,642; 4,229,537; and 4,330,440 are suitably employed for capture-reagent immobilization. In some embodiments, the immobilized capture reagents are coated on a microtiter plate. In some embodiments, the solid phase used is a multi-well microtiter plate that can be used to analyze several samples at one time, for example, a MICROTEST™ or MAXISORP™ 96-well ELISA plate such as that sold as NUNC MAXISORB™ or IMMULONT™.

The solid phase is coated with the capture reagents as defined above, which may be linked by a non-covalent or covalent interaction or physical linkage as desired. Techniques for attachment include those described in U.S. Pat. No. 4,376,110 and the references cited therein. If covalent, the plate or other solid phase is incubated with a cross-linking agent together with the capture reagent under conditions well known in the art such as for one hour at room temperature.

Commonly used cross-linking agents for attaching the capture reagents to the solid-phase substrate include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-((p-azidophenyl)-dithio)propioimidate yield photoactivatable intermediates capable of forming cross-links in the presence of light.

If 96-well plates are utilized, they may be coated with the mixture of capture reagents typically diluted in a buffer such as 0.05 M sodium carbonate by incubation for at least about 10 hours. In some embodiments, incubation is at least overnight, at temperatures of about 4-20° C., or about 4-8° C., and at a pH of about 8-12, about 9-10, or about 9.6. If shorter coating times (1-2 hours) are desired, one can use 96-well plates with nitrocellulose filter bottoms (Millipore MULTISCREEN™) or coat at 37° C. The plates may be stacked and coated long in advance of the assay itself, and then the assay can be carried out simultaneously on several samples in a manual, semi-automatic, or automatic fashion, such as by using robotics.

The coated plates are then typically treated with a blocking agent that binds non-specifically to and saturates the binding sites to prevent unwanted binding of the free ligand to the excess sites on the wells of the plate. Examples of appropriate blocking agents for this purpose include, e.g., gelatin, bovine serum albumin, egg albumin, casein, and non-fat milk. The blocking treatment typically takes place under conditions of ambient temperatures for about 1-4 hours, or about 1.5 to 3 hours.

After coating and blocking, the standard (purified KRas, KRas-GDP, and/or alkylated KRas) or the biological sample to be analyzed, appropriately diluted, is added to the immobilized phase. In certain embodiments the dilution rate is about 5-15%, or about 10%, by volume. Buffers that may be used for dilution for this purpose include (a) phosphate-buffered saline (PBS) containing 0.5% BSA, 0.05% TWEEN 20™ detergent (P20), 0.05% PROCLIN™ 300 antibiotic, 5 mM EDTA, 0.25% 3-((3-cholamidopropyl) dimethylammonio)-1-propanesulphonate (CHAPS) surfactant, 0.2% beta-gamma globulin, and 0.35M NaCl; (b) PBS containing 0.5% bovine serum albumin (BSA), 0.05% P20, and 0.05% PROCLIN™ 300, pH 7; (c) PBS containing 0.5% BSA, 0.05% P20, 0.05% PROCLIN™ 300, 5 mM EDTA, and 0.35 M NaCl, pH 6.35; (d) PBS containing 0.5% BSA, 0.05% P20, 0.05% PROCLIN™ 300, 5 mM EDTA, 0.2% beta-gamma globulin, and 0.35 M NaCl; and (e) PBS containing 0.5% BSA, 0.05% P20, 0.05% PROCLIN™ 300, 5 mM EDTA, 0.25% CHAPS, and 0.35 M NaCl. PROCLIN™ 300 acts as a preservative, and TWEEN 20™ acts as a detergent to eliminate non-specific binding.

The amount of capture reagents employed is sufficiently large to give a good signal in comparison with the standards, but not in molar excess compared to the maximum expected level of KRas, KRas-GDP, KRas-GTP, and/or alkylated KRas, including specifically $KRas^{G12C}$, $KRas^{G12D}$, $KRas^{G12V}$, $KRas^{G12R}$, $KRas^{G13D}$, or $KRas^{Q61H}$ as described herein, in the sample. In certain embodiments, the amount of biological sample added is such that the immobilized capture reagents are in molar excess of the maximum molar concentration of free KRas, KRas-GDP, KRas-GTP, and/or alkylated KRas, including specifically $KRas^{G12C}$, $KRas^{G12D}$, $KRas^{G12V}$, $KRas^{G12R}$, $KRas^{G13D}$, or $KRas^{Q61H}$ as described herein, anticipated in the biological sample after appropriate dilution of the sample. This anticipated level depends mainly on any known correlation between the concentration levels of the free KRas, KRas-GDP, KRas-GTP, and/or alkylated KRas, including specifically $KRas^{G12C}$, $KRas^{G12D}$, $KRas^{G12V}$, $KRas^{G12R}$, $KRas^{G13D}$, or $KRas^{Q61H}$ as described herein, in the particular biological sample being analyzed with the clinical condition of the patient. Thus, for example, an adult patient may have a maximum expected concentration of free KRas, KRas-GDP, KRas-GTP, and/or alkylated KRas, including specifically $KRas^{G12C}$, $KRas^{G12D}KRas^{G12V}$, $KRas^{G12R}$, $KRas^{G13D}$, or $KRas^{Q61H}$ as described herein, in his/her serum that is quite high, whereas a child will be expected to have a lower level of free KRas, KRas-GDP, KRas-GTP, and/or alkylated KRas, including specifically $KRas^{G12C}$, $KRas^{G12D}$, $KRas^{G12V}$, $KRas^{G12R}$, $KRas^{G13D}$, or $KRas^{Q61H}$ as described herein, in his/her serum based on the doses given.

The concentration of the capture reagents may be determined by the concentration range of interest of KRas, KRas-GDP, KRas-GTP, and/or alkylated KRas, including specifically $KRas^{G12C}$, $KRas^{G12D}$, $KRas^{G12V}$, $KRas^{G12R}$, $KRas^{G13D}$, or $KRas^{Q61H}$ as described herein, taking any necessary dilution of the biological sample into account. The final concentration of the capture reagents may also be determined empirically to maximize the sensitivity of the assay over the range of interest. Generally, the molar excess is suitably less than about ten-fold of the maximum expected molar concentration of KRas, KRas-GDP, KRas-GTP, and/or alkylated KRas, including specifically $KRas^{G12C}$, $KRas^{G12D}$, $KRas^{G12V}KRas^{G12R}$, $KRas^{G13D}$, or $KRas^{Q61H}$ as described herein, in the biological sample after any appropriate dilution of the sample.

The conditions for incubation of sample and immobilized capture reagent are selected to maximize sensitivity of the assay and to minimize dissociation, and to ensure that any KRas, KRas-GDP, KRas-GTP, and/or alkylated KRas, including specifically $KRas^{G12C}$, $KRas^{G12D}$, $KRas^{G12V}$, $KRas^{G12R}$, $KRas^{G13D}$, or $KRas^{Q61H}$ as described herein, present in the sample binds to the immobilized capture reagent. The incubation is accomplished at fairly constant temperatures, ranging from about 0° C. to about 40° C., for example at or about room temperature. The time for incubation is generally no greater than about 10 hours. In various embodiments, the incubation time is from about 0.5 to 3 hours, or from about 1.5-3 hours at or about room temperature to maximize binding of KRas, KRas-GDP, KRas-GTP, and/or alkylated KRas, including specifically $KRas^{G12C}$, $KRas^{G12D}$, $KRas^{G12V}$, $KRas^{G12R}$, $KRas^{G13D}$, or $KRas^{Q61H}$ as described herein, to the capture reagents. The duration of incubation may be longer if a protease inhibitor is added to prevent proteases in the biological fluid from degrading KRas, KRas-GDP, KRas-GTP, and/or alkylated KRas, including specifically $KRas^{G12C}$, $KRas^{G12D}$, $KRas^{G12V}$, $KRas^{G12R}$, $KRas^{G13D}$, or $KRas^{Q61H}$ as described herein.

At this stage, the pH of the incubation mixture will ordinarily be in the range of about 4-9.5, or in the range of about 6-9, or about 7 to 8. The pH of the incubation buffer is chosen to maintain a significant level of specific binding of the capture reagents to the KRas, KRas-GDP, KRas-GTP, and/or alkylated KRas being captured. Various buffers may be employed to achieve and maintain the desired pH during this step, including borate, phosphate, carbonate, TRIS-HCl or TRIS-phosphate, acetate, barbital, and the like. The particular buffer employed is not critical to the invention, but in individual assays one buffer may be preferred over another.

Optional Second Step

In an optional second step of the assay method, the biological sample is separated (for example by washing) from the immobilized capture reagents to remove uncaptured KRas, KRas-GDP, KRas-GTP, and/or alkylated KRas. The solution used for washing is generally a buffer ("washing buffer") with a pH determined using the considerations and buffers described above for the incubation step, with a pH range of about 6-9. The washing may be done three or more times. The temperature of washing is generally from refrigerator to moderate temperatures, with a constant temperature maintained during the assay period, typically from about 0-40° C., or about 4-30° C. For example, the wash buffer can be placed in ice at 4° C. in a reservoir before the washing, and a plate washer can be utilized for this step. A cross-linking agent or other suitable agent may also be added at this stage to allow the now-bound KRas, KRas-GDP, KRas-GTP, and/or alkylated KRas to be covalently attached to the capture reagents if there is any concern that the captured KRas, KRas-GDP, KRas-GTP, and/or alkylated KRas may dissociate to some extent in the subsequent steps.

Third Step

In the next step, the immobilized capture reagents with any bound KRas, KRas-GDP, KRas-GTP, and/or alkylated KRas present are contacted with detectable antibody at a temperature of about 20-40° C., or about 36-38° C., with the exact temperature and time for contacting the two being dependent primarily on the detection means employed. For example, when 4-methylumbelliferyl-β-galactoside (MUG), streptavidin-HRP, or streptavidin-β-galactosidase is used as the means for detection, the contacting may be carried out overnight (e.g., about 15-17 hours or more) to amplify the signal to the maximum. While the detectable antibody may be a polyclonal or monoclonal antibody, preferably it is a monoclonal antibody, to reduce background noise. In some embodiments, the same anti-KRas antibody is used for coat and detection in the assay. In other embodiments, different anti-KRas antibodies can be used for coat and detection which are selected so that the background noise is minimized.

In some embodiments, the detectable antibody is an antibody from a non-human species that binds to human antibodies. In some embodiments, the detectable antibody is an anti-huIgG Fc antibody. In some embodiments, the detectable antibody is a mouse anti-huIgG Fcγ antibody. In some embodiments, the detectable antibody is directly detectable. In certain embodiments, the detectable antibody is biotinylated. In such cases, the detection means for the biotinylated label may be avidin or streptavidin-HRP, and the readout of the detection means may be fluorimetric or colorimetric. In some embodiments, the antibody is conjugated to HRP, and the detection means is colorimetric.

A molar excess of detectable antibody with respect to the maximum concentration of free KRas, KRas-GDP, KRas-GTP, and/or alkylated KRas expected (as described above) is added to the plate after it is washed. This antibody (which is directly or indirectly detectable) is a monoclonal antibody, although any antibody can be employed. The affinity of the detectable antibody must be sufficiently high that small amounts of the free KRas, KRas-GDP, KRas-GTP, and/or alkylated KRas can be detected, but not so high that it causes the KRas, KRas-GDP, KRas-GTP, and/or alkylated KRas to be pulled from the capture reagents.

Fourth Step

In the last step of the assay method, the level of any free KRas, KRas-GDP, KRas-GTP, and/or alkylated KRas from the sample that is now bound to the capture reagents is measured using a detection means for the detectable antibody. If the biological sample is from a clinical patient, the measuring step comprises comparing the reaction that occurs as a result of the above three steps with a standard curve to determine the level of KRas, KRas-GDP, KRas-GTP, and/or alkylated KRas compared to the known amount.

The antibody added to the immobilized capture reagents will be either directly labeled, or detected indirectly by addition, after washing off of excess first antibody, of a molar excess of a second, labeled antibody directed against IgG of the animal species of the first antibody. In the latter, indirect assay, labeled antisera against the first antibody are added to the sample so as to produce the labeled antibody in situ.

The label used for either the first or second antibody is any detectable functionality that does not interfere with the binding of free KRas, KRas-GDP, KRas-GTP, and/or alkylated KRas to the anti-KRas antibodies, including specifically $KRas^{G12C}$ $KRas^{G12D}$, $KRas^{G12V}$, $KRas^{G12R}$, $KRas^{G13D}$, or $KRas^{Q61H}$ as described herein.

Examples of suitable labels are those numerous labels known for use in immunoassay, including moieties that may be detected directly, such as fluorochrome, chemiluminscent, and radioactive labels, as well as moieties, such as enzymes, that must be reacted or derivatized to be detected. Examples of such labels include the radioisotopes $^{32}P$, $^{14}C$, $^{125}I$, $^{3}H$, and $^{131}I$, fluorophores such as rare-earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, HRP, alkaline phosphatase, beta-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin (detectable by, e.g., avidin, streptavidin, streptavidin-HRP, and streptavidin-β-galactosidase with MUG), spin labels, bacteriophage labels, stable free radicals, and the like.

Conventional methods are available to bind these labels covalently to proteins or polypeptides. For instance, coupling agents such as dialdehydes, carbodiimides, dimaleimides, bis-imidates, bis-diazotized benzidine, and the like may be used to tag the antibodies with the above-described fluorescent, chemiluminescent, and enzyme labels. See, for example, U.S. Pat. No. 3,940,475 (fluorimetry) and U.S. Pat. No. 3,645,090 (enzymes); Hunter et al., Nature, 144:945 (1962); David et al., Biochemistry, 13:1014-1021 (1974); Pain et al., J. Immunol. Methods, 40:219-230 (1981); and Nygren, J. Histochem. and Cytochem., 30:407-412 (1982).

The conjugation of such label, including the enzymes, to the antibody is a standard manipulative procedure for one of ordinary skill in immunoassay techniques. See, for example, O'Sullivan et al. "Methods for the Preparation of Enzyme-antibody Conjugates for Use in Enzyme Immunoassay," in Methods in Enzymology, ed. J. J. Langone and H. Van Vunakis, Vol. 73 (Academic Press, New York, New York, 1981), pp. 147-166. Suitable commercially available labeled antibodies may also be used.

Following the addition of last labeled antibody, the amount of bound antibody is determined by removing excess unbound labeled antibody through washing and then measuring the amount of the attached label using a detection method appropriate to the label, and correlating the measured amount with the amount of the KRas, KRas-GDP, KRas-GTP, and/or alkylated KRas in the biological sample. For example, in the case of enzymes, the amount of color developed and measured will be a direct measurement of the amount of the KRas, KRas-GDP, KRas-GTP, and/or alkylated KRas present. Specifically, if HRP is the label, the color may be detected using the substrate TMD, using a 450 nm read wavelength and a 620 or 630 nm reference wavelength.

In one example, after an enzyme-labeled second antibody directed against the first unlabeled antibody is washed from the immobilized phase, color or chemiluminescence is developed and measured by incubating the immobilized capture reagent with a substrate of the enzyme. Then the concentration of the KRas, KRas-GDP, KRas-GTP, and/or alkylated KRas is calculated by comparing with the color or chemiluminescence generated by the standard KRas, KRas-GDP, KRas-GTP, and/or alkylated KRas run in parallel.

ii. Immunohistochemistry (IHC)

In some embodiments, the anti-KRas antibodies of the present disclosure are used to detect KRas, KRas-GDP, KRas-GTP, and/or alkylated KRas, including specifically $KRas^{G12C}$, $KRas^{G12D}$, $KRas^{G12V}$, $KRas^{G12R}$, $KRas^{G13D}$, or $KRas^{Q61H}$ as described herein, in immunohistochemistry (IHC). Accordingly, in some embodiments, provided herein is a method of detecting KRas, such as KRas-GDP, KRas-GTP, and/or alkylated KRas in a tissue sample using immunohistochemistry. Immunohistochemistry (IHC) is the localization of targets (e.g. antigens such as KRas, KRas-GDP, KRas-GTP, and/or alkylated KRas) and/or subsets of cells presenting a target in tissue sections by the use of binding domains (such as anti-KRas antibodies) which are either directly labeled (direct IHC) or indirectly labeled (indirect IHC), which binding domains react with their target through specific target-binding-domain interactions. These interactions are then visualized by the mentioned label.

It is envisaged that in some embodiments of the methods of the present invention, said immunohistochemistry is characterized by the following steps:

(a) providing a means (for example a slide) comprising said tissue sample comprising the subset of cells and/or said subset of cells to which the binding domain (e.g., an anti-KRas antibody) has bound to;
(b) optionally fixing said tissue sample;
(c) optionally dehydrating said tissue sample;
(d) optionally allowing the tissue sample to be paraffinized;
(e) directly or indirectly detecting the binding domain (e.g., an anti-KRas antibody) and thereby the subset of cells.

"Fixing" or "fixation" means a fixation procedure which is suitable to prepare the target/subset of cells/tissue sample comprising said subset of cells for a subsequent IHC procedure. A "fixation" is particularly carried out in order to ensure the preservation of tissue architecture and cell morphology. Suitable fixation conditions are well-known and also disclosed herein. Alternatively, it is also envisaged that the tissue/subset is preserved by way of deep-freezing (e.g. in liquid nitrogen).

All the above pre-treatment steps/measures are within the scope of the term "fixation", i.e. fixation specifically includes fixation with fixing agents like formaldehyde, paraformaldehyde; and/or deep-freezing of the tissue sample/subset of cells, and/or optionally also the embedding of the tissue/subset of cells in paraffin or similar agents. It must be understood that the gist of the present invention lies in the surprising finding that it is advantageous that the binding domain (e.g. the primary antibody which is specific for a target) is allowed to bind to its target before the tissue/subset etc. presenting said target is subject to a fixation procedure, as the fixation procedure might effect the amount and/or quality of the target thereby altering the result in an unwanted fashion.

The tissue/subset can also be paraffinized (usually after the fixation).

Means and methods to put the different IHC protocols into practice are well-known to the skilled person and have been, and will/can be adapted to the specific tissue/subset of cells/target which is of interest, without further ado.

iii. Surface Plasmon Resonance

In one embodiment, the antibody or antigen binding fragment thereof described herein may facilitate identification of new chemical matter and/or the development of chemical matter to produce drug candidates as described herein. In one embodiment, the SWII pocket of KRas is opened and/or stabilized as described herein. In one embodiment, opening and/or stabilizing the SWII pocket of KRas can increase the probability of higher affinity compound binding which in turn allows a higher fraction of weakly bound compounds to be detected. In embodiments, an antibody or antigen binding fragment thereof described herein may not increase the affinity of compound binding but instead stabilizes KRas conformation.

Surface plasmon resonance (SPR) or various forms of surface interferometry generate an optical evanescent field at a sensing surface that is sensitive to the accumulation of biomolecules at the sensing surface by monitoring the associated changes in the average refractive index close to the sensing surface. The evanescent field exponentially decays moving away from the surface and defines the refractive index sensitivity depth of the surface. Typically the penetration depth of this field is in the order of 200-300 nM providing a three dimensional probed volume that can be fully exploited by using bound hydrogels to support bimolecular complex formation and hydrogel coated sensor chips are widely available.

A hydrogel can be created by chemically grafting polysaccharide chains (e.g. linear but some branching is acceptable) onto the planar surface to form a hydrogel that extends 10-200 nm from the sensing surface. In one embodiment, these chains are derivitized to contain reactive groups allowing target molecules to be coupled to the hydrogel. In one embodiment, a target can be coupled to concentrations of 20-50 mg/ml within the hydrogel but 5-fold above and below this limit is possible. The response obtained is proportional to the molecular volume of the molecule that is bound, the number of target molecules present and the refractive index contrast between the molecule and the surrounding buffer.

In one aspect provided herein is a biosensing surface for measuring binding of a KRas inhibitor compound to a KRas mutant described herein. In one embodiment, the surface is prebound to an antibody or antigen binding fragment thereof described herein. In one embodiment provided herein is a biosensing surface for measuring binding of compounds to a KRas mutant described herein wherein:

the biosensing surface comprises a hydrogel into which a KRas protein and the antibody or antigen binding fragment thereof described herein are co-localized;

the KRas protein and the antibody or antigen binding fragment thereof have sufficient degrees of freedom within the hydrogen to engage each other to form affinity complexes;

wherein the local concentration of the KRas protein and the antibody or antigen binding fragment thereof exceeds the dissociation affinity constant by at least 10-fold, wherein the local concentration promotes formation of the affinity complex;

wherein the fraction of unbound KRas protein and antibody or antigen binding fragment thereof is less than about 50%;

wherein the KRas inhibitor compound is injected onto the biosensing surface for at least 5 seconds; and wherein binding of the KRas inhibitor compound to the antibody or antigen binding fragment thereof is measured over at least one sensing channel.

In one embodiment of the surface, the fraction of unbound KRas protein and antibody or antigen binding fragment thereof is less than about 40%, 30%, 25%, 20%, or 10%.

In some embodiments, the hydrogel is about 10 nm-500 nm, 10 nm-300 nm, 10-250 nm, or about 10-200 nm in thickness. In some embodiments, the hydrogen comprises streptavidin.

In one embodiment, the KRas protein is biotinylated. In some embodiments, the KRas protein is $KRas^{G12C}$. In some embodiments, the KRas protein is $KRas^{G12D}$. In some embodiments, the KRas protein is $KRas^{G12V}$. In some embodiments, the KRas protein is $KRas^{G12C}$. In some embodiments, the KRas protein is $KRas^{G12R}$. In some embodiments, the KRas protein is $KRas^{G13D}$. In some embodiments, the KRas protein is $KRas^{Q61H}$ In one embodiment, the KRas protein is at a concentration of about 50-1000 nM, 50-750 nM, 50-500 nM, 100-1000 nM, 100-750 nM, 100-500 nM, or about 100-250 nM in a buffer before applying to the biosensing surface. In some embodiments, the concentration of the KRas protein in the hydrogel is about 0.5-2 mM, 0.5-1.5 mM, 0.5-1 mM, 0.75-2 mM, 0.75-1.5 mM, 0.75-1 mM, 0.9-2 mM, or 0.9-1.5 mM.

In some embodiments, the antibody or antigen binding fragment thereof is a Fab as described herein. In one embodiment, the antibody or antigen binding fragment thereof is injected at a concentration of about 50, 100, 150, 200, 250, 500, or 1000 nM. In one embodiment, the antibody or antigen binding fragment thereof is injected at a concentration of about 150-200 nM. In one embodiment, the antibody or antigen binding fragment thereof is a Fab of 2H11.

In some embodiments, the biosensing surface is attached to a BIACORE sensor chip. In some embodiments, the measuring is performed over at least 2 channels. In one such embodiment, at least one channel is a reference (e.g. blank) sensing channel.

In one embodiment, the KRas inhibitor compound is injected at a concentration of about 0.025 μM-500 μM, 0.025 μM-250 μM, 0.025 μM-100 μM, 0.025 μM-50 μM, 0.025 μM-25 μM, 0.025 μM-10 μM, 0.03 μM-500 μM, 0.03 μM-250 μM, 0.03 μM-100 μM, 0.03 μM-50 μM, 0.03 μM-25 μM, 0.03 μM-10 μM, 0.05 uM-500 uM, 0.05 μM-250 μM, 0.05 μM-100 μM, 0.05 μM-50 μM, 0.05 μM-25 μM, or 0.05 μM-10 μM. In some embodiments, the KRas inhibitor compound is injected at a concentration set forth above at a rate of about 10, 25, 50, 100, 150, or about 250 μL/min. In some embodiments, the KRas inhibitor compound is injected for about 5, 7, 8, 9, 10, 15, 20, or about 25 seconds at a rate and concentrations described herein. In one embodiment, the KRas inhibitor compound is injected onto the hydrogel for about 10 seconds at a rate of about 100 μL/min at a concentration of about 0.04-10 μM. In some embodiments, the KRas inhibitor compound is provided as a series of different concentrations (e.g. a series of 2, 3, 4, 5, 6, 7, 8, or 9 different concentrations). In some embodiments, each different concentration is injected over the hydrogel as described herein.

In another aspect provided herein is a method of screening compounds for anti-KRas inhibitor activity, the method comprising measuring the binding of a compound to a KRas mutant protein described, wherein the KRas mutant protein is bound to an antibody or antigen binding fragment thereof as described herein, wherein the binding is measured using a biosensing surface described herein.

In one embodiment, the KRas and an antibody or antigen binding fragment thereof described herein are coupled simultaneously in the hydrogel. In another embodiment, the KRas is added prior to coupling with the antibody or antigen binding fragment thereof described herein. In still another embodiment, the antibody or antigen binding fragment thereof is added prior to coupling with KRas.

Further provided herein is a method of measuring binding of a KRas mutant protein to an antibody or antigen binding fragment thereof described herein, wherein the method comprises:

contacting a biosensing surface described herein with a KRas protein described herein to form a KRas-bound biosensing surface;

contacting the KRas-bound biosensing surface with an antibody or antigen binding fragment thereof described herein or a Fab thereof, wherein the anti-KRas antibody is at a molar excess compared to the KRas protein; and detecting the binding and affinity of the antibody or antigen binding fragment thereof to the KRas protein using surface plasmon resonance.

In one such embodiment, the biosensing surface is coated with avidin. In another such embodiment, the KRas protein is biotinylated.

Further provided herein is a method of measuring binding of a KRas mutant protein to an anti-KRas antibody described herein, wherein the method comprises:

contacting a biosensing surface described herein with an antibody or antigen binding fragment thereof described herein to form an anti-KRas antibody-bound biosensing surface;

contacting the anti-KRas antibody-bound biosensing surface with a KRas protein described herein, wherein the anti-KRas antibody is at a molar excess compared to the KRas protein; and detecting the binding and affinity of the antibody or antigen binding fragment thereof to the KRas protein using surface plasmon resonance.

In one such embodiment, the biosensing surface is coated with avidin. In another such embodiment, the antibody or antigen binding fragment thereof is biotinylated.

iv. Methods of Detecting KRas-GDP in a Sample

Provided herein are methods of detecting KRas-GDP in a sample. In some embodiments, the anti-KRas antibodies of the present disclosure bind to human KRas wherein the antibodies bind to the KRas bound to GDP (KRas-GDP) with a higher affinity than to the KRas bound to GTP (KRas-GTP). Accordingly, in some embodiments, the anti-KRas antibodies are used to detect KRas-GDP in a sample. In some embodiments, KRas-GDP is detected using a variety of techniques known in the art, as described above. In some embodiments, KRas-GDP is detected using ELISA. In some embodiments, KRas-GDP is detected using immunohistochemistry, as provided herein. In some embodiments, KRas-GDP is detected using surface plasmon resonance (SPR). In some embodiments, KRas-GDP is detected using a BIOACORE SPR instrument. In some embodiments, KRas-GDP is detected using flow cytometry. In some embodiments, KRas-GDP is detected using fluorescence-activated cell sorting (FACS). In some embodiments, KRas-GDP is detected using immunoprecipitation. In some embodiments, KRas-GDP is detected using affinity electrophoresis, such as an electrophoretic mobility shift assay. In some embodiments, KRas-GDP is detected using fluorescence polarization/anisotropy. In some embodiments, KRas-GDP is detected using affinity purification coupled to mass spectrometry. In some embodiments, KRas-GDP is detected using Bio-layer interferometry. In some embodiments, KRas-GDP is detected using microscale thermophoresis (MST). In some embodiments, KRas-GDP is detected using a labeled KRas antibody.

Provided herein is a method for detecting KRas-GDP in a sample wherein the KRas is a KRas mutant. In some embodiments, the KRas mutant is an oncogenic KRas. In some embodiments, the KRas mutant is $KRas^{G12C}$. In some embodiments, the KRas mutant is $KRas^{G12R}$. In some embodiments, the KRas mutant is $KRas^{G12V}$. In some embodiments, the KRas mutant is $KRas^{Q61H}$. In some embodiments, the KRas mutant is $KRas^{G12D}$. In some embodiments, the KRas mutant is $KRas^{G13D}$.

In some embodiments, any of the anti-KRas antibodies described herein are used to detect KRas-GDP in a sample. In some embodiments, the anti-KRas antibody is a Class I antibody. In some embodiments, the anti-KRas antibody is a Class II antibody. In some embodiments, the anti-KRas antibody is an alkylated conformation-specific antibody. In some embodiments, the anti-KRas antibody is an alkylation-inducing antibody. In some embodiments, the anti-KRas antibody opens the SWII pocket. In some embodiments, the anti-KRas antibody stabilizes the SWII pocket. In some embodiments, the anti-KRas antibody is 1E5. In some embodiments, the anti-KRas antibody is 2H11. In some embodiments, the anti-KRas antibody is 2A3. In some embodiments, the anti-KRas antibody is 3A12. In some embodiments, the anti-KRas antibody is 4G12. In some embodiments, the anti-KRas antibody is 1A5. In some embodiments, the anti-KRas antibody is 1D6. In some embodiments, the anti-KRas antibody is 2C1. In some embodiments, the anti-KRas antibody is 1A6. In some embodiments, the anti-KRas antibody is 1B7. In some embodiments, the anti-KRas antibody is 1F4. For example, in some embodiments the anti-KRas antibody comprises a light chain variable region comprising a CDR-L1 comprising the amino acid sequence SGSSSNIGSNYVY (SEQ ID NO:9), a CDR-L2 comprising the amino acid sequence RNNQRPS (SEQ ID NO:10), and a CDR-L3 comprising the amino acid sequence AAWDERLSGWV (SEQ ID NO:11) and a heavy chain variable region comprising a CDR-H1 comprising the amino acid sequence SSNWWS (SEQ ID NO:12), a CDR-H2 comprising the amino acid sequence EIYHSGSTNYNPSLKS (SEQ ID NO:13), and a CDR-H3 comprising the amino acid sequence GSSSWYDLGPFDY (SEQ ID NO:14). In some embodiments the anti-KRas antibody comprises a light chain variable region comprising a CDR-L1 comprising the amino acid sequence SGSSSNIGSNYVY (SEQ ID NO:9), a CDR-L2 comprising the amino acid sequence RNNQRPS (SEQ ID NO:10), and a CDR-L3 comprising the amino acid sequence AAWDERLSGWV (SEQ ID NO:11) and a heavy chain variable region comprising a CDR-H1 comprising the amino acid sequence GSSIWSSN (SEQ ID NO:91), a CDR-H2 comprising the amino acid sequence EIYHSGSTNYNPSLKS (SEQ ID NO:13), and a CDR-H3 comprising the amino acid sequence GSSSWYDLGPFDY (SEQ ID NO:14). In some embodiments the anti-KRas antibody comprises a light chain variable region comprising a CDR-L1 comprising the amino acid sequence SGSSSNIGSNYVY (SEQ ID NO:9), a CDR-L2 comprising the amino acid sequence RNNQRPS (SEQ ID NO:10), and a CDR-L3 comprising the amino acid sequence AAWDERLSGWV (SEQ ID NO:11) and a heavy chain variable region comprising a CDR-H1 comprising the amino acid sequence GSNISSSN (SEQ ID NO:92), a CDR-H2 comprising the amino acid sequence EIYHSGSTNYNPSLKS (SEQ ID NO:13), and a CDR-H3 comprising the amino acid sequence GSSSWYDLGPFDY (SEQ ID NO:14). In some embodiments the anti-KRas antibody comprises a light chain variable region comprising a CDR-L1 comprising the amino acid sequence SGSSSNIGSNYVY (SEQ ID NO:9), a CDR-L2 comprising the amino acid sequence RNNQRPS (SEQ ID NO:10), and a CDR-L3 comprising the amino acid sequence AAWDERLSGWV (SEQ ID NO:11) and a heavy chain variable region comprising a CDR-H1 comprising the amino acid sequence GSSIFSSN (SEQ ID NO:93), a CDR-H2 comprising the amino acid sequence EIYHSGSTNYNPSLKS (SEQ ID NO:13), and a CDR-H3 comprising the amino acid sequence GSSSWYDLGPFDY (SEQ ID NO:14). In some embodiments the anti-KRas antibody comprises a light chain variable region comprising a CDR-L1 comprising the amino acid sequence SGSSSNIGSNYVY (SEQ ID NO:9), a CDR-L2 comprising the amino acid sequence RNNQRPS (SEQ ID NO:10), and a CDR-L3 comprising the amino acid sequence AAWDERLSGWV (SEQ ID NO:11) and a heavy chain variable region comprising a CDR-H1 comprising the amino acid sequence GSSIMSSN (SEQ ID NO:94), a CDR-H2 comprising the amino acid sequence EIYHSGSTNYNPSLKS (SEQ ID NO:13), and a CDR-H3 comprising the amino acid sequence GSSSWYDLGPFDY (SEQ ID NO:14). In some embodiments the anti-KRas antibody comprises a light chain variable region comprising a CDR-L1 comprising the amino acid sequence SGSSSNIGSNYVY (SEQ ID NO:9), a CDR-L2 comprising the amino acid sequence RNNQRPS (SEQ ID NO:10), and a CDR-L3 comprising the amino acid sequence AAWDERLSGWV (SEQ ID NO:11) and a heavy chain variable region comprising a CDR-H1 comprising the amino acid sequence GSSIYSSN (SEQ ID NO:95), a CDR-H2 comprising the amino acid sequence EIYHSGSTNYNPSLKS (SEQ ID NO:13), and a CDR-H3 comprising the amino acid sequence GSSSWYDLGPFDY (SEQ ID NO:14). In some embodiments the anti-KRas antibody comprises a light chain variable region comprising a CDR-L1 comprising the amino acid sequence SGSSSNIGSNYVY (SEQ ID NO:9), a CDR-L2 comprising the amino acid sequence RNNQRPS (SEQ ID NO:10), and a CDR-L3 comprising the amino acid sequence AAWDERLSGWV (SEQ ID NO:11) and a heavy chain variable region comprising a CDR-H1 comprising the amino acid sequence GGNIWSSN (SEQ ID NO:96), a CDR-H2 comprising the amino acid sequence EIYHSGSTNYNPSLKS (SEQ ID NO:13), and a CDR-H3 comprising the amino acid sequence GSSSWYDLGPFDY (SEQ ID NO:14). In some embodiments the anti-KRas antibody comprises a light chain variable region comprising a CDR-L1 comprising the amino acid sequence SGSSSNIGSNYVY (SEQ ID NO:9), a CDR-L2 comprising the amino acid sequence RNNQRPS (SEQ ID NO:10), and a CDR-L3 comprising the amino acid sequence AAWDERLSGWV (SEQ ID NO:11) and a heavy chain variable region comprising a CDR-H1 comprising the amino acid sequence KGSIWASH (SEQ ID NO:97), a CDR-H2 comprising the amino acid sequence EIYHSGSTNYNPSLKS (SEQ ID NO:13), and a CDR-H3 comprising the amino acid sequence GSSSWYDLGPFDY (SEQ ID NO:14). In some embodiments the anti-KRas antibody comprises a light chain variable region comprising a CDR-L1 comprising the amino acid sequence SGSSSNIGSNYVY (SEQ ID NO:9), a CDR-L2 comprising the amino acid sequence RNNQRPS (SEQ ID NO:10), and a CDR-L3 comprising the amino acid sequence AAWDERLSGWV (SEQ ID NO:11) and a heavy chain variable region comprising a CDR-H1 comprising the amino acid sequence KGSIWSSN (SEQ ID NO:98), a CDR-H2 comprising the amino acid sequence EIYHSG-STNYNPSLKS (SEQ ID NO:13), and a CDR-H3 comprising the amino acid sequence GSSSWYDLGPFDY (SEQ ID NO:14). In some embodiments, the anti-KRas antibody comprises a light chain variable region comprising a CDR-L1 comprising the amino acid sequence RASQGIRNDLG (SEQ ID NO:1), a CDR-L2 comprising the amino acid sequence AASSLQS (SEQ ID NO:2), and a CDR-L3 comprising the amino acid sequence LQDHDYPLT (SEQ ID NO:3), and a heavy chain variable region comprising a CDR-H1 comprising the amino acid sequence SYSMN (SEQ ID NO:4), a CDR-H2 comprising the amino acid sequence YISSSSSTIYYADSVKG (SEQ ID NO:5), and a CDR-H3 comprising the amino acid sequence GFYVRNWFDP (SEQ ID NO:6). In some embodiments, the anti-KRas antibody comprises a light chain variable region comprising a CDR-L1 comprising the amino acid sequence RASQGISSYLA (SEQ ID NO:17), a CDR-L2 comprising the amino acid sequence AASSLQS (SEQ ID NO:18), and a CDR-L3 comprising the amino acid sequence QQYYSYPFT (SEQ ID NO:19), and a heavy chain variable region comprising a CDR-H1 comprising the amino acid sequence SYAMS (SEQ ID NO: 20), a CDR-H2 comprising the amino acid sequence AISSSGSSTYYADSVKG (SEQ ID NO: 21), and a CDR-H3 comprising the amino acid sequence DQGGYGYPGESWFDY (SEQ ID NO: 22). In some embodiments, the anti-KRas antibody comprises a light chain variable region comprising a CDR-L1 comprising the amino acid sequence RASQSISSYLN (SEQ ID NO:25), a CDR-L2 comprising the amino acid sequence AASSLQS (SEQ ID NO:26), and a CDR-L3 comprising the amino acid sequence QQSYSPPWT (SEQ ID NO:27), and a heavy chain variable region comprising a CDR-H1 comprising the amino acid sequence SYSMN (SEQ ID NO:28), a CDR-H2 comprising the amino acid sequence SIS-SSSSYIYYADSVKG (SEQ ID NO:29), and a CDR-H3 comprising the amino acid sequence AFYSYMDV (SEQ ID NO:30). In some embodiments, the anti-KRas antibody comprises a light chain variable region comprising a CDR-L1 comprising the amino acid sequence RSSQSLLHSNGY-NYLD (SEQ ID NO:33), a CDR-L2 comprising the amino acid sequence LGSNRAS (SEQ ID NO:34), and a CDR-L3 comprising the amino acid sequence MQALQTPLT (SEQ ID NO:35), and a heavy chain variable region comprising a CDR-H1 comprising the amino acid sequence SSNWWS (SEQ ID NO:36), a CDR-H2 comprising the amino acid sequence EIYHSGSTNYNPSLKS (SEQ ID NO:37), and a CDR-H3 comprising the amino acid sequence ERTIL-TGYYGFDY (SEQ ID NO:38). In some embodiments, the anti-KRas antibody comprises a light chain variable region comprising a CDR-L1 comprising the amino acid sequence SGSSSNIGNNYVS (SEQ ID NO:41), a CDR-L2 comprising the amino acid sequence DNNKRPS (SEQ ID NO:42), and CDR-L3 comprising the amino acid sequence GTWDSSLTGYV (SEQ ID NO:43), and a heavy chain variable region comprising a CDR-H1 comprising the amino acid sequence SYAIS (SEQ ID NO:44), a CDR-H2 comprising the amino acid sequence GIIPIFGTANYAQKFQG (SEQ ID NO:45), and a CDR-H3 comprising the amino acid sequence YYDFWSGYPGGLFDV (SEQ ID NO:46). In some embodiments, the anti-KRas antibody comprises a light chain variable region comprising a CDR-L1 comprising the amino acid sequence SGSSSNIGSNYVY (SEQ ID NO:81), a CDR-L2 comprising the amino acid sequence RNNQRPS (SEQ ID NO:82), and a CDR-L3 comprising the amino acid sequence AAWDDSLSGWV (SEQ ID NO: 83) and a heavy chain variable region comprising a CDR-H1 comprising the amino acid sequence SYSMN (SEQ ID NO:84), a CDR-H2 comprising the amino acid sequence YISSSSSTIYYADSVKG (SEQ ID NO:85), and a CDR-H3 comprising the amino acid sequence SFGPYAFDV (SEQ ID NO:86). In some embodiments, the anti-KRas antibody comprises a light chain variable region comprising a CDR-L1 comprising the amino acid sequence SGSSS-NIGNNYVS (SEQ ID NO:49), a CDR-L2 comprising the amino acid sequence DNNKRPS (SEQ ID NO:50), and a CDR-L3 comprising the amino acid sequence GTWDSSLTGWV (SEQ ID NO: 51), and a heavy chain variable region comprising a CDR-H1 comprising the amino acid sequence SYAIS (SEQ ID NO:52), a CDR-H2 comprising the amino acid sequence GIIPIFGTANYAQKFQG (SEQ ID NO:53), and a CDR-H3 comprising the amino acid sequence YYDFWSGYPGGLFDV (SEQ ID NO:54). In some embodiments, the anti-KRas antibody comprises a light chain variable region comprising a CDR-L1 comprising the amino acid sequence QGDSLRSYYAS (SEQ ID NO:57), a CDR-L2 comprising the amino acid sequence GKNNRPS (SEQ ID NO:58), and a CDR-L3 comprising the amino acid sequence NSRDSSGNHWV (SEQ ID NO: 59), and a heavy chain variable region comprising a CDR-H1 comprising the amino acid sequence SYSMN (SEQ ID NO:60), a CDR-H2 comprising the amino acid sequence SISSSSSYIYYADSVKG (SEQ ID NO:61), and a CDR-H3 comprising the amino acid sequence TNNYGYRYFDY (SEQ ID NO:62). In some embodiments, the anti-KRas antibody comprises a light chain variable region comprising a CDR-L1 comprising the amino acid sequence QGD-SLRSYYAS (SEQ ID NO:65), a CDR-L2 comprising the amino acid sequence GKNNRPS (SEQ ID NO:66), and a CDR-L3 comprising the amino acid sequence NSRD-STDNHLWV (SEQ ID NO: 67), and a heavy chain variable region comprising a CDR-H1 comprising the amino acid sequence SYSMN (SEQ ID NO:68), a CDR-H2 comprising the amino acid sequence SISSSSSYIYYADSVKG (SEQ ID NO:69), and a CDR-H3 comprising the amino acid sequence ATSSGYYYFDY (SEQ ID NO:70). In some embodiments, the anti-KRas antibody comprises a light chain variable region comprising a CDR-L1 comprising the amino acid sequence SGSSSNIGNNYVS (SEQ ID NO:73), a CDR-L2 comprising the amino acid sequence DNNKRPS (SEQ ID NO:74), and a CDR-L3 comprising the amino acid sequence GTWDNSLSVWV (SEQ ID NO: 75), and a heavy chain variable region comprising a CDR-H1 comprising the amino acid sequence SYSMN (SEQ ID NO:76), a CDR-H2 comprising the amino acid sequence YISSSSSTIYYADSVKG (SEQ ID NO:77), and a CDR-H3 comprising the amino acid sequence GKGIVGWGFFGMDV (SEQ ID NO:78).

In some embodiments, the methods provided herein can be used to quantify (or determine the amount of) KRas-GDP in a sample. In some embodiments, the methods provided herein can be used to measure the abundance of KRas-GDP in a sample. In some embodiments, the methods provided herein can be used to measure the abundance of KRas-GDP bound to a KRas inhibitor as described herein in a sample.

In some embodiments, the amount of KRas-GDP is determined relative to a standard. For example, in some embodiments, a quantitative western blot can be used to quantify KRas-GDP abundance. In some embodiments, KRas-GDP is quantified using ELISA. In some embodiments, KRas-GDP is quantified using immunohistochemistry. In some embodiments, KRas-GDP is quantified using flow cytometry. In some embodiments, KRas-GDP is quantified using fluorescence-activated cell sorting (FACS). In some embodiments, KRas-GDP is quantified following immunoprecipitation. In some embodiments, KRas-GDP is quantified using affinity electrophoresis, such as an electrophoretic mobility shift assay. In some embodiments, KRas-GDP is quantified using affinity purification coupled to mass spectrometry. In some embodiments, KRas-GDP is quantified following purification. In some embodiments, KRas-GDP is quantified following purification by high performance liquid chromatography (HPLC). In some embodiments, KRas-GDP is quantified following purification by size exclusion chromatography.

In some embodiments, the method comprises detecting KRas-GDP in a sample. In some embodiments, KRas-GDP is detected in a biological sample. In some embodiments, a biological sample is a biological fluid, such as whole blood or whole blood components including red blood cells, white blood cells, platelets, serum and plasma, ascites, vitreous fluid, lymph fluid, synovial fluid, follicular fluid, seminal fluid, amniotic fluid, milk, saliva, sputum, tears, perspiration, mucus, cerebrospinal fluid, urine and other constituents of the body that may contain KRas-GDP. In various embodiments, the sample is a body sample from any animal. In various embodiments, the sample is a sample from a human. In some embodiments, the sample is from a mammal. In some embodiments, the sample is from a human subject, for example, when detecting KRas-GDP in a clinical sample. In some embodiments, the biological sample is from clinical patients or a patient with an oncogenic KRas mutation. In some embodiments, the biological sample is from clinical patients or a patient with an oncogenic KRas mutation, where the patient has been dosed with a KRas inhibitor as described herein. In some embodiments, the biological sample is from clinical patients or a patient with a $KRas^{G12C}$ oncogenic mutation. In some embodiments, the biological sample is from clinical patients or a patient with a $KRas^{G12D}$ oncogenic mutation. In some embodiments, the biological sample is from clinical patients or a patient with a $KRas^{G12V}$ oncogenic mutation. In some embodiments, the biological sample is from clinical patients or a patient with a $KRas^{G12R}$ oncogenic mutation. In some embodiments, the biological sample is from clinical patients or a patient with a $KRas^{G13D}$ oncogenic mutation. In some embodiments, the biological sample is a from clinical patients or patient with a $KRas^{Q61H}$ oncogenic mutation. In certain embodiments, the biological sample is serum or plasma. In certain embodiments, the biological sample is serum from a clinical patient. In certain embodiments the biological sample is urine. In certain embodiments, the biological sample is urine from a clinical patient.

In some embodiments, KRas-GDP is detected in a sample from a cancer patient. In some embodiments, KRas-GDP is detected in a sample from a cancer patient having a $KRas^{G12C}$ oncogenic mutation. In some embodiments, KRas-GDP is detected in a sample from a cancer patient having a $KRas^{G12D}$ oncogenic mutation. In some embodiments, KRas-GDP is detected in a sample from a cancer patient having a $KRas^{G12V}$ oncogenic mutation. In some embodiments, KRas-GDP is detected in a sample from a cancer patient having a $KRas^{G12R}$ oncogenic mutation. In some embodiments, KRas-GDP is detected in a sample from a cancer patient having a $KRas^{G13D}$ oncogenic mutation. In some embodiments, KRas-GDP is detected in a sample from a cancer patient having a $KRas^{Q61H}$ oncogenic mutation.

In some embodiments, the methods provided herein can be used to quantify (or determine the amount of) KRas-GTP in a sample. In some embodiments, the methods provided herein can be used to measure the abundance of KRas-GTP in a sample. In some embodiments, the methods provided herein can be used to measure the abundance of KRas-GTP bound to a KRas inhibitor as described herein in a sample. In some embodiments, the amount of KRas-GTP is determined relative to a standard. For example, in some embodiments, a quantitative western blot can be used to quantify KRas-GTP abundance. In some embodiments, KRas-GTP is quantified using ELISA. In some embodiments, KRas-GTP is quantified using immunohistochemistry. In some embodiments, KRas-GTP is quantified using flow cytometry. In some embodiments, KRas-GTP is quantified using fluorescence-activated cell sorting (FACS). In some embodiments, KRas-GTP is quantified following immunoprecipitation. In some embodiments, KRas-GTP is quantified using affinity electrophoresis, such as an electrophoretic mobility shift assay. In some embodiments, KRas-GTP is quantified using affinity purification coupled to mass spectrometry. In some embodiments, KRas-GTP is quantified following purification. In some embodiments, KRas-GTP is quantified following purification by high performance liquid chromatography (HPLC). In some embodiments, KRas-GTP is quantified following purification by size exclusion chromatography.

In some embodiments, the method comprises detecting KRas-GTP in a sample. In some embodiments, KRas-GTP is detected in a biological sample. In some embodiments, a biological sample is a biological fluid, such as whole blood or whole blood components including red blood cells, white blood cells, platelets, serum and plasma, ascites, vitreous fluid, lymph fluid, synovial fluid, follicular fluid, seminal fluid, amniotic fluid, milk, saliva, sputum, tears, perspiration, mucus, cerebrospinal fluid, urine and other constituents of the body that may contain KRas-GTP. In various embodiments, the sample is a body sample from any animal. In various embodiments, the sample is a sample from a human. In some embodiments, the sample is from a mammal. In some embodiments, the sample is from a human subject, for example, when detecting KRas-GTP in a clinical sample. In some embodiments, the biological sample is from clinical patients or a patient with an oncogenic KRas mutation. In some embodiments, the biological sample is from clinical patients or a patient with an oncogenic KRas mutation, where the patient has been dosed with a KRas inhibitor as described herein. In some embodiments, the biological sample is from clinical patients or a patient with a $KRas^{G12C}$ oncogenic mutation. In some embodiments, the biological sample is from clinical patients or a patient with a $KRas^{G12D}$ oncogenic mutation. In some embodiments, the biological sample is from clinical patients or a patient with a $KRas^{G12V}$ oncogenic mutation. In some embodiments, the biological sample is from clinical patients or a patient with a $KRas^{G12R}$ oncogenic mutation. In some embodiments, the biological sample is from clinical patients or a patient with a $KRas^{G13D}$ oncogenic mutation. In some embodiments, the biological sample is a from clinical patients or patient with a $KRas^{Q61H}$ oncogenic mutation. In certain embodiments, the biological sample is serum or plasma. In certain embodiments, the biological sample is serum from a clinical patient. In certain embodiments the biological sample is urine. In certain embodiments, the biological sample is urine from a clinical patient.

In some embodiments, KRas-GTP is detected in a sample from a cancer patient. In some embodiments, KRas-GTP is detected in a sample from a cancer patient having a $KRas^{G12C}$ oncogenic mutation. In some embodiments, KRas-GTP is detected in a sample from a cancer patient having a $KRas^{G12D}$ oncogenic mutation. In some embodiments, KRas-GTP is detected in a sample from a cancer patient having a $KRas^{G12V}$ oncogenic mutation. In some embodiments, KRas-GTP is detected in a sample from a cancer patient having a $KRas^{G12R}$ oncogenic mutation. In some embodiments, KRas-GTP is detected in a sample from a cancer patient having a $KRas^{G13D}$ oncogenic mutation. In some embodiments, KRas-GTP is detected in a sample from a cancer patient having a $KRas^{Q61H}$ oncogenic mutation.

In some embodiments, the biological sample is from clinical patients or a patient treated with a $KRas^{G12C}$ covalent inhibitor (e.g., a compound that alkylates Cys12). In some embodiments, the biological sample is from clinical patients or a patient treated with a $KRas^{G12C}$ covalent inhibitor (e.g., a compound that alkylates Cys12), and the level of alkylation of $KRas^{G12C}$ is determined as described herein. In some embodiments, the biological sample is from clinical patients or a patient treated with a $KRas^{G12D}$ covalent inhibitor (e.g. an inhibitor that covalently binds to Asp12). In some embodiments, the biological sample is from clinical patients or a patient treated with a $KRas^{G12D}$ covalent inhibitor and the level of covalent binding of the inhibitor to $KRas^{G12D}$ is determined as described herein. In some embodiments, the biological sample is from clinical patients or a patient treated with a $KRas^{G13D}$ covalent inhibitor (e.g. an inhibitor that covalently binds to Asp13). In some embodiments, the biological sample is from clinical patients or a patient treated with a $KRas^{G13D}$ covalent inhibitor, and the level of covalent binding of the inhibitor to $KRas^{G13D}$ is determined as described herein.

In some embodiments, the biological sample is from clinical patients or a patient treated with a $KRas^{G12D}$ non-covalent inhibitor. In some embodiments, the biological sample is from clinical patients or a patient treated with a $KRas^{G12V}$ non-covalent inhibitor. In some embodiments, the biological sample is from clinical patients or a patient treated with a $KRas^{G12R}$ non-covalent inhibitor. In some embodiments, the biological sample is from clinical patients or a patient treated with a $KRas^{G13D}$ non-covalent inhibitor. In some embodiments, the biological sample is from clinical patients or a patient treated with a $KRas^{Q61H}$ non-covalent inhibitor. In some embodiments, the biological sample is from clinical patients or a patient treated with a $KRas^{G12C}$ SWII ligand. In some embodiments, the biological sample is from clinical patients or a patient treated with a KRas SWII ligand. In some embodiments, the biological sample is from clinical patients or a patient treated with an anti-KRas antibody.

In some embodiments, KRas-GDP is detected as part of a method of monitoring the treatment of a cancer in a patient. In some such embodiments, the method of monitoring the treatment of a cancer in a patient is performed using a biomarker assay as described herein. In some embodiments, KRas-GDP is detected as part of a method of monitoring the treatment of a $KRas^{G12C}$ mediated cancer in a patient, as described herein. In some embodiments, the patient has been treated a $KRas^{G12C}$ specific covalent inhibitor. In some embodiments, the $KRas^{G12C}$ specific covalent inhibitor is ARS-1952. In some embodiments, the $KRas^{G12C}$ specific covalent inhibitor is ARS-853. In some embodiments, the $KRas^{G12C}$ specific covalent inhibitor is MRTX849. In some embodiments, the $KRas^{G12C}$ specific covalent inhibitor is AMG-510. In some embodiments, the $KRas^{G12C}$ specific covalent inhibitor is GDC-6036. In some embodiments, the $KRas^{G12C}$ specific covalent inhibitor is ARS-3248. In some embodiments, the $KRas^{G12C}$ specific covalent inhibitor is LY3499446. In some embodiments, the $KRas^{G12C}$ specific covalent inhibitor is JNJ-74699157. In some embodiments, the patient has been treated a $KRas^{G12D}$ specific covalent inhibitor. In some embodiments, the patient has been treated a $KRas^{G12V}$ specific covalent inhibitor. In some embodiments, the patient has been treated a $KRas^{G12R}$ specific covalent inhibitor. In some embodiments, the patient has been treated a $KRas^{G13D}$ specific covalent inhibitor. In some embodiments, the patient has been treated a $KRas^{Q61H}$ specific covalent inhibitor.

In some embodiments, KRas-GDP or KRas-GTP is detected as part of a method of monitoring the treatment of a $KRas^{G12D}$ mediated cancer in a patient, as described herein. In some embodiments, the patient has been treated a $KRas^{G12D}$ specific covalent inhibitor. In some embodiments, the patient has been treated a $KRas^{G12D}$ specific non-covalent inhibitor. In some embodiments, KRas-GDP or KRas-GTP is detected as part of a method of monitoring the treatment of a $KRas^{G13D}$ mediated cancer in a patient, as described herein. In some embodiments, the patient has been treated a $KRas^{G13D}$ specific covalent inhibitor. In some embodiments, the patient has been treated a $KRas^{G13D}$ specific non-covalent inhibitor. In some embodiments, KRas-GDP or KRas-GTP is detected as part of a method of monitoring the treatment of a $KRas^{G12V}$ mediated cancer in a patient, as described herein. In some embodiments, the patient has been treated a $KRas^{G12V}$ specific non-covalent inhibitor. In some embodiments, KRas-GDP or KRas-GTP is detected as part of a method of monitoring the treatment of a $KRas^{G12R}$ mediated cancer in a patient, as described herein. In some embodiments, the patient has been treated a $KRas^{G12R}$ specific non-covalent inhibitor. In some embodiments, KRas-GDP or KRas-GTP is detected as part of a method of monitoring the treatment of a $KRas^{Q61H}$ mediated cancer in a patient, as described herein. In some embodiments, the patient has been treated a $KRas^{Q61H}$ specific non-covalent inhibitor.

v. Methods of Detecting KRas-GDP and KRas-GTP in a Sample

Also provided herein are methods of detecting KRas-GDP and KRas-GTP in a sample. In some embodiments, the relative amounts of KRas-GDP and KRas-GTP in a sample are determined. In some embodiments, the relative abundances of KRas-GDP and KRas-GTP in a sample are determined. In some embodiments, the proportion of KRas-GDP to KRas-GTP in a sample is determined. In some embodiments, the anti-KRas antibodies of the present disclosure are used in combination with an anti-KRas antibody that binds KRas-GTP with a higher affinity than KRas-GDP. In some embodiments, an anti-KRas antibody that binds KRas-GDP is labeled with a first label, and an anti-KRas antibody that preferentially binds KRas-GTP is labeled with a second label. In some embodiments, the first and second label are detected. In some embodiments, the detection and quantification of the signal from both the first and second labels allows for the separate quantification of both KRas-GDP and KRas-GTP levels in a sample. In some embodiments, the anti-KRas antibody that binds KRas-GDP and the anti-KRas antibody that preferentially binds KRas-GTP are not necessarily labeled with separate labels. In some embodiments, the amount of KRas-GDP and KRas-GTP is determined relative to a standard.

In some embodiments, KRas-GDP and KRas-GTP are detected by a variety of means known in the art, as described above. In some embodiments, KRas-GDP and KRas-GTP are detected using ELISA. In some embodiments, KRas-GDP and KRas-GTP are detected using immunohistochemistry, as provided herein. In some embodiments, KRas-GDP and KRas-GTP are detected using surface plasmon resonance (SPR). In some embodiments, KRas-GDP and KRas-GTP are detected using a BIOACORE SPR instrument. In some such embodiments, the KRas-GTP and/or KRas-GDP are detected using a biosensing surface as provided herein. In some embodiments, KRas-GDP and KRas-GTP are detected using flow cytometry. In some embodiments, KRas-GDP and KRas-GTP are detected using fluorescence-activated cell sorting (FACS). In some embodiments, KRas-GDP and KRas-GTP are detected using immunoprecipitation. In some embodiments, KRas-GDP and KRas-GTP are detected using affinity electrophoresis, such as an electrophoretic mobility shift assay. In some embodiments, KRas-GDP and KRas-GTP are detected using fluorescence polarization/anisotropy. In some embodiments, KRas-GDP and KRas-GTP are detected using affinity purification coupled to mass spectrometry. In some embodiments, KRas-GDP and KRas-GTP are detected using Bio-layer interferometry. In some embodiments, KRas-GDP and KRas-GTP are detected using microscale thermophoresis (MST).

As described above, in some embodiments, any of the anti-KRas antibodies described herein are used to detect KRas-GDP in a sample. In some embodiments, any of the anti-KRas antibodies described herein are used to detect KRas-GTP in a sample. In some embodiments, the anti-KRas antibody is a Class I antibody. In some embodiments, the anti-KRas antibody is a Class II antibody. In some embodiments, the anti-KRas antibody is 1E5. In some embodiments, the anti-KRas antibody is 2H11. In some embodiments, the anti-KRas antibody is 2A3. In some embodiments, the anti-KRas antibody is 3A12. In some embodiments, the anti-KRas antibody is 4G12. In some embodiments, the anti-KRas antibody is 1A5. In some embodiments, the anti-KRas antibody is 1D6. In some embodiments, the anti-KRas antibody is 2C1. In some embodiments, the anti-KRas antibody is 1A6. In some embodiments, the anti-KRas antibody is 1B7. In some embodiments, the anti-KRas antibody is 1F4. In some embodiments, the anti-KRas antibody is 1E5, 2H11, 2A3, 3A12, 1F4, 4G12, Ab1, Ab2, Ab3, Ab4, Ab5, Ab6, Ab7, or Ab8. In some embodiments, the anti-KRas antibody is 2H11, Ab1, Ab2, Ab3, Ab4, Ab5, Ab6, Ab7, or Ab8. In some embodiments, the anti-KRas antibody is Ab1, Ab2, Ab3, Ab4, Ab5, Ab6, Ab7, or Ab8. In some embodiments, the anti-KRas antibody is Ab1. In some embodiments, the anti-KRas antibody is Ab2. In some embodiments, the anti-KRas antibody is Ab3. In some embodiments, the anti-KRas antibody is Ab4. In some embodiments, the anti-KRas antibody is Ab5. In some embodiments, the anti-KRas antibody is Ab6. In some embodiments, the anti-KRas antibody is Ab7. In some embodiments, the anti-KRas antibody is Ab8.

In some embodiments, the anti-KRas antibody that binds KRas-GTP is a commercially available antibody. In some embodiments, the anti-KRas antibody that binds KRas-GTP is iDab6 (Tanaka, T. et al., *EMBO J* 2007; 26:3250-3259). In some embodiments, the anti-KRas antibody that binds KRas-GTP is Anti-Ras antibody EP1125Y (Abcam, ab52939). In some embodiments, the anti-KRas antibody that binds KRas-GTP is a KRas-2B specific Rabbit polyclonal antibody (Proteintech, Cat. No 16155-1-AP). In some embodiments, the anti-KRas antibody that binds KRas-GTP is Ras10 (Millipore, Cat. No 05-516). In some embodiments, the anti-KRas antibody that binds KRas-GTP is 3B10-2F2 (Sigma-Aldrich, Cat. No WH0003845M1). In some embodiments, the anti-KRas antibody that binds KRas-GTP is 234-4.2 (Millipore, Cat. No OP24).

vi. Methods of Obtaining a KRas Inhibitor

Also provided herein are methods of obtaining a KRas inhibitor. In some embodiments, the anti-KRas antibodies of the present disclosure stabilize and/or open the KRas SWII pocket. In some embodiments, the anti-KRas antibodies of the present disclosure stabilize and/or open the KRas SWII pocket of $KRas^{G12C}$, $KRas^{G12D}$, $KRas^{G12V}$, $KRas^{G12R}$, $KRas^{G13D}$, or $KRas^{Q61H}$. In some embodiments, an anti-KRas antibody of the present disclosure may be used to induce the open conformation of the SWII pocket. In some embodiments, the anti-KRas antibodies of the present disclosure may be used to induce the open conformation of the SWII pocket of $KRas^{G12C}$, $KRas^{G12D}$, $KRas^{G12V}$, $KRas^{G12R}$, $KRas^{G13D}$, or $KRas^{Q61H}$. In some embodiments the anti-KRas antibodies of the present disclosure lock the KRas pocket in an open conformation. In some embodiments, this allows for the screening of molecules that specifically target the open SWII pocket. In some embodiments, this allows for the screening of molecules that specifically target the open SWII pocket of $KRas^{G12C}$, $KRas^{G12D}$, $KRas^{G12V}$, $KRas^{G12R}$, $KRas^{G13D}$, or $KRas^{Q61H}$. In some embodiments, the anti-KRas antibody stabilizes the open conformation of the SWII pocket, and allows for the identification of a small molecule that covalently binds the SWII pocket. In some embodiments, the anti-KRas antibody stabilizes the open conformation of the SWII pocket, and allows for the identification of a small molecule that covalently binds the SWII pocket of $KRas^{G12C}$, $KRas^{G12D}$, $KRas^{G12V}$, $KRas^{G12R}$, $KRas^{G13D}$, or $KRas^{Q61H}$. For example, in some embodiments, KRas may be bound by an anti-KRas antibody of the present disclosure that induces the open conformation of the SWII pocket, and the KRas bound by an anti-KRas antibody may be used to obtain KRas inhibitors.

Accordingly, provided herein is a method for obtaining a KRas inhibitor comprising contacting an anti-KRas antibody with KRas, screening a library of compounds, and identifying a compound that binds to KRas. In some embodiments, the compound that binds to KRas inhibits KRas. In some embodiments, the KRas inhibitor inhibits a KRas mutant. In some embodiments, the KRas inhibitor inhibits an oncogenic KRas. In some embodiments, the KRas inhibitor inhibits $KRas^{G12C}$. In some embodiments, the KRas inhibitor inhibits $KRas^{G12R}$. In some embodiments, the KRas inhibitor inhibits $KRas^{G12V}$. In some embodiments, the KRas inhibitor inhibits $KRas^{Q61H}$. In some embodiments, the KRas inhibitor inhibits $KRas^{G12D}$. In some embodiments, the KRas inhibitor inhibits $KRas^{G13D}$.

In some embodiments, any of the anti-KRas antibodies of the present disclosure may be used in a method of obtaining a KRas inhibitor of a KRas mutant described herein. In some embodiments, the anti-KRas antibody is a Class I or a Class II antibody as provided herein. In some embodiments, the anti-KRas antibody is 1E5. In some embodiments, the anti-KRas antibody is 2H111. In some embodiments, the anti-KRas antibody is 2A3. In some embodiments, the anti-KRas antibody is 3A12. In some embodiments, the anti-KRas antibody is 4G12. In some embodiments, the anti-KRas antibody is 1A5. In some embodiments, the anti-KRas antibody is 1D6. In some embodiments, the anti-KRas antibody is 2C1. In some embodiments, the anti-KRas antibody is 1A6. In some embodiments, the anti-KRas antibody is 1B7. In some embodiments, the anti-KRas antibody is 1F4. In some embodiments, the anti-KRas antibody is 1E5, 2H111, 2A3, 3A12, 1F4, 4G12, Ab1, Ab2, Ab3, Ab4, Ab5, Ab6, Ab7, or Ab8. In some embodiments, the anti-KRas antibody is 2H11, Ab1, Ab2, Ab3, Ab4, Ab5, Ab6, Ab7, or Ab8. In some embodiments, the anti-KRas antibody is Ab1, Ab2, Ab3, Ab4, Ab5, Ab6, Ab7, or Ab8. In some embodiments, the anti-KRas antibody is Ab1. In some embodiments, the anti-KRas antibody is Ab2. In some embodiments, the anti-KRas antibody is Ab3. In some embodiments, the anti-KRas antibody is Ab4. In some embodiments, the anti-KRas antibody is Ab5. In some embodiments, the anti-KRas antibody is Ab6. In some embodiments, the anti-KRas antibody is Ab7. In some embodiments, the anti-KRas antibody is Ab8.

In some embodiments, high-throughput screening (HTS) is performed to identify a KRas inhibitor. In some embodiments, a chemical library is screened to identify a KRas inhibitor. In some embodiments, a library of natural products, or naturally occurring compounds is screened to identify a KRas inhibitor. In some embodiments, a peptide library is screened to identify a KRas inhibitor. In some embodiments, a peptidomimetic library is screened to identify a KRas inhibitor. In some embodiments, a library of antibodies or antigen-binding fragments is screened to identify a KRas inhibitor. In some embodiments, a library of small molecules is screened. In some embodiments, a library of covalent inhibitors is screened. In some embodiments, a library of non-covalent inhibitors is screened.

In some embodiments, the KRas inhibitor is obtained due to the identification of the KRas inhibitor in a screen. In some embodiments, the KRas inhibitor is identified due to its binding of KRas. In some embodiments, binding of KRas is detected through one of a variety of techniques known in the art for detecting protein-small molecule interactions (see, for example, McFedries, A., et al. *Chem. Biol.* 2013 20:5). In some embodiments, binding of KRas is detected using differential scanning fluorimetry (DSF). In some embodiments, binding of KRas is detected using a thermostability shift assay. In some embodiments, binding of KRas is detected using affinity capture coupled to stable isotope labeling of amino acids in cell culture (SILAC).

In some embodiments, the KRas inhibitor is identified due to its alteration of mutant KRas (e.g. a mutant KRas as described herein) activity in an assay of KRas activity. In some embodiments, an assay of KRas activity is designed based on the biology of KRas. In some embodiments, the KRas inhibitor is identified due to its alteration of the nucleotide-binding affinity of KRas. In some embodiments, the KRas inhibitor is identified due to its alteration of the ability of KRas to activate a RAF kinase. In some embodiments, the KRas inhibitor is identified due to its blocking of KRas RAF kinase activation. In some embodiments, the KRas inhibitor is identified due to its blocking of KRas binding a RAF kinase. In some embodiments, the KRas inhibitor is identified due to its blocking of a reporter that indicates KRas activation, for example, a GLUT1 transcriptional reporter.

In some embodiments, the KRas inhibitor covalently binds to a mutant KRas described herein. In some embodiments, the KRas inhibitor is a covalent inhibitor (e.g. an inhibitor that alkylates KRas). In some embodiments, the KRas inhibitor covalently binds a residue of the SWII pocket. In some embodiments, the KRas inhibitor binds to and alkylates the SWII pocket. In some embodiments, the KRas inhibitor alkylates a residue that is exposed to the surface of KRas when the SWII pocket is open. In some embodiments, the KRas inhibitor covalently modifies a residue of the SWII pocket. In some embodiments, the KRas inhibitor binds a cysteine residue in the SWII pocket of a mutant KRas described herein. In some embodiments, the KRas inhibitor alkylates a cysteine residue the SWII pocket of a mutant KRas described herein. In some embodiments, the KRas inhibitor binds a cysteine residue of the KRas SWII pocket. In some embodiments, the KRas inhibitor alkylates a cysteine residue of the KRas SWII pocket. In some embodiments, the KRas inhibitor allosterically inhibits KRas. In some embodiments, the KRas inhibitor prevents mutant KRas from entering the active, GTP-bound state. In some embodiments, the KRas inhibitor locks mutant KRas in the inactive, GDP-bound state. In some embodiments, the KRas inhibitor alters the nucleotide-binding affinity of mutant KRas. In some embodiments, the KRas inhibitor causes mutant KRas to preferentially bind GDP over GTP. In some embodiments, the KRas inhibitor causes mutant KRas to enter the inactive form of KRas. In some embodiments, the KRas inhibitor blocks GEF-catalyzed nucleotide exchange. In some embodiments, the KRas inhibitor blocks signaling downstream of mutant KRas. In some embodiments, the KRas inhibitor is an alkylating agent. In some embodiments, the KRas inhibitor inhibits $KRas^{G12C}$ and binds residue Cys12. In some embodiments, the mutant KRas described herein is $KRas^{G12D}$, $KRas^{G12R}$, $KRas^{G12V}$, $KRas^{G13C}$, or $KRas^{Q61H}$ In some embodiments, a KRas inhibitor is identified, where such an inhibitor binds to a mutant KRas described herein. In some embodiments, a molecular probe of KRas is identified. In some embodiments, the KRas inhibitor is a small molecule, such as an organic compound or an inorganic compound. In some embodiments, the small molecule is a naturally occurring small molecule or a synthetic small molecule. In some embodiments, the KRas inhibitor is a protein. In some embodiments, the KRas inhibitor is a peptide. In some embodiments, the KRas inhibitor is an antibody or an antibody fragment. In some embodiments, the KRas inhibitor is a nucleic acid. In some embodiments, a KRas inhibitor obtained by the methods of the present disclosure may be used as a drug to treat cancers associated with KRas mutation. In some embodiments, the KRas inhibitor is used as a drug to treat a $KRas^{G12C}$ mediated cancer.

vii. Methods of Detecting Alkylation of KRas-GDP in a Biological Sample

Provided herein are KRas alkylated conformation-specific antibodies that specifically bind the alkylated form of KRas. Accordingly, in some embodiments of the present disclosure, anti-KRas antibodies are used to detect the alkylation of KRas-GDP in a biological sample. In some embodiments, anti-KRas antibodies are used to detect the covalent binding (e.g. alkylation) of $KRas^{G12C}$ by the binding of covalent inhibitors in a biological sample. In some embodiments, the detection is done using a biomarker assay as described herein to measure target engagement. In some embodiments, a Class I antibody is used to detect alkylation of $KRas^{G12C}$. In some embodiments, a Class I antibody is used to detect covalent binding of $KRas^{G12D}$. In some embodiments, a Class I antibody is used to detect non-covalent binding of $KRas^{G12D}$. In some embodiments, a Class I antibody is used to detect non-covalent binding of $KRas^{G12V}$. In some embodiments, a Class I antibody is used to detect non-covalent binding of $KRas^{G12R}$. In some embodiments, a Class I antibody is used to detect non-covalent binding of $KRas^{G13D}$. In some embodiments, a Class I antibody is used to detect non-covalent binding of $KRas^{Q61H}$. In some embodiments, 1A5, 1D6, 2C1, 1A6, 1F4, or 1B7 is used to detect alkylated KRas or KRas non-covalently bound to a KRas non-covalent inhibitor as described herein. In some embodiments, 1E5, 2H11, 2A3, 3A12, 1F4, 4G12, Ab1, Ab2, Ab3, Ab4, Ab5, Ab6, Ab7, or Ab8 is used to detect alkylated KRas or KRas non-covalently bound to a KRas non-covalent inhibitor as described herein. In some embodiments, 2H11, Ab1, Ab2, Ab3, Ab4, Ab5, Ab6, Ab7, or Ab8 is used to detect alkylated KRas or KRas non-covalently bound to a KRas non-covalent inhibitor as described herein. In some embodiments, Ab1, Ab2, Ab3, Ab4, Ab5, Ab6, Ab7, or Ab8 is used to detect alkylated KRas or KRas non-covalently bound to a KRas non-covalent inhibitor as described herein.

In some embodiments, a method of detecting covalent binding (e.g., alkylation) of $KRas^{G12C}$ in a subject treated with a $KRas^{G12C}$ specific covalent inhibitor is provided, wherein the method comprises (a) administering any of the anti-KRas antibodies disclosed herein to the subject after treatment with the $KRas^{G12C}$ specific covalent inhibitor; and (b) detecting the antibody or antigen binding fragment thereof bound to the alkylated KRas. In some embodiments, the $KRas^{G12C}$ specific covalent inhibitor is ARS-1952. In some embodiments, the $KRas^{G12C}$ specific covalent inhibitor is ARS-853. In some embodiments, the $KRas^{G12C}$ specific covalent inhibitor is ARS-1620, MRTX849. In some embodiments, the $KRas^{G12C}$ specific covalent inhibitor is AMG-510. In some embodiments, the $KRas^{G12C}$ specific covalent inhibitor is GDC-6036. In some embodiments, the $KRas^{G12C}$ specific covalent inhibitor is ARS-3248. In some embodiments, the $KRas^{G12C}$ specific covalent inhibitor is LY3499446. In some embodiments, the $KRas^{G12C}$ specific covalent inhibitor is JNJ-74699157. In some embodiments, the $KRas^{G12C}$ specific covalent inhibitor is LY3537982.

In some embodiments, a method of detecting covalent binding of a covalent KRas inhibitor to $KRas^{G12D}$ in a subject treated with a $KRas^{G12D}$ specific covalent inhibitor is provided, wherein the method comprises (a) administering any of the anti-KRas antibodies disclosed herein to the subject after treatment with the $KRas^{G12D}$ specific covalent inhibitor; and (b) detecting the antibody or antigen binding fragment thereof bound to the KRas. In some embodiments, a method of detecting non-covalent binding of a non-covalent KRas inhibitor to $KRas^{G12D}$ in a subject treated with a $KRas^{G12D}$ specific non-covalent inhibitor is provided, wherein the method comprises (a) administering any of the anti-KRas antibodies disclosed herein to the subject after treatment with the $KRas^{G12D}$ specific non-covalent inhibitor; and (b) detecting the antibody or antigen binding fragment thereof bound to the KRas.

In some embodiments, the alkylation of KRas-GDP is detected by a variety of means known in the art, as described above. In some embodiments, the alkylation of KRas-GDP is detected using ELISA. In some embodiments, the alkylation of KRas-GDP is detected using immunohistochemistry, as provided herein. In some embodiments, the alkylation of KRas-GDP is detected using surface plasmon resonance (SPR). In some embodiments, the alkylation of KRas-GDP is detected using a BIOACORE SPR instrument. In some embodiments, the alkylation of KRas-GDP is detected using flow cytometry. In some embodiments, the alkylation of KRas-GDP is detected using fluorescence-activated cell sorting (FACS). In some embodiments, the alkylation of KRas-GDP is detected using immunoprecipitation. In some embodiments, the alkylation of KRas-GDP is detected using affinity electrophoresis, such as an electrophoretic mobility shift assay. In some embodiments, the alkylation of KRas-GDP is detected using fluorescence polarization/anisotropy. In some embodiments, the alkylation of KRas-GDP is detected using affinity purification coupled to mass spectrometry. In some embodiments, the alkylation of KRas-GDP is detected using Bio-layer interferometry. In some embodiments, the alkylation of KRas-GDP is detected using microscale thermophoresis (MST).

In some embodiments, the alkylation of KRas-GDP is detected in a biological sample. In some embodiments, a biological sample is a biological fluid, such as whole blood or whole blood components including red blood cells, white blood cells, platelets, serum and plasma, ascites, vitreous fluid, lymph fluid, synovial fluid, follicular fluid, seminal fluid, amniotic fluid, milk, saliva, sputum, tears, perspiration, mucus, cerebrospinal fluid, urine and other constituents of the body that may contain alkylated KRas. In various embodiments, the sample is a body sample from any animal. In various embodiments, the sample is a sample from a human.

In some embodiments, the sample is from a mammal. In some embodiments, the sample is from a human subject, for example, when detecting KRas-GDP alkylation state in a clinical sample. In some embodiments, the biological sample is from clinical patients or a patient with an oncogenic KRas mutation. In some embodiments, the biological sample is from clinical patients or a patient treated with a $KRas^{G12C}$ oncogenic mutation. In certain embodiments, the biological sample is serum or plasma. In certain embodiments, the biological sample is serum from a clinical patient. In certain embodiments the biological sample is urine. In certain embodiments, the biological sample is urine from a clinical patient.

viii. Methods of Detecting Alkylation of KRas-GDP In Vivo

In some embodiments of the present inventions, anti-KRas antibodies are used to detect the alkylation of KRas-GDP in vivo. In some embodiments, detection of KRas-GDP is in vivo when it occurs in a living cell, tissue, or organism. In some embodiments, the anti-KRas antibody is used to detect the alkylation of KRas-GDP in vivo in a cell. In some embodiments, the anti-KRas antibody is used to detect the alkylation of KRas-GDP in vivo in a cell culture. In some embodiments, the anti-KRas antibody is used to detect the alkylation of KRas-GDP in vivo in a tissue. In some embodiments, the anti-KRas antibody is used to detect the alkylation of KRas-GDP in vivo in a tissue. In some embodiments, the anti-KRas antibodies may be used to detect alkylated KRas-GDP in vivo in tumor cells. In some embodiments, the anti-KRas antibody is used to detect the alkylation of KRas-GDP in vivo in an organism. In some embodiments, the organism is a mammal. In some embodiments, the organism is a rodent. In some embodiments, the organism is a mouse. In some embodiments, the organism is a humans. The detection of alkylation of KRas-GDP in vivo may be accomplished by a variety of means known in the art, as described above. In some embodiments, the alkylation of KRas-GDP in vivo is detected by immunohistochemistry. In some embodiments, a Class I antibody is used to detect alkylation of KRasG12C. In some embodiments, 1A5, 1D6, 2C1, 1A6, 1F4, or 1B7 is used to detect alkylated KRas. In some embodiments, 1E5, 2H11, 2A3, 3A12, 1F4, 4G12, Ab1, Ab2, Ab3, Ab4, Ab5, Ab6, Ab7, or Ab8 is used to detect alkylated KRas. In some embodiments, 2H111, Ab1, Ab2, Ab3, Ab4, Ab5, Ab6, Ab7, or Ab8 is used to detect alkylated KRas. In some embodiments, Ab1, Ab2, Ab3, Ab4, Ab5, Ab6, Ab7, or Ab8 is used to detect alkylated KRas.

ix. Methods of Treatment and Monitoring Treatments

In some embodiments of the present disclosure, a method of treating a KRas mediated cancer is provided. In some embodiments, a method of treating a KRas$^{G12C}$ mediated cancer is provided. In some embodiments, the method comprises administering to a patient having such a cancer any of the anti-KRas antibodies disclosed herein. In some embodiments, the anti-KRas antibody is 1E5. In some embodiments, the anti-KRas antibody is 2H11. In some embodiments, the anti-KRas antibody is 2A3. In some embodiments, the anti-KRas antibody is 3A12. In some embodiments, the anti-KRas antibody is 4G12. In some embodiments, the anti-KRas antibody is 1A5. In some embodiments, the anti-KRas antibody is 1D6. In some embodiments, the anti-KRas antibody is 2C1. In some embodiments, the anti-KRas antibody is 1A6. In some embodiments, the anti-KRas antibody is 1B7. In some embodiments, the anti-KRas antibody is 2H11, Ab1, Ab2, Ab3, Ab4, Ab5, Ab6, Ab7, or Ab8. In some embodiments, the anti-KRas antibody is Ab1, Ab2, Ab3, Ab4, Ab5, Ab6, Ab7, or Ab8. In some embodiments, the anti-KRas antibody is Ab1. In some embodiments, the anti-KRas antibody is Ab2. In some embodiments, the anti-KRas antibody is Ab3. In some embodiments, the anti-KRas antibody is Ab4. In some embodiments, the anti-KRas antibody is Ab5. In some embodiments, the anti-KRas antibody is Ab6. In some embodiments, the anti-KRas antibody is Ab7. In some embodiments, the anti-KRas antibody is Ab8. In some embodiments, a therapeutically effective about of the anti-KRas antibody is administered. In some embodiments, the KRas$^{G12C}$ mediated cancer is NSCLC. In some embodiments, the KRas$^{G12C}$ mediated cancer is colon cancer. In some embodiments, the KRas$^{G12C}$ mediated cancer is pancreatic cancer. In some embodiments, the patient is a human patient.

In some embodiments, the patient had previously received a KRas inhibitor (e.g. covalent KRas inhibitor or non-covalent KRas inhibitor as described herein). In some embodiments, a KRas inhibitor is co-administered to the patient. In some embodiments, the KRas inhibitor is a SWII inhibitor. In some embodiments, the KRas inhibitor is a SWII ligand. In some embodiments, the KRas inhibitor is a covalent KRas inhibitor. In one embodiment, the covalent KRas inhibitor alkylates the SWII pocket of KRas as described herein. In some embodiments, the anti-KRas antibody improves the affinity of SWII inhibitors for KRas. In some embodiments, the anti-KRas antibody improves the affinity of SWII ligands for KRas. In some embodiments, the anti-KRas antibody improves the affinity of the KRas inhibitor (e.g. a covalent or non-covalent KRas inhibitor as described herein) for KRas. In some embodiments, the patient had previously received a KRas$^{G12C}$ inhibitor. In some embodiments, a KRas$^{G12C}$ inhibitor is co-administered to the patient. In some embodiments, the KRas$^{G12C}$ inhibitor is a SWII inhibitor. In some embodiments, the KRas$^{G12C}$ inhibitor is a SWII ligand. In some embodiments, the KRas$^{G12C}$ inhibitor is a covalent inhibitor. In some embodiments, the anti-KRas antibody improves the affinity of SWII inhibitors for KRas$^{G12C}$. In some embodiments, the anti-KRas antibody improves the affinity of SWII ligands for KRas$^{G12C}$. In some embodiments, the anti-KRas antibody improves the affinity of the KRas inhibitor for KRas$^{G12C}$. In some embodiments, the patient had previously received a KRas$^{G12D}$ covalent-inhibitor. In some embodiments, the patient had previously received a KRas$^{G12D}$ non-covalent-inhibitor. In some embodiments, a KRas$^{G12D}$inhibitor (e.g. covalent or non-covalent) is co-administered to the patient. In some embodiments, the KRas$^{G12D}$ inhibitor is a SWII inhibitor. In some embodiments, the KRas$^{G12D}$ inhibitor is a SWII ligand. In some embodiments, the anti-KRas antibody improves the affinity of SWII inhibitors for KRas$^{G12D}$. In some embodiments, the anti-KRas antibody improves the affinity of SWII ligands for KRas$^{G12D}$. In some embodiments, the anti-KRas antibody improves the affinity of the KRas inhibitor for KRas$^{G12D}$. In some embodiments, the anti-KRas antibody improves the affinity of the KRas inhibitor for KRas$^{G12V}$. In some embodiments, the anti-KRas antibody improves the affinity of the KRas inhibitor for KRas$^{G12R}$. In some embodiments, the anti-KRas antibody improves the affinity of the KRas inhibitor for KRas$^{G13D}$. In some embodiments, the anti-KRas antibody improves the affinity of the KRas inhibitor for KRas$^{Q61H}$.

In some embodiments, a method of monitoring the treatment of a cancer in a patient is provided. In some embodiments, a method of monitoring the treatment of a KRas$^{G12C}$ mediated cancer in a patient is provided. In some embodiments, a method of monitoring the progress of treatment of a KRas$^{G12C}$ mediated cancer in a patient is provided. In some embodiments, direct target engagement (e.g., binding of KRas$^{G12C}$) is monitored. In some embodiments, monitoring the treatment of a KRas$^{G12C}$ mediated cancer is followed by selecting a treatment dose to maximize efficacy while minimizing toxicity. In some embodiments, the patient has been treated with a covalent KRas$^{G12C}$ inhibitor. In some embodiments, the patient has been treated with a KRas$^{G12C}$ SWII ligand. In some embodiments, the patient has been treated with a KRas$^{G12C}$ covalent inhibitor. In some embodiments, an anti-KRas antibody may be used to detect the alkylation of KRas$^{G12C}$. In some embodiments, a Class I antibody is used to detect alkylation of KRas$^{G12C}$. In some embodiments, 1A5, 1D6, 2C1, 1A6, 1F4, or 1B7 is used to detect alkylated KRas. In some embodiments, 1E5, 2H11, 2A3, 3A12, 1F4, 4G12, Ab1, Ab2, Ab3, Ab4, Ab5, Ab6, Ab7, or Ab8 is used to detect alkylated KRas. In some embodiments, 2H11, Ab1, Ab2, Ab3, Ab4, Ab5, Ab6, Ab7, or Ab8 is used to detect alkylated KRas. In some embodiments, Ab1, Ab2, Ab3, Ab4, Ab5, Ab6, Ab7, or Ab8. In some embodiments, Ab1 is used to detect alkylated KRas. In some embodiments, detection of binding of the anti-KRas antibody is measured using any of the techniques described above. In some embodiments, detection of binding of the anti-KRas antibody is measured using surface plasmon resonance. In some embodiments, the anti-KRas antibody is be used to detect the alkylation of KRas$^{G12C}$ in a sample from the patient. In some embodiments, the sample is a clinical sample. In certain embodiments, a biological sample is a biological fluid, such as whole blood or whole blood components including red blood cells, white blood cells, platelets, serum and plasma, ascites, vitreous fluid, lymph fluid, synovial fluid, follicular fluid, seminal fluid, amniotic fluid, milk, saliva, sputum, tears, perspiration, mucus, cerebrospinal fluid, urine and other constituents of the body that may contain alkylated KRas$^{G12C}$. In some embodiments, binding of the anti-KRas antibody indicates that KRas$^{G12C}$ has been alkylated. In some embodiments, binding of the anti-KRas antibody indicates that KRas$^{G12C}$ has been drugged. In some embodiments, binding of the anti-KRas antibody indicates that KRas$^{G12C}$ has been covalently bound by a SWII ligand. In some embodiments, the treatment of cancer in a patient is monitored by assessing the relative level of KRas$^{G12C}$ alkylation. In some embodiments, the treatment of cancer in a patient is monitored by assessing the proportion of alkylated KRas$^{G12C}$.

x. Methods of Crystallizing KRas

In another aspect provided herein is a method of crystallizing KRas, wherein the KRas is optionally bound to a KRas inhibitor as described herein, the method comprising contacting an anti-KRas antibody described herein with KRas (e.g. KRas$^{G12C}$, KRas$^{G12D}$, KRas$^{G12V}$, KRas$^{G12R}$, KRas$^{G13D}$, or KRas$^{Q61H}$) and resolving a crystal structure of the complex. In one embodiment, the anti-KRas antibody opens and/or stabilizes the SWII pocket as described herein. In another embodiment, the anti-KRas antibody stabilizes a KRas-GDP form as described herein. In still another embodiment, the anti-KRas antibody opens and/or stabilizes the SWII pocket as described herein wherein a KRas inhibitor is covalently or non-covalently bound to at least one residue in the SWII pocket.

Further provided herein are anti-KRas antibodies that co-complex with KRas, thereby acting as a crystallization chaperone. A "crystallization chaperone" as used herein refers to an auxiliary protein that binds to a target of interest, enhances and modulates crystal packing, and/or provides high-quality phasing information. In one embodiment, the binding of an anti-KRas antibody to KRas as described herein increases crystal formation when compared to KRas alone. In one embodiment, the anti-KRas antibody is a Fab as described herein.

C. Kits

The assay methods of this invention can be provided in the form of a kit. In one embodiment, such a kit comprises an anti-KRas antibody or a composition comprising an anti-KRas antibody as described herein. In some embodiments, such a kit is a packaged combination including the basic elements of: a capture reagent comprised of an anti-KRas antibody against mutant KRas, KRas-GDP, and/or alkylated KRas, including specifically KRas$^{G12C}$, KRas$^{G12D}$, KRas$^{G12V}$, KRas$^{G12R}$, KRas$^{G13D}$, or KRas$^{Q61H}$ as described herein; a detectable (labeled or unlabeled) antibody that binds to KRas, KRas-GDP, and/or alkylated KRas, including specifically KRas$^{G12C}$, KRas$^{G12D}$, KRas$^{G12V}$, KRas$^{G12R}$, KRas$^{G13D}$, or KRas$^{Q61H}$ as described herein; and instructions on how to perform the assay method using these reagents. These basic elements are defined hereinabove.

The kit may further comprise a solid support for the capture reagents, which may be provided as a separate element or on which the capture reagents are already immobilized.

Hence, the capture antibodies in the kit may be immobilized on a solid support, or they may be immobilized on such support that is included with the kit or provided separately from the kit. In some embodiments, the capture reagents are coated on or attached to a solid material (for example, a microtiter plate, beads or a comb). The detectable antibodies may be labeled antibodies detected directly or unlabeled antibodies that are detected by labeled antibodies directed against the unlabeled antibodies raised in a different species. Where the label is an enzyme, the kit will ordinarily include substrates and cofactors required by the enzyme; where the label is a fluorophore, a dye precursor that provides the detectable chromophore; and where the label is biotin, an avidin such as avidin, streptavidin, or streptavidin conjugated to HRP or β-galactosidase with MUG.

In various embodiments, the anti-KRas antibody is one or more of any of the anti-KRas antibodies disclosed herein. For example, in some embodiments the anti-KRas antibody comprises a light chain variable region comprising a CDR-L1 comprising the amino acid sequence SGSSSNIGSNYVY (SEQ ID NO:9), a CDR-L2 comprising the amino acid sequence RNNQRPS (SEQ ID NO:10), and a CDR-L3 comprising the amino acid sequence AAWDERLSGWV (SEQ ID NO: 11) and a heavy chain variable region comprising a CDR-H1 comprising the amino acid sequence SSNWWS (SEQ ID NO:12), a CDR-H2 comprising the amino acid sequence EIYHSGSTNYNPSLKS (SEQ ID NO:13), and a CDR-H3 comprising the amino acid sequence GSSSWYDLGPFDY (SEQ ID NO:14). In some embodiments the anti-KRas antibody comprises a light chain variable region comprising a CDR-L1 comprising the amino acid sequence SGSSSNIGSNYVY (SEQ ID NO:9), a CDR-L2 comprising the amino acid sequence RNNQRPS (SEQ ID NO:10), and a CDR-L3 comprising the amino acid sequence AAWDERLSGWV (SEQ ID NO: 11) and a heavy chain variable region comprising a CDR-H1 comprising the amino acid sequence GSSIWSSN (SEQ ID NO:91), a CDR-H2 comprising the amino acid sequence EIYHSGSTNYNPSLKS (SEQ ID NO:13), and a CDR-H3 comprising the amino acid sequence GSSSWYDLGPFDY (SEQ ID NO:14). In some embodiments the anti-KRas antibody comprises a light chain variable region comprising a CDR-L1 comprising the amino acid sequence SGSSSNIGSNYVY (SEQ ID NO:9), a CDR-L2 comprising the amino acid sequence RNNQRPS (SEQ ID NO:10), and a CDR-L3 comprising the amino acid sequence AAWDERLSGWV (SEQ ID NO: 11) and a heavy chain variable region comprising a CDR-H1 comprising the amino acid sequence GSNISSSN (SEQ ID NO:92), a CDR-H2 comprising the amino acid sequence EIYHSGSTNYNPSLKS (SEQ ID NO:13), and a CDR-H3 comprising the amino acid sequence GSSSWYDLGPFDY (SEQ ID NO:14). In some embodiments the anti-KRas antibody comprises a light chain variable region comprising a CDR-L1 comprising the amino acid sequence SGSSSNIGSNYVY (SEQ ID NO:9), a CDR-L2 comprising the amino acid sequence RNNQRPS (SEQ ID NO:10), and a CDR-L3 comprising the amino acid sequence AAWDERLSGWV (SEQ ID NO: 11) and a heavy chain variable region comprising a CDR-H1 comprising the amino acid sequence GSSIFSSN (SEQ ID NO:93), a CDR-H2 comprising the amino acid sequence EIYHSGSTNYNPSLKS (SEQ ID NO:13), and a CDR-H3 comprising the amino acid sequence GSSSWYDLGPFDY (SEQ ID NO:14). In some embodiments the anti-KRas antibody comprises a light chain variable region comprising a CDR-L1 comprising the amino acid sequence SGSSSNIGSNYVY (SEQ ID NO:9), a CDR-L2 comprising the amino acid sequence RNNQRPS (SEQ ID NO:10), and a CDR-L3 comprising the amino acid sequence AAWDERLSGWV (SEQ ID NO: 11) and a heavy chain variable region comprising a CDR-H1 comprising the amino acid sequence GSSIMSSN (SEQ ID NO:94), a CDR-H2 comprising the amino acid sequence EIYHSGSTNYNPSLKS (SEQ ID NO:13), and a CDR-H3 comprising the amino acid sequence GSSSWYDLGPFDY (SEQ ID NO:14). In some embodiments the anti-KRas antibody comprises a light chain variable region comprising a CDR-L1 comprising the amino acid sequence SGSSSNIGSNYVY (SEQ ID NO:9), a CDR-L2 comprising the amino acid sequence RNNQRPS (SEQ ID NO:10), and a CDR-L3 comprising the amino acid sequence AAWDERLSGWV (SEQ ID NO: 11) and a heavy chain variable region comprising a CDR-H1 comprising the amino acid sequence GSSIYSSN (SEQ ID NO:95), a CDR-H2 comprising the amino acid sequence EIYHSGSTNYNPSLKS (SEQ ID NO:13), and a CDR-H3 comprising the amino acid sequence GSSSWYDLGPFDY (SEQ ID NO:14). In some embodiments the anti-KRas antibody comprises a light chain variable region comprising a CDR-L1 comprising the amino acid sequence SGSSSNIG-SNYVY (SEQ ID NO:9), a CDR-L2 comprising the amino acid sequence RNNQRPS (SEQ ID NO:10), and a CDR-L3 comprising the amino acid sequence AAWDERLSGWV (SEQ ID NO: 11) and a heavy chain variable region comprising a CDR-H1 comprising the amino acid sequence GGNIWSSN (SEQ ID NO:96), a CDR-H2 comprising the amino acid sequence EIYHSGSTNYNPSLKS (SEQ ID NO:13), and a CDR-H3 comprising the amino acid sequence GSSSWYDLGPFDY (SEQ ID NO:14). In some embodiments the anti-KRas antibody comprises a light chain variable region comprising a CDR-L1 comprising the amino acid sequence SGSSSNIGSNYVY (SEQ ID NO:9), a CDR-L2 comprising the amino acid sequence RNNQRPS (SEQ ID NO:10), and a CDR-L3 comprising the amino acid sequence AAWDERLSGWV (SEQ ID NO: 11) and a heavy chain variable region comprising a CDR-H1 comprising the amino acid sequence KGSIWASH (SEQ ID NO:97), a CDR-H2 comprising the amino acid sequence EIYHSG-STNYNPSLKS (SEQ ID NO:13), and a CDR-H3 comprising the amino acid sequence GSSSWYDLGPFDY (SEQ ID NO:14). In some embodiments the anti-KRas antibody comprises a light chain variable region comprising a CDR-L1 comprising the amino acid sequence SGSSSNIG-SNYVY (SEQ ID NO:9), a CDR-L2 comprising the amino acid sequence RNNQRPS (SEQ ID NO:10), and a CDR-L3 comprising the amino acid sequence AAWDERLSGWV (SEQ ID NO: 11) and a heavy chain variable region comprising a CDR-H1 comprising the amino acid sequence KGSIWSSN (SEQ ID NO:98), a CDR-H2 comprising the amino acid sequence EIYHSGSTNYNPSLKS (SEQ ID NO:13), and a CDR-H3 comprising the amino acid sequence GSSSWYDLGPFDY (SEQ ID NO:14). In some embodiments, the anti-KRas antibody comprises a light chain variable region comprising a CDR-L1 comprising the amino acid sequence RASQGIRNDLG (SEQ ID NO:1), a CDR-L2 comprising the amino acid sequence AASSLQS (SEQ ID NO: 2), and a CDR-L3 comprising the amino acid sequence LQDHDYPLT (SEQ ID NO:3), and a heavy chain variable region comprising a CDR-H1 comprising the amino acid sequence SYSMN (SEQ ID NO:4), a CDR-H2 comprising the amino acid sequence YISSSSSTIYYADSVKG (SEQ ID NO: 5), and a CDR-H3 comprising the amino acid sequence GFYVRNWFDP (SEQ ID NO:6). In some embodiments, the anti-KRas antibody comprises a light chain variable region comprising a CDR-L1 comprising the amino acid sequence RASQGISSYLA (SEQ ID NO:17), a CDR-L2 comprising the amino acid sequence AASSLQS (SEQ ID NO:18), and a CDR-L3 comprising the amino acid sequence QQYYSYPFT (SEQ ID NO:19), and a heavy chain variable region comprising a CDR-H1 comprising the amino acid sequence SYAMS (SEQ ID NO:20), a CDR-H2 comprising the amino acid sequence AISSSGSSTYYADSVKG (SEQ ID NO:21), and a CDR-H3 comprising the amino acid sequence DQGGYGYPGESWFDY (SEQ ID NO:22). In some embodiments, the anti-KRas antibody comprises a light chain variable region comprising a CDR-L1 comprising the amino acid sequence RASQSISSYLN (SEQ ID NO:25), a CDR-L2 comprising the amino acid sequence AASSLQS (SEQ ID NO:26), and a CDR-L3 comprising the amino acid sequence QQSYSPPWT (SEQ ID NO:27), and a heavy chain variable region comprising a CDR-H1 comprising the amino acid sequence SYSMN (SEQ ID NO:28), a CDR-H2 comprising the amino acid sequence SIS-SSSSYIYYADSVKG (SEQ ID NO:29), and a CDR-H3 comprising the amino acid sequence AFYSYMDV (SEQ ID NO:30). In some embodiments, the anti-KRas antibody comprises a light chain variable region comprising a CDR-L1 comprising the amino acid sequence RSSQSLLHSNGY-NYLD (SEQ ID NO:33), a CDR-L2 comprising the amino acid sequence LGSNRAS (SEQ ID NO:34), and a CDR-L3 comprising the amino acid sequence MQALQTPLT (SEQ ID NO:35), and a heavy chain variable region comprising a CDR-H1 comprising the amino acid sequence SSNWWS (SEQ ID NO:36), a CDR-H2 comprising the amino acid sequence EIYHSGSTNYNPSLKS (SEQ ID NO:37), and a CDR-H3 comprising the amino acid sequence ERTIL-TGYYGFDY (SEQ ID NO:38). In some embodiments, the anti-KRas antibody comprises a light chain variable region comprising a CDR-L1 comprising the amino acid sequence SGSSSNIGNNYVS (SEQ ID NO:41), a CDR-L2 comprising the amino acid sequence DNNKRPS (SEQ ID NO:42), and CDR-L3 comprising the amino acid sequence GTWDSSLTGYV (SEQ ID NO: 43), and a heavy chain variable region comprising a CDR-H1 comprising the amino acid sequence SYAIS (SEQ ID NO:44), a CDR-H2 comprising the amino acid sequence GIIPIFGTANYAQKFQG (SEQ ID NO:45), and a CDR-H3 comprising the amino acid sequence YYDFWSGYPGGLFDV (SEQ ID NO:46). In some embodiments, the anti-KRas antibody comprises a light chain variable region comprising a CDR-L1 comprising the amino acid sequence SGSSSNIGSNYVY (SEQ ID NO:81), a CDR-L2 comprising the amino acid sequence RNNQRPS (SEQ ID NO:82), and a CDR-L3 comprising the amino acid sequence AAWDDSLSGWV (SEQ ID NO: 83) and a heavy chain variable region comprising a CDR-H1 comprising the amino acid sequence SYSMN (SEQ ID NO:84), a CDR-H2 comprising the amino acid sequence YISSSSSTIYYADSVKG (SEQ ID NO:85), and a CDR-H3 comprising the amino acid sequence SFGPYAFDV (SEQ ID NO:86). In some embodiments, the anti-KRas antibody comprises a light chain variable region comprising a CDR-L1 comprising the amino acid sequence SGSSS-NIGNNYVS (SEQ ID NO:49), a CDR-L2 comprising the amino acid sequence DNNKRPS (SEQ ID NO:50), and a CDR-L3 comprising the amino acid sequence GTWDSSLTGWV (SEQ ID NO: 51), and a heavy chain variable region comprising a CDR-H1 comprising the amino acid sequence SYAIS (SEQ ID NO:52), a CDR-H2 comprising the amino acid sequence GIIPIFGTANYAQKFQG (SEQ ID NO:53), and a CDR-H3 comprising the amino acid sequence YYDFWSGYPGGLFDV (SEQ ID NO:54). In some embodiments, the anti-KRas antibody comprises a light chain variable region comprising a CDR-L1 comprising the amino acid sequence QGDSLRSYYAS (SEQ ID NO:57), a CDR-L2 comprising the amino acid sequence GKNNRPS (SEQ ID NO:58), and a CDR-L3 comprising the amino acid sequence NSRDSSGNHWV (SEQ ID NO: 59), and a heavy chain variable region comprising a CDR-H1 comprising the amino acid sequence SYSMN (SEQ ID NO:60), a CDR-H2 comprising the amino acid sequence SISSSSSYIYYADSVKG (SEQ ID NO:61), and a CDR-H3 comprising the amino acid sequence TNNYGYRYFDY (SEQ ID NO:62). In some embodiments, the anti-KRas antibody comprises a light chain variable region comprising a CDR-L1 comprising the amino acid sequence QGD-SLRSYYAS (SEQ ID NO:65), a CDR-L2 comprising the amino acid sequence GKNNRPS (SEQ ID NO:66), and a CDR-L3 comprising the amino acid sequence NSRD-STDNHLWV (SEQ ID NO: 67), and a heavy chain variable region comprising a CDR-H1 comprising the amino acid sequence SYSMN (SEQ ID NO:68), a CDR-H2 comprising the amino acid sequence SISSSSSYIYYADSVKG (SEQ ID NO:69), and a CDR-H3 comprising the amino acid sequence ATSSGYYYFDY (SEQ ID NO:70). In some embodiments, the anti-KRas antibody comprises a light chain variable region comprising a CDR-L1 comprising the amino acid sequence SGSSSNIGNNYVS (SEQ ID NO:73), a CDR-L2 comprising the amino acid sequence DNNKRPS (SEQ ID NO:74), and a CDR-L3 comprising the amino acid sequence GTWDNSLSVWV (SEQ ID NO: 75), and a heavy chain variable region comprising a CDR-H1 comprising the amino acid sequence SYSMN (SEQ ID NO:76), a CDR-H2 comprising the amino acid sequence YISSSSSTIYYADSVKG (SEQ ID NO:77), and a CDR-H3 comprising the amino acid sequence GKGIVGWGFFGMDV (SEQ ID NO:78).

The kit also typically contains KRas, KRas-GDP, KRas-GTP, and/or alkylated KRas as a standard as well as other additives such as stabilizers, washing and incubation buffers, and the like.

The components of the kit will be provided in predetermined ratios, with the relative amounts of the various reagents suitably varied to provide for concentrations in solution of the reagents that substantially maximize the sensitivity of the assay. Particularly, the reagents may be provided as dry powders, usually lyophilized, including excipients, which on dissolution will provide for a reagent solution having the appropriate concentration for combining with the sample to be tested.

In some embodiments, a kit comprising an anti-KRas antibody as described herein for use in a method as described herein (e.g., in a method of detecting KRas, KRas-GDP, and/or alkylated KRas, including specifically KRas$^{G12C}$, KRas$^{G12D}$, KRas$^{G12V}$, KRas$^{G12R}$, KRas$^{G13D}$, or KRas$^{Q61H}$ as described herein), is provided. In some embodiments, the kit further comprises an anti-KRas antibody coated or attached to a comb for use in a method of detecting KRas, KRas-GDP, KRas-GTP, and/or alkylated KRas.

In some embodiments, a kit for use in a method of monitoring the treatment of cancer in a patient, as described herein, is provided. In some embodiments, a kit for use in a biomarker assay for measuring target engagement of one or more KRas inhibitors described herein to a KRas protein (e.g. KRas$^{G12C}$), as described herein, is provided. In some embodiments, a kit for use in a method of detecting alkylation of KRas-GDP or KRas-GTP in a biological sample, as described herein, is provided. In some embodiments, a kit comprises one or more KRas alkylated conformation-specific antibodies that specifically bind the alkylated form of KRas. Accordingly, in some embodiments of the present disclosure, a kit comprises one or more anti-KRas antibodies that are used to detect the alkylation of KRas-GDP in a biological sample. In some embodiments, a kit comprises one or more anti-KRas antibodies that are used to detect the covalent binding (e.g. alkylation) of KRas$^{G12C}$ by the binding of covalent inhibitors in a biological sample. In some embodiments, a kit comprises reagents to detect KRas, KRas-GDP, KRas-GTP, and/or alkylated KRas, including specifically KRas$^{G12C}$, KRas$^{G12D}$, KRas$^{G12V}$, KRas$^{G12R}$, KRas$^{G13D}$, or KRas$^{Q61H}$ as described herein, according to a biomarker assay as described herein, to measure target engagement. In some embodiments, a kit comprises a Class I antibody used to detect alkylation of KRas$^{G12C}$. In some embodiments, a kit comprises a Class I antibody used to detect covalent binding of KRas$^{G12D}$. In some embodiments, a kit comprises a Class I antibody used to detect non-covalent binding of KRas$^{G12D}$. In some embodiments, a kit comprises a Class I antibody used to detect non-covalent binding of KRas$^{G12V}$. In some embodiments, a kit comprises a Class I antibody used to detect non-covalent binding of KRas$^{G12R}$. In some embodiments, a kit comprises a Class I antibody used to detect non-covalent binding of KRas$^{G13D}$. In some embodiments, a kit comprises a Class I antibody used to detect non-covalent binding of KRas$^{Q61H}$. In some embodiments, a kit comprises 1A5, 1D6, 2C1, 1A6, 1F4, or 1B7, used to detect alkylated KRas or KRas non-covalently bound to a KRas non-covalent inhibitor as described herein. In some embodiments, a kit comprises 1E5, 2H11, 2A3, 3A12, 1F4, 4G12, Ab1, Ab2, Ab3, Ab4, Ab5, Ab6, Ab7, or Ab8, used to detect alkylated KRas or KRas non-covalently bound to a KRas non-covalent inhibitor as described herein. In some embodiments, a kit comprises 2H11, Ab1, Ab2, Ab3, Ab4, Ab5, Ab6, Ab7, or Ab8, used to detect alkylated KRas or KRas non-covalently bound to a KRas non-covalent inhibitor as described herein. In some embodiments, a kit comprises Ab1, Ab2, Ab3, Ab4, Ab5, Ab6, Ab7, or Ab8, used to detect alkylated KRas or KRas non-covalently bound to a KRas non-covalent inhibitor as described herein.

In some embodiments, a kit for use in a method of detecting covalent binding (e.g., alkylation) of KRas$^{G12C}$ in a subject treated with a KRas$^{G12C}$ specific covalent inhibitor is provided, wherein the method comprises (a) administering any of the anti-KRas antibodies disclosed herein to the subject after treatment with the KRas$^{G12C}$ specific covalent inhibitor; and (b) detecting the antibody or antigen binding fragment thereof bound to the alkylated KRas. In some embodiments, the KRas$^{G12C}$ specific covalent inhibitor is ARS-1952. In some embodiments, the KRas$^{G12C}$ specific covalent inhibitor is ARS-853. In some embodiments, the KRas$^{G12C}$ specific covalent inhibitor is ARS-1620, MRTX849. In some embodiments, the KRas$^{G12C}$ specific covalent inhibitor is AMG-510. In some embodiments, the KRas$^{G12C}$ specific covalent inhibitor is GDC-6036. In some embodiments, the KRas$^{G12C}$ specific covalent inhibitor is ARS-3248. In some embodiments, the KRas$^{G12C}$ specific covalent inhibitor is LY3499446. In some embodiments, the KRas$^{G12C}$ specific covalent inhibitor is JNJ-74699157. In some embodiments, the KRas$^{G12C}$ specific covalent inhibitor is LY3537982.

In some embodiments, a kit for use a method of detecting covalent binding of a covalent KRas inhibitor to KRas$^{G12D}$ in a subject treated with a KRas$^{G12D}$ specific covalent inhibitor is provided, wherein the method comprises (a) administering any of the anti-KRas antibodies disclosed herein to the subject after treatment with the KRas$^{G12D}$ specific covalent inhibitor; and (b) detecting the antibody or antigen binding fragment thereof bound to the KRas. In some embodiments, a kit for use in a method of detecting non-covalent binding of a non-covalent KRas inhibitor to KRas$^{G12D}$ in a subject treated with a KRas$^{G12D}$ specific non-covalent inhibitor is provided, wherein the method comprises (a) administering any of the anti-KRas antibodies disclosed herein to the subject after treatment with the KRas$^{G12D}$ specific non-covalent inhibitor; and (b) detecting the antibody or antigen binding fragment thereof bound to the KRas, is provided.

In some embodiments, a kit comprises reagents and instructions to detect the alkylation of KRas-GDP using one or more of a variety of means known in the art, as described herein. In some embodiments, a kit comprises reagents and instructions to detect the alkylation of KRas-GDP using an ELISA. In some embodiments, a kit comprises reagents and instructions to detect the alkylation of KRas-GDP using immunohistochemistry, as provided herein. In some embodiments, a kit comprises reagents and instructions to detect the alkylation of KRas-GDP using surface plasmon resonance (SPR). In some embodiments, a kit comprises reagents and instructions to detect the alkylation of KRas-GDP using a BIOACORE SPR instrument. In some embodiments, a kit comprises reagents and instructions to detect the alkylation of KRas-GDP using flow cytometry. In some embodiments, a kit comprises reagents and instructions to detect the alkylation of KRas-GDP using fluorescence-activated cell sorting (FACS). In some embodiments, a kit comprises reagents and instructions to detect the alkylation of KRas-GDP using immunoprecipitation. In some embodiments, a kit comprises reagents and instructions to detect the alkylation of KRas-GDP using affinity electrophoresis, such as an electrophoretic mobility shift assay. In some embodiments, a kit comprises reagents and instructions to detect the alkylation of KRas-GDP using fluorescence polarization/anisotropy. In some embodiments, a kit comprises reagents and instructions to detect the alkylation of KRas-GDP using affinity purification coupled to mass spectrometry. In some embodiments, a kit comprises reagents and instructions to detect the alkylation of KRas-GDP using Bio-layer interferometry. In some embodiments, a kit comprises reagents and instructions to detect the alkylation of KRas-GDP using microscale thermophoresis (MST).

In some embodiments, a kit for use in detecting the alkylation of KRas-GDP in a biological sample. In some embodiments, a kit is provided for use in detecting the alkylation of KRas-GDP in a biological sample, wherein the biological sample is a biological fluid, such as whole blood or whole blood components including red blood cells, white blood cells, platelets, serum and plasma, ascites, vitreous fluid, lymph fluid, synovial fluid, follicular fluid, seminal fluid, amniotic fluid, milk, saliva, sputum, tears, perspiration, mucus, cerebrospinal fluid, urine and other constituents of the body that may contain alkylated KRas. In some embodiments, the sample is a body sample from any animal. In some embodiments, the sample is a sample from a human.

In some embodiments, a kit for use in detecting the alkylation of KRas-GDP in a sample from a mammal is provided. In some embodiments, the sample is from a human subject, for example, when detecting KRas-GDP alkylation state in a clinical sample. In some embodiments, the biological sample is from clinical patients or a patient with an oncogenic KRas mutation. In some embodiments, the biological sample is from clinical patients or a patient treated with a $KRas^{G12C}$ oncogenic mutation. In certain embodiments, the biological sample is serum or plasma. In certain embodiments, the biological sample is serum from a clinical patient. In certain embodiments the biological sample is urine. In certain embodiments, the biological sample is urine from a clinical patient.

EMBODIMENTS

Embodiment No 1. An isolated antibody or antigen binding fragment thereof that binds to a human KRas, wherein the antibody specifically binds to the KRas bound to GDP (KRas-GDP) with a higher affinity than to the KRas bound to GTP (KRas-GTP).

Embodiment No 2. An isolated antibody or antigen binding fragment thereof that binds to a human KRas, wherein the antibody specifically binds to the KRas bound to GTP (KRas-GTP) with a higher affinity than to the KRas bound to GDP (KRas-GDP).

Embodiment No 3. The isolated antibody or antigen binding fragment thereof of embodiment 1 or embodiment 2, wherein the antibody or antigen binding fragment thereof is a KRas alkylated conformation specific antibody.

Embodiment No 4. The isolated antibody or antigen binding fragment thereof of any one of embodiments 1-3, wherein the antibody or antigen binding fragment thereof opens and stabilizes the SWII pocket.

Embodiment No 5. The isolated antibody or antigen binding fragment thereof of any one of embodiments 1-4, wherein the human KRas is a KRas mutant selected from the group consisting of $KRas^{G12C}$, $KRas^{G12V}$, $KRas^{G12R}$, $KRas^{Q61H}$, $KRas^{G12D}$ and, $KRas^{G13D}$.

Embodiment No 6. The isolated antibody or antigen binding fragment thereof of embodiment 5, wherein the human KRas is a KRas mutant selected from the group consisting of $KRas^{G12C}$, KRas G12V $KRas^{G12D}$, and $KRas^{G13D}$.

Embodiment No 7. The isolated antibody or antigen binding fragment thereof embodiment 6, wherein the KRas mutant is $KRas^{G12C}$.

Embodiment No 8. The isolated antibody or antigen binding fragment thereof of embodiment 7, wherein the $KRas^{G12C}$-GDP is alkylated with a $KRas^{G12C}$ specific covalent inhibitor.

Embodiment No 9. The isolated antibody or antigen binding fragment thereof of embodiment 8, wherein the isolated antibody or antigen binding fragment is an alkylated conformation specific KRas antibody that binds to $KRas^{G12C}$-GDP alkylated with MRTX849, AMG-510, GDC-6036, ARS-3248, LY3499446, LY3537982, or JNJ-74699157.

Embodiment No 10. The isolated antibody or antigen binding fragment thereof of any one of embodiments 1-9, wherein the antibody or antigen binding fragment thereof stabilizes the SWII pocket of a KRas mutant protein.

Embodiment No 11. The isolated antibody or antigen binding fragment thereof of any one of embodiments 1-10, wherein the antibody or antigen binding fragment thereof comprises (a) a light chain variable region comprising:
  (i) CDR-L1 comprising the amino acid sequence SGSSSNIGSNYVY (SEQ ID NO:9);
  (ii) CDR-L2 comprising the amino acid sequence RNNQRPS (SEQ ID NO:10);
  (iii) CDR-L3 comprising the amino acid sequence AAWDERLSGWV (SEQ ID NO:11); and
(b) a heavy chain variable region comprising:
  (i) CDR-H1 comprising the amino acid sequence SSNWWS (SEQ ID NO:12);
  (ii) CDR-H2 comprising the amino acid sequence EIYHSGSTNYNPSLKS (SEQ ID NO:13); and
  (iii) CDR-H3 comprising the amino acid sequence GSSSWYDLGPFDY (SEQ ID NO: 14).

Embodiment No 12. The isolated antibody or antigen binding fragment thereof of embodiment 11, wherein the light chain variable region comprises the amino acid sequence of SEQ ID NO:15 and the heavy chain variable region comprises the amino acid sequence of SEQ ID NO: 16.

Embodiment No 13. The isolated antibody or antigen binding fragment thereof of any one of embodiments 1-10, wherein the antibody or antigen binding fragment thereof comprises (a) a light chain variable region comprising:
  (i) CDR-L1 comprising the amino acid sequence SEQ ID NO:9;
  (ii) CDR-L2 comprising the amino acid sequence SEQ ID NO:10;

(iii) CDR-L3 comprising the amino acid sequence SEQ ID NO: 11; and (b) a heavy chain variable region comprising:

(i) CDR-H1 comprising one of the amino acid sequences selected from the group consisting of SEQ ID NO:91, SEQ ID NO:92, SEQ ID NO:93, SEQ ID NO:94, SEQ ID NO:95, SEQ ID NO:96, SEQ ID NO:97, and SEQ ID NO: 98;

(ii) CDR-H2 comprising the amino acid sequence SEQ ID NO: 13; and (iii) CDR-H3 comprising the amino acid sequence SEQ ID NO: 14.

Embodiment No 14. The isolated antibody or antigen binding fragment thereof of embodiment 13, wherein the light chain variable region comprises the amino acid sequence of SEQ ID NO:15 and the heavy chain variable region comprises one of the amino acid sequences selected from the group consisting of SEQ ID NO:99, SEQ ID NO: 100, SEQ ID NO:101, SEQ ID NO:102, SEQ ID NO:103, SEQ ID NO:104, SEQ ID NO:105, and SEQ ID NO: 106.

Embodiment No 15. The isolated antibody or antigen binding fragment thereof of any one of embodiments 1-10, wherein the antibody comprises (a) a light chain variable region comprising:

(i) CDR-L1 comprising the amino acid sequence RASQGIRNDLG (SEQ ID NO: 1);

(ii) CDR-L2 comprising the amino acid sequence AASSLQS (SEQ ID NO:2);

(iii) CDR-L3 comprising the amino acid sequence LQDHDYPLT (SEQ ID NO: 3); and (b) a heavy chain variable region comprising:

(i) CDR-H1 comprising the amino acid sequence SYSMN (SEQ ID NO:4);

(ii) CDR-H2 comprising the amino acid sequence YISSSSSTIYYADSVKG (SEQ ID NO:5); and (iii) CDR-H3 comprising the amino acid sequence GFYVRNWFDP (SEQ ID NO:6).

Embodiment No 16. The isolated antibody or antigen binding fragment thereof of embodiment 15, wherein the light chain variable region comprises the amino acid sequence of SEQ ID NO:7 and the heavy chain variable region comprises the amino acid sequence of SEQ ID NO: 8.

Embodiment No 17. The isolated antibody or antigen binding fragment thereof of any one of embodiments 1-10, wherein the antibody or antigen binding fragment thereof comprises (a) a light chain variable region comprising:

(i) CDR-L1 comprising the amino acid sequence RASQGISSYLA (SEQ ID NO: 17);

(ii) CDR-L2 comprising the amino acid sequence AASSLQS (SEQ ID NO: 18);

(iii) CDR-L3 comprising the amino acid sequence QQYYSYPFT (SEQ ID NO: 19); and (b) a heavy chain variable region comprising:

(i) CDR-H1 comprising the amino acid sequence SYAMS (SEQ ID NO:20);

(ii) CDR-H2 comprising the amino acid sequence AISSSGSSTYYADSVKG (SEQ ID NO:21); and (iii) CDR-H3 comprising the amino acid sequence DQGGYGYPGESWFDY (SEQ ID NO:22).

Embodiment No 18. The isolated antibody or antigen binding fragment thereof of embodiment 17, wherein the light chain variable region comprises the amino acid sequence of SEQ ID NO:23 and the heavy chain variable region comprises the amino acid sequence of SEQ ID NO:24.

Embodiment No 19. The isolated antibody or antigen binding fragment thereof of any one of embodiments 1-10, wherein the antibody or antigen binding fragment thereof comprises (a) a light chain variable region comprising:

(i) CDR-L1 comprising the amino acid sequence RASQSISSYLN (SEQ ID NO:25);

(ii) CDR-L2 comprising the amino acid sequence AASSLQS (SEQ ID NO:26);

(iii) CDR-L3 comprising the amino acid sequence QQSYSPPWT (SEQ ID NO:27); and (b) a heavy chain variable region comprising:

(i) CDR-H1 comprising the amino acid sequence SYSMN (SEQ ID NO:28);

(ii) CDR-H2 comprising the amino acid sequence SISSSSSYIYYADSVKG (SEQ ID NO:29); and (iii) CDR-H3 comprising the amino acid sequence AFYSYMDV (SEQ ID NO:30).

Embodiment No 20. The isolated antibody or antigen binding fragment thereof of embodiment 19, wherein the light chain variable region comprises the amino acid sequence of SEQ ID NO:31 and the heavy chain variable region comprises the amino acid sequence of SEQ ID NO: 32.

Embodiment No 21. The isolated antibody or antigen binding fragment thereof of any one of embodiments 1-10, wherein the antibody or antigen binding fragment thereof comprises (a) a light chain variable region comprising:

(i) CDR-L1 comprising the amino acid sequence RSSQSLLHSNGYNYLD (SEQ ID NO:33);

(ii) CDR-L2 comprising the amino acid sequence LGSNRAS (SEQ ID NO:34);

(iii) CDR-L3 comprising the amino acid sequence MQALQTPLT (SEQ ID NO:35); and (b) a heavy chain variable region comprising:

(i) CDR-H1 comprising the amino acid sequence SSNWWS (SEQ ID NO:36);

(ii) CDR-H2 comprising the amino acid sequence EIYHSGSTNYNPSLKS (SEQ ID NO:37); and (iii) CDR-H3 comprising the amino acid sequence ERTILTGYYGFDY (SEQ ID NO:38).

Embodiment No 22. The isolated antibody or antigen binding fragment thereof of embodiment 21, wherein the light chain variable region comprises the amino acid sequence of SEQ ID NO:39 and the heavy chain variable region comprises the amino acid sequence of SEQ ID NO:40.

Embodiment No 23. The isolated antibody or antigen binding fragment thereof of any one of embodiments 1-10, wherein the antibody or antigen binding fragment thereof comprises (a) a light chain variable region comprising:

(i) CDR-L1 comprising the amino acid sequence SGSSSNIGNNYVS (SEQ ID NO:41);

(ii) CDR-L2 comprising the amino acid sequence DNNKRPS (SEQ ID NO:42);

(iii) CDR-L3 comprising the amino acid sequence GTWDSSLTGYV (SEQ ID NO:43); and (b) a heavy chain variable region comprising:

(i) CDR-H1 comprising the amino acid sequence SYAIS (SEQ ID NO:44);

(ii) CDR-H2 comprising the amino acid sequence GIIPIFGTANYAQKFQG (SEQ ID NO:45); and (iii) CDR-H3 comprising the amino acid sequence YYDFWSGYPGGLFDV (SEQ ID NO:46).

Embodiment No 24. The isolated antibody or antigen binding fragment thereof of embodiment 23, wherein the light chain variable region comprises the amino acid sequence of SEQ ID NO:47 and the heavy chain variable region comprises the amino acid sequence of SEQ ID NO:48.

Embodiment No 25. The isolated antibody or antigen binding fragment thereof of any one of embodiments 1-10, wherein the antibody comprises (a) a light chain variable region comprising:
 (i) CDR-L1 comprising the amino acid sequence SGSSSNIGSNYVY (SEQ ID NO:81);
 (ii) CDR-L2 comprising the amino acid sequence RNNQRPS (SEQ ID NO:82);
 (iii) CDR-L3 comprising the amino acid sequence AAWDDSLSGWV (SEQ ID NO:83); and
(b) a heavy chain variable region comprising:
 (i) CDR-H1 comprising the amino acid sequence SYSMN (SEQ ID NO:84);
 (ii) CDR-H2 comprising the amino acid sequence YISSSSSTIYYADSVKG (SEQ ID NO:85); and
 (iii) CDR-H3 comprising the amino acid sequence SFGPYAFDV (SEQ ID NO:86).

Embodiment No 26. The isolated antibody or antigen binding fragment thereof of embodiment 25, wherein the light chain variable region comprises the amino acid sequence of SEQ ID NO:87 and the heavy chain variable region comprises the amino acid sequence of SEQ ID NO: 88.

Embodiment No 27. The isolated antibody or antigen binding fragment thereof of any one of embodiments 1-10, wherein the antibody or antigen binding fragment thereof comprises (a) a light chain variable region comprising:
 (i) CDR-L1 comprising the amino acid sequence SGSSSNIGNNYVS (SEQ ID NO:49);
 (ii) CDR-L2 comprising the amino acid sequence DNNKRPS (SEQ ID NO:50);
 (iii) CDR-L3 comprising the amino acid sequence GTWDSSLTGWV (SEQ ID NO:51); and
(b) a heavy chain variable region comprising:
 (i) CDR-H1 comprising the amino acid sequence SYAIS (SEQ ID NO:52);
 (ii) CDR-H2 comprising the amino acid sequence GIIPIFGTANYAQKFQG (SEQ ID NO:53); and
 (iii) CDR-H3 comprising the amino acid sequence YYDFWSGYPGGLFDV (SEQ ID NO:54).

Embodiment No 28. The isolated antibody or antigen binding fragment thereof of embodiment 27, wherein the light chain variable region comprises the amino acid sequence of SEQ ID NO:55 and the heavy chain variable region comprises the amino acid sequence of SEQ ID NO:56.

Embodiment No 29. The isolated antibody or antigen binding fragment thereof of any one of embodiments 1-10, wherein the antibody or antigen binding fragment thereof comprises (a) a light chain variable region comprising:
 (i) CDR-L1 comprising the amino acid sequence QGDSLRSYYAS (SEQ ID NO:57);
 (ii) CDR-L2 comprising the amino acid sequence GKNNRPS (SEQ ID NO:58);
 (iii) CDR-L3 comprising the amino acid sequence NSRDSSGNHWV (SEQ ID NO:59); and
(b) a heavy chain variable region comprising:
 (i) CDR-H1 comprising the amino acid sequence SYSMN (SEQ ID NO:60);
 (ii) CDR-H2 comprising the amino acid sequence SISSSSSYIYYADSVKG (SEQ ID NO:61); and
 (iii) CDR-H3 comprising the amino acid sequence TNNYGYRYFDY (SEQ ID NO:62).

Embodiment No 30. The isolated antibody or antigen binding fragment of embodiment 29, wherein the light chain variable region comprises the amino acid sequence of SEQ ID NO:63 and the heavy chain variable region comprises the amino acid sequence of SEQ ID NO:64.

Embodiment No 31. The isolated antibody or antigen binding fragment thereof of any one of embodiments 1-10, wherein the antibody or antigen binding fragment thereof comprises (a) a light chain variable region comprising:
 (i) CDR-L1 comprising the amino acid sequence QGDSLRSYYAS (SEQ ID NO:65);
 (ii) CDR-L2 comprising the amino acid sequence GKNNRPS (SEQ ID NO:66);
 (iii) CDR-L3 comprising the amino acid sequence NSRDSTDNHLWV (SEQ ID NO:67); and
(b) a heavy chain variable region comprising:
 (i) CDR-H1 comprising the amino acid sequence SYSMN (SEQ ID NO:68);
 (ii) CDR-H2 comprising the amino acid sequence SISSSSSYIYYADSVKG (SEQ ID NO:69); and
 (iii) CDR-H3 comprising the amino acid sequence ATSSGYYYFDY (SEQ ID NO:70).

Embodiment No 32. The isolated antibody or antigen binding fragment thereof of embodiment 31, wherein the light chain variable region comprises the amino acid sequence of SEQ ID NO:71 and the heavy chain variable region comprises the amino acid sequence of SEQ ID NO:72.

Embodiment No 33. The isolated antibody or antigen binding fragment thereof of any one of embodiments 1-10, wherein the antibody or antigen binding fragment thereof comprises (a) a light chain variable region comprising:
 (i) CDR-L1 comprising the amino acid sequence SGSSSNIGNNYVS (SEQ ID NO:73);
 (ii) CDR-L2 comprising the amino acid sequence DNNKRPS (SEQ ID NO:74);
 (iii) CDR-L3 comprising the amino acid sequence GTWDNSLSVWV (SEQ ID NO:75); and
(b) a heavy chain variable region comprising:
 (i) CDR-H1 comprising the amino acid sequence SYSMN (SEQ ID NO:76);
 (ii) CDR-H2 comprising the amino acid sequence YISSSSSTIYYADSVKG (SEQ ID NO:77); and
 (iii) CDR-H3 comprising the amino acid sequence GKGIVGWGFFGMDV (SEQ ID NO:78).

Embodiment No 34. The isolated antibody or antigen binding fragment thereof of embodiment 33, wherein the light chain variable region comprises the amino acid sequence of SEQ ID NO:79 and the heavy chain variable region comprises the amino acid sequence of SEQ ID NO: 80.

Embodiment No 35. An isolated antibody or antigen binding fragment thereof that binds to human KRas-GDP, wherein the isolated antibody or antigen binding fragment thereof binds to amino acids W99, K5, L6, V7, S39, D54, L54, Y71, T74, and/or G75 of human KRas.

Embodiment No 36. An isolated antibody or antigen binding fragment thereof that binds to human KRas-GTP, wherein the isolated antibody or antigen binding fragment thereof binds to amino acids W99, K5, L6, V7, S39, D54, L54, Y71, T74, and/or G75 of human KRas.

Embodiment No 37. Isolated nucleic acid(s) encoding a light chain variable domain and a heavy chain variable domain of the antibody or antigen binding fragment of any one of embodiments 1-36.

Embodiment No 38. A vector comprising the nucleic acid(s) of embodiment 37.

Embodiment No 39. A host cell comprising the vector of embodiment 28.

Embodiment No 40. The isolated antibody or antigen binding fragment thereof of any one of embodiments 1-36, wherein the antibody or antigen binding fragment thereof is conjugated to a detectable label.

Embodiment No 41. A process for making an antibody or fragment thereof that binds to KRas-GDP comprising culturing the host cell of embodiment 36 under conditions suitable for expression of the vector encoding the antibody and recovering the antibody.

Embodiment No 42. A process for making an antibody or fragment thereof that binds to KRas-GtP comprising culturing the host cell of embodiment 36 under conditions suitable for expression of the vector encoding the antibody and recovering the antibody.

Embodiment No 43. A method of screening for an antibody that binds to $KRas^{G12C}$-GDP with higher affinity than $KRas^{G12C}$-GTP comprising (a) contacting an antibody library with
  i) $KRas^{G12C}$-GDP,
  ii) alkylated $KRas^{G12C}$-GDP with a $KRas^{G12C}$ specific covalent inhibitor, and
  iii) $KRas^{G12C}$ bound to a non-hydrolysable GTP analog and
(b) selecting an antibody that binds to the alkylated $KRas^{G12C}$-GDP and the unalkylated KRasG12C-GDP with higher affinity than KRasG12C bound to the non-hydrolysable GTP analog.

Embodiment No 44. A method of screening for an antibody that binds to $KRas^{G12C}$-GTP with higher affinity than $KRas^{G12C}$-GDP comprising (a) contacting an antibody library with
  i) $KRas^{G12C}$-GTP,
  ii) alkylated $KRas^{G12C}$-GTP with a $KRas^{G12C}$ specific covalent inhibitor, and
  iii) $KRas^{G12C}$ bound to a non-hydrolysable GDP analog and
(b) selecting an antibody that binds to the alkylated $KRas^{G12C}$-GTP and the unalkylated $KRas^{G12C}$-GTP with higher affinity than $KRas^{G12C}$ bound to the non-hydrolysable GDP analog.

Embodiment No 45. The method of embodiment 43 or embodiment 44, wherein the library is a synthetic phage library.

Embodiment No 46. A method for detecting KRas-GDP in a biological sample comprising contacting the biological sample with the antibody or antigen binding fragment thereof of any one of embodiments 1-36.

Embodiment No 47. The method of embodiment 46, further comprising contacting the biological sample with an antibody that binds to KRas-GTP, wherein the amount of KRas-GDP and the amount of KRas-GTP are determined.

Embodiment No 48. A method for detecting KRas-GTP in a biological sample comprising contacting the biological sample with the antibody or antigen binding fragment thereof of any one of embodiments 1-36.

Embodiment No 49. The method of embodiment 46, further comprising contacting the biological sample with an antibody that binds to KRas-GDP, wherein the amount of KRas-GTP and the amount of KRas-GDP are determined.

Embodiment No 50. A kit comprising the KRas antibody or antigen binding fragment thereof of any one of embodiments 1-36 conjugated to a detectable label and instructions for detecting said antibody or antigen binding fragment thereof.

Embodiment No 51. A method of obtaining an inhibitor of a KRas mutant comprising contacting the antibody or antigen binding fragment thereof of any one of embodiments 1-36 with the KRas mutant, screening compounds, and identifying compounds that bind to the KRas mutant bound to the antibody or antigen binding fragment thereof.

Embodiment No 52. The method of embodiment 51, wherein the compounds comprise molecules that covalently modify KRas at the SWII pocket.

Embodiment No 53. The method of embodiment 52, wherein the compounds comprise a covalent inhibitor that alkylates at least one residue in the SWII pocket.

Embodiment No 54. The method of embodiment 51, wherein the compounds comprise molecules that non-covalently modify KRas at the SWII pocket.

Embodiment No 55. The method of any one of embodiments 51-54, wherein the KRas mutant is $KRas^{G12C}$, $KRas^{G12V}$, $KRas^{G12D}$, $KRas^{G13D}$, $KRas^{G12R}$, or $KRas^{Q61H}$ Embodiment No 56. A method of detecting alkylation of KRas comprising contacting a biological sample with the antibody or antigen binding fragment thereof of any one of embodiments 1-36 and detecting the antibody or antigen binding fragment thereof bound to alkylated KRas.

Embodiment No 57. The method of embodiment 56, wherein the detection comprises detection of $KRas^{G12C}$.

Embodiment No 58. The method of embodiment 56 or 57, wherein the antibody or antigen binding fragment thereof is a KRas alkylated conformation specific antibody.

Embodiment No 59. A method of detecting alkylation of KRas in a mammal comprising administering the antibody or antigen binding fragment thereof of any one of embodiments 1-36 to the mammal and detecting the antibody or antigen binding fragment thereof bound to the alkylated KRas.

Embodiment No 60. A method of detecting alkylation of KRas in a patient treated with a KRas inhibitor, the method comprising:

(a) obtaining a sample from the patient;
(b) contacting the sample with the antibody or antigen binding fragment thereof of any one of embodiments 1-36;
(c) measuring an amount of KRas bound by the antibody or antigen binding fragment thereof.

Embodiment No 61. The method of embodiment 60, wherein the KRas inhibitor is MRTX849, AMG-510, GDC-6036, ARS-3248, LY3499446, LY3537982, or JNJ-74699157.

Embodiment No 62. The method of embodiment 60 or 61, wherein the amount of KRas bound by the antibody or antigen binding fragment thereof determines a dosage of the KRas inhibitor to administer to the patient.

Embodiment No 63. The method of any one of embodiments 59-62, wherein the detection comprises detection of $KRas^{G12C}$.

Embodiment No 64. The method of any one of embodiments 59-63, wherein the antibody or antigen binding fragment thereof is a KRas alkylated conformation specific antibody.

Embodiment No 65. The method of any one of embodiments 59-63, wherein the mammal is a human.

Embodiment No 66. A method of detecting alkylation of KRas$^{G12C}$ in a subject treated with a KRas$^{G12C}$ specific covalent inhibitor, the method comprising:

(a) administering the antibody or antigen binding fragment thereof of any one of antibodies 1E5, 2H11, 2A3, 3A12, 1F4, 4G12, Ab1, Ab2, Ab3, Ab4, Ab5, Ab6, Ab7, or Ab8 to the subject after treatment with the KRas$^{G12C}$ specific covalent inhibitor; and (b) detecting the antibody or antigen binding fragment thereof bound to the alkylated KRas.

Embodiment No 67. The method of embodiment 66, wherein the KRas$^{G12C}$ specific covalent inhibitor is ARS-1952, ARS-853, ARS-1620, MRTX849, AMG-510, GDC-6036, ARS-3248, LY3499446, LY3537982, or JNJ-74699157.

Embodiment No 68. The method of embodiment 67, wherein the antibody or antigen binding fragment thereof is a KRas alkylated conformation specific antibody.

Embodiment No 69. A method of treating a KRas$^{G12C}$ mediated cancer, the method comprising administering to a patient having such a cancer, the antibody or antigen binding fragment thereof of any one of embodiments 1-36.

Embodiment No 70. The method of embodiment 69, wherein the KRas$^{G12C}$ mediated cancer is NSCLC, colon cancer, or pancreatic cancer.

Embodiment No 71. A crystallization chaperone comprising the antibody or antigen binding fragment thereof of any one of embodiments 1-36.

Embodiment No 72. A method for crystallizing KRas, wherein the KRas is optionally bound to a KRas inhibitor, the method comprising contacting the antibody or antigen binding fragment thereof of any one of embodiments 1-36 with KRas and resolving a crystal structure of the complex.

Embodiment No 73. The method of embodiment 72, wherein the KRas is KRas$^{G12C}$, KRas$^{G12D}$, KRas$^{G12V}$, KRas$^{G12R}$, KRas$^{G13D}$, or KRas$^{Q61H}$.

Embodiment No 74. A biosensing surface for measuring binding of compounds to a KRas wherein:

(i) the biosensing surface comprises a hydrogel into which a KRas protein and the antibody or antigen binding fragment thereof of any one of embodiments 1-36 are co-localized;

(ii) the KRas and the antibody or antigen binding fragment thereof have sufficient degrees of freedom within the hydrogel to engage each other to form affinity complexes;

(iii) the local concentration of the KRas and the antibody or antigen binding fragment thereof exceeds the dissociation affinity constant by at least 10-fold, wherein the local concentration promotes formation of the affinity complex;

(iv) the fraction of unbound KRas protein and anti-KRas antibody is less than about 50%;

(v) the KRas inhibitor compound is injected onto the biosensing surface for at least 5 seconds; and (vi) wherein binding of the KRas inhibitor compound to the anti-KRas antibody is measured over at least one sensing channel.

Embodiment No 75. The biosensing surface of embodiment 74, wherein the hydrogel is about 10 nm-500 nm, 10 nm-300 nm, 10-250 nm, or about 10-200 nm in thickness.

Embodiment No 76. The biosensing surface of embodiment 74 or 75, wherein KRas is biotinylated.

Embodiment No 77. The biosensing surface of any one of embodiments 74-76, wherein the biosensing surface is attached to a BIACORE sensor chip.

Embodiment No 78. A method of screening compounds for anti-KRas inhibitor activity, the method comprising measuring the binding of a compound to KRas, wherein the KRas is bound to an anti-KRas antibody, and wherein the binding is measured using the biosensing surface of any one of embodiments 74-77.

Embodiment No 79. A method of measuring binding of a KRas mutant protein to an anti-KRas antibody described herein, wherein the method comprises:

(i) contacting the biosensing surface of any one of embodiments 74-77 with KRas to form a KRas-bound biosensing surface;

(ii) contacting the KRas-bound biosensing surface with the antibody or antigen binding fragment thereof of any one of embodiments 1-36, wherein the antibody or antigen binding fragment thereof is at a molar excess compared to the KRas protein; and (iii) detecting the binding and affinity of the antibody or antigen binding fragment thereof to KRas using surface plasmon resonance.

Embodiment No 80. A method of measuring binding of a KRas mutant protein to an anti-KRas antibody described herein, wherein the method comprises:

(i) contacting the biosensing surface of any one of embodiments 74-77 with the antibody or antigen binding fragment thereof of any one of embodiments 1-36 to form an anti-KRas antibody-bound biosensing surface;

(ii) contacting the anti-KRas antibody-bound biosensing surface with KRas, wherein the antibody or antigen binding fragment thereof is at a molar excess compared to the KRas protein; and (iii) detecting the binding and affinity of the antibody or antigen binding fragment thereof to KRas using surface plasmon resonance.

Embodiment No 81. A method of measuring target engagement of a KRas inhibitor to a KRas protein comprising (a) obtaining a sample from a patient;

(b) contacting the sample with an anti-KRas antibody or antigen-binding fragment thereof described herein; and (c) measuring the level of KRas bound by the anti-KRas antibody.

EXAMPLES

The present disclosure is described in further detail in the following examples which are not in any way intended to limit the scope of the disclosure as claimed. The attached figures are meant to be considered as integral parts of the specification and description of the disclosure. The following examples are offered to illustrate, but not to limit the claimed disclosure.

Example 1: Selection and Epitope-Mapping of Anti-KRas Antibodies

The following example describes the selection and characterization of anti-KRas antibodies that recognize or induce the open conformation of KRas$^{G12C}$.

Materials and Methods

Phage Selection

Figure 1B:
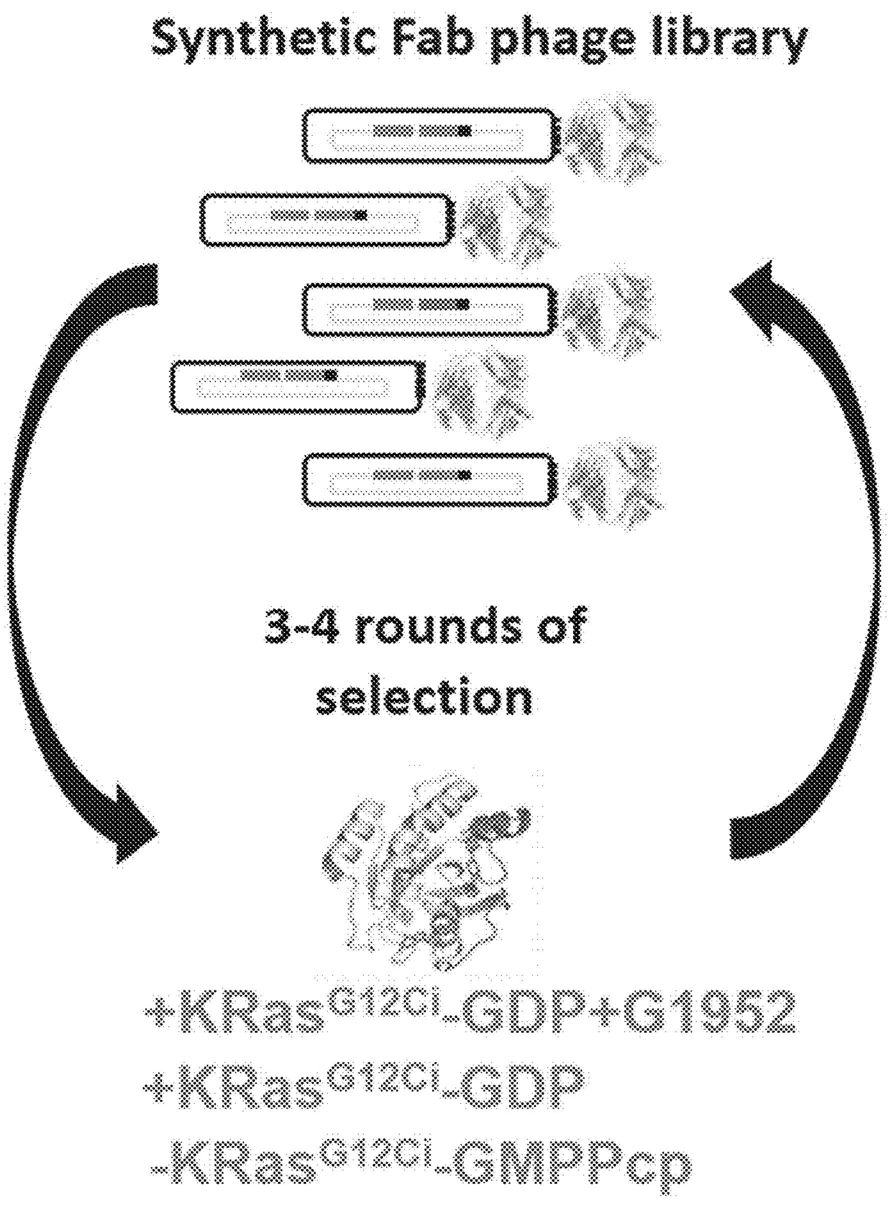
FIG. 1B shows the in vitro phage display selection strategy used to identify alkylated $KRas^{G12C}$-GDP specific monoclonal antibodies.

An in vitro selection strategy was developed using synthetic antibody libraries and three distinct KRas$^{G12C}$ conformations: alkylated and unalkylated KRas$^{G12C}$-GDP and KRas$^{G12C}$-GMPPcp (a non-hydrolysable GTP mimetic) (FIG. 1B). Amino acid residues T2 through K169 of KRas isoform B were used. Four rounds of biopanning were performed in which the synthetic phage libraries were incubated in solution with biotinylated KRas$^{G12C}$-GDP alkylated with GNE-1952. In order to drive selections towards the alkylated, open conformation of KRas$^{G12C}$-GDP, selections were done in the presence of excess of non-biotinylated KRas$^{G12C}$-GDP and KRas$^{G12C}$-GMPPcp in solution.

Selections were performed using existing synthetic Fab phage display libraries (C. V. Lee et al., *J Mol Biol* 2004; 340:1073-1093; W. C. Liang et al., *J Mol Biol* 2007; 366:815-829). The pooled library was cycled through three to four rounds of binding in solution to biotinylated KRas$^{G12Ci}$-GDP+GNE1952 (ranging from 500 nM initially down to 10 nM). The solution was captured on NeutrAvidin beads (Promega), blocked with 5 μM biotin, washed 3 times for 30 s each in PBS+0.5% BSA+0.1% Tween 20 (PBSBT), and eluted with 100 mM HCl. The eluted phage was neutralized with 1M TRIS-HCl pH 8.0 prior to overnight amplification in *E. coli* XL1-blue (Stratagene) with the addition of M13-KO7 helper phage (New England Biolabs). To enrich for binders specific to the alkylated KRas$^{G12C}$, selections were done in the presence of excess of either soluble KRas$^{G12C}$-GDP or KRas$^{G12C}$-GMPPcp at 1 μM. After selections, individual colonies were picked and grown overnight at 30° C. in 96-well deep well plates in 2×YT media supplemented with carbenicillin and helper phage. Phage supernatant was used in phage ELISAs against KRas$^{G12Ci}$-GDP+GNE1952, KRas$^{G12C}$-GDP, and KRas$^{G12C}$-GMPPcp to identify target-specific clones.

Antibody and Fab Production

IgGs were generated for eleven unique clones. Sequences from lead phage clones were obtained by Sanger sequencing. IgG (human IgG1) expression constructs for the light chain and heavy chain for each clone were obtained by gene synthesis. IgGs were produced by transient transfection of 293 cells and purified with affinity chromatography followed by SEC using standard methods (MabSelect SuRe; GE Healthcare, Piscataway, NJ, USA). Bacterial expression Fab constructs were generated by gene synthesis. Recombinant Fabs were generated as previously described (T. N. Lombana, M. Dillon, J. Bevers, 3rd, C. Spiess, *Sci Rep* 2015; 5:17488).

Antibody Enzyme-Linked Immunosorbent Assay (ELISA) Against Alkylated KRas$^{G12C}$ To identify anti-KRas antibodies that recognize GNE-1952 bound KRas$^{G12C}$-GDP, the ability of the eleven monoclonal antibodies (mAbs) to recognize KRas$^{G12C}$ alkylated with two additional compounds (ARS-853 and ARS-1620) was measured (M. P. Patricelli et al., *Cancer Discov* 2016; 6:316-329; P. Lito et al., *Science* 2016; 351:604-608). Biotinylated KRas$^{G12C}$-GDP+GNE-1952 and KRas$^{G12C}$-GDP was coated on NeutrAvidin ELISA plates (Thermo Scientific) in triplicate at 0.3 μg/mL in PBS overnight at 4° C. Plates were washed with PBSBT and serial dilutions of anti-KRas antibodies (both the selected anti-KRas antibodies described herein and commercially available anti-bodies) starting at 10 μg/mL were added for 1-2 hours at 25° C. with shaking. After washing, a species matched Fc-specific HRP 2° antibody was added for 1 hour at 25° C. with shaking. After washing with PBSBT, plates were developed with TMB substrate for 5 minutes and detected at 650 nm.

Antibody Surface Plasmon Resonance (SPR)

SPR experiments were carried out on the Mass-1 (Bruker) at 25° C. using HBS-P+(GE Healthcare) running buffer. 1 μg/mL of the anti-KRas antibodies were captured using an anti-HuIgG1 Fc capture kit (GE Healthcare). KRas$^{G12C}$-GDP+GNE-1952, KRas$^{G12C}$-GDP, KRas$^{G12C}$-GDP+ARS1620, KRas$^{G12C}$-GDP+ARS853, and KRas$^{WT}$-GDP were added as analytes in solution at a flow rate of 30 L/min. KRas$^{G12}$-GDP+GNE-1952 was titrated using a dilution series from 500-0 nM. KRas$^{G12C}$-GDP was titrated using a dilution series from 5000-0 nM. KRas$^{G12C}$-GDP+ARS1620 was titrated using a dilution series from 1000-0 nM. KRas$^{G12C}$-GDP+ARS853 was titrated using a dilution series from 200-0 nM. KRasWT-GDP was titrated using a dilution series from 2000-0 nM. Sensorgrams were fit to a 1:1 *Langmuir* model to identify kinetic parameters.

Epitope Binning

Figure 1C:
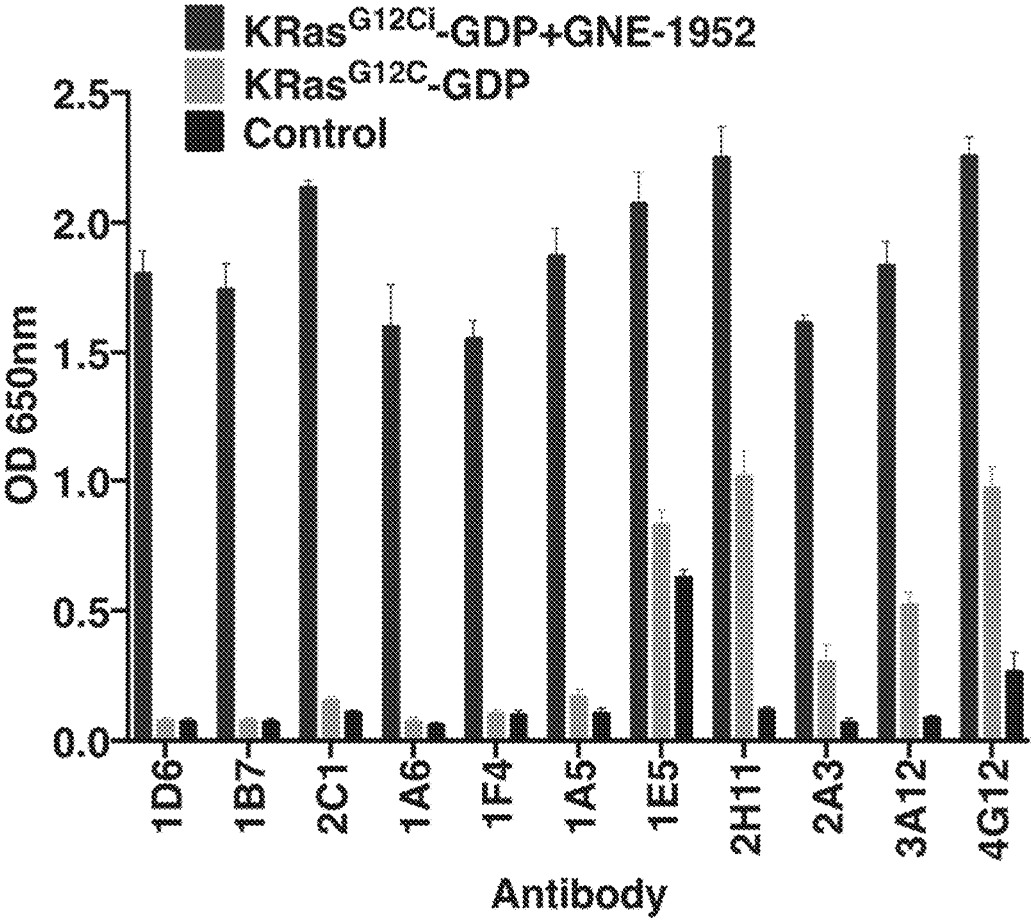
FIG. 1C shows enzyme-linked immunosorbent assay (ELISA) data for selected anti-KRas monoclonal antibodies binding to $KRas^{G12C}$-GDP+GNE1952, unalkylated $KRas^{G12C}$-GDP and a negative control.
Figure 1D:
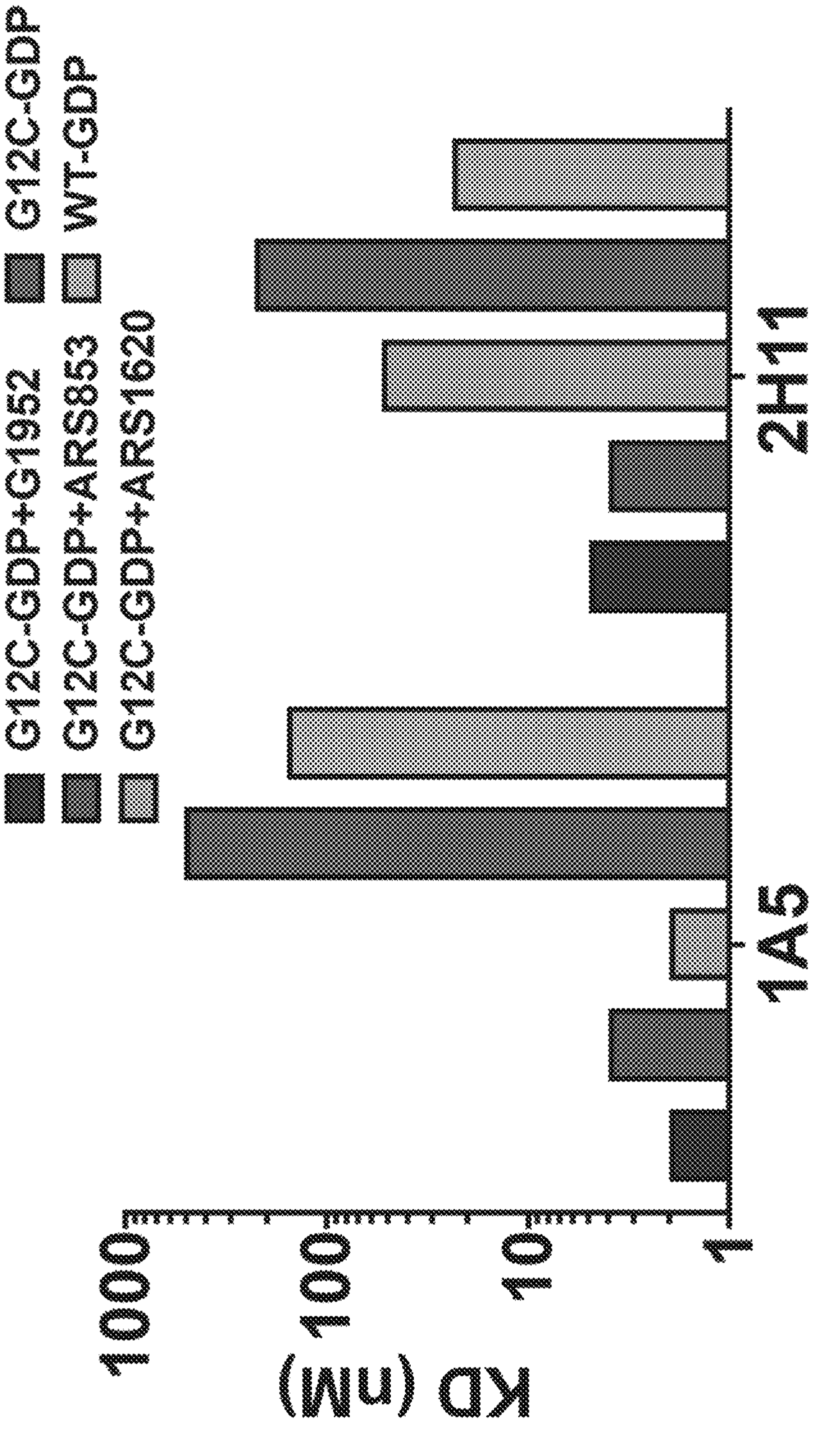
FIG. 1D shows data from a surface plasmon resonance (SPR) analysis of the selected anti-KRas antibodies 1A5 (left side of x-axis) and 2H11 (right side of x-axis) binding KRas when alkylated with different agents.
Figure 1E:
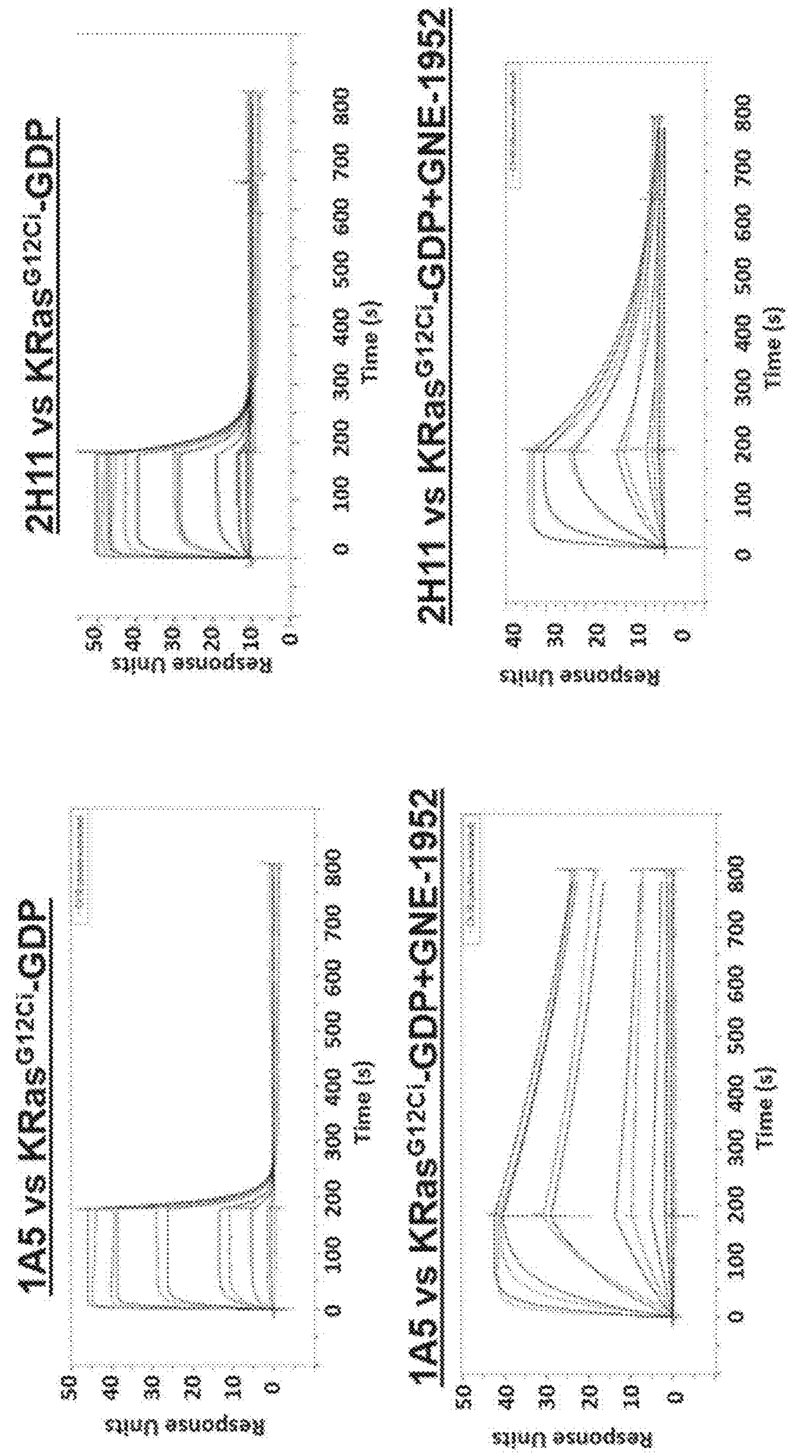
FIG. 1E shows representative SPR traces of selected anti-KRas antibodies 1A5 and 2H11 against $KRas^{G12C}$-GDP+GNE1952 and $KRas^{G12C}$-GDP. Time in seconds is plotted on the x-axis, and response units are plotted on the y-axis.
Figure 1F:
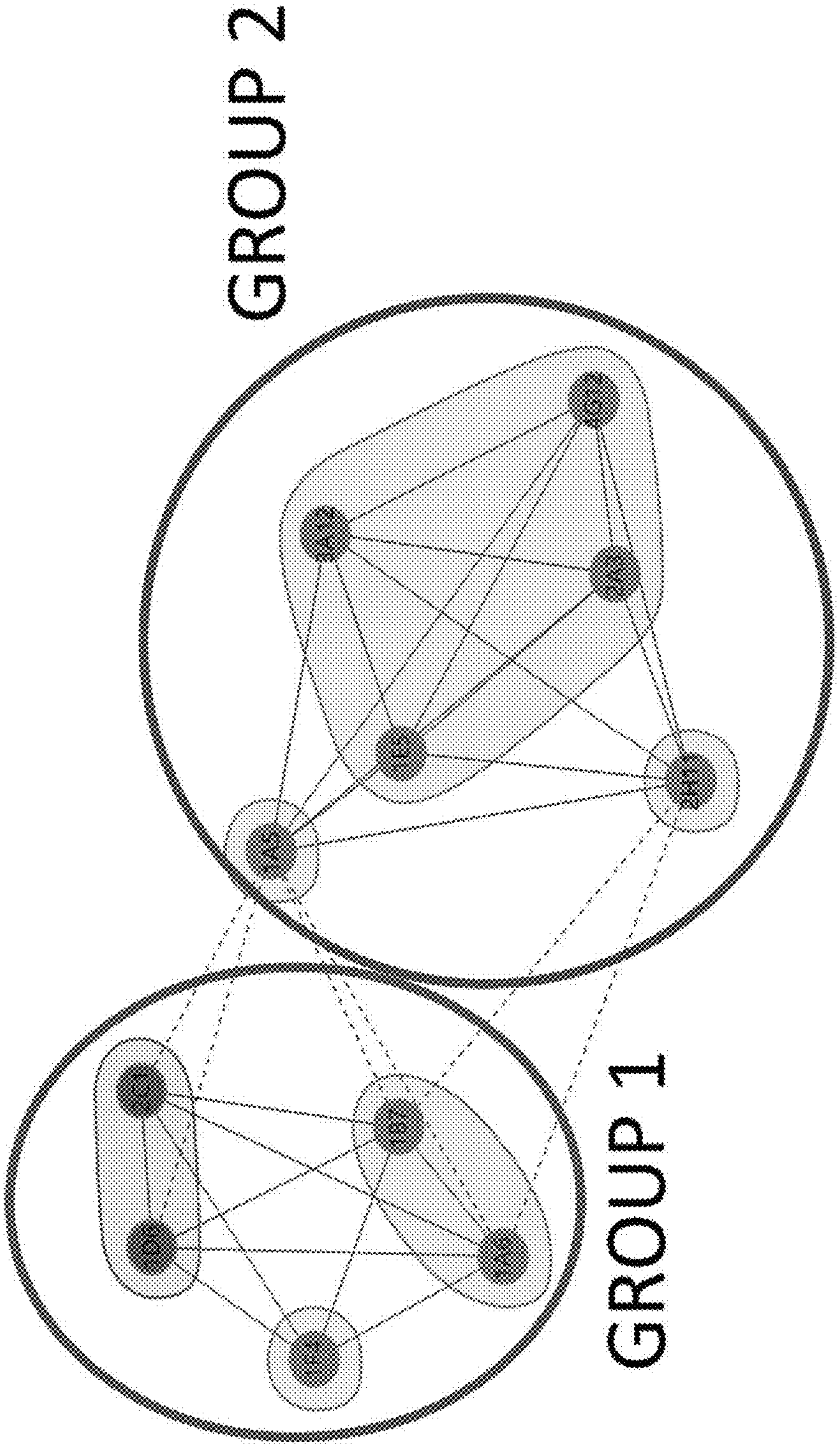
FIG. 1F shows epitope binning results for the selected anti-KRas antibodies.

Epitope binning experiments were performed in HBS-P+ (GE Healthcare) running buffer at 25° C. on an array-based imager (*IBIS* MX96, Netherlands, as described previously (Y. N. Abdiche et al., PLoS One 2014; 9:e92451). Briefly, 10 μg/mL of anti-KRas antibody was amine coupled onto surface in 10 mM sodium acetate pH 4.5 and the surface was quenched with 1M ethanolamine. Epitope binning experiments were done by initially flowing 2 μM KRas$^{G12C}$-GDP+GNE1952 over the immobilized antibodies, and then, adding 10 μg/mL of each of the anti-KRas antibodies in solution. Enough time was allowed for association of the antigen prior to the addition of the antibody. Prior to the addition of the next antibody in solution, the surface was regenerated with 10 mM glycine pH 2.5 (FIG. 1F).

Immunoprecipitation

Figure 1G:
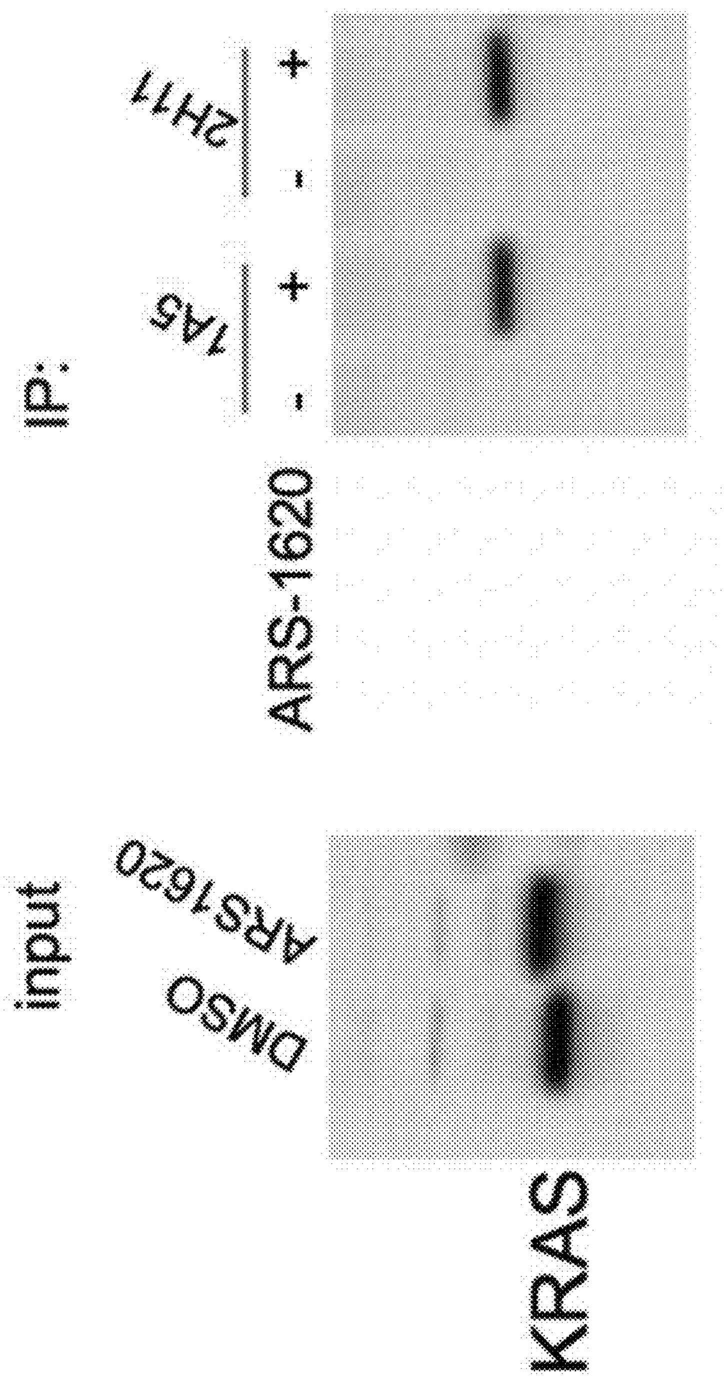
FIG. 1G shows immunoprecipitation of alkylated $KRas^{G12C}$-GDP by the selected anti-KRas antibodies 1A5 and 2H11 from cells treated with ARS-1620 and unalkylated $KRas^{G12C}$-GDP.

An immunoprecipitation experiment was performed with 1A5 and 2H11 on cells treated with ARS-1620 or DMSO control (FIG. 1G).

Results

A phage display selection was performed to select for anti-KRas antibodies that bind the unique conformation of KRas$^{G12C}$ alkylated upon covalent modification by SWII covalent inhibitors. After phage ELISA screens to confirm specificity, IgGs were generated for eleven unique clones and their binding specificities were characterized by ELISA (FIG. TC) and surface plasmon resonance (SPR) (FIG. 1D, FIG. TE, and Table TA). All mAbs bound to GNE-1952-alkylated KRas$^{G12C}$-GDP with affinities in the range of $K_D$~1-139 nM (Table TA). The binding specificities of the selected mAbs and the commercially available anti-KRas antibody iDab6 (Tanaka, T. et al., *EMBO J* 2007; 26:3250-3259) to KRas-GTP were also measured (Table 1B).

One group (clones 1D6, 1B7, 2C1, 1A6, and 1F4) was selective to GNE-1952-bound KRas$^{G12C}$-GDP conformation while the second group (clones 1A5, 1E5, 2A3, 2H11, 3A12, and 4G12) appeared to be pan-alkylation selective, recognizing GNE-1952, ARS-853, and ARS-1620 bound KRas$^{G12C}$-GDP conformations (Table TA). Epitope mapping analysis revealed that these two groups bound two distinct but partially overlapping epitopes on GNE-1952-bound KRas$^{G12C}$-GDP (FIG. 1F).

TABLE 1A

Affinity of anti-KRas antibodies for different KRas proteins bound to GDP, with "NB" indicating no binding, and "ND" indicating no data

| Clone | $KRas^{G12Ci}$-GDP + GNE-1952 Affinity (nM) | $KRas^{G12Ci}$-GDP + ARS-853 Affinity (nM) | $KRas^{G12Ci}$-GDP + ARS-1620 Affinity (nM) | $KRas^{G12C}$-GDP Affinity (nM) | $KRas^{WT}$-GDP Affinity (nM) |
|---|---|---|---|---|---|
| 1D6 | 10 | NB | NB | NB | NB |
| 1B7 | 139 | NB | NB | NB | NB |
| 2C1 | 7 | NB | NB | NB | NB |
| 1A6 | 61 | NB | NB | NB | NB |
| 1F4 | 39 | NB | NB | NB | NB |
| 1A5 | 2 | 4 | 2 | 513 | 159 |
| 1E5 | 5 | NB | 107 | 1700 | 411 |
| 2A3 | 10 | 195 | 21 | 216 | 71 |
| 2H11 | 5 | 4 | 54 | 230 | 42 |
| 3A12 | 2 | 772 | 94 | 121 | 24 |
| 4G12 | 1 | 441 | NB | 366 | 61 |
| iDab6 | 924 | ND | ND | 35 | 12900 |

TABLE 1B

Affinity of anti-KRas antibodies for KRas proteins bound to GTP, with "NB" indicating no binding, and "ND" indicating no data

| Clone | $KRas^{G12C}$-GTP Affinity (nM) | $KRas^{WT}$-GTP Affinity (nM) |
|---|---|---|
| 1D6 | NB | ND |
| 1B7 | NB | ND |
| 2C1 | NB | ND |
| 1A6 | NB | ND |
| 1F4 | NB | ND |
| 1A5 | 535 | NB |
| 1E5 | 1800 | NB |
| 2A3 | 313 | 7 |
| 2H11 | 344 | NB |
| 3A12 | 123 | NB |
| 4G12 | 215 | NB |
| iDab6 | 172 | 172 |

The Class I anti-KRas antibody 1A5 had high specificity for alkylated $KRas^{G12C}$-GDP with >100-fold improved affinity compared to unalkylated $KRas^{G12C}$-GDP. Class I anti-KRas antibodies required the presence of a covalently bound SWII ligand to bind, and they recognized and bound to this form with high specificity. In contrast, Class II anti-KRas antibodies, (1E5, 2H11, 2A3, 3A12, and 4G12) showed binding to both alkylated $KRas^{G12C}$-GDP and unalkylated $KRas^{G12C}$-GDP by ELISA and SPR (FIG. 1C, FIG. 1D and Table 1A). Class II anti-KRas antibodies did not require the presence of a covalently bound SWII ligand to bind.

An immunoprecipitation experiment was performed with 1A5 and 2H111 on cells treated with ARS-1620 or DMSO control. Both Class I and II anti-KRas antibodies specifically immunoprecipitated alkylated $KRas^{G12C}$-GDP but not unalkylated $KRas^{G12C}$-GDP (FIG. 1G).

The methods described herein generated a panel of novel anti-KRas antibodies that detect the unique open conformation induced by alkylation of $KRas^{G12C}$ with diverse chemotypes.

Example 2: Amino Acid Sequences of Anti-KRas Antibodies

The amino acid sequences of the selected anti-KRas antibodies were determined using standard techniques. The light chain complementary-determining regions (CDRs) of the anti-KRas antibodies are provided in Table 2, and the heavy chain CDRs of the anti-KRas antibodies are provided in Table 3. The light chain variable region sequences of the anti-KRas antibodies are provided in Table 4, and the heavy chain variable region sequences of the anti-KRas antibodies are provided in Table 5.

TABLE 2

Light chain CDR sequences of anti-KRas antibodies

| Antibody | CDR L1 | CDR L2 | CDR L3 |
|---|---|---|---|
| 1A5 | RASQGIRNDLG (SEQ ID NO: 1) | AASSLQS (SEQ ID NO: 2) | LQDHDYPLT (SEQ ID NO: 3) |
| 1D6 | RASQGISSYLA (SEQ ID NO: 17) | AASSLQS (SEQ ID NO: 18) | QQYYSYPFT (SEQ ID NO: 19) |
| 2C1 | RASQSISSYLN (SEQ ID NO: 25) | AASSLQS (SEQ ID NO: 26) | QQSYSPPWT (SEQ ID NO: 27) |
| 4G12 | RSSQSLLHSNGYNYLD (SEQ ID NO: 33) | LGSNRAS (SEQ ID NO: 34) | MQALQTPLT (SEQ ID NO: 35) |
| 1A6 | SGSSSNIGNNYVS (SEQ ID NO: 41) | DNNKRPS (SEQ ID NO: 42) | GTWDSSLTGYV (SEQ ID NO: 43) |
| 1B7 | SGSSSNIGNNYVS (SEQ ID NO: 49) | DNNKRPS (SEQ ID NO: 50) | GTWDSSLTGWV (SEQ ID NO: 51) |

TABLE 2-continued

Light chain CDR sequences of anti-KRas antibodies

| Antibody | CDR L1 | CDR L2 | CDR L3 |
|---|---|---|---|
| 1E5 | QGDS LRSY YAS (SEQ ID NO: 57) | GKNN RPS (SEQ ID NO: 58) | NSRD SSGN HWV (SEQ ID NO: 59) |
| 2A3 | QGDS LRSY YAS (SEQ ID NO: 65) | GKNN RPS (SEQ ID NO: 66) | NSRD STDN HLWV (SEQ ID NO: 67) |
| 2H11 | SGSS SNIG SNYV Y (SEQ ID NO: 9) | RNNQ RPS (SEQ ID NO: 10) | AAWD ERLS GWV (SEQ ID NO: 11) |
| 3A12 | SGSS SNIG NNYV S (SEQ ID NO: 73) | DNNK RPS (SEQ ID NO: 74) | GTWD NSLS VWV (SEQ ID NO: 75) |
| 1F4 | SGSS SNIG SNYV Y (SEQ ID NO: 81) | RNNQ RPS (SEQ ID NO: 82) | AAWD DSLS GWV (SEQ ID NO: 83) |
| Ab1 | SGSS SNIG SNYV Y (SEQ ID NO: 9) | RNNQ RPS (SEQ ID NO: 10) | AAWD ERLS GWV (SEQ ID NO: 11) |
| Ab2 | SGSS SNIG SNYV Y (SEQ ID NO: 9) | RNNQ RPS (SEQ ID NO: 10) | AAWD ERLS GWV (SEQ ID NO: 11) |
| Ab3 | SGSS SNIG SNYV Y (SEQ ID NO: 9) | RNNQ RPS (SEQ ID NO: 10) | AAWD ERLS GWV (SEQ ID NO: 11) |
| Ab4 | SGSS SNIG SNYV Y (SEQ ID NO: 9) | RNNQ RPS (SEQ ID NO: 10) | AAWD ERLS GWV (SEQ ID NO: 11) |
| Ab5 | SGSS SNIG SNYV Y (SEQ ID NO: 9) | RNNQ RPS (SEQ ID NO: 10) | AAWD ERLS GWV (SEQ ID NO: 11) |
| Ab6 | SGSS SNIG SNYV Y (SEQ ID NO: 9) | RNNQ RPS (SEQ ID NO: 10) | AAWD ERLS GWV (SEQ ID NO: 11) |

TABLE 2-continued

Light chain CDR sequences of anti-KRas antibodies

| Antibody | CDR L1 | CDR L2 | CDR L3 |
|---|---|---|---|
| Ab7 | SGSS SNIG SNYV Y (SEQ ID NO: 9) | RNNQ RPS (SEQ ID NO: 10) | AAWD ERLS GWV (SEQ ID NO: 11) |
| Ab8 | SGSS SNIG SNYV Y (SEQ ID NO: 9) | RNNQ RPS (SEQ ID NO: 10) | AAWD ERLS GWV (SEQ ID NO: 11) |

TABLE 3

Heavy chain CDR sequences of anti-KRas antibodies

| Antibody | CDR H1 | CDR H2 | CDR H3 |
|---|---|---|---|
| 1A5 | SYSM N (SEQ ID NO: 4) | YISS SSST IYYA DSVK G (SEQ ID NO: 5) | GFYV RNWF DP (SEQ ID NO: 6) |
| 1D6 | SYAM S (SEQ ID NO: 20) | AISS SGSS TYYA DSVK G (SEQ ID NO: 21) | DQGG YGYP GESW FDY (SEQ ID NO: 22) |
| 2C1 | SYSM N (SEQ ID NO: 28) | SISS SSSY IYYA DSVK G (SEQ ID NO: 29) | AFYS YMDV (SEQ ID NO: 30) |
| 4G12 | SSNW WS (SEQ ID NO: 36) | EIYH SGST NYNP SLKS (SEQ ID NO: 37) | ERTI LTGY YGFD Y (SEQ ID NO: 38) |
| 1A6 | SYAI S (SEQ ID NO: 44) | GIIP IFGT ANYA QKFQ G (SEQ ID NO: 45) | YYDF WSGY PGGL FDV (SEQ ID NO: 46) |
| 1B7 | SYAI S (SEQ ID NO: 52) | GIIP IFGT ANYA QKFQ G (SEQ ID NO: 53) | YYDF WSGY PGGL FDV (SEQ ID NO: 54) |

TABLE 3-continued

Heavy chain CDR sequences of anti-KRas antibodies

| Antibody | CDR H1 | CDR H2 | CDR H3 |
|---|---|---|---|
| 1E5 | SYSMN (SEQ ID NO: 60) | SISSSSSYIYYADSVKG (SEQ ID NO: 61) | TNNYGYRYFDY (SEQ ID NO: 62) |
| 2A3 | SYSMN (SEQ ID NO: 68) | SISSSSSYIYYADSVKG (SEQ ID NO: 69) | ATSSGYYYFDY (SEQ ID NO: 70) |
| 2H11 | SSNWWS (SEQ ID NO: 12) | EIYHSGSTNYNPSLKS (SEQ ID NO: 13) | GSSSWYDLGPFDY (SEQ ID NO: 14) |
| 3A12 | SYSMN (SEQ ID NO: 76) | YISSSSSTIYYADSVKG (SEQ ID NO: 77) | GKGIVGWGFFGMDV (SEQ ID NO: 78) |
| 1F4 | SYSMN (SEQ ID NO: 84) | YISSSSSTIYYADSVKG (SEQ ID NO: 85) | SFGPYAFDV (SEQ ID NO: 86) |
| Ab1 | GSSIWSSN* (SEQ ID NO: 91) | EIYHSGSTNYNPSLKS (SEQ ID NO: 13) | GSSSWYDLGPFDY (SEQ ID NO: 14) |
| Ab2 | GSNISSSN* (SEQ ID NO: 92) | EIYHSGSTNYNPSLKS (SEQ ID NO: 13) | GSSSWYDLGPFDY (SEQ ID NO: 14) |
| Ab3 | GSSIFSSN* (SEQ ID NO: 93) | EIYHSGSTNYNPSLKS (SEQ ID NO: 13) | GSSSWYDLGPFDY (SEQ ID NO: 14) |
| Ab4 | GSSIMSSN* (SEQ ID NO: 94) | EIYHSGSTNYNPSLKS (SEQ ID NO: 13) | GSSSWYDLGPFDY (SEQ ID NO: 14) |

TABLE 3-continued

Heavy chain CDR sequences of anti-KRas antibodies

| Antibody | CDR H1 | CDR H2 | CDR H3 |
|---|---|---|---|
| Ab5 | GSSIYSSN* (SEQ ID NO: 95) | EIYHSGSTNYNPSLKS (SEQ ID NO: 13) | GSSSWYDLGPFDY (SEQ ID NO: 14) |
| Ab6 | GGNIWSSN* (SEQ ID NO: 96) | EIYHSGSTNYNPSLKS (SEQ ID NO: 13) | GSSSWYDLGPFDY (SEQ ID NO: 14) |
| Ab7 | KGSIWASH* (SEQ ID NO: 97) | EIYHSGSTNYNPSLKS (SEQ ID NO: 13) | GSSSWYDLGPFDY (SEQ ID NO: 14) |
| Ab8 | KGSIWSSN* (SEQ ID NO: 98) | EIYHSGSTNYNPSLKS (SEQ ID NO: 13) | GSSSWYDLGPFDY (SEQ ID NO: 14) |

*= Chothia numbering

TABLE 4

Light chain variable region sequences of anti-KRas antibodies

| Antibody | Light Chain Variable Region Sequence |
|---|---|
| 1A5 | AIQMTQSPSSLSASVGDRVTITCRASQGIRNDLGWYQQKPGKAPKLLIYAASSLQSGVPSRFSGSGSGTDFTLTISSLQPEDFATYYCLQDHDYPLTFGQGTKVEIK (SEQ ID NO: 7) |
| 1D6 | DIQMTQSPSSLSASVGDRVTITCRASQGISSYLAWYQQKPGKAPKLLIYAASSLQSGVPSRFSGSGSGTDFTLTISSLQPEDFATYYCQQYYSYPFTFGQGTKVEIK (SEQ ID NO: 23) |
| 2C1 | DIQMTQSPSSLSASVGDRVTITCRASQSISSYLNWYQQKPGKAPKLLIYAASSLQSGVPSRFSGSGSGTDFTLTISSLQPEDFATYYCQQSYSPPWTFGQGTKVEIK (SEQ ID NO: 31) |

TABLE 4-continued

Light chain variable region sequences of anti-KRas antibodies

| Antibody | Light Chain Variable Region Sequence |
|---|---|
| 4G12 | DIVMTQSPLSLPVTPGEPAS ISCRSSQSLLHSNGYNYLDW YLQKPGQSPQLLIYLGSNRA SGVPDRFSGSGSGTDFTLKI SRVEAEDVGVYYCMQALQTP LTFGQGTKVEIK (SEQ ID NO: 39) |
| 1A6 | SVLTQPPSVSAAPGQKVTIS CSGSSSNIGNNYVSWYQQLP GTAPKLLIYDNNKRPSGIPD RFSGSKSGTSATLGITGLQT GDEADYYCGTWDSSLTGYVF GGGTKLTVL (SEQ ID NO: 47) |
| 1B7 | SVLTQPPSVSAAPGQKVTIS CSGSSSNIGNNYVSWYQQLP GTAPKLLIYDNNKRPSGIPD RFSGSKSGTSATLGITGLQT GDEADYYCGTWDSSLTGWVF GGGTKLTVL (SEQ ID NO: 55) |
| 1E5 | LTQDPAVSVALGQTVRITCQ GDSLRSYYASWYQQKPGQAP VLVIYGKNNRPSGIPDRFSG SSSGNTASLTITGAQAEDEA DYYCNSRDSSGNHWVFGGGT KLTVL (SEQ ID NO:63) |
| 2A3 | ELTQDPAVSVALGQTVRITC QGDSLRSYYASWYQQKPGQA PVLVIYGKNNRPSGIPDRFS GSSSGNTASLTITGAQAEDE ADYYCNSRDSTDNHLWVFGG GTKLTVL (SEQ ID NO: 71) |
| 2H11 | SVLTQPPSASGTPGQRVTIS CSGSSSNIGSNYVYWYQQLP GTAPKLLIYRNNQRPSGVPD RFSGSKSGTSASLAISGLRS EDEADYYCAAWDERLSGWVF GGGTKLTVL (SEQ ID NO: 15) |
| 3A12 | SVLTQPPSVSAAPGQKVTIS CSGSSSNIGNNYVSWYQQLP GTAPKLLIYDNNKRPSGIPD RFSGSKSGTSATLGITGLQT GDEADYYCGTWDNSLSVWVF GGGTKLTVL (SEQ ID NO: 79) |
| 1F4 | VLTQPPSASGTPGQRVTISC SGSSSNIGSNYVYWYQQLPG TAPKLLIYRNNQRPSGVPDR FSGSKSGTSASLAISGLRSE DEADYYCAAWDDSLSGWVFG GGTKLTVL (SEQ ID NO: 87) |
| Ab1 | SVLTQPPSASGTPGQRVTIS CSGSSSNIGSNYVYWYQQLP GTAPKLLIYRNNQRPSGVPD RFSGSKSGTSASLAISGLRS EDEADYYCAAWDERLSGWVF GGGTKLTVL (SEQ ID NO: 15) |
| Ab2 | SVLTQPPSASGTPGQRVTIS CSGSSSNIGSNYVYWYQQLP GTAPKLLIYRNNQRPSGVPD RFSGSKSGTSASLAISGLRS EDEADYYCAAWDERLSGWVF GGGTKLTVL (SEQ ID NO: 15) |
| Ab3 | SVLTQPPSASGTPGQRVTIS CSGSSSNIGSNYVYWYQQLP GTAPKLLIYRNNQRPSGVPD RFSGSKSGTSASLAISGLRS EDEADYYCAAWDERLSGWVF GGGTKLTVL (SEQ ID NO: 15) |
| Ab4 | SVLTQPPSASGTPGQRVTIS CSGSSSNIGSNYVYWYQQLP GTAPKLLIYRNNQRPSGVPD RFSGSKSGTSASLAISGLRS EDEADYYCAAWDERLSGWVF GGGTKLTVL (SEQ ID NO: 15) |
| Ab5 | SVLTQPPSASGTPGQRVTIS CSGSSSNIGSNYVYWYQQLP GTAPKLLIYRNNQRPSGVPD RFSGSKSGTSASLAISGLRS EDEADYYCAAWDERLSGWVF GGGTKLTVL (SEQ ID NO: 15) |
| Ab6 | SVLTQPPSASGTPGQRVTIS CSGSSSNIGSNYVYWYQQLP GTAPKLLIYRNNQRPSGVPD RFSGSKSGTSASLAISGLRS EDEADYYCAAWDERLSGWVF GGGTKLTVL (SEQ ID NO: 15) |
| Ab7 | SVLTQPPSASGTPGQRVTIS CSGSSSNIGSNYVYWYQQLP GTAPKLLIYRNNQRPSGVPD RFSGSKSGTSASLAISGLRS EDEADYYCAAWDERLSGWVF GGGTKLTVL (SEQ ID NO: 15) |
| Ab8 | SVLTQPPSASGTPGQRVTIS CSGSSSNIGSNYVYWYQQLP GTAPKLLIYRNNQRPSGVPD RFSGSKSGTSASLAISGLRS EDEADYYCAAWDERLSGWVF GGGTKLTVL (SEQ ID NO: 15) |

TABLE 5

Heavy chain variable region sequences of anti-KRas antibodies

| Antibody | Heavy Chain Variable Region Sequence |
|---|---|
| 1A5 | EVQLVESGGGLVQPGGSLRL SCAASGFTFSSYSMNWVRQA PGKGLEWVSYISSSSSTIYY ADSVKGRFTISRDNAKNSLY LQMNSLRAEDTAVYYCARGF YVRNWFDPWGQGTLVTVSS (SEQ ID NO: 8) |

TABLE 5-continued

Heavy chain variable region sequences of anti-KRas antibodies

| Antibody | Heavy Chain Variable Region Sequence |
|---|---|
| 1D6 | EVQLVESGGGLVQPGGSLRL SCAASGFTFSSYAMSWVRQA PGKGLEWVSAISSSGGSSTYY ADSVKGRFTISRDNSKNTLY LQMNSLRAEDTAVYYCARDQ GGYGYPGESWFDYWGQGTLV TVSS (SEQ ID NO: 24) |
| 2C1 | EVQLVESGGGLVKPGGSLRL SCAASGFTFSSYSMNWVRQA PGKGLEWVSSISSSSSYIYY ADSVKGRFTISRDNAKNSLY LQMNSLRAEDTAVYYCARAF YSYMDVWGQGTLVTVSS (SEQ ID NO: 32) |
| 4G12 | EVQLQESGPGLVKPPGTLSL TCAVSGGSISSSNWWSWVRQ PPGKGLEWIGEIYHSGSTNY NPSLKSRVTISVDKSKNQFS LKLSSVTAADTAVYYCARER TILTGYYGFDYWGQGTLVTV SS (SEQ ID NO: 40) |
| 1A6 | EVQLVQSGAEVKKPGSSVKV SCKASGGTFSSYAISWVRQA PGQGLEWMGGIIPIFGTANY AQKFQGRVTITADESTSTAY MELSSLRSEDTAVYYCARYY DFWSGYPGGLFDVWGQGTLV TVSS (SEQ ID NO: 48) |
| 1B7 | EVQLVQSGAEVKKPGSSVKV SCKASGGTFSSYAISWVRQA PGQGLEWMGGIIPIFGTANY AQKFQGRVTITADESTSTAY MELSSLRSEDTAVYYCARYY DFWSGYPGGLFDVWGQGTLV TVSS (SEQ ID NO: 56) |
| 1E5 | EVQLVESGGGLVKPGGSLRL SCAASGFTFSSYSMNWVRQA PGKGLEWVSSISSSSSYIYY ADSVKGRFTISRDNAKNSLY LQMNSLRAEDTAVYYCARTN NYGYRYFDYWGQGTLVTVSS (SEQ ID NO: 64) |
| 2A3 | EVQLVESGGGLVKPGGSLRL SCAASGFTFSSYSMNWVRQA PGKGLEWVSSISSSSSYIYY ADSVKGRFTISRDNAKNSLY LQMNSLRAEDTAVYYCARAT SSGYYYFDYWGQGTLVTVSS (SEQ ID NO: 72) |
| 2H11 | EVQLQESGPGLVKPPGTLSL TCAVSGGSISSSNWWSWVRQ PPGKGLEWIGEIYHSGSTNY NPSLKSRVTISVDKSKNQFS LKLSSVTAADTAVYYCARGS SSWYDLGPFDYWGQGTLVTV SS (SEQ ID NO: 16) |
| 3A12 | EVQLVESGGGLVQPGGSLRL SCAASGFTFSSYSMNWVRQA PGKGLEWVSYISSSSSTIYY ADSVKGRFTISRDNAKNSLY LQMNSLRAEDTAVYYCARGK GIVGWGFFGMDVWGQGTLVT VSS (SEQ ID NO: 80) |
| 1F4 | EVQLVESGGGLVQPGGSLRL SCAASGFTFSSYSMNWVRQA PGKGLEWVSYISSSSSTIYY ADSVKGRFTISRDNAKNSLY LQMNSLRAEDTAVYYCARSF GPYAFDVWGQGTLVTVSS (SEQ ID NO: 88) |
| Ab1 | EVQLQESGPGLVKPPGTLSL TCAVSGSSIWSSNWWSWVRQ PPGKGLEWIGEIYHSGSTNY NPSLKSRVTISVDKSKNQFS LKLSSVTAADTAVYYCARGS SSWYDLGPFDYWGQGTLVTV SS (SEQ ID NO: 99) |
| Ab2 | EVQLQESGPGLVKPPGTLSL TCAVSGSNISSSNWWSWVRQ PPGKGLEWIGEIYHSGSTNY NPSLKSRVTISVDKSKNQFS LKLSSVTAADTAVYYCARGS SSWYDLGPFDYWGQGTLVTV SS (SEQ ID NO: 100) |
| Ab3 | EVQLQESGPGLVKPPGTLSL TCAVSGSSIFSSNWWSWVRQ PPGKGLEWIGEIYHSGSTNY NPSLKSRVTISVDKSKNQFS LKLSSVTAADTAVYYCARGS SSWYDLGPFDYWGQGTLVTV SS (SEQ ID NO: 101) |
| Ab4 | EVQLQESGPGLVKPPGTLSL TCAVSGSSIMSSNWWSWVRQ PPGKGLEWIGEIYHSGSTNY NPSLKSRVTISVDKSKNQFS LKLSSVTAADTAVYYCARGS SSWYDLGPFDYWGQGTLVTV SS (SEQ ID NO: 102) |
| Ab5 | EVQLQESGPGLVKPPGTLSL TCAVSGSSIYSSNWWSWVRQ PPGKGLEWIGEIYHSGSTNY NPSLKSRVTISVDKSKNQFS LKLSSVTAADTAVYYCARGS SSWYDLGPFDYWGQGTLVTV SS (SEQ ID NO: 103) |
| Ab6 | EVQLQESGPGLVKPPGTLSL TCAVSGGNIWSSNWWSWVRQ PPGKGLEWIGEIYHSGSTNY NPSLKSRVTISVDKSKNQFS LKLSSVTAADTAVYYCARGS SSWYDLGPFDYWGQGTLVTV SS (SEQ ID NO: 104) |

TABLE 5-continued

Heavy chain variable region sequences of anti-KRas antibodies

| Antibody | Heavy Chain Variable Region Sequence |
| --- | --- |
| Ab7 | EVQLQESGPGLVKPPGTLSL TCAVSKGSIWASHWWSWVRQ PPGKGLEWIGEIYHSGSTNY NPSLKSRVTISVDKSKNQFS LKLSSVTAADTAVYYCARGS SSWYDLGPFDYWGQGTLVTV SS (SEQ ID NO: 105) |
| Ab8 | EVQLQESGPGLVKPPGTLSL TCAVSKGSIWSSNWWSWVRQ PPGKGLEWIGEIYHSGSTNY NPSLKSRVTISVDKSKNQFS LKLSSVTAADTAVYYCARGS SSWYDLGPFDYWGQGTLVTV SS (SEQ ID NO: 106) |

Based on the crystal structure of the 2H11 antibody, the binding affinity was further improved to KRas-GDP and KRas-GTP. Portions of the antibody were randomized using NNK codons and in vitro phage selections were performed to identify variants with improved affinity. Unique sequences were reformatted into IgGs. The off-rates of each variant was measure to different KRas proteins by SPR as described herein. Table 6 demonstrates that each variant exhibits a slower off-rate to at least one of the KRas proteins, indicating that the affinity was improved.

TABLE 6

Off-rate of CLAMP variants against different KRas proteins

| | $KRas^{G12Ci}$-GDP + GNE-1952 kd (1/s) | Fold improvement | $KRas^{G12C}$ GDP kd (1/s) | Fold improvement | $KRas^{G12C}$ GMPPcP kd (1/s) | Fold improvement |
| --- | --- | --- | --- | --- | --- | --- |
| 2H11 | 5.60E−03 | 1.00 | 2.10E−02 | 1.00 | 1.70E−02 | 1.00 |
| Ab1 | 5.90E−04 | 9.49 | 1.70E−03 | 12.35 | 1.80E−03 | 9.44 |
| Ab2 | 2.70E−02 | 0.21 | 5.40E−03 | 3.89 | 5.90E−03 | 2.88 |
| Ab3 | 8.40E−04 | 6.67 | 5.20E−03 | 4.04 | 5.30E−03 | 3.21 |
| Ab4 | 8.50E−04 | 6.59 | 6.20E−03 | 3.39 | 6.30E−03 | 2.70 |
| Ab5 | 6.80E−04 | 8.24 | 4.80E−03 | 4.38 | 4.80E−03 | 3.54 |
| Ab6 | 3.10E−03 | 1.81 | 2.20E−02 | 0.95 | 2.10E−02 | 0.81 |
| Ab7 | 8.40E−04 | 6.67 | 4.10E−03 | 5.12 | 4.00E−03 | 4.25 |
| Ab8 | 6.60E−04 | 8.48 | 3.80E−03 | 5.53 | 3.50E−03 | 4.86 |

Example 3: Tethering of KRas to CLAMP to Improve Affinity

Fusions comprising the KRas protein to the Fab, scFv, or IgG of the CLAMP described herein were also made. This fusion protein may result in an increased local concentration of KRas near the Fab and could exhibit increased affinity. The sequences below were constructed in which KRas was fused to the N-terminus of either the LC or HC of a 2H11 Fab.

Avi.TEV.KRas.G4S4.2H11.Fab.LC
Heavy chain sequence:
(Seq ID No: 107)
EVQLQESGPGLVKPPGILSLICAVSGGSISSSNWW

SWVRQPPGKGLEWIGEIYHSGSTNYNPSLKSRVTI

-continued

SVDKSKNQFSLKLSSVTAADTAVYYCARGSSSWYD

LGPFDYWGQGTLVTVSSASTKGPSVFPLAPSSKST

SGGTAALGCLVKDYFPEPVTVSWNSGALTSGVHTF

PAVLQSSGLYSLSSVVTVPSSSLGTQTYICNVNHK

PSNTKVDKKVEPKSCDKTHT

Light chain sequence:
(Seq ID No: 108)
GLNDIFEAQKIEWHEGSENLYFQSTEYKLVVVGAG

GVGKSALTIQLIQNHFVDEYDPTIEDSYRKQVVID

GETSLLDILDTAGQEEYSAMRDQYMRTGEGFLLVF

AINNTKSFEDIHHYREQIKRVKDSEDVPMVLVGNK

SDLPSRTVDTKQAQDLARSYGIPFIETSAKTRQGV

DDAFYTLVREIRKHKEKGGGGSGGGGSGGGGSGGG

GSSVLIQPPSASGTPGQRVTISCSGSSSNIGSNYV

YWYQQLPGTAPKLLIYRNNQRPSGVPDRFSGSKSG

TSASLAISGLRSEDEADYYCAAWDERLSGWVFGGG

TKLTVLGQPKAAPSVTLFPPSSEELQANKATLVCL

-continued

ISDFYPGAVTVAWKADSSPVKAGVETTTPSKQSNN

KYAASSYLSLTPEQWKSHKSYSCQVTHEGSTVEKT

VAPTECS

Avi.TEV.KRas.G484.2H11.Fab.HC
Heavy chain sequence:
(Seq ID No: 109)
GLNDIFEAQKIEWHEGSENLYFQSTEYKLVVVGAG

GVGKSALTIQLIQNHFVDEYDPTIEDSYRKQVVID

GETSLLDILDTAGQEEYSAMRDQYMRTGEGFLLVF

AINNTKSFEDIHHYREQIKRVKDSEDVPMVLVGNK

SDLPSRTVDTKQAQDLARSYGIPFIETSAKTRQGV

-continued

DDAFYTLVREIRKHKEKGGGGSGGGGSGGGGSGGG

GSEVQLQESGPGLVKPPGILSLICAVSGGSISSSN

WWSWVRQPPGKGLEWIGEIYHSGSTNYNPSLKSRV

TISVDKSKNQFSLKLSSVTAADTAVYYCARGSSSW

YDLGPFDYWGQGTLVTVSSASTKGPSVFPLAPSSK

STSGGTAALGCLVKDYFPEPVTVSWNSGALTSGVH

TFPAVLQSSGLYSLSSVVTVPSSSLGTQTYICNVN

HKPSNTKVDKKVEPKSCDKTHT

Light chain sequence:

(Seq ID No: 110)

SVLTQPPSASGTPGQRVTISCSGSSSNIGSNYVYW

YQQLPGTAPKLLIYRNNQRPSGVPDRFSGSKSGTS

ASLAISGLRSEDEADYYCAAWDERLSGWVFGGGTK

LTVLGQPKAAPSVTLFPPSSEELQANKATLVCLIS

DFYPGAVTVAWKADSSPVKAGVETTTPSKQSNNKY

AASSYLSLTPEQWKSHKSYSCQVTHEGSTVEKTVA

PTECS

Example 4: Detecting KRas$^{G12C}$ Alkylation in Cells

The following example describes the detection of alkylated KRas$^{G12C}$ in KRas$^{G12C}$ mutant cancer cells using the anti-KRas antibody 1A5.

Materials and Methods

Immunofluorescence and High Content Imaging Cells (20000 to 40000 cells per well depending on the cell line) were seeded into Poly-L-Lysine Coated 96-well plates (Cell Carrier Ultra; Perkin Elmer) and supplemented with complete medium (RPMI with 2% L-Glutamine and 10% FBS). The next day, cells were treated with KRas$^{G12C}$ inhibitors at indicated concentrations and incubated for the indicated length of time. At the end of treatment, cells were washed twice with cold 1×PBS, fixed with 3% paraformaldehyde for 20 minutes at room temperature, washed for 10 minutes with 1×PBS, and the PFA was quenched with 50 mM $NH_4Cl$ for 10 minutes at room temperature. Cells were washed again with 1×PBS twice for 5 minutes, then permeabilized with 1× Perm/Wash Buffer (BD, Fisher Scientific) for 20 minutes at room temperature. Cells were then incubated with primary antibody diluted in Perm/Wash buffer at indicated concentration for 2 hours at room temperature. Cells were then washed three times with Perm/Wash buffer for 10 minutes each, and the incubated with conjugated fluorescence secondary antibody for 20 to 60 minutes (Alexa488 anti-human and Alexa647 anti-rabbit or anti-rat at 1:500 from Jackson ImmunoResearch Laboratories Inc.) 100 ml of 300 nM DAPI was added to each well for 15 minutes and then cells were washed twice with Perm/Wash buffer, and once with 1×PBS prior to imaging.

Imaging was done on the Opera Phenix™ HCS machine (PerkinElmer Inc.) using the 40× water immersion lens and the confocal mode for better membrane scanning ability. 4-5 fields were acquired for each well to enable better quantitative analysis of fluorescence intensities, and analysis and quantification were conducted on the Harmony® (PerkinElmer Inc.) software.

Western Blotting. HCC1171 cells (20000/mL) were seeded into T-75 ultra-low adherence ULA plates (Corning® Inc.) with complete medium (RPMI with 2% L-Glutamine and 10% FBS) and allowed to grow overnight. The next day, cells were treated with 5 mM ARS853 for 18-24 hours. The next day cells were pelleted and washed twice with 1×PBS and replenished with compound-free complete medium with or without 50 mg/mL Cycloheximide (Sigma) as a control for new protein synthesis for 24 or 48 hours. Cells were then collected for the end of treatment, washed once with 1×PBS and lysed with Ripa Buffer (Thermofisher Scientific™) with Halt™ proteases and phosphatases inhibitors (Thermofisher Scientific™) to collect protein. Pierce™ BCA assay (Thermofisher Scientific™) was used to quantify proteins, which were then run on Novex™ 4-20% Tris-Glycine gels for 3 hours at 100V, and transferred using the Trans-Blot® Turbo™ Transfer System (Bio-Rad Laboratories). Membranes were blocked with Li-Cor Odyssey® TBS blocking buffer for 1 hour, incubated with primary antibodies (Proteintech: KRAS antibody #12063-1-AP, Cell Signaling Technology: pERK(Thr 202/Tyr 204) #9101, Total ERK #9102, pS6 (Ser 235/236) #2211, and HSP90 #4874) overnight, then washed 3 times, 10 min, with TBST before adding the secondary antibodies (Li-Cor). Membranes were finally washed 3 times with TBST buffer and imaged on the Li-Cor Odyssey@ CLx machine.

In vivo fluorescence-activated cell sorting (FACS). To evaluate tumor pharmacodynamics, harvested tumors were digested with Liberase DL (0.2 U/ml, Sigma-Aldrich, SKU No. 5466202001) and DNase 1(40 U/ml, Sigma-Aldrich, SKU No. 10104159001) for 30 minutes, 37° C. using gentleMACS™ dissociator (Miltenyi Biotec). Single cell suspensions were prepared and stained for EpCAM (clone EBAl, BD Biosciences, Catalog No. 743544) and Fixable Viability Dye (ebioscience) for 30 minutes at 4° C. and washed. Cells were fixed with Cytofix Buffer (BD Biosciences, Catalog No. 51-2090KZ) for 30 minutes at 4° C. and washed with Perm/Wash buffer (BD Biosciences, Catalog No. 51-2091KZ). Intracellular staining was performed for 1A5-488, pS6 (Clone N7-548, BD Biosciences, Catalog No. 561457) for 60 minutes at 4° C. and washed with perm wash buffer and resuspended in FACS buffer. Cells were analyzed on the BD Symphony FACS machine. Data were analyzed using GraphPad prism software version 7 (GraphPad, San Diego, CA); Flowjo 10.5.3 (FlowJo, BD, CA).

Whether the 1A5 anti-KRas antibody could be used to specifically visualize alkylated KRas$^{G12C}$ in KRas$^{G12C}$ mutant cancer cells was tested. Immunofluorescence (IF) staining of H1171 KRas$^{G12C}$ cells but not HCT116 KRas$^{G13D}$ cells treated with a variety of G12C covalent molecules including GNE-1952, ARS-853, ARS-1620, and AMG 510 were detected with the 1A5 anti-KRas antibody (FIG. 2A-2C) in a dose dependent manner further confirming the ability of 1A5 to recognize a common conformation induced by multiple KRas$^{G12C}$ covalent molecules.

Figure 2A:
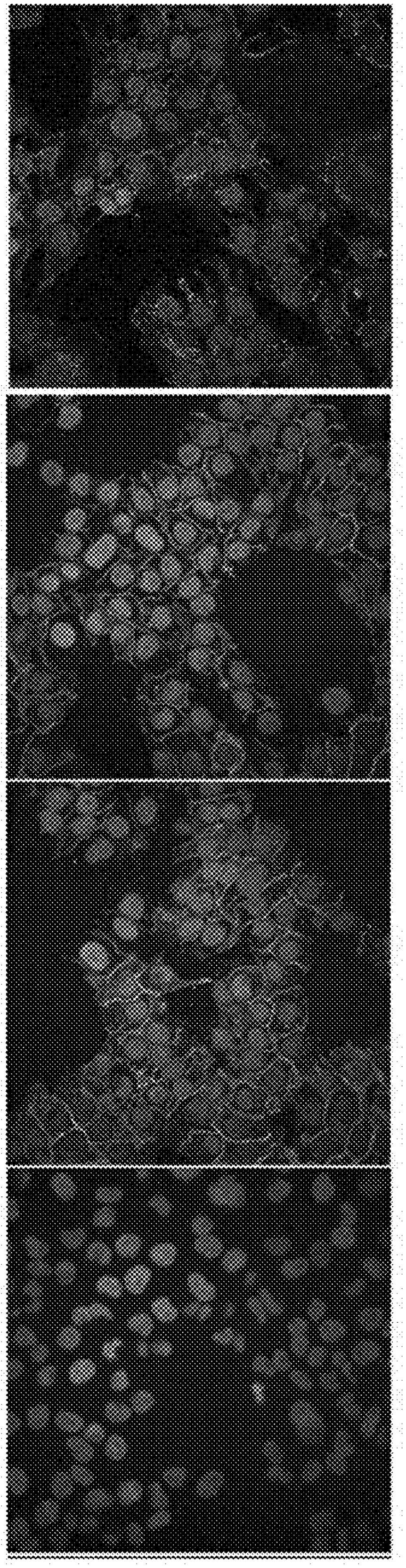
FIG. 2A shows 1A5 anti-KRas antibody binding $KRas^{G12C}$ in cells treated with various covalent molecules compared to a DMSO control, in H1171 $KRAS^{G12C}$ mutant cancer cells using immunofluorescence (IF) assays.
Figure 2B:
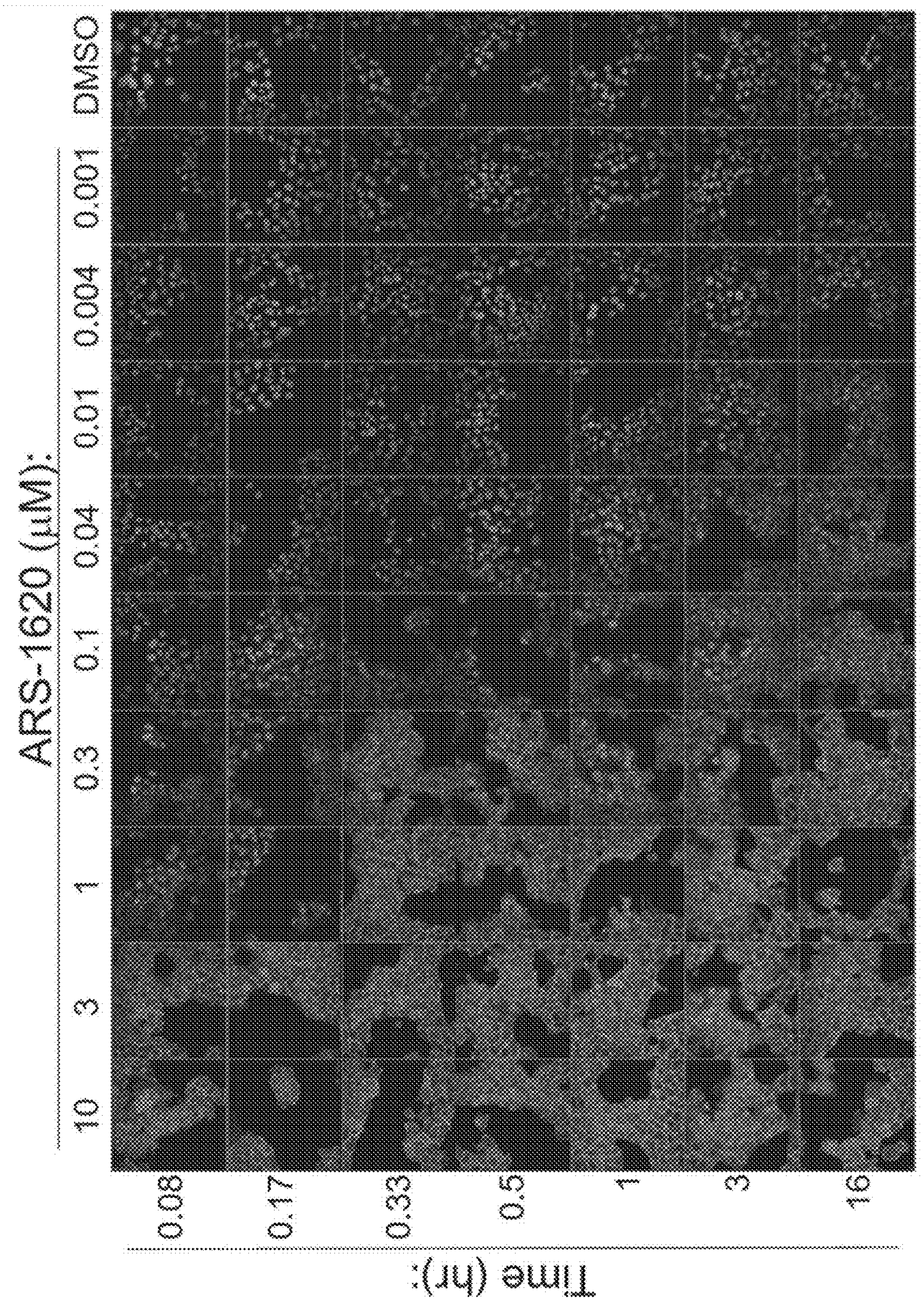
FIG. 2B shows staining with 1A5 anti-KRas antibody of $KRas^{G12C}$ upon ARS-1620 treatment in H1171 $KRAS^{G12C}$ mutant cancer cells over a range of time (indicated in hours on the y-axis) and dose of ARS-1620 (indicated in μM along the x-axis, compared to a DMSO control).
Figure 2C:
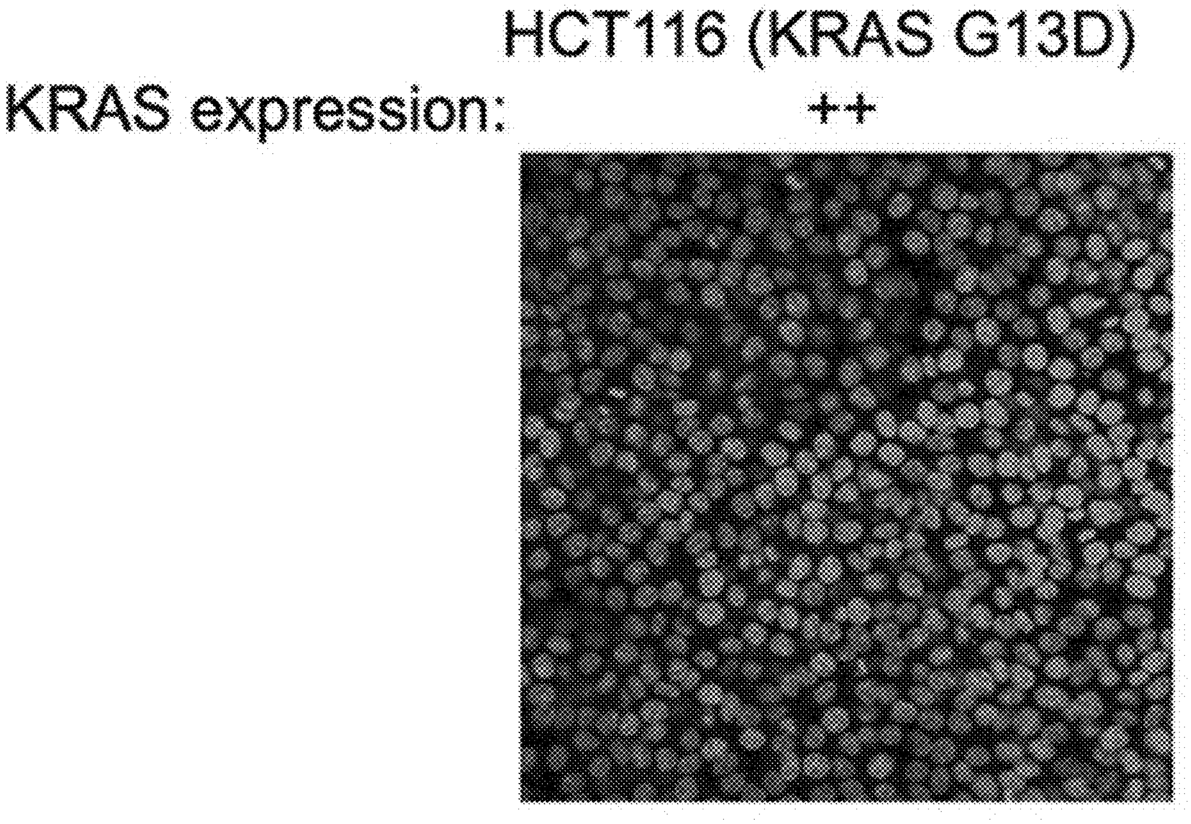
FIG. 2C shows the lack of observable KRas staining by 1A5 anti-KRas antibody in HCT116 $KRas^{G13D}$ cells treated with a $KRas^{G12C}$ inhibitor GNE-1952.
Figure 2D:
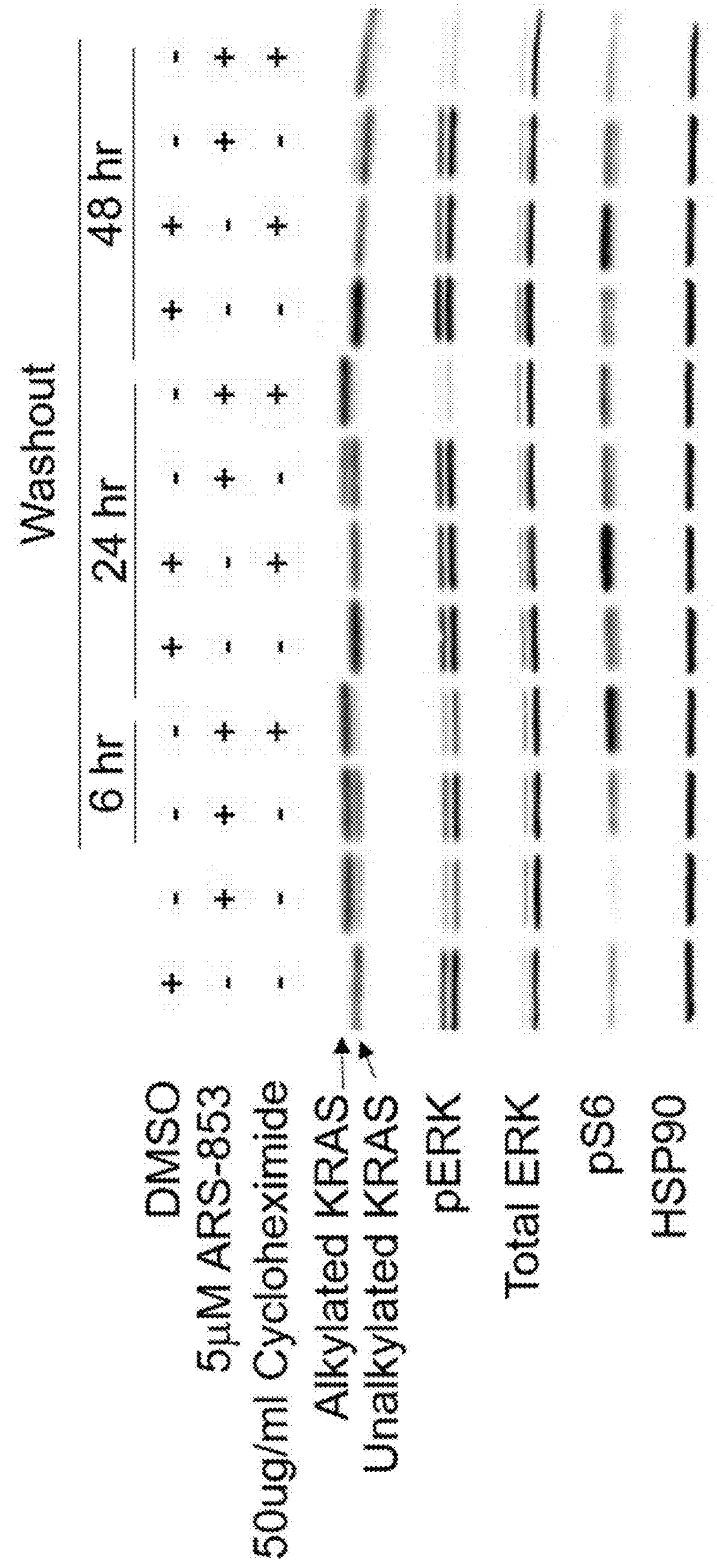
FIG. 2D shows an immunoblot analysis for alkylated KRas inhibition of KRas pathway marker, pERK, pS6 in a bulk population of H1171 $KRAS^{G12C}$ mutant cancer cells. Cells were treated with DMSO, 5 μM ARS-853, and/or 50 μg/ml cyclohexamide, as indicated. Samples were collected either after treatment, or after 6, 24, or 48 hours after the washout of the treatment, as indicated.
Figure 2E:
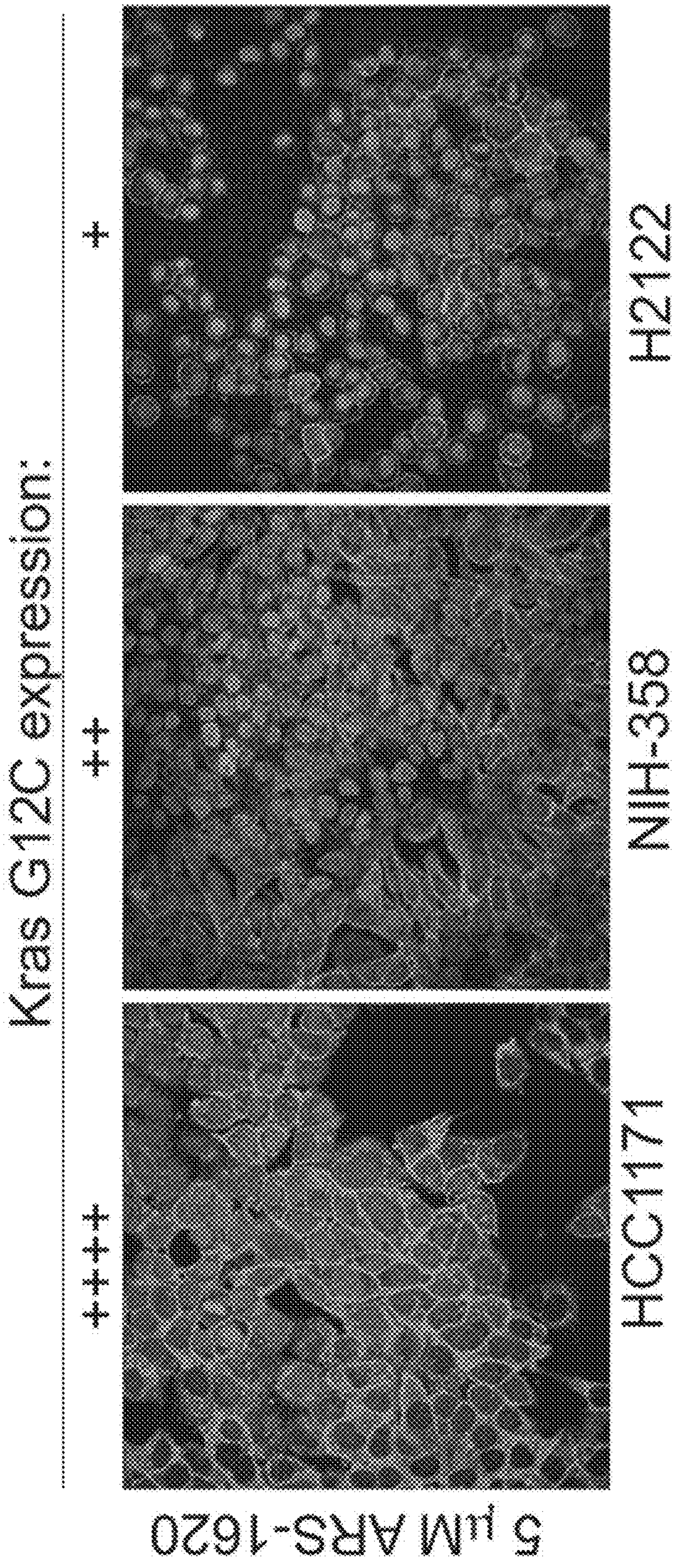
FIG. 2E shows 1A5 binding $KRas^{G12C}$ across different $KRAS^{G12C}$ mutant cancer cell models in immunofluorescence assays. Cells were treated with 5 μM ARS-1620. The relative amount of $KRas^{G12C}$ expression in each cancer cell model is indicated with + signs.

The kinetics of KRas$^{G12C}$ alkylation was quantified in cells (FIG. 2B). These results agreed with values obtained with immunoblotting for alkylated KRas (FIG. 2D) and inhibition of KRas pathway markers such as pERK and pMEK in a bulk population of cells. IF staining of alkylated KRas$^{G12C}$ with 1A5 in individual cells provided additional information, revealing that the kinetics of KRas$^{G12C}$ alkylation surprisingly occurred in very synchronous fashion at both the membrane as well as punctate compartments of cells (FIG. 2A, FIG. 2B). Since antibodies specific for RAS-GDP do not exist, staining with the 1A5 anti-KRas antibody provides information on the localization on where KRas$^{G12C}$-GDP was located in cells when it was alkylated. The 1A5 anti-KRas antibody could also detect alkylated KRas$^{G12C}$-GDP in a number of KRas$^{G12C}$ lines expressing very low levels of KRas$^{G12C}$ protein (FIG. 2E).

Figure 2F:
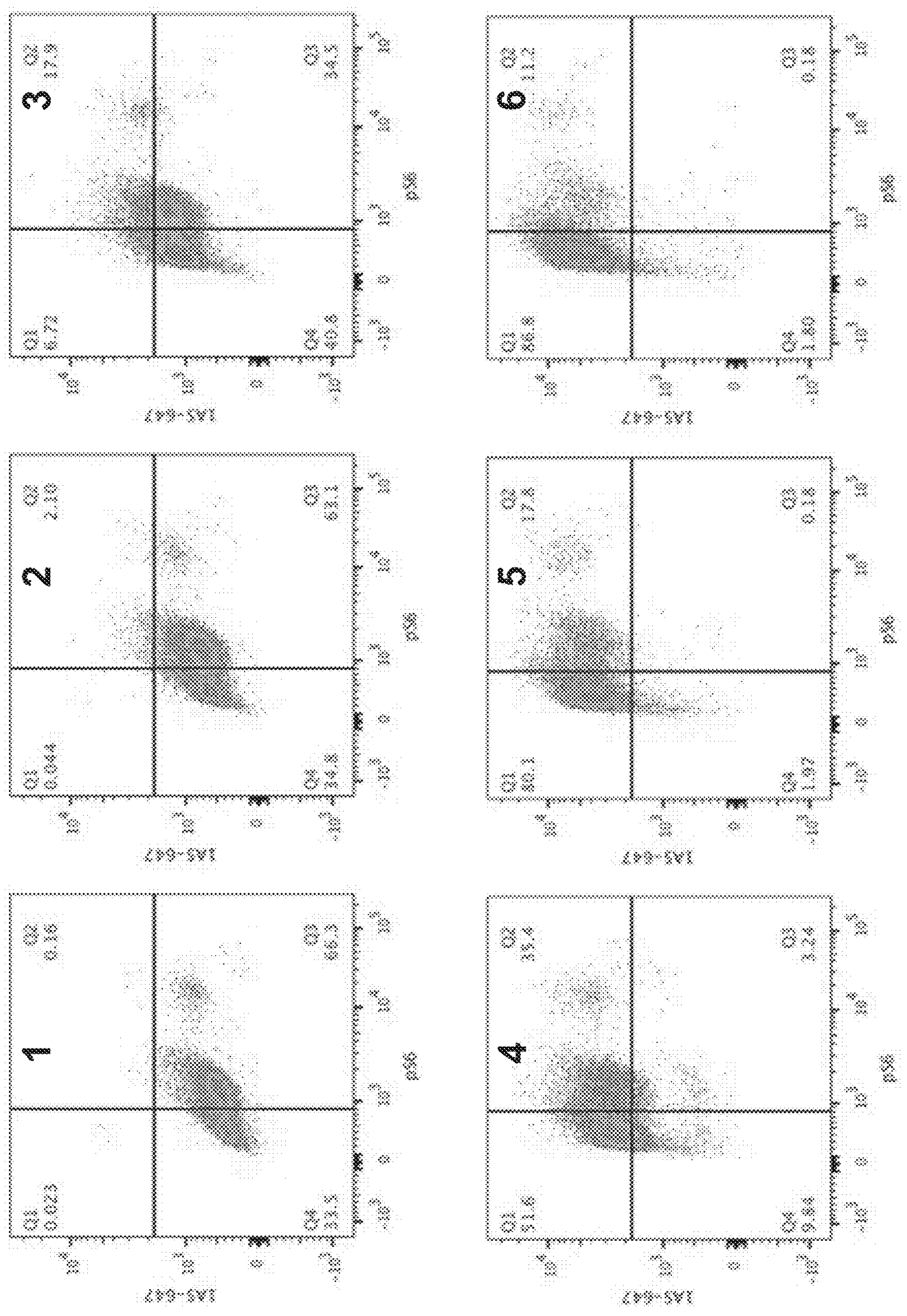
FIG. 2F shows flow cytometry measurements of 1A5 staining (y-axis) and pS6 staining (x-axis) in H1171 $KRAS^{G12C}$ mutant cancer cells treated with increasing doses of ARS-1620, compared to a DMSO control (left).

Since FACS enables single cell analysis and potential to correlate alkylation levels with pharmacodynamic effects on downstream signaling, application of the 1A5 anti-KRas antibody for FACS staining was evaluated. 1A5 anti-KRas antibody specifically detected increasing levels of alkylated KRas$^{G12C}$-GDP as levels of the compound increased (FIG. 2F). Furthermore, cells were co-stained with an anti-pS6 antibody, a downstream marker of KRAS activity, and as expected, there was a dose-dependent decrease in pS6 levels in most of the population (FIG. 2F).

Example 5: Comparison of Selected Anti-KRas Antibodies to Commercially Available Anti-KRas Antibodies The following example describes a comparison of the conformational specificity of KRas-binding by the selected anti-KRas antibodies disclosed herein to a set of commercially available anti-KRas antibodies.

Materials and Methods

Commercially available anti-KRas antibodies. Commercial antibodies used were as follows: iDab6 (Tanaka, T. et al., *EMBO J* 2007; 26:3250-3259) with a Rabbit IgG, Anti-Ras antibody (EP1125Y) (Abcam, ab52939), KRas-2B specific Rabbit polyclonal (Proteintech, Cat. No 16155-1-AP), Ras10 (Millipore, Cat. No 05-516), 3B10-2F2 (Sigma-Aldrich, Cat. No WH0003845M1), and 234-4.2 (Millipore, Cat. No OP24) (FIGS. 3A-3D). Antibody ELISA against alkylated KRas$^{G12C}$. Biotinylated KRas$^{G12C}$-GDP+GNE-1952 and KRas$^{G12C}$-GDP was coated on NeutrAvidin ELISA plates (Thermo Scientific) in triplicate at 0.3 μg/mL in PBS overnight at 4° C. Plates were washed with PBSBT and serial dilutions of anti-KRas antibodies starting at 10 μg/mL were added for 1-2 hours at 25° C. with shaking. After washing, a species matched Fc-specific HRP 2° antibody was added for 1 hour at 25° C. with shaking. After washing with PBSBT, plates were developed with TMB substrate for 5 minutes and detected at 650 nm.

Immunoprecipitation. Immunoprecipitation of alkylated and un-alkylated KRas$^{G12C}$ in H1171 KRAS$^{G12C}$ mutant cancer cells treated with DMSO or ARS-1620 by the selected anti-KRas antibodies 1A5 and 2H11, and a set of commercially available antibodies was performed.

A set of commercially available antibodies to KRas was surveyed to determine their conformational specificity. Two antibodies were identified (Abcam EP1125Y and Ras10) that had comparable affinity for both unalkylated and alkylated KRasG12C by immunoprecipitation and ELISA (FIG. 3A, FIG. 3B) suggesting these antibodies were not conformation specific. In contrast, the iDab6 antibody, which was reported to be highly specific for HRasGTP, showed little to no binding to the alkylated KRas$^{G12C}$-GDP, but bound to both GDP and GMPPcP bound forms with a preference for the GDP bound form by ELISA (FIG. 3B), and could only immunoprecipate the unalkylated KRas$^{G12C}$ in cells (FIG. 3A) (Tanaka, T. et al., *EMBO J* 2007; 26:3250-3259). Since the iDab6 antibody binds an epitope that spans both the SWI and SWII regions, the SWII conformation induced by alkylation of KRas$^{G12C}$-GDP likely prevents iDab6 binding. Only 1A5 and 2H11 bound preferentially to alkylated KRas$^{G12C}$.

Example 6: 1A5 Anti-KRas Antibody Binds KRas in Cells

The following example provides a comparison of the ability of the selected anti-KRas antibody 1A5 to a commercially available anti-KRas antibody to bind KRas in cells.

Materials and Methods

Figure 3A:
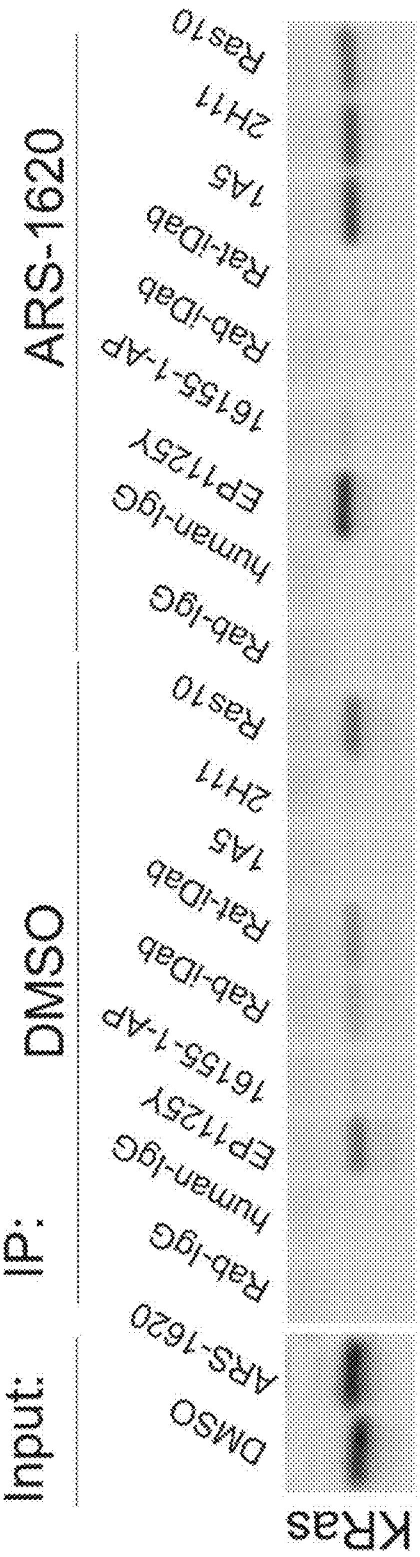
FIG. 3A shows the differential immunoprecipitation of alkylated and un-alkylated $KRas^{G12C}$ in H1171 $KRAS^{G12C}$ mutant cancer cells treated with DMSO or ARS-1620 by the selected anti-KRas antibodies 1A5 and 2H11, compared to a set of commercially available antibodies.
Figure 3B:
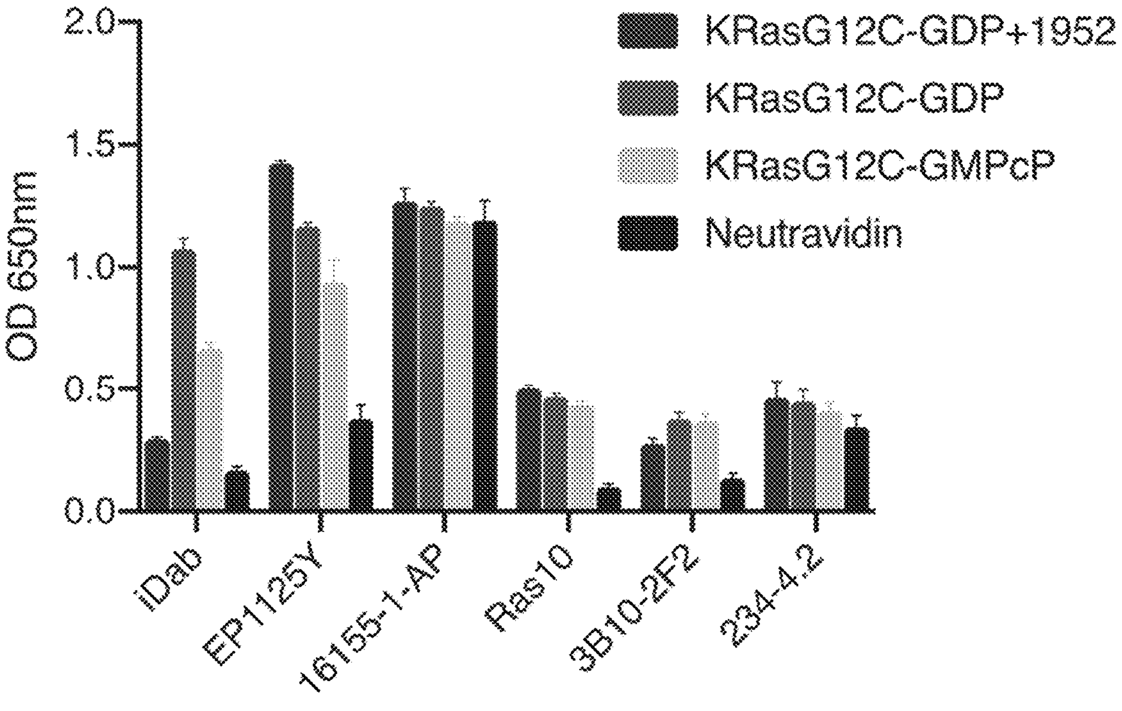
FIG. 3B shows an ELISA with a set of commercially available antibodies (indicated on the x-axis) on $KRas^{G12C}$-GDP+GNE1952 compared to unalkylated $KRas^{G12C}$-GDP, $KRas^{G12C}$-GMPcP, and NeutrAvidin alone.
Figure 3C:
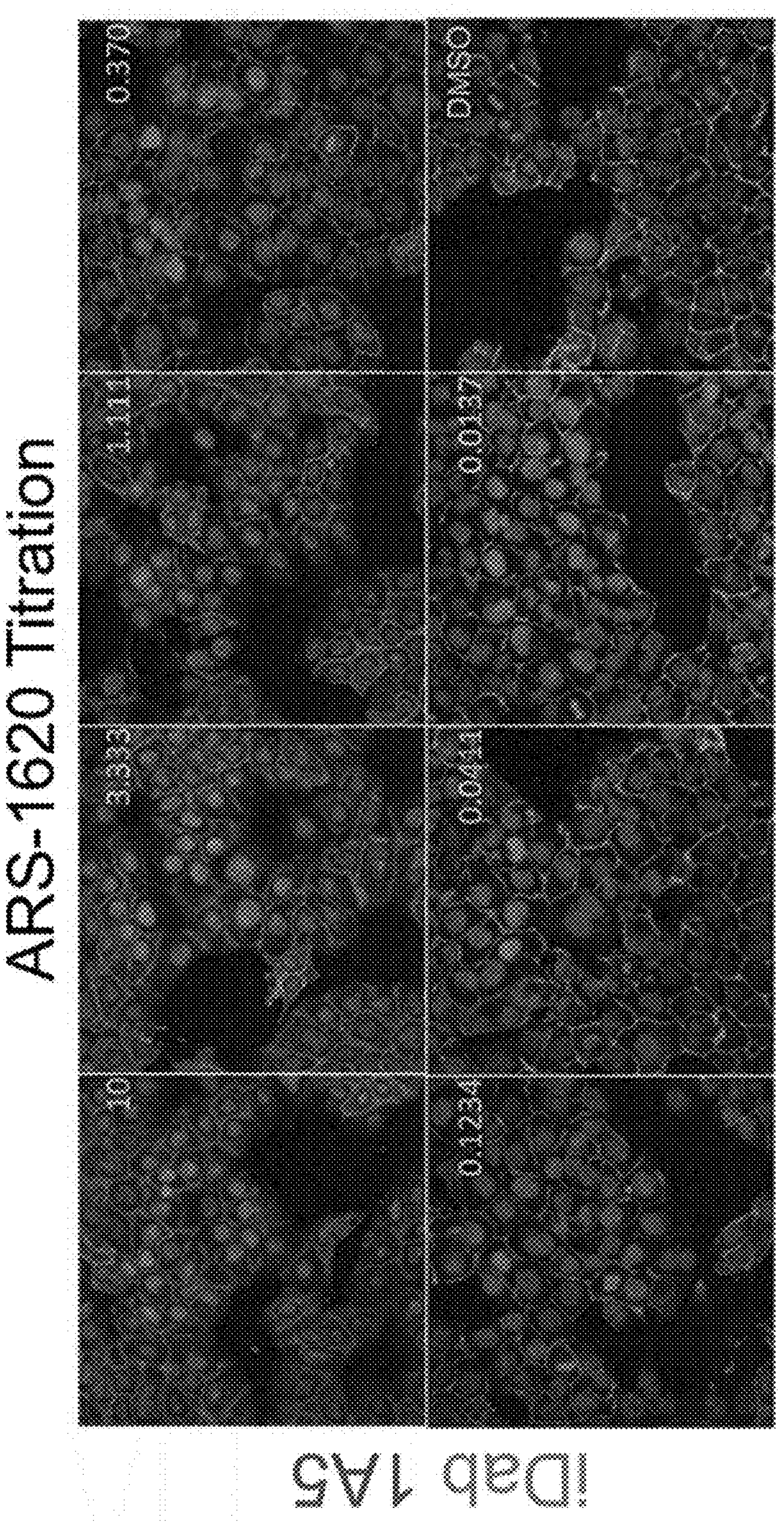
FIG. 3C shows immunofluorescence with the 1A5 anti-KRas antibody (top row) and iDab6 (bottom row) over a dose titration of ARS-1620. DAPI-stained DNA is shown in blue. The dose of ARS-1620 in nM is indicated on each image.

Immunofluorescence and High Content Imaging. Cells (20000 to 40000 cells per well depending on the cell line) were seeded into Poly-L-Lysine Coated 96-well plates (Cell Cater Ultra; Perkin Elmer) and supplemented with complete medium (RPMI with 2% L-Glutamine and 10% FBS). The next day, cells were treated with KRAS$^{G12C}$ inhibitors at indicated concentrations and incubated for the indicated length of time. At the end of treatment, cells were washed twice with cold 1×PBS, fixed with 3% paraformaldehyde for 20 minutes at room temperature, washed for 10 minutes with 1×PBS, and the PFA was quenched with 50 mM $NH_4Cl$ for minutes at room temperature. Cells were washed again with 1×PBS twice for 5 minutes, then permeabilized with 1× Perm/Wash Buffer (BD, Fisher Scientific) for 20 minutes at room temperature. Cells were then incubated with primary antibody (1A5 or iDab6 or both) diluted in Perm/Wash buffer at indicated concentration for 2 hours at room temperature. Cells were then washed three times with Perm/Wash buffer for 10 minutes each, and the incubated with conjugated fluorescence secondary antibody for 20 to 60 minutes (Alexa488 anti-human and Alexa647 anti-rabbit or anti-rat at 1:500 from Jackson ImmunoResearch Laboratories Inc.) 100 ml of 300 nM DAPI was added to each well for 15 minutes and then cells were washed twice with Perm/Wash buffer, and once with 1×PBS prior to imaging (FIG. 3C).

Imaging was done on a Opera Phenix™ HCS machine (PerkinElmer Inc.) using the 40× water immersion lens and the confocal mode for better membrane scanning ability. 4-5 fields were acquired for each well to enable better quantitative analysis of fluorescence intensities, and analysis and quantification were conducted on the Harmony® (PerkinElmer Inc.) software.

For washout experiment, cells were plated as described previously and treated with KRAS$^{G12C}$ inhibitor for 18-24 hours. One plate was imaged after 24 hours as control and the other plates were washed twice with cold 1×PBS, and incubated for either 24 or 48 hours with 150 mL of complete compound-free medium and stained and imaged as described above.

Whether the 1A5 and iDab6 (Tanaka, T. et al., *EMBO J* 2007; 26:3250-3259) antibodies could be used in combination to co-stain and visualize both unalkylated and alkylated KRas$^{G12C}$ within the same cell was tested. Immunofluorescence (IF) experiments were conducted with H1171 cells treated with a dose titration of ARS-1620 using both 1A5 anti-KRas antibody and iDab6 antibodies. Similar to previous IF experiments with 1A5, an increase in 1A5 staining was detected that correlated with high concentrations of ARS-1620 treatment. In contrast, the increase in 1A5 staining coincided with decreased staining with the iDab6 antibody (FIG. 3C).

Co-staining with both antibodies allowed for the monitoring of the re-synthesis of KRas$^{G12C}$. Treatment of KRas$^{G12C}$ cells with ARS-1620 for 16 hours resulted in almost complete alkylation of KRas$^{G12C}$ by IF and immunoblot analysis (FIG. 2D). Upon washing out drug, the appearance of unalkylated KRas$^{G12C}$ started to appear at 24 hours (FIG. 2D) which coincided with a decrease in 1A5 anti-KRas antibody and an increase in iDab6 antibody staining.

Thus, the 1A5 anti-KRas antibody can be used to study $KRas^{G12C}$ alkylation as well as track $KRas^{G12C}$-GDP in cells.

Example 7: Dose-Dependent In Vivo Detection of Alkylated $KRas^{G12C}$ with ARS-1620 Treatment in High and Low $KRas^{G12C}$-Expressing Mouse Models The following example describes the binding of anti-KRas antibodies to $KRas^{G12C}$ in vivo in mouse models.

Materials and Methods

In vivo tumor studies. Female C.B-17 SCID (Inbred) mice that were 16-17 weeks old and weighed 24-27 g were obtained from Charles River Lab. They were inoculated with five million NCI-H358 non-small cell lung carcinoma cells (suspended in a 1:1 mixture of Hank's Balanced Salt Solution containing Matrigel at a 1:1 ratio) in both the left and right flank subcutaneously. Tumors were monitored until they reached a mean tumor volume of 400-600 $mm^3$. Mice were given single dose of 0 (Vehicle—100% Labrasol), 50, or 200 mg/kg ARS1620 orally (PO) by gavage in a volume of 100 μL. Plasma and tumor samples were collected at 8 or 24 hours post-dose.

In vivo FACs assays. To evaluate tumor pharmacodynamics, harvested tumors were digested with Liberase DL (0.2 U/ml, Sigma-Aldrich) and DNase I (40 U/ml, Sigma-Aldrich) for 30 minutes, 37° C. using gentleMACS™ dissociator (Miltenyi Biotec). Single cell suspensions were prepared and stained for EpCAM (clone EBAl, BD Biosciences) and Fixable Viability Dye (ebioscience) for 30 minutes at 4° C. and washed. Cells were fixed with Cytofix Buffer (BD Biosciences) for 30 minutes at 4° C. and washed with Perm/Wash buffer (BD Biosciences). Intracellular staining was performed for 1A5-488, pS6 (Clone N7-548, BD Biosciences) for 60 minutes at 4° C. and washed with perm wash buffer and resuspended in FACS buffer. Cells were analyzed on the BD Symphony, FACS machine. Data were analyzed using GraphPad prism software version 7 (GraphPad, San Diego, CA); Flowjo 10.5.3 (FlowJo, BD, CA).

Figure 4A:
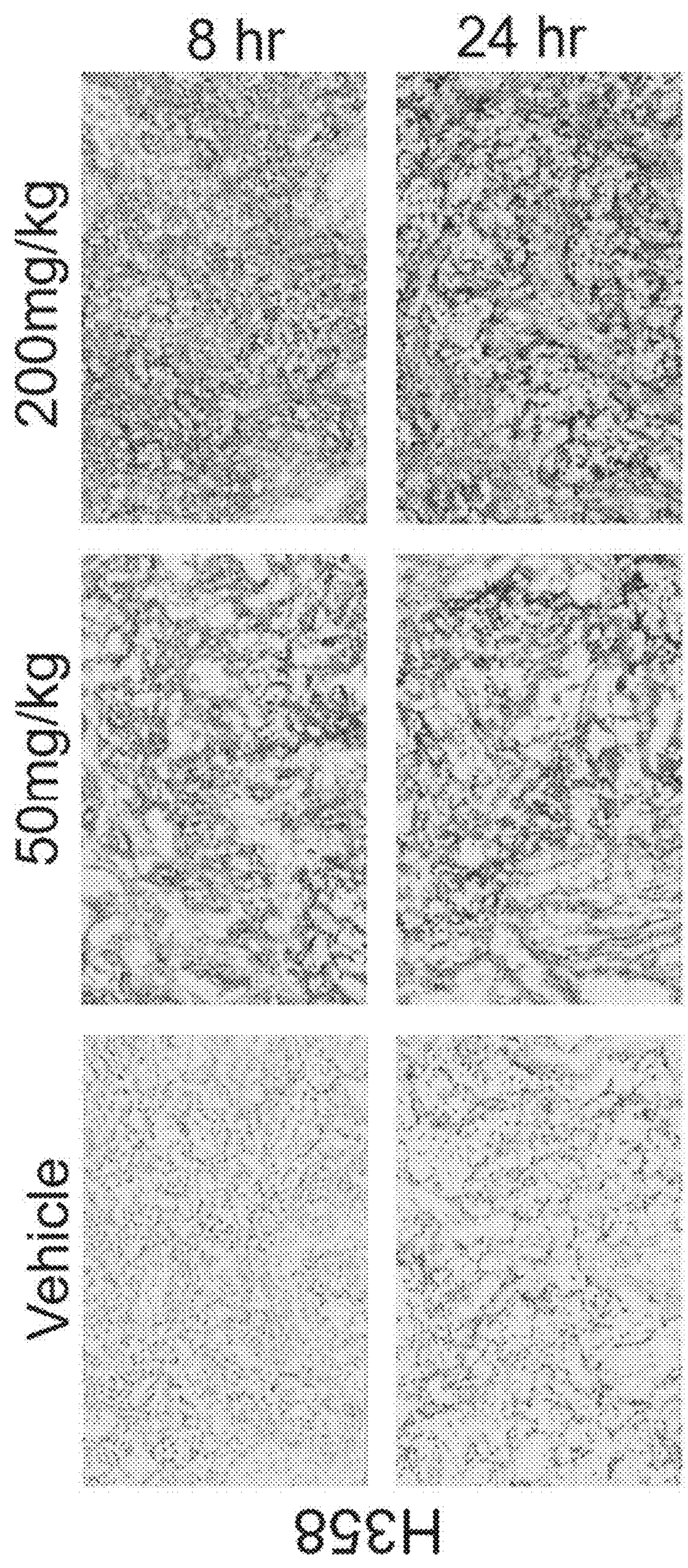
FIG. 4A shows immunohistochemistry with 1A5 anti-KRas antibody on NCI-H358 (high $KRas^{G12C}$-expressing) xenografts in female C/B17 SCID mice following 8 hour and 24 hour treatment with ARS-1620 at 50 mg/kg or 200 mg/kg, compared to a vehicle only control.
Figure 4B:
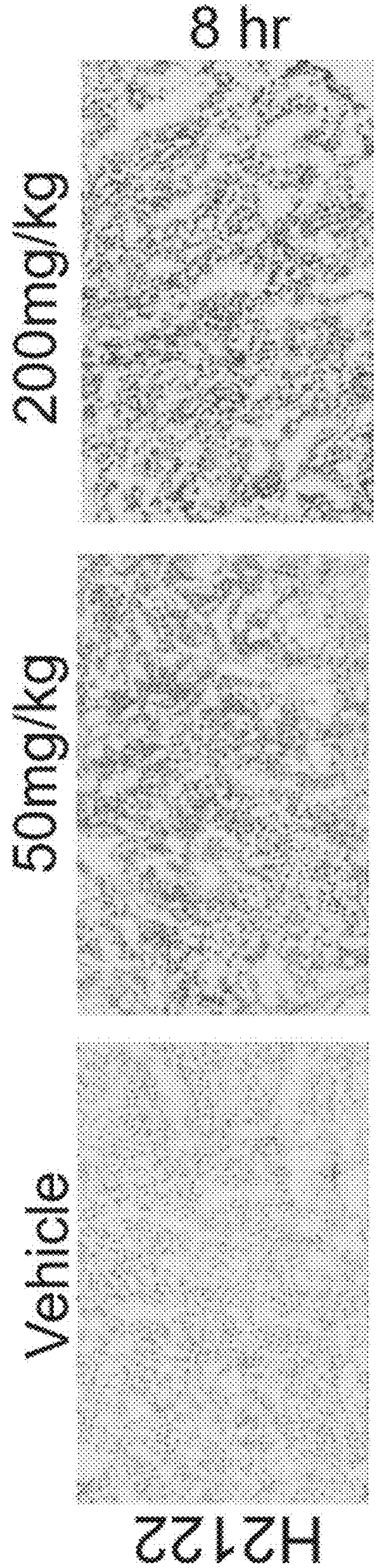
FIG. 4B shows NCI-H2122 (low $KRas^{G12C}$-expressing) xenografts in female CRL nude mice following 8 hour treatment with ARS-1620 at 50 mg/kg or 200 mg/kg, compared to a vehicle only control.
Figure 4C:
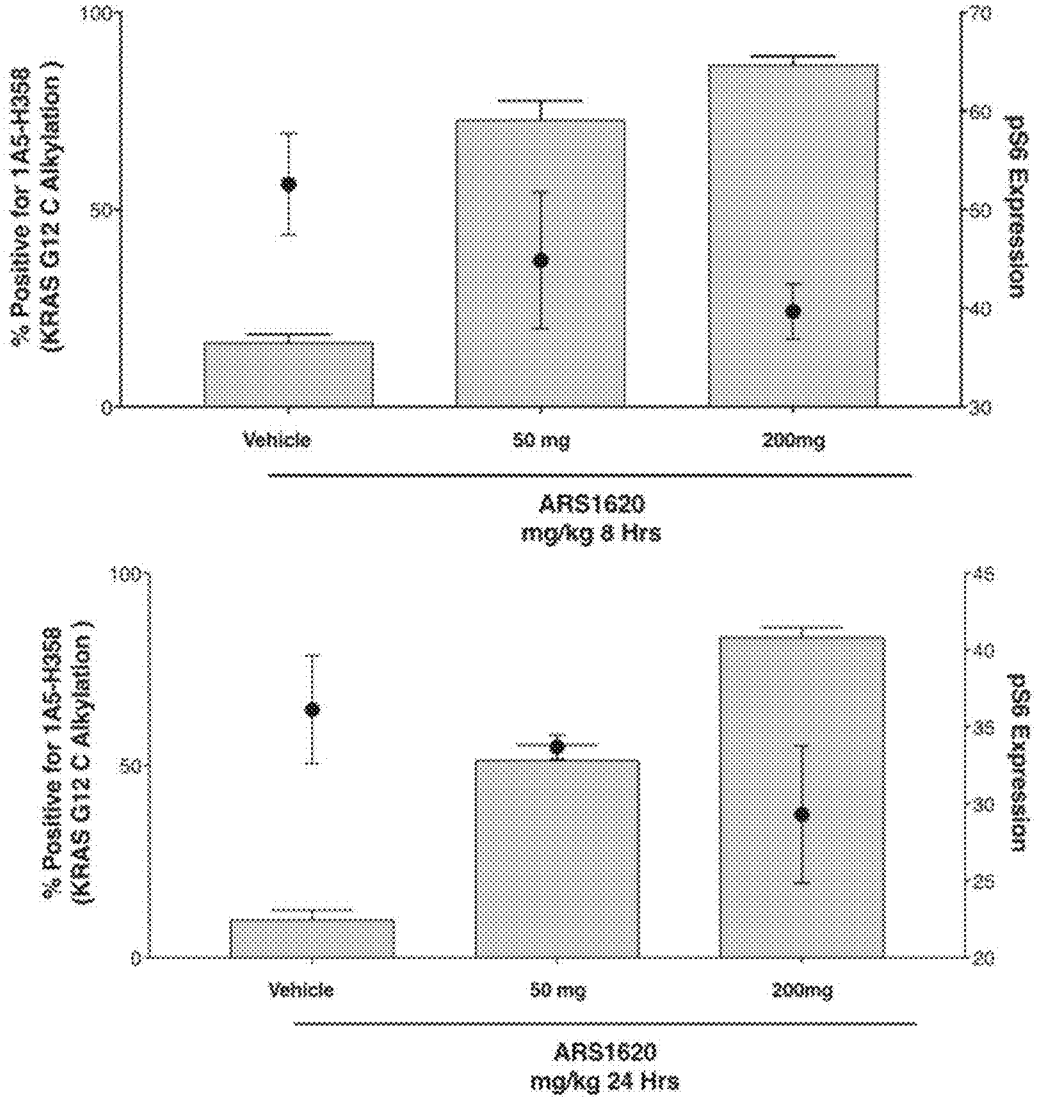
FIG. 4C shows the percentage of NCI-H358 xenograft cells positive for the 1A5, as measured by flow cytometry, in grey bars (left y-axis). Relative expression of pS6 (a KRAS pathway marker) is shown in black circles (x-axis). Samples were treated with 50 mg/kg or 200 mg/kg ARS-1620 or a vehicle only control for 8 or 24 hours.

Alkylated $KRas^{G12C}$ was readily detectable in tumor samples prepared as fresh frozen (FP) tissues (FIG. 4A). Tumors expressing lower amounts of alkylated $KRas^{G12C}$ were also detected by the 1A5 anti-KRas antibody (FIG. 4B). Similar to in vitro cell experiments, the 1A5 anti-KRas antibody could also detect alkylated $KRas^{G12C}$ in FACS experiments in ex vivo tumor samples and could be multiplexed with the MAPK marker pS6 (FIG. 4C). These results show that the 1A5 anti-KRas antibody enables measurement of direct target engagement of $KRas^{G12C}$ inhibitors in $KRas^{G12C}$ tumor samples and multiplex analysis with markers of RAS pathway activation.

The following example describes experiments testing whether the ability of Class II selected anti-KRas antibodies (e.g., 2H11) to recognize the alkylation-induced KRas unalkylated $KRas^{G12C}$ could be used to improve the affinity for small molecule compound binding in the pocket.

Figure 5A:
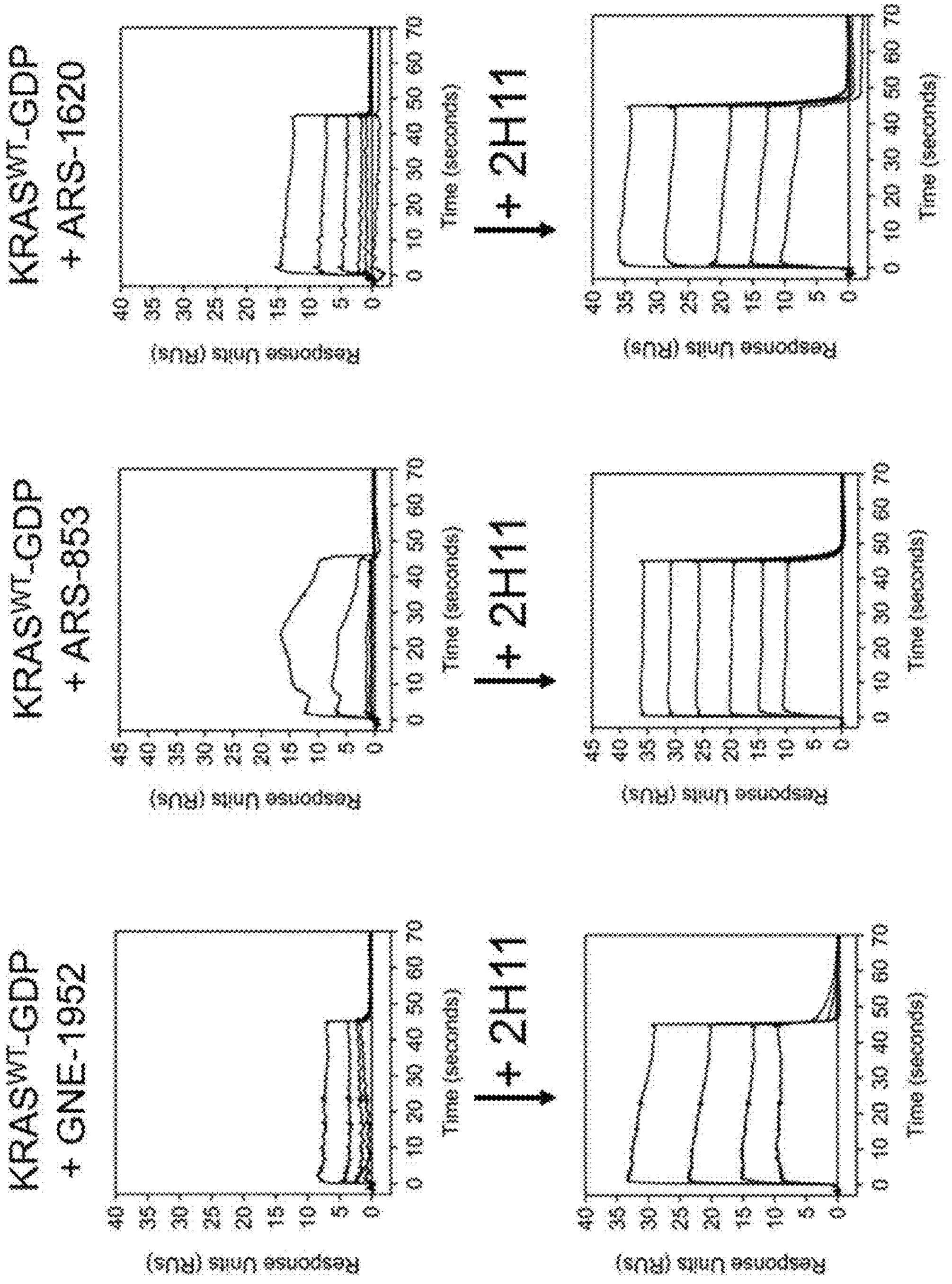
FIG. 5A shows SPR data from $KRas^{WT}$ treated with GNE-1952, ARS-853, or ARS-1620 at concentrations ranging from 1 to 50 μM in the absence (top row) or presence (bottom row) of the 2H11 anti-KRas antibody.
Figure 5B:
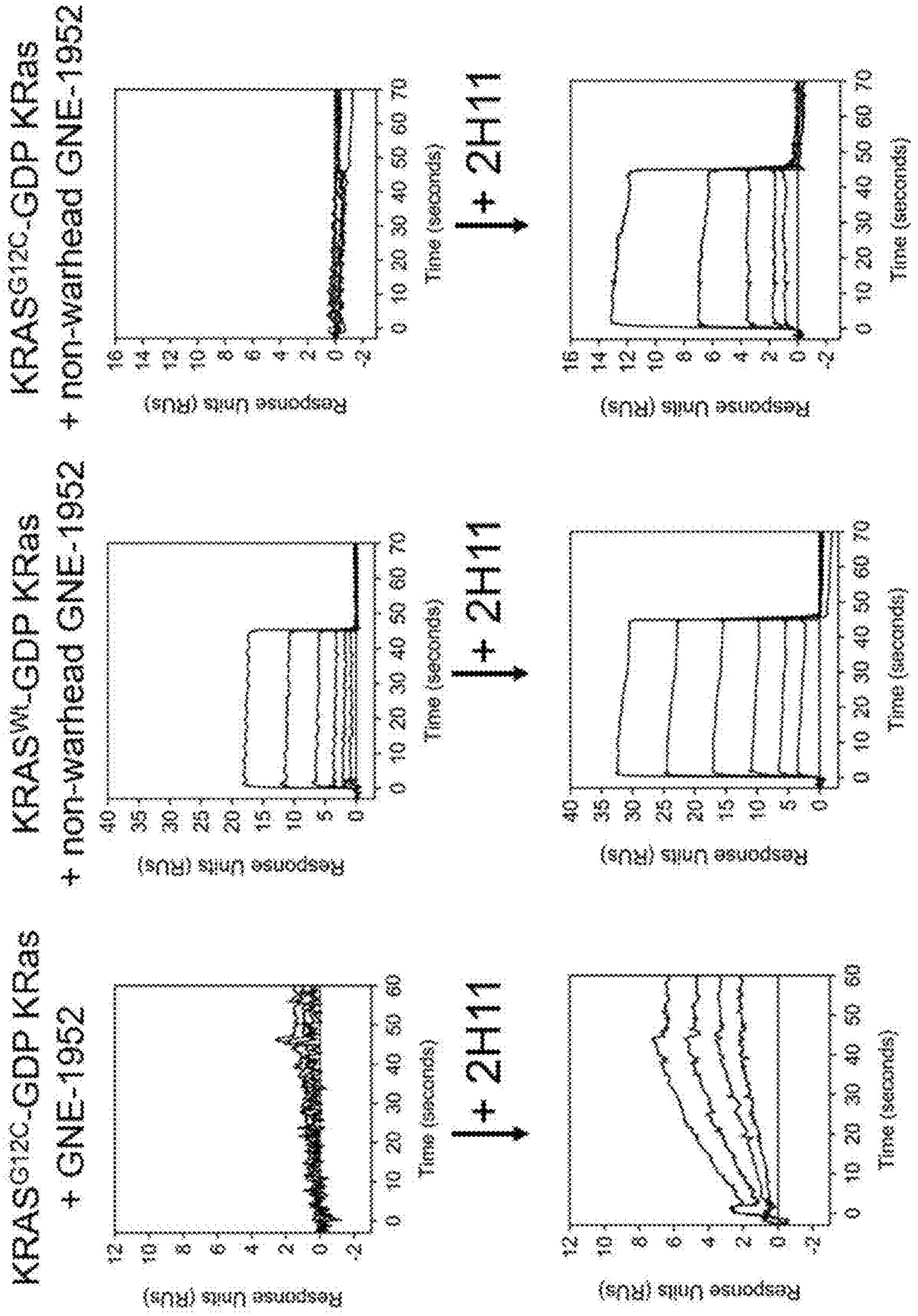
FIG. 5B shows SPR data from $KRas^{G12C}$ or $KRas^{WT}$ treated with GNE-1952 or a "non-warhead" form of GNE-1952 (lacking the reactive acrylamide function), in the absence (top row) or presence (bottom row) of the 2H11 anti-KRas antibody. In each SPR plot in FIGS. 5A-5B, time in seconds is plotted on the x-axis, and response units are plotted on the y-axis).

Example 8: Selected Anti-KRas Antibodies Improve SWII Ligand Affinity to $KRas^{G12C}$ and $KRas^{WT}$ Materials and Methods Surface plasmon resonance (SPR) experiments with 2H11 anti-KRas antibody. A series S SA (streptavidin) chip was inserted into a Biacore T200 (GE Health Sciences). The instrument was primed into running buffer (50 mM HEPES pH 7.5, 150 mM NaCl, 0.2% (w/v) PEG-3350, 0.1% CM-dextran (w/v), 0.1 mM TCEP, 10 mM MgCl2, 100 nM GDP, and 2% (v/v) DMSO). $KRas^{G12C}$ was pre-blocked at the 12 position with covalent binding $KRas^{G12C}$ alkylator was captured to yield 2000-2500 response units (RU) on flow channel 1 (FC1) and FC3 to serve as the reference for $KRas^{WT}$ and $KRas^{G12C}$ and allow affinity measurement exclusively at the Switch II (SWII) pocket. $KRas^{WT}$ or $KRas^{G12C}$ was captured on FC2 and FC4 within 100 RU of the reference channel capture level and data was collected in FC 2-1, FC 4-3 mode. All channels were subsequently blocked by injecting 100 μg/mL amine-PEG-biotin (Thermo Fisher). 2H11 was injected 2 times at 200 nM for 120 seconds at the start of the run to saturate FC3 and FC4, and injected every 14 cycles at 100 nM throughout the run to ensure complete occupancy. Analyte samples were tested 50 3M—1.75 3M in 2-fold dose response with 20-30 second contact time and 30 second dissociation. Data was analyzed in with a 1:1 affinity model in Biacore S200 Evaluation Software 1.0 and figures were made in Scrubber 2 (Biologic Software) (FIG. 5A and FIG. 5B).

A surface plasmon resonance (SPR) assay was developed to specifically detect binding to the SWII pocket using a SWII-blocked reference. The affinity of various SWII covalent molecules were tested (i.e., GNE-1952, ARS-853, ARS-1620), as well as a version of GNE-1952 lacking the acrylamide function, with $KRas^{G12C}$-GDP in the presence and absence of 2H11 anti-KRas antibody. Additionally, $KRas^{WT}$-GDP was included to test whether 2H11 could stabilize the SWII pocket in other KRas variants. The affinity was greatly enhanced in the presence of the 2H11 anti-KRas antibody (FIG. 5A and FIG. 5B). The 2H11 anti-KRas antibody increased the affinity of chemically diverse $KRas^{G12C}$ alkylators, further confirming that it was not biased towards one particular chemotype and suggesting that it may stabilize an open conformation of the SWII pocket in the absence of ligand.

Example 9: Crystal Structures of Anti-KRas Antibody:$KRas^{G12C}$ Complexes

The following example describes the determination of crystal structures of $KRas^{G12C}$ in complex with anti-KRas antibodies.

Materials and Methods $KRas^{G12C}$ protein expression and purification. The N-terminal His-tagged $KRas^{G12C}$ (1-169) constructs with and without cysteine mutations (S39C, C51S, C80L, C118S) were cloned into pET-52b vector and transformed into BL21 (DE3) cells. Cells were grown at 37° C. to an OD600 absorbance of 0.5 in LB media containing 50 μg/mL of carbenicillin and then transferred to 16° C. prior to induction with 0.3 mM IPTG at an OD600 absorbance of 0.8. Cells were harvested 16 hours post induction and the pellet was lysed by passing through a microfluidizer in a buffer containing 50 mM Hepes pH 8.0, 500 mM NaCl, 5 mM MgCl2, 10 mM Imidazole, 10% Glycerol, 1 mM TCEP, 1 mM PMSF, benzonase and EDTA-free-protease inhibitors. Cell lysates were clarified by spinning at 12,000K for 1 hour. Clarified cell lysates were loaded onto a HiTrap column in a buffer containing 20 mM Hepes pH 8.0, 300 mM NaCl, 10% Glycerol, 5 mM MgCl2, 1 mM TCEP and bound KRas protein was eluted with 300 mM Imidazole. The N-terminal His-tag was cleaved by incubating with TEV protease and removed through a nickel column. The KRas protein was polished by a size-exclusion S75 column (GE Healthcare) in a buffer of 20 mM Hepes pH 8.0, 150 mM NaCl, 5 mM MgCl2. The purity of KRas is greater than 95% as assayed by SDS-PAGE. To load GDP on KRas, it was first incubated with 40 mM EDTA and 2 mM GDP at 20° C. for 1-2 hours. It was then buffer exchanged to an EDTA-free and nucleotide-free buffer. KRas and 2H11 Fab were then complexed 1:1 and further purified by a size-exclusion S75 column in a buffer of 20 mM Hepes pH 8.0, 150 mM NaCl, 5 mM $MgCl_2$.

$KRas^{G12C}$ protein alkylation by GNE-1952. To alkylate KRas with GNE-1952, $KRas^{G12C}$ was incubated overnight at 20° C. with 5 mM GDP, 20 mM EDTA and 150 uM GNE-1952 in a buffer of 20 mM Hepes pH 8.0, 150 mM NaCl, 10% Glycerol and 2 mM TCEP. Complete alkylation was confirmed by observing shift in mass via mass spectrometry. The KRas was buffer exchanged by a size-exclusion S75 16/60 column to a buffer of 20 mM Hepes pH 7.0, 150 mM NaCl and 10% Glycerol. KRas G12C and 2H11 Fab were then complexed 1:1 and further purified by size-exclusion S75 column in a buffer of 20 mM Hepes pH 8.0, 150 mM NaCl.

Crystallization of $KRas^{G12C}$ and 2H11 Fab. Diffraction quality crystals of $KRas^{G12C}$/2H11 were grown at 19° C. from 1.0 µL+1.0 µL vapor diffusion sitting drops containing 10 mg/mL KRas and 24 mg/mL 2H11 Fab against a crystallization buffer of 0.1 M Sodium cacodylate pH 6.5, 40% 2-methyl 2,4-pentanediol (MPD), 7% Peg 8000, 0.5% ethyl acetate, 10 mM spermine tetrahydrochloride. Crystals appeared in two weeks and typically grew to 150×20×30 µM.

Diffraction quality crystals of $KRas^{G12C}$/GNE-1952/2H11 were grown at 19° C. from 1.0 µL+1.0 µL vapor diffusion sitting drops containing 15 mg/mL of KRas/2H11 complex against a crystallization buffer of 0.1 M MES pH 6.0, 21% Peg 4K and 0.2 M Lithium Sulfate. Crystals appeared in 10 days and grew to a size of 100×15×30 µM.

$KRas^{G12C}$/GNE-1952 crystals were grown at 19° C. from 1.0 µL+1.0 µL vapor diffusion sitting drops containing $KRas^{G12C}$/GNE-1952 against a crystallization buffer of 0.10% n-Octyl-B-D-glucoside, 0.1 M Sodium Citrate pH 5.5, 22% PEG 3350.

To prepare for diffraction data collection, 10% Glycerol was added to the crystallization buffer as cryobuffer before flash freezing the crystals for above three cases.

Diffraction Data Collection and Structure Determination.

The diffraction data of $KRas^{G12C}$/GNE-1952, $KRas^{G12C}$/2H11, and $KRas^{G12C}$/GNE-1952/2H11 crystals were collected using monochromatic X-rays at Stanford Synchrotron Radiation Lightsource (SSRL) beamline or Advanced Light Source (ALS) beam line 5.0.2 using PILATUS3 6M detector. Rotation method was applied to a single crystal for each of the complete data set. The crystals were kept at cryogenic temperature throughout the data collection process. Data reduction was done using the program XDS (Kabsch, W., *Acta crystallographica. Section D, Biological crystallography* 2010; 66:125-132) and the CCP4 program suite (A. J. McCoy et al., *Journal of applied crystallography* 2007; 40: 658-674).

Data reduction statistics are shown in Table 7. In Table 7, values in parentheses are of the highest resolution shell, $Rsym=\Sigma|I_h i-Ih|/\Sigma I_{hi}$ (where $I_{hi}$ is the scaled intensity of the ith symmetry-related observation of reflection h and $I_h$ is the mean value), $Rcryst=\Sigma_h|F_{oh}-F_{ch}|/\Sigma_h F_{oh}$ (where $F_{oh}$ and $F_{ch}$ are the observed and calculated structure factor amplitudes for reflection h), and the value of Rfree is calculated for 5 randomly chosen reflections not included in the refinement.

TABLE 7

| Crystallography statistics | | | |
|---|---|---|---|
| Protein complex | $KRas^{G12C}$/GNE-1952 | $KRas^{G12C}$/2H11 | $KRas^{G12C}$/GNE-1952/2H11 |
| PDB code | TBD (2016_02_03_SSRL_122, CRY21253) | TBD (2018_02_28_ALS_502, CRY25665) | TBD (2019_07_24_SSRL_122, CRY30160) |
| Space group | P1 | C2 | $P2_1$ |
| Unit cell | a = 33.6 Å, b = 44.0 Å, c = 65.3 Å, α = 89.0°, β = 85.0°, γ = 80.0° | a = 149.9 Å, b = 68.8 Å, c = 101.0 Å, α = γ = 90°, β = 114.1° | a = 59.2 Å, b = 51.9 Å, c = 107.5 Å, α = γ = 90°, β = 131.0° |
| Resolution | 2.15 Å | 2.20 Å | 2.00 Å |
| Total measured reflections | 69746 (639) | 317770 (3618) | 151246 (1545) |
| Completeness (%) | 89.3 (92.2) | 99.7 (97.3) | 97.9 (99.3) |
| Redundancy | 3.9 (3.9) | 6.7 (6.9) | 3.5 (3.6) |
| I/σ | 8.4 (1.7) | 11.6 (1.9) | 15.5 (2.1) |
| Rsym | 0.118 (0.782) | 0.075 (0.945) | 0.045 (0.592) |
| $CC_{1/2}$ | 0.996 (0.745) | 0.997 (0.807) | 0.999 (0.778) |
| Refinement | | | |
| Resolution range | 50-2.15 Å | 50-2.20 Å | 50-2.00 Å |
| Rcryst/Rfree | 0.213/0.257 | 0.208/0.225 | 0.216/0.255 |
| Non-hydrogen atoms | 2978 | 4788 | 4888 |
| Water molecules | 148 | 104 | 257 |

TABLE 7-continued

| Crystallography statistics | | | |
|---|---|---|---|
| Protein complex | $KRas^{G12C}$/GNE-1952 | $KRas^{G12C}$/2H11 | $KRas^{G12C}$/GNE-1952/2H11 |
| Average B | 39.1 Å | 79.7 Å | 41.5 Å |
| r.m.s.d. bond lengths | 0.002 Å | 0.004 Å | 0.006 Å |
| r.ms.d. angles | 0.539° | 0.991° | 0.863° |
| Ramachandran | 0.915/0.078/ 0.003/0.003 | 0.883/0.110/ 0.002/0.006 | 0.892/0.100/ 0/0.008 |

The structures were phased by molecular replacement (MR) using program Phaser (A. J. McCoy et al., *Journal of applied crystallography* 2007; 40: 658-674). A previously published crystal structure of $KRas^{G12D}$ (PDB code 4DSU) and a Fab structure Fab structure (PDB code 3R1G) were used as the MR search models. Manual rebuilding was performed with graphics program COOT (P. Emsley, K. Cowtan, *Acta crystallographica. Section D, Biological crystallography* 2004; 60:2126-2132). The structures were further refined iteratively using program REFMAC5 (G. N. Murshudov, A. A. Vagin, E. J. Dodson, *Acta crystallographica. Section D, Biological crystallography* 1997; 53:240-255) and PHENIX (P. D. Adams et al., *Acta crystallographica. Section D, Biological crystallography* 2010; 66:213-221) using maximum likelihood target functions, anisotropic individual B-factor refinement and TLS refinement, and to achieve final statistics shown in Table 7.

Figure 6A:
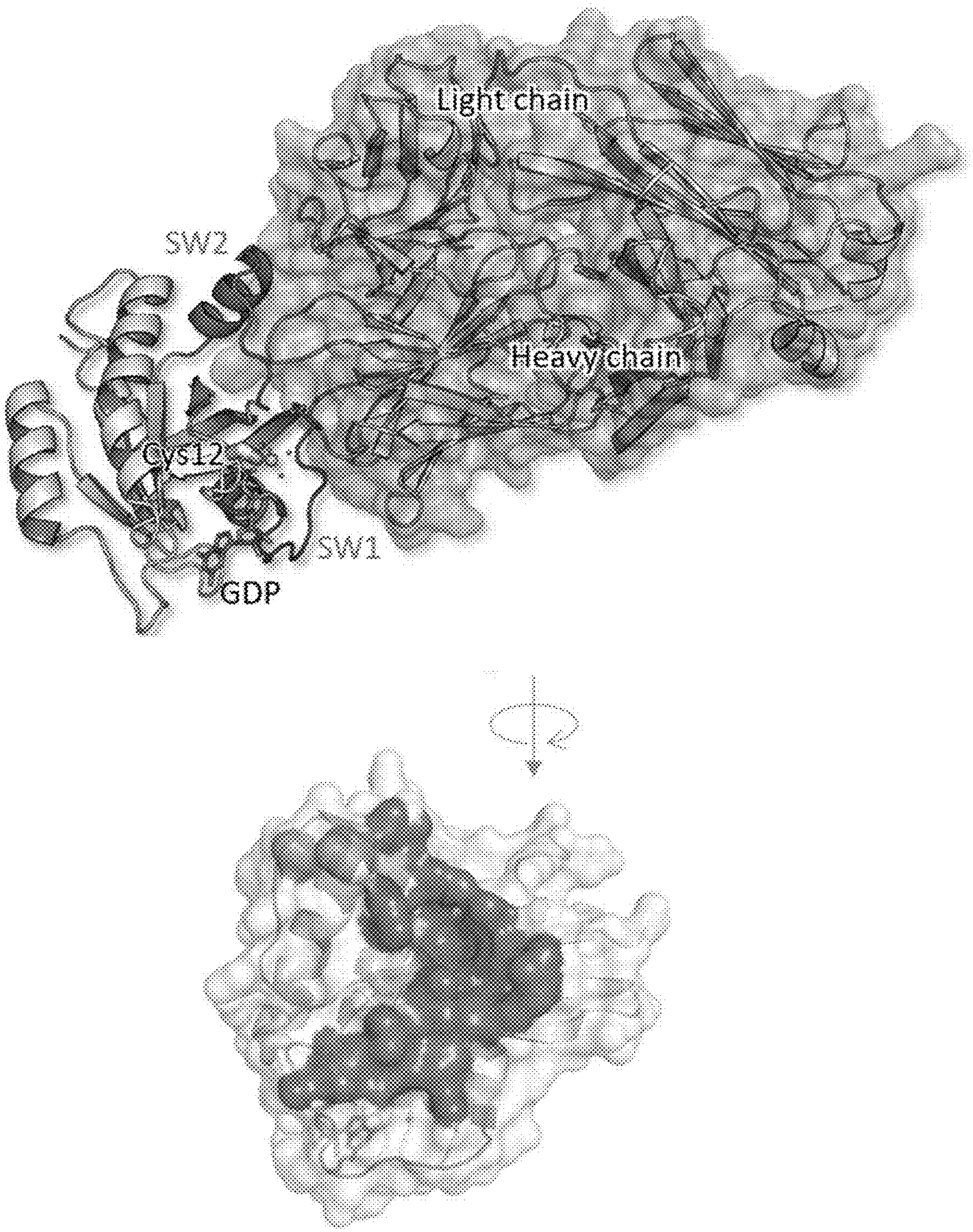
FIGS. 6A-6F show crystal structures of anti-KRas antibody:$KRas^{G12C}$ complexes.
Figure 6B:
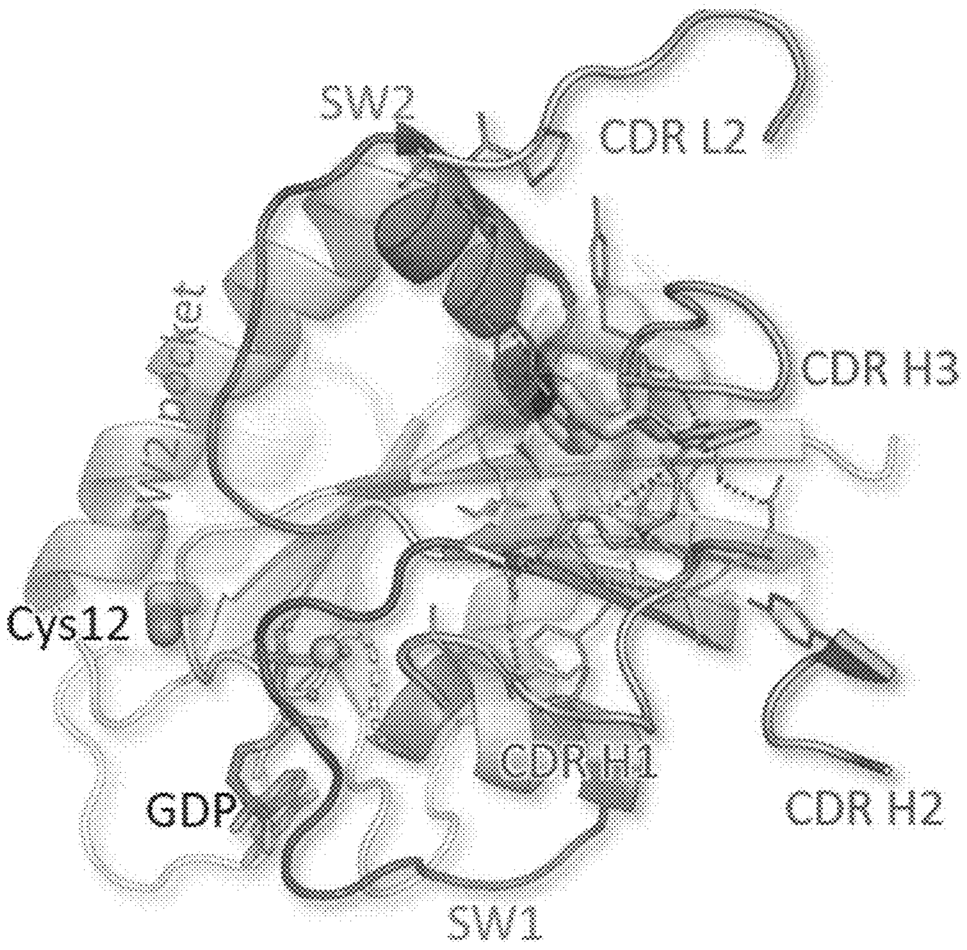
Figure 6C:
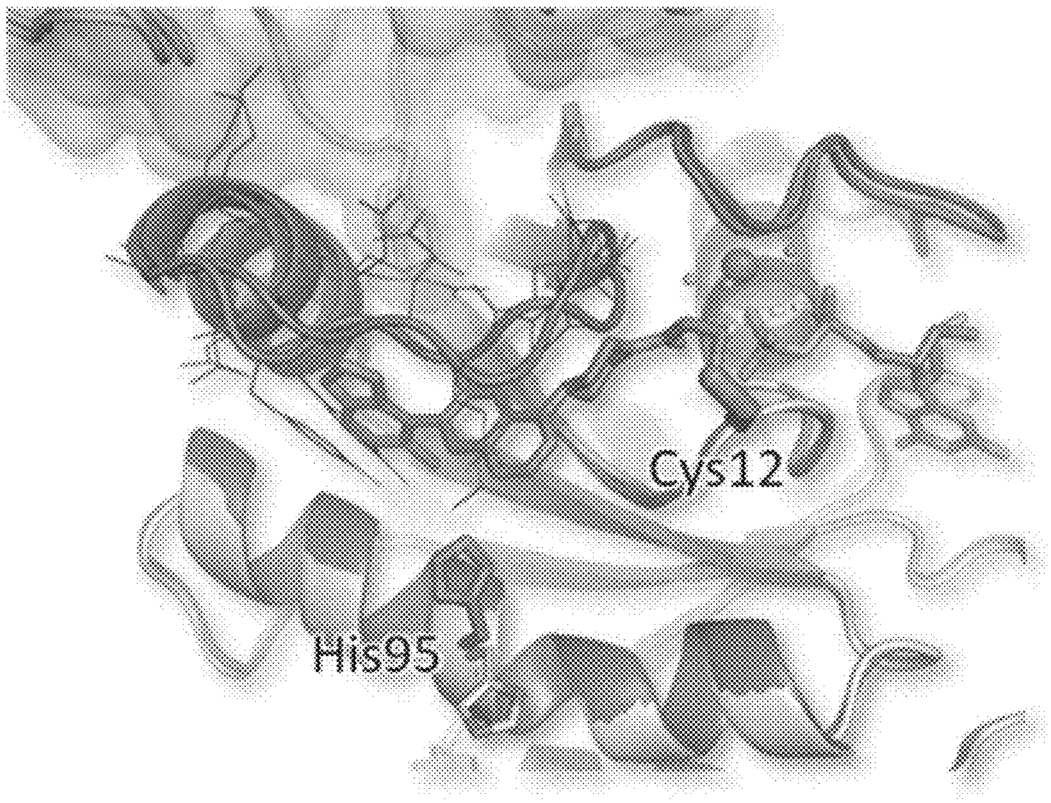
Figure 6D:
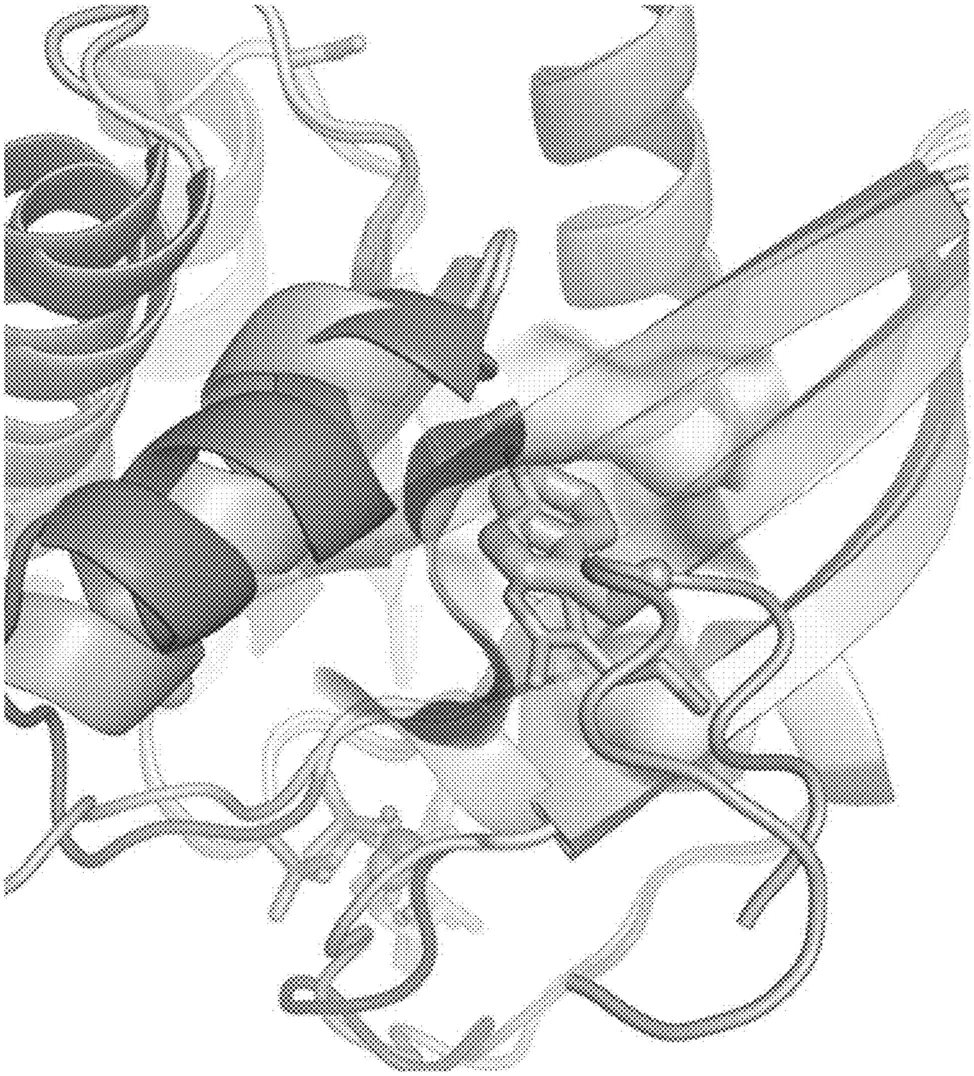
Figure 6E:
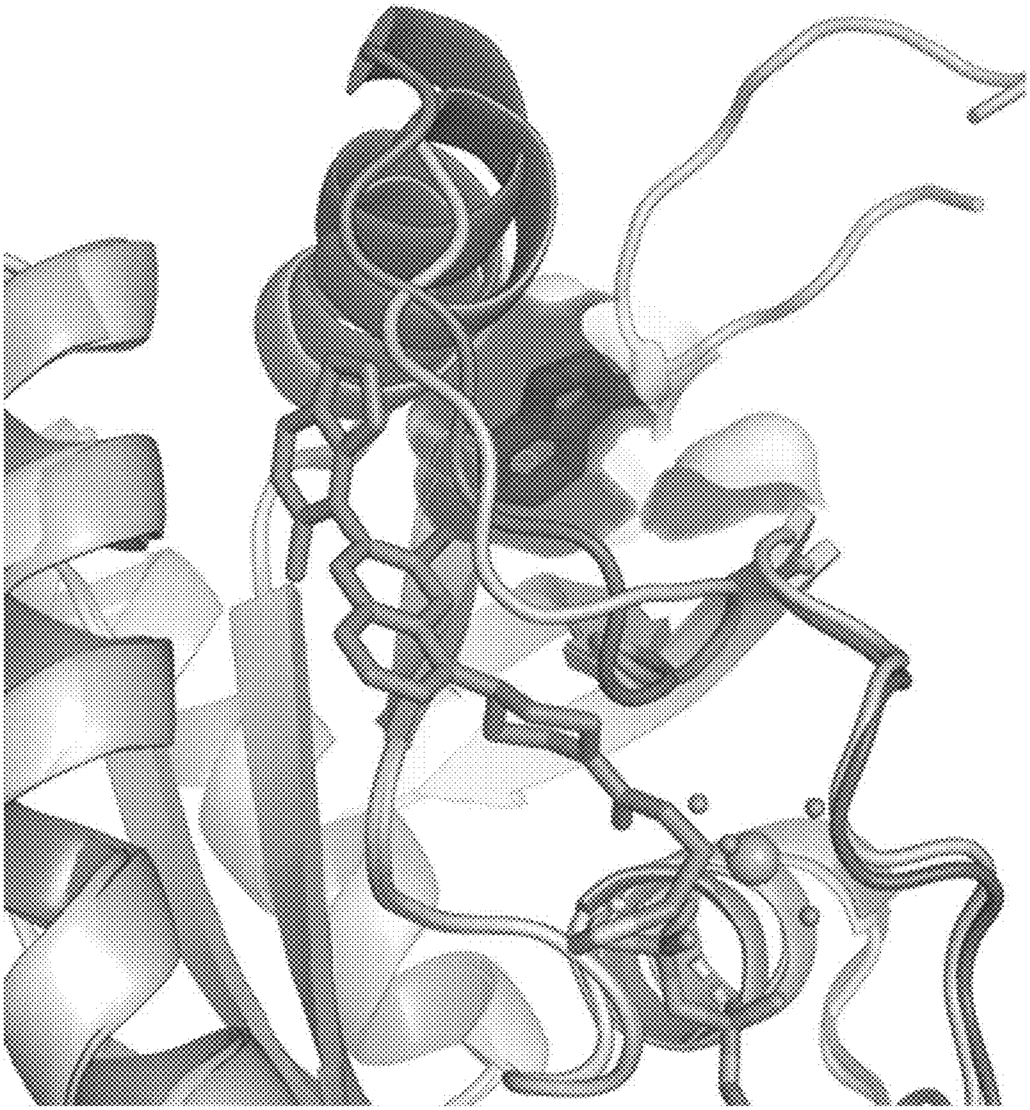
Figure 6F:
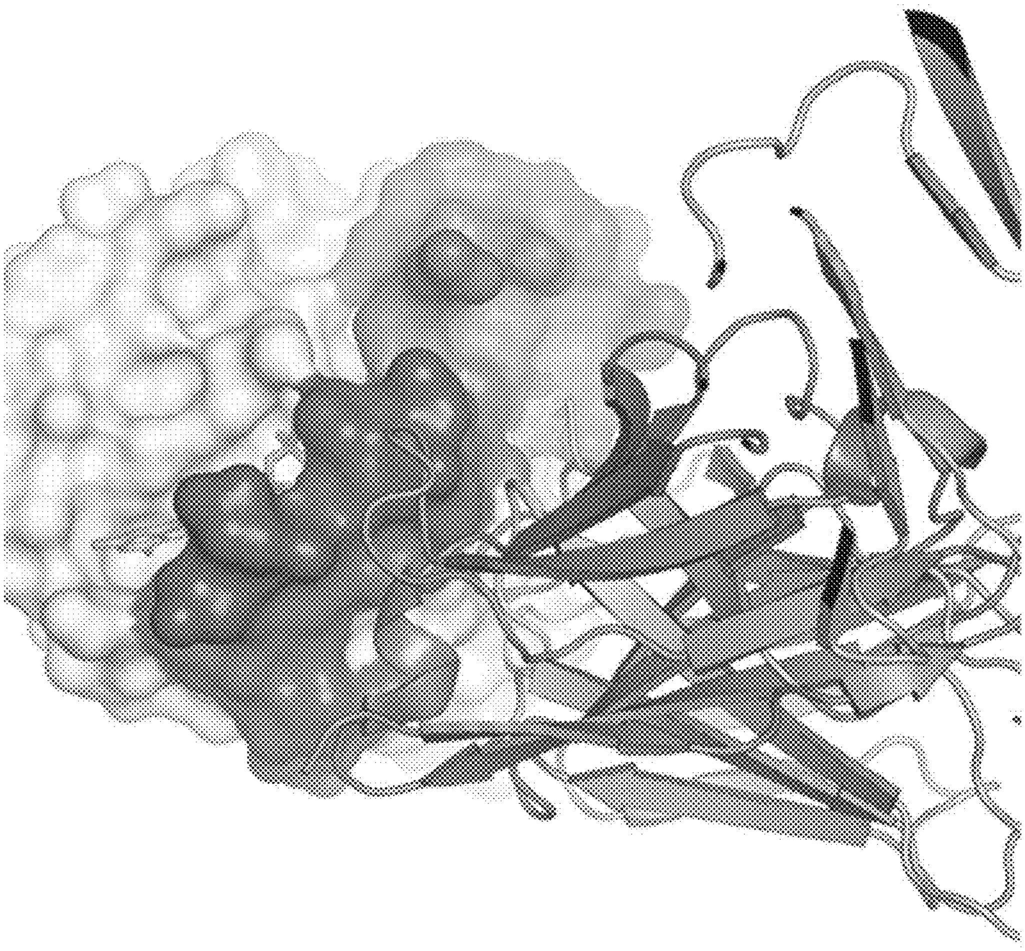

To gain further insights into the unique mode of action of the 2H11 anti-KRas antibody, the crystal structure of $KRas^{G12C}$-GDP in complex with 2H11 Fab was determined at 2.2 Å resolution (FIG. 6A). 2H11 approaches $KRas^{G12C}$ from the outer surface of SWII and does stabilize an open conformation of the SWII pocket. Fab binding buries ~745 $Å^2$ of surface area, with a shape complementarity score of 0.64. The epitope comprises residues from SWI, SWII and the center core beta-sheet. 2H11 complementarity-determining regions (CDRs) H1 and H3 contribute a majority of the direct contacts to $KRas^{G12C}$ (FIG. 6B). The 13-residue long H3 loop binds to the SWII region. At the center of epitope, HC.Trp99 anchors in a small hydrophobic pocket surrounded by $KRas^{G12C}$ residues Lys5, Leu6, Val7, Ser39, Asp54, Leu56, Tyr71, Thr74, Gly75 (FIG. 6C). This pocket was previously discovered to bind indole containing small-molecules which inhibit SOS-dependent nucleotide exchange (T. Maurer et al., *Proc Natl Acad Sci USA* 2012; 109:5299-5304; Q. Sun et al., *Angew Chem Int Ed Engl* 2012; 51:6140-6143). Interestingly, the antibody exploited this site with a chemically similar tryptophan side chain. The CDRH1 binds to the vicinity of SWI region by packing against a portion of the Ras-binding domain (RBD) binding site. Unlike iDab6, 2H11 makes little direct contact with SWI residues (FIG. 6F), therefore was less sensitive to the type of bound nucleotide. CDR L2 and H2 participate in KRas recognition by making a small number of van der Waals contacts. L2 was particularly interesting as it touches the C-terminal tip of the SWII helix, hence providing additional stabilization to SWII loop but without overly restricting the conformation. As shown in FIG. 6E, the most flexible part of SWII, Gln60-Ala66, was completely free from direct contact with 2H11, therefore it maintains certain level of conformational flexibility that permits binding of various ligands in the SWII pocket. For example, comparison of the $KRas^{G12C}$-GDP/2H11 complex structure with GNE-1952 bound $KRas^{G12C}$-GDP structure (FIG. 6D) indicates that the stabilized SWII pocket was sufficiently open to accommodate the inhibitor and the flexibility in SWII permits slight closure inward to fully wrap around the ligand. To validate this hypothesis, the crystal structure of 2H11 in complex with GNE-1952 alkylated $KRas^{G12C}$ was determined. The presence of GNE-1952 indeed was associated with shifts of mainchain and sidechain conformation in SWII residues (FIG. 6C), while the rest of KRas and the Fab CDRs structure remain constant. An important sidechain flip occurs at His95 upon compound binding, which forms a hydrogen bond with the quinazoline nitrogen. This interaction appears to be common for quinazoline scaffold compounds and was unaltered by 2H11 Fab binding (M. P. Patricelli et al., *Cancer Discov* 2016; 6:316-329).

Example 10: Extension of Selected Anti-KRas Antibodies to Other KRas Mutants

The following example describes the ability of the selected anti-KRas antibodies to bind various KRas mutants.

Materials and Methods

Antibody ELISA against alkylated $KRas^{G12C}$. Biotinylated $KRas^{G12C}$-GDP+GNE-1952 and $KRas^{G12C}$-GDP was coated on NeutrAvidin ELISA plates (Thermo Scientific) in triplicate at 0.3 μg/mL in PBS overnight at 4° C. Plates were washed with PBSBT and serial dilutions of anti-KRas antibodies starting at 10 μg/mL were added for 1-2 hours at 25° C. with shaking. After washing, a species matched Fc-specific HRP 2° antibody was added for 1 hour at 25° C. with shaking. After washing with PBSBT, plates were developed with TMB substrate for 5 minutes and detected at 650 nm.

Antibody ELISA against mutant KRas-GDP proteins. KRas-GDP proteins were directly coated in triplicate at 10 μg/mL on Maxisorb plates (Thermo Scientific) in PBS overnight at 4° C. Plates were blocked for 2 hours at 25° C. using 4% BSA. Serial dilutions of 1A5 and 2H11 antibodies starting at 10 μg/mL were added for 1-2 hours at 25° C. with shaking. Plates were developed and read as described above.

Figure 7:
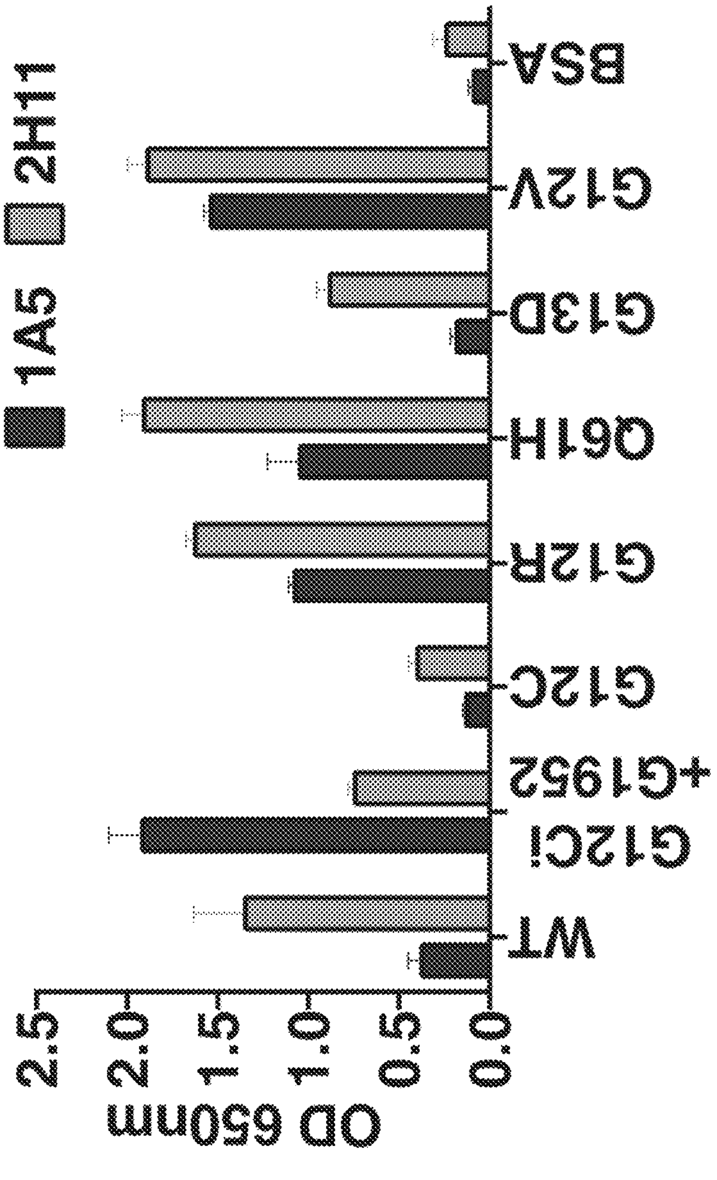
FIG. 7 shows ELISA experiments with 1A5 and 2H11 anti-KRas antibodies binding to a panel of KRas-GDP mutants. The genotype of KRas (or the BSA control) is indicated on the x-axis, and $OD_{650}$ nm is indicated on the y-axis.

To explore whether 2H11 could also recognize the GDP bound states and potentially stabilize the open conformation of the SWII region in KRas mutants other than $KRas^{G12C}$, binding of antibodies 1A5 and 2H11 to a panel of KRas mutants was evaluated by ELISA (FIG. 7). Quite strikingly, 2H11 exhibited strong binding to $KRas^{G12V}$-GDP, $KRas^{G12R}$-GDP, and $KRas^{Q61H}$-GDP, and much weaker binding to $KRas^{G13D}$-GDP and $KRas^{WT}$-GDP (FIG. 7). Given that 2H11 anti-KRas antibody binds multiple KRas mutants and can increase the affinity of SWII pocket binders, it may enable the identification of novel ligands to target other RAS mutants.

Example 11: CLAMP Cooperativity SPR Assay Using Target and CLAMP Co-Capture

A BIACORE 5200 (GE Healthcare Life Sciences) was set to an analysis temperature of 20° C. and a series-S SA sensor chip (i.e. a hydrogel coated sensing chip with pre-coated Streptavidin) was docked. The system was primed three times with assay buffer containing 50 mM (4-(2-hydroxy-ethyl)-1-piperazineethanesulfonic acid), pH 7.5; 150 mM NaCl; 0.2% polyethylene glycol (average molecular weight of 3350 Da), 0.1% carboxymethlated-dextran; 10 mM magnesium chloride, 100 nM nucleotide (GDP, GTP or nucleotide analog), 0.1 mM (tris(2-carboxyethyl)phosphine). Biotinylated mutant KRas (i.e. $KRas^{G12V}$-GDP, $KRas^{G12D}$-GDP, $KRas^{G12R}$-GDP and $KRas^{G13D}$-GDP), were expressed recombinantly and purified in-house and for a given mutant KRas, was diluted to give a final concentration within the range 100-500 nM in assay buffer. This mutant KRas sample was then injected over a sensing channel giving a capture density in the range of 2000 RU to 3000 RU. This is equivalent to a hydrogel concentration of ~0.9-1.5 mM inside the optically interrogated hydrogel volume. A second sensing channel remained uncoated in order to provide a reference sensing channel. Excess unoccupied biotin sites were saturated by injecting 1 μM biotin.

A series of nine doubling dilutions from a 10 mM stock (dissolved in dimethylsulfoxide) of test compound, a SWII pocket-binding compound, were prepared using assay buffer as diluent giving a concentration range from 0.039-to-10 μM. The dimethylsulfoxide concentration in each sample and in the running buffer was matched at 1% (v/v). A set of dilutions were prepared in this way for all tested compounds. A series of six samples prepared from assay buffer containing a range of dimethylsulfoxide concentrations were prepared to order to provide solvent correction standards. Each dilution series was injected for 10 seconds at 100 μL/min over all sensing channels, from low-to high-concentration, producing a single cycle containing a full dose response. The cycle was double referenced by first subtracting the cycle for the un-coated sensing channel and then subtracting a blank single cycle, which was a sample that did not contain compound. Each compound injection series was followed by a blank injection cycle allowing near neighbor blanks to be used for blank selection.

Figure 8:
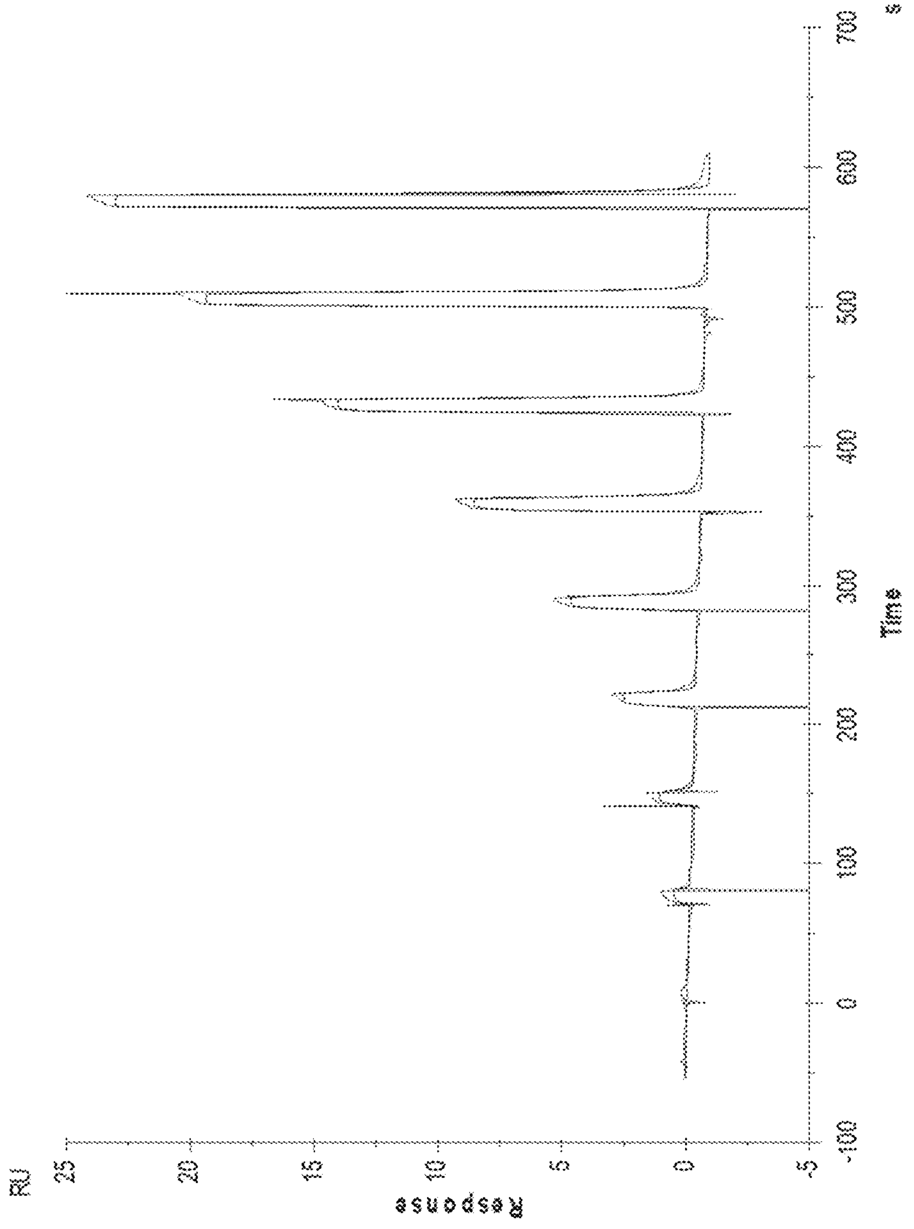
FIG. 8 shows an exemplary single cycle kinetic cycle for kinetic analysis of a single SWII binding compound without 2H11 co-capture. Time in seconds is indicated on the x-axis, and response in relative units (RU) is indicated on the y-axis. A single-site pseudo-first order model was fit giving $k_{on}$ of $3.29\times10^5$ (1/Ms), $k_{off}$ of 1.3 (1/s) and $K_D$ of ~4 μM.

The data was exported into Biaevaluation software (GE Healthcare Life Sciences) and a kinetic model fit was performed to in order to obtain the interaction constants. The data for a single compound is shown in FIG. 8. This assay was performed without the use of 2H11 Fab and therefore returned the interaction constants for compound binding to $KRas^{G12V}$-GDP without co-operative amplification of affinity.

As shown in FIG. 8, the increasing concentrations of compound resulted in a dose-dependent response that approached saturation of the $KRas^{G12V}$-GDP-coated surface. A single-site pseudo-first order model was fit giving $k_{on}$ of $3.29\times10^5$ (1/Ms), $k_{off}$ of 1.3 (1/s) and $K_D$ of ~4 μM. It can be observed that the fitted model curve superimposed well onto experimental response cycle.

To determine the co-cooperativity enhancement factor of the 2H11 Fab, the above assay was repeated but with the inclusion of a 2H11-Fab-biotin capture step after capture of the KRas mutant(s) but before biotin blocking.

2H11-Fab-biotin was injected at 200 nM until the binding response reached an approximate plateau and resulted in ~2500-3000 RU (0.5 mM Fab) of co-captured 2H11 onto the pre-coated mutant KRas-surface. This represented a mole ratio of 2H11 Fab:KRas of 1:2 and effectively results in an equal fraction of weak binding sites (i.e. KRas without 2H11 Fab bound) and high affinity binding sites (i.e. KRas-2H11 Fab complexes). Co-capture of sufficient Fab to yield a stoichiometric equivalence, or an excess of Fab, resulted in homogenous KRas-2H11 Fab complexes and was possible with further optimization.

Figure 9:
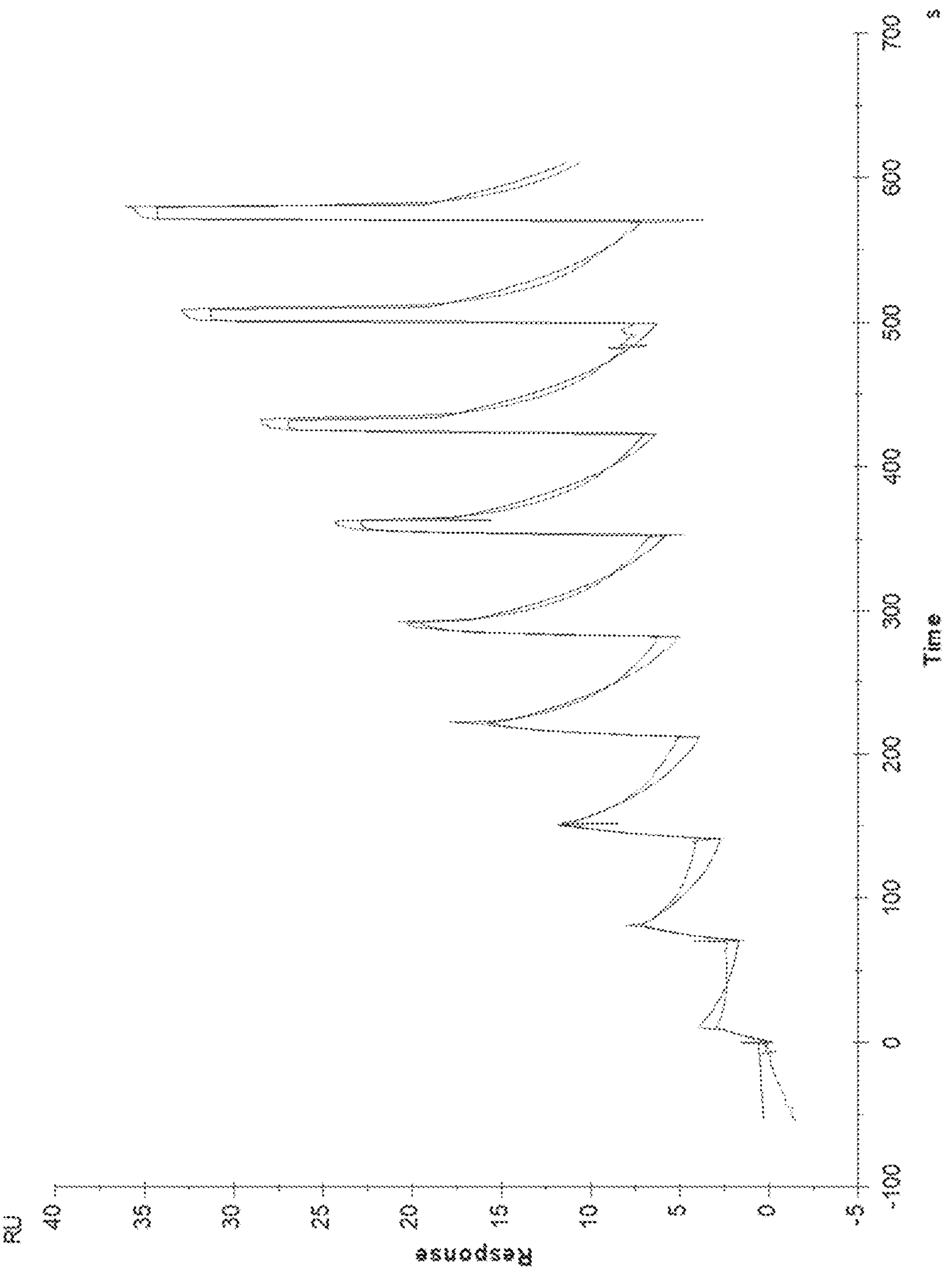
FIG. 9 shows an exemplary single cycle kinetic cycle for kinetic analysis of a single SWII binding compound with 2H11 Fab-co-capture. Time in seconds is indicated on the x-axis, and response in relative units (RU) is indicated on the y-axis. A two-site pseudo-first order model was fit to data and returned the interaction constants for the high affinity site as $k_{on}$ of $6.6\times10^5$ (1/Ms), $k_{off}$ as 0.025 (1/s) and $K_D$ of ~0.04 μM.
Figure 10:
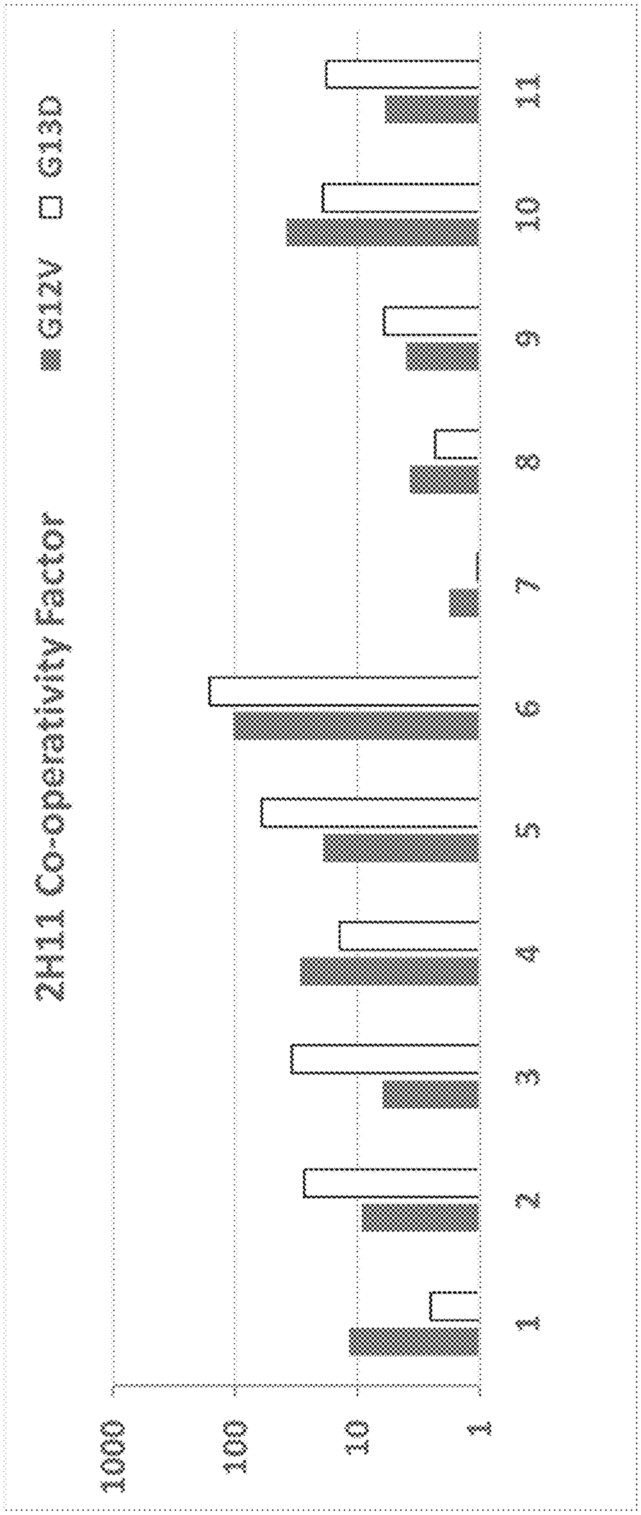
FIG. 10 shows 2H11-Fab co-cooperativity factor values for eleven SWII binding compounds, as indicated on the x-axis, binding to $KRas^{G12V}$-GDP (gray bars) and $KRas^{G13D}$-GDP (white bars), as determined using the co-capture SPR assay.

The analysis was performed as outlined above, but the 1:1 model was replaced with a two-site site binding model (heterogeneous ligand) that allowed the kinetics and affinity of both sites to be determined from a fit to a single cycle kinetic curve, as shown in FIG. 9. As shown in FIG. 9, the increasing concentrations of compound resulted in a biphasic dose-dependent response. A two-site pseudo-first order model was fit to data and returned the interaction constants for the high affinity site as $k_{on}$ of $6.6\times10^5$ (1/Ms), $k_{off}$ as 0.025 (1/s) and $K_D$ of ~0.04 μM. It can be observed that the fitted model curve superimposes well onto experimental response cycle. Compound binding to the high affinity stabilized SWII site is readily identified from the slower dissociation phase curvature at the end of each injection, which is indicative of a more stable complex. Binding to the weak affinity, non-stabilized SWII site appears to superimpose but with fast dissociation. As expected, binding to the higher affinity stabilized SWII KRas becomes saturated at low concentrations while binding to the non-stabilized weak affinity sites remains unsaturated even at the highest test concentration of 10 μM. This analysis was repeated for a selection of SWII binding compounds. The cooperativity factors were expressed as the $K_D$ ratio for stabilized:non-stabilized SWII binding, and FIG. 10 summarizes the co-cooperativity factors for a selection of compounds.

Curvature at the start and at the end of each injection, in FIG. 8, contains kinetic information and helps define the kinetic rate constants and the plateau regions in the middle of each injection define the equilibrium response at each dose. A 1:1 pseudo-first order model was fit to the data, shown superimposed to obtain the association rate constant, the dissociation rate constant and the affinity constant.

In non-co-capture SPR, the antibody can be pre-bound before exposure to the compounds to be tested and can be injected over the target-coated sensing surfaces where both the concentration and contact time are chosen to allow the antibody described herein to fully saturate (i.e. essentially no unbound target remaining). However, this approach has disadvantages. At high target concentrations, it was not possible to load a stoichiometric equivalent (e.g. one-Fab arm per target) concentration of full sized antibody (150 kDa) into the target-coated hydrogel. This loading limit may be a result of hydrogel exclusion effects driven by over-crowding and the complex interplay of molecular size exclusion, isoelectric point, electrostatics, hydrogel chain density and target density.

Biosensor-based assays for screening and compound binding characterization generally require several hours or more to run to completion, during which time the antibody is free to dissociate from the surface into the continuously flowing buffer stream. Therefore, periodic injections of antibody are required in order to re-saturate the surface. Periodic re-saturation is impractical when the antibody KRas complex has a relatively short half-life (e.g. <15 min) and at best leads to highly variable occupancy during the assay. Thus, the co-capture techniques described herein are more efficient and better at determining interaction and compound affinity.

What is claimed is:

1. An isolated antibody or antigen binding fragment thereof, comprising:
 (a) a light chain variable region comprising:
  (i) CDR-L1 comprising the amino acid sequence SGSSSNIGSNYVY (SEQ ID NO:9);
  (ii) CDR-L2 comprising the amino acid sequence RNNQRPS (SEQ ID NO:10); and
  (iii) CDR-L3 comprising the amino acid sequence AAWDERLSGWV (SEQ ID NO: 11);
 and
 (b) a heavy chain variable region comprising:
  (i) CDR-H1 comprising the amino acid sequence SSNWWS (SEQ ID NO:12);
  (ii) CDR-H2 comprising the amino acid sequence EIYHSGSTNYNPSLKS (SEQ ID NO: 13); and
  (iii) CDR-H3 comprising the amino acid sequence GSSSWYDLGPFDY (SEQ ID NO: 14).

2. The isolated antibody or antigen binding fragment thereof of claim 1, wherein the light chain variable region comprises the amino acid sequence of SEQ ID NO:15 and the heavy chain variable region comprises the amino acid sequence of SEQ ID NO:16.

3. An isolated antibody or antigen binding fragment thereof, comprising:
 (a) a light chain variable region comprising:
  (i) CDR-L1 comprising the amino acid sequence SEQ ID NO:9;
  (ii) CDR-L2 comprising the amino acid sequence SEQ ID NO:10; and
  (iii) CDR-L3 comprising the amino acid sequence SEQ ID NO:11; and
 (b) a heavy chain variable region comprising:
  (i) CDR-H1 comprising one of the amino acid sequences selected from the group consisting of SEQ ID NO:91, SEQ ID NO: 92, SEQ ID NO:93, SEQ ID NO:94, SEQ ID NO: 95, SEQ ID NO:96, SEQ ID NO:97, and SEQ ID NO:98;
  (ii) CDR-H2 comprising the amino acid sequence SEQ ID NO:13; and
  (iii) CDR-H3 comprising the amino acid sequence SEQ ID NO:14.

4. The isolated antibody or antigen binding fragment thereof of claim 3, wherein the light chain variable region comprises the amino acid sequence of SEQ ID NO:15 and the heavy chain variable region comprises one of the amino acid sequences selected from the group consisting of SEQ ID NO: 99, SEQ ID NO: 100, SEQ ID NO: 101, SEQ ID NO: 102, SEQ ID NO: 103, SEQ ID NO: 104, SEQ ID NO:105, and SEQ ID NO:106.

5. An isolated antibody or antigen binding fragment thereof, comprising:
 (a) a light chain variable region comprising:
  (i) CDR-L1 comprising the amino acid sequence RASQGIRNDLG (SEQ ID NO:1);
  (ii) CDR-L2 comprising the amino acid sequence AASSLQS (SEQ ID NO:2); and
  (iii) CDR-L3 comprising the amino acid sequence LQDHDYPLT (SEQ ID NO:3); and
 (b) a heavy chain variable region comprising:
  (i) CDR-H1 comprising the amino acid sequence SYSMN (SEQ ID NO:4);
  (ii) CDR-H2 comprising the amino acid sequence YISSSSTIYYADSVKG (SEQ ID NO: 5); and
  (iii) CDR-H3 comprising the amino acid sequence GFYVRNWFDP (SEQ ID NO:6).

6. The isolated antibody or antigen binding fragment thereof of claim 5, wherein the light chain variable region comprises the amino acid sequence of SEQ ID NO:7 and the heavy chain variable region comprises the amino acid sequence of SEQ ID NO:8.

7. An isolated antibody or antigen binding fragment thereof, comprising:
 (a) a light chain variable region comprising:
  (i) CDR-L1 comprising the amino acid sequence RASQGISSYLA (SEQ ID NO:17);
  (ii) CDR-L2 comprising the amino acid sequence AASSLQS (SEQ ID NO:18); and
  (iii) CDR-L3 comprising the amino acid sequence QQYYSYPFT (SEQ ID NO:19); and
 (b) a heavy chain variable region comprising:
  (i) CDR-H1 comprising the amino acid sequence SYAMS (SEQ ID NO:20);
  (ii) CDR-H2 comprising the amino acid sequence AISSSGSSTYYADSVKG (SEQ ID NO: 21); and
  (iii) CDR-H3 comprising the amino acid sequence DQGGYGYPGESWFDY (SEQ ID NO: 22).

8. The isolated antibody or antigen binding fragment thereof of claim 7, wherein the light chain variable region comprises the amino acid sequence of SEQ ID NO:23 and the heavy chain variable region comprises the amino acid sequence of SEQ ID NO:24.

9. An isolated antibody or antigen binding fragment thereof, comprising:
 (a) a light chain variable region comprising:
  (i) CDR-L1 comprising the amino acid sequence RASQSISSYLN (SEQ ID NO:25);
  (ii) CDR-L2 comprising the amino acid sequence AASSLQS (SEQ ID NO:26); and
  (iii) CDR-L3 comprising the amino acid sequence QQSYSPPWT (SEQ ID NO:27); and
 (b) a heavy chain variable region comprising:
  (i) CDR-H1 comprising the amino acid sequence SYSMN (SEQ ID NO:28);
  (ii) CDR-H2 comprising the amino acid sequence SISSSSSYIYYADSVKG (SEQ ID NO: 29); and
  (iii) CDR-H3 comprising the amino acid sequence AFYSYMDV (SEQ ID NO:30).

10. The isolated antibody or antigen binding fragment thereof of claim 9, wherein the light chain variable region comprises the amino acid sequence of SEQ ID NO:31 and the heavy chain variable region comprises the amino acid sequence of SEQ ID NO:32.

11. An isolated antibody or antigen binding fragment thereof, comprising:

(a) a light chain variable region comprising:

(i) CDR-L1 comprising the amino acid sequence RSSQSLLHSNGYNYLD (SEQ ID NO: 33);

(ii) CDR-L2 comprising the amino acid sequence LGSNRAS (SEQ ID NO:34); and (iii) CDR-L3 comprising the amino acid sequence MQALQTPLT (SEQ ID NO:35); and (b) a heavy chain variable region comprising:

(i) CDR-H1 comprising the amino acid sequence SSNWWS (SEQ ID NO:36);

(ii) CDR-H2 comprising the amino acid sequence EIYHSGSTNYNPSLKS (SEQ ID NO: 37); and (iii) CDR-H3 comprising the amino acid sequence ERTILTGYYGFDY (SEQ ID NO: 38).

12. The isolated antibody or antigen binding fragment thereof of claim 11, wherein the light chain variable region comprises the amino acid sequence of SEQ ID NO:39 and the heavy chain variable region comprises the amino acid sequence of SEQ ID NO:40.

13. An isolated antibody or antigen binding fragment thereof, comprising:

(a) a light chain variable region comprising:

(i) CDR-L1 comprising the amino acid sequence SGSSSNIGNNYVS (SEQ ID NO: 41);

(ii) CDR-L2 comprising the amino acid sequence DNNKRPS (SEQ ID NO:42); and (iii) CDR-L3 comprising the amino acid sequence GTWDSSLTGYV (SEQ ID NO: 43); and (b) a heavy chain variable region comprising:

(i) CDR-H1 comprising the amino acid sequence SYAIS (SEQ ID NO:44);

(ii) CDR-H2 comprising the amino acid sequence GIIPIFGTANYAQKFQG (SEQ ID NO: 45); and (iii) CDR-H3 comprising the amino acid sequence YYDFWSGYPGGLFDV (SEQ ID NO: 46).

14. The isolated antibody or antigen binding fragment thereof of claim 13, wherein the light chain variable region comprises the amino acid sequence of SEQ ID NO:47 and the heavy chain variable region comprises the amino acid sequence of SEQ ID NO:48.

15. An isolated antibody or antigen binding fragment thereof, comprising:

(a) a light chain variable region comprising:

(i) CDR-L1 comprising the amino acid sequence SGSSSNIGSNYVY (SEQ ID NO: 81);

(ii) CDR-L2 comprising the amino acid sequence RNNQRPS (SEQ ID NO:82); and (iii) CDR-L3 comprising the amino acid sequence AAWDDSLSGWV (SEQ ID NO: 83);

and (b) a heavy chain variable region comprising:

(i) CDR-H1 comprising the amino acid sequence SYSMN (SEQ ID NO:84);

(ii) CDR-H2 comprising the amino acid sequence YISSSSSTIYYADSVKG (SEQ ID NO: 85); and (iii) CDR-H3 comprising the amino acid sequence SFGPYAFDV (SEQ ID NO:86).

16. The isolated antibody or antigen binding fragment thereof of claim 15, wherein the light chain variable region comprises the amino acid sequence of SEQ ID NO:87 and the heavy chain variable region comprises the amino acid sequence of SEQ ID NO:88.

17. An isolated antibody or antigen binding fragment thereof, comprising:

(a) a light chain variable region comprising:

(i) CDR-L1 comprising the amino acid sequence SGSSSNIGNNYVS (SEQ ID NO: 49);

(ii) CDR-L2 comprising the amino acid sequence DNNKRPS (SEQ ID NO:50); and (iii) CDR-L3 comprising the amino acid sequence GTWDSSLTGWV (SEQ ID NO: 51);

and (b) a heavy chain variable region comprising:

(i) CDR-H1 comprising the amino acid sequence SYAIS (SEQ ID NO:52);

(ii) CDR-H2 comprising the amino acid sequence GIIPIFGTANYAQKFQG (SEQ ID NO: 53); and (iii) CDR-H3 comprising the amino acid sequence YYDFWSGYPGGLFDV (SEQ ID NO: 54).

18. The isolated antibody or antigen binding fragment thereof of claim 17, wherein the light chain variable region comprises the amino acid sequence of SEQ ID NO:55 and the heavy chain variable region comprises the amino acid sequence of SEQ ID NO:56.

19. An isolated antibody or antigen binding fragment thereof, comprising:

(a) a light chain variable region comprising:

(i) CDR-L1 comprising the amino acid sequence QGDSLRSYYAS (SEQ ID NO:57);

(ii) CDR-L2 comprising the amino acid sequence GKNNRPS (SEQ ID NO:58); and (iii) CDR-L3 comprising the amino acid sequence NSRDSSGNHWV (SEQ ID NO: 59);

and (b) a heavy chain variable region comprising:

(i) CDR-H1 comprising the amino acid sequence SYSMN (SEQ ID NO:60);

(ii) CDR-H2 comprising the amino acid sequence SISSSSSYIYYADSVKG (SEQ ID NO: 61); and (iii) CDR-H3 comprising the amino acid sequence TNNYGYRYFDY (SEQ ID NO: 62).

20. The isolated antibody or antigen binding fragment of claim 19, wherein the light chain variable region comprises the amino acid sequence of SEQ ID NO:63 and the heavy chain variable region comprises the amino acid sequence of SEQ ID NO:64.

21. An isolated antibody or antigen binding fragment thereof, comprising:

(a) a light chain variable region comprising:

(i) CDR-L1 comprising the amino acid sequence QGDSLRSYYAS (SEQ ID NO:65);

(ii) CDR-L2 comprising the amino acid sequence GKNNRPS (SEQ ID NO:66); and (iii) CDR-L3 comprising the amino acid sequence NSRDSTDNHLWV (SEQ ID NO: 67); and (b) a heavy chain variable region comprising:

(i) CDR-H1 comprising the amino acid sequence SYSMN (SEQ ID NO:68);

(ii) CDR-H2 comprising the amino acid sequence SISSSSSYIYYADSVKG (SEQ ID NO: 69); and (iii) CDR-H3 comprising the amino acid sequence ATSSGYYYFDY (SEQ ID NO: 70).

22. The isolated antibody or antigen binding fragment thereof of claim 21, wherein the light chain variable region comprises the amino acid sequence of SEQ ID NO:71 and the heavy chain variable region comprises the amino acid sequence of SEQ ID NO:72.

23. An isolated antibody or antigen binding fragment thereof, comprising:

(a) a light chain variable region comprising:
(i) CDR-L1 comprising the amino acid sequence SGSSSNIGNNYVS (SEQ ID NO: 73);
(ii) CDR-L2 comprising the amino acid sequence DNNKRPS (SEQ ID NO:74); and
(iii) CDR-L3 comprising the amino acid sequence GTWDNSLSVWV (SEQ ID NO: 75); and
(b) a heavy chain variable region comprising:
(i) CDR-H1 comprising the amino acid sequence SYSMN (SEQ ID NO:76);
(ii) CDR-H2 comprising the amino acid sequence YISSSSSTIYYADSVKG (SEQ ID NO: 77); and
(iii) CDR-H3 comprising the amino acid sequence GKGIVGWGFFGMDV (SEQ ID NO: 78).

24. The isolated antibody or antigen binding fragment thereof of claim 23, wherein the light chain variable region comprises the amino acid sequence of SEQ ID NO:79 and the heavy chain variable region comprises the amino acid sequence of SEQ ID NO:80.

25. A method for detecting KRas-GDP in a biological sample, the method comprising contacting the biological sample with an antibody or antigen binding fragment thereof of any one of claims 1, 5 and 23.

26. The method of claim 25, further comprising contacting the biological sample with an antibody that binds to KRas-GTP, wherein the amount of KRas-GDP and the amount of KRas-GTP are determined.

27. A method for detecting KRas-GTP in a biological sample, the method comprising contacting the biological sample with an antibody or antigen binding fragment thereof of any one of claims 1, 5 and 23.

28. The method of claim 27, further comprising contacting the biological sample with an antibody that binds to KRas-GDP, wherein the amount of KRas-GTP and the amount of KRas-GDP are determined.

29. A method of obtaining an inhibitor of a KRas mutant, the method comprising:
contacting the antibody or antigen binding fragment thereof of any one of claims 1, 5 and 23 with the KRas mutant,
screening compounds, and
identifying compounds that bind to the KRas mutant bound to the antibody or antigen binding fragment thereof.

30. The method of claim 29, wherein the compounds comprise molecules that covalently modify KRas at the SWII pocket.

31. The method of claim 29, wherein the compounds comprise a covalent inhibitor that alkylates at least one residue in the SWII pocket.

32. The method of claim 29, wherein the compounds comprise molecules that non-covalently modify KRas at the SWII pocket.

33. The method of claim 29, wherein the KRas mutant is $KRas^{G12C}$, $KRas^{G12V}$, $KRas^{G12D}$, $KRas^{G13D}$, $KRas^{G12R}$ or $KRas^{Q61H}$.

34. A method of detecting alkylation of KRas, the method comprising:
contacting a biological sample with the antibody or antigen binding fragment thereof of any one of claims 1, 5 and 23; and
detecting the antibody or antigen binding fragment thereof bound to alkylated KRas.

35. The method of claim 34, wherein the KRas is $KRas^{G12C}$.

36. The method of claim 34, wherein the antibody or antigen binding fragment thereof is a KRas alkylated conformation specific antibody.

37. A method of detecting alkylation of KRas in a patient, the method comprising:
administering the antibody or antigen binding fragment thereof of any one of claims 1, 5 and 23 to the patient; and
detecting the antibody or antigen binding fragment thereof bound to the alkylated KRas.

38. A method of detecting alkylation of KRas in a patient treated with a KRas inhibitor, the method comprising:
(a) obtaining a sample from the patient;
(b) contacting the sample with the antibody or antigen binding fragment thereof of any one of claims 1, 5 and 23; and
(c) measuring an amount of KRas bound by the antibody or antigen binding fragment thereof.

39. The method of claim 38, wherein the KRas inhibitor is MRTX849, AMG-510, GDC-6036, ARS-3248, LY3499446, LY3537982, or JNJ-74699157.

40. The method of claim 38, wherein the amount of KRas bound by the antibody or antigen binding fragment thereof determines a dosage of the KRas inhibitor to administer to the patient.

41. The method of claim 37, wherein the KRas is $KRas^{G12C}$.

42. The method of claim 37, wherein the antibody or antigen binding fragment thereof is a KRas alkylated conformation specific antibody.

43. A method of treating a $KRas^{G12C}$ mediated cancer, the method comprising:
administering, to a patient having a $KRas^{G12C}$ mediated cancer, the antibody or antigen binding fragment thereof of any one of claims 1, 5 and 23.

44. The method of claim 43, wherein the $KRas^{G12C}$ mediated cancer is NSCLC, colon cancer, or pancreatic cancer.

45. A method for crystallizing KRas, wherein the KRas is optionally bound to a KRas inhibitor, the method comprising:
contacting the antibody or antigen binding fragment thereof of any one of claims 1, 5 and 23 with Kras; and
resolving a crystal structure of the complex.

46. The method of claim 45, wherein the KRas is $KRas^{G12C}$, $KRas^{G12D}$, $KRas^{G12V}$, $KRas^{G12R}$, $KRas^{G13D}$, or $KRas^{Q61H}$.

47. A system for measuring binding of an inhibitor compound to a KRas, the system comprising:
(a) a sensor chip; and
(b) a biosensing surface attached to the sensor chip;
wherein the biosensing surface comprises:
a hydrogel into which a KRas protein and the antibody or antigen binding fragment thereof of any one of claims 1, 2, 5, 6, 23 and 24 are co-localized, wherein:
the KRas protein and the antibody or antigen binding fragment thereof have sufficient degrees of freedom within the hydrogel to engage each other to form affinity complexes;
the local concentration of the KRas and the antibody or antigen binding fragment thereof exceeds the dissociation affinity constant by at least 10-fold, wherein the local concentration promotes formation of the affinity complexes; and
the fraction of unbound KRas protein and anti-KRas antibody is less than about 50%; and wherein the sensor chip comprises at least one sensing channel for measuring binding of the inhibitor compound to the anti-KRas antibody, wherein the inhibitor compound has been injected onto the biosensing surface.

48. The system of claim 47, wherein the hydrogel is about 10-500 nm, 10-300 nm, 10-250 nm, or about 10-200 nm in thickness.

49. The system of claim 47, wherein KRas is biotinylated.

50. A method of measuring binding of a KRas mutant protein to an anti-KRas antibody, wherein the method comprises:

(i) contacting the KRas mutant protein with a biosensing surface to form a KRas-bound biosensing surface;

(ii) contacting the KRas-bound biosensing surface with the antibody or antigen binding fragment thereof of any one of claims 1, 5, and 23, wherein the antibody or antigen binding fragment thereof is at a molar excess compared to the KRas mutant protein; and (iii) detecting the binding affinity of the antibody or antigen binding fragment thereof to the KRas mutant protein using surface plasmon resonance, wherein the biosensing surface is attached to a sensor chip, and wherein the biosensing surface comprises a hydrogel into which a KRas mutant protein and the antibody or antigen binding fragment thereof are co-localized.

* * * * *